US006764677B1

(12) United States Patent
Sharp et al.

(10) Patent No.: US 6,764,677 B1
(45) Date of Patent: Jul. 20, 2004

(54) TANGO 294, A LIPASE-LIKE PROTEIN

(75) Inventors: John D. Sharp, Arlington, MA (US); Thomas M. Barnes, Brookline, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/578,063

(22) Filed: May 24, 2000

Related U.S. Application Data

(63) Continuation-in-part of application No. 09/333,159, filed on Jun. 14, 1999.

(51) Int. Cl.[7] .................................................. A61K 38/43
(52) U.S. Cl. ..................... 424/94.1; 530/350; 435/69.1; 435/69.7; 514/2
(58) Field of Search .......................... 530/350; 536/23.1

(56) References Cited

U.S. PATENT DOCUMENTS 5,807,726 A * 9/1998 Blanchard et al.

FOREIGN PATENT DOCUMENTS

| | | |
|---|---|---|
| EP | 0 911 399 A | 4/1999 |
| JP | WO 95/14772 | 1/1995 |
| WO | WO 96/34873 | 11/1996 |
| WO | WO 98/45436 | 10/1998 |
| WO | WO 99/06550 | 2/1999 |
| WO | WO 00/06698 | 2/2000 |

OTHER PUBLICATIONS

S. Vukicevic et al. Induction of nephrogenic mesenchyme by osteogenic protein 1 (bone morphogenetic protein 7). 1996. Proc. Natl. Acad. Sci. USA, 93: 9021–26.*
J. Skolnick et al. From genes to protein structure and function: novel applications of computational approaches in the genomic era. 2000. Trends in Biotechnology, 18(1): 34–39.*
S. E. Brenner. Errors in genome annotation. 1999. Trends in Genetics, 15(4): 132–33.*
R.A. Anderson et al. Cloning and expression of cDNA encoding human lysosomal acid lipase/cholesteryl ester hydrolase. 1991. J. Biol. Chem., 266(33):22479–84.*
H. Du et al. Locus HSU08464, Jun. 23, 1994. Accessed Aug. 27, 2001 (see attached computer printout).*
Elsbach, 1998, Journal of Leukocyte Biology, 64:14–18.
Mahadeva et al., 1997, Chest 112:1699–1701.
GenPept Accession No. P04634.
GenPept Accession No. P80035.
GenPept Accession No. P07098.
GenPept Accession No. P38571.
GenPept Accession No. P34298.
GenBank Accession No. AA506741.
GenBank Accession No. AA670682.
GenBank Accession No. AA499001.
GenBank Accession No. AA794194.
GenBank Accession No. AA756504.
GenBank Accession No. Z95116.
GenBank Accession No. A1095706.
GenBank Accession No. A1090561.
GenBank Accession No. A1278132.
GenBank Accession No. X63723.
GenBank Accession No. X63723.
GenBank Accession No. X85991.
GenBank Accession No. AA81246.
GenBank Accession No. Z1568200.
GenBank Accession No. AA029404.
GenBank Accession No. W25986.
GenBank Accession No. AA779337.
GenBank Accession No. AA082143.
GenBank Accession No. AA779337.
GenBank Accession No. W65734.
GenBank Accession No. AA059511.
GenBank Accession No. Aa153748.
GenBank Accession No. AL021937.
GenBank Accession No. A1527813.
GenBank Accession No. X76488.
GenBank Accession No. W80832.
GenBank Accession No. AA630445.

* cited by examiner

*Primary Examiner*—Dong Jiang
(74) *Attorney, Agent, or Firm*—Millennium Pharmaceuticals, Inc.

(57) ABSTRACT

The invention provides isolated nucleic acids encoding a variety of proteins having diagnostic, preventive, therapeutic, and other uses. These nucleic and proteins are useful for diagnosis, prevention, and therapy of a number of human and other animal disorders. The invention also provides antisense nucleic acid molecules, expression vectors containing the nucleic acid molecules of the invention, host cells into which the expression vectors have been introduced, and non-human transgenic animals in which a nucleic acid molecule of the invention has been introduced or disrupted. The invention still further provides isolated polypeptides, fusion polypeptides, antigenic peptides and antibodies. Diagnostic, screening, and therapeutic methods utilizing compositions of the invention are also provided. The nucleic acids and polypeptides of the present invention are useful as modulating agents in regulating a variety of cellular processes.

20 Claims, 95 Drawing Sheets

```
                                 M   A   P   P   A   A   R   L   A   L   L     11
GTCGACCCACGCGTCCGCCCACGCGTCCGGCCC ATG GCG CCG CCC GCC GCC CGC CTC GCC CTG CTC     66

S   A   A   A   L   T   L   A   A   R   P   A   P   S   P   G   L   G   P   G     31
TCC GCC GCG GCG CTC ACG CTG GCG GCC CGG CCC GCG CCT AGC CCC GGC CTC GGC CCC GGA  126

P   E   C   F   T   A   N   G   A   D   Y   R   G   T   Q   N   W   T   A   L     51
CCC GAG TGT TTC ACA GCC AAT GGT GCG GAT TAT AGG GGA ACA CAG AAC TGG ACA GCA CTA  186

Q   G   G   K   P   C   L   F   W   N   E   T   F   Q   H   P   Y   N   T   L     71
CAA GGC GGG AAG CCA TGT CTG TTT TGG AAC GAG ACT TTC CAG CAT CCA TAC AAC ACT CTG  246

K   Y   P   N   G   E   G   G   L   G   E   H   N   Y   C   R   N   P   D   G     91
AAA TAC CCC AAC GGG GAG GGG GGC CTG GGT GAG CAC AAC TAT TGC AGA AAT CCA GAT GGA  306

D   V   S   P   W   C   Y   V   A   E   H   E   D   G   V   Y   W   K   Y   C    111
GAC GTG AGC CCC TGG TGC TAT GTG GCA GAG CAC GAG GAT GGT GTC TAC TGG AAG TAC TGT  366

E   I   P   A   C   Q   M   P   G   N   L   G   C   Y   K   D   H   G   N   P    131
GAG ATA CCT GCT TGC CAG ATG CCT GGA AAC CTT GGC TGC TAC AAG GAT CAT GGA AAC CCA  426

P   P   L   T   G   T   S   K   T   S   N   K   L   T   I   Q   T   C   I   S    151
CCT CCT CTA ACT GGC ACC AGT AAA ACG TCC AAC AAA CTC ACC ATA CAA ACT TGC ATC AGT  486

F   C   R   S   Q   R   F   K   F   A   G   M   E   S   G   Y   A   C   F   C    171
TTT TGT CGG AGT CAG AGG TTC AAG TTT GCT GGG ATG GAG TCA GGC TAT GCT TGC TTC TGT  546
```

Fig. 1A

```
 G   N   N   P   D   Y   W   K   Y   G   E   A   A   S   T   E   C   N   S   V   191
GGA AAC AAT CCT GAT TAC TGG AAG TAC GGG GAG GCA GCC AGT ACC GAA TGC AAC AGC GTC  606

 C   F   G   D   H   T   Q   P   C   G   G   D   G   R   I   I   L   F   D   T   211
TGC TTC GGG GAT CAC ACC CAA CCC TGT GGT GGC GAT GGC AGG ATC ATC CTC TTT GAT ACT  666

 L   V   G   A   C   G   G   N   Y   S   A   M   S   S   V   V   Y   S   P   D   231
CTC GTG GGC GCC TGC GGT GGG AAC TAC TCA GCC ATG TCT TCT GTG GTC TAT TCC CCT GAC  726

 F   P   D   T   Y   A   T   G   R   V   C   Y   W   T   I   R   V   P   G   A   251
TTC CCC GAC ACC TAT GCC ACG GGG AGG GTC TGC TAC TGG ACC ATC CGG GTT CCG GGG GCC  786

 S   H   I   H   F   S   F   P   L   F   D   I   R   D   S   A   D   M   V   E   271
TCC CAC ATC CAC TTC AGC TTC CCC CTA TTT GAC ATC AGG GAC TCG GCG GAC ATG GTG GAG  846

 L   L   D   G   Y   T   H   R   V   L   A   R   F   H   G   R   S   R   P   P   291
CTT CTG GAT GGC TAC ACC CAC CGT GTC CTA GCC CGC TTC CAC GGG AGG AGC CGC CCA CCT  906

 L   S   F   N   V   S   L   D   F   V   I   L   Y   F   F   S   D   R   I   N   311
CTG TCC TTC AAC GTC TCT CTG GAC TTC GTC ATC TTG TAT TTC TTC TCT GAT CGC ATC AAT  966

 Q   A   Q   G   F   A   V   L   Y   Q   A   V   K   E   E   L   P   Q   E   R   331
CAG GCC CAG GGA TTT GCT GTT TTA TAC CAA GCC GTC AAG GAA GAA CTG CCA CAG GAG AGG 1026
```

Fig. 1B

```
 P   A   V   N   Q   T   V   A   E   V   I   T   E   Q   A   N   L   S   V   S   351
CCC GCT GTC AAC CAG ACG GTG GCC GAG GTG ATC ACG GAG CAG GCC AAC CTC AGT GTC AGC 1086

 A   A   R   S   S   K   V   L   Y   V   I   T   T   S   P   S   H   P   P   Q   371
GCT GCC CGG TCC TCC AAA GTC CTC TAT GTC ATC ACC ACC AGC CCC AGC CAC CCA CCT CAG 1146

 T   V   P   G   S   N   S   W   A   P   P   M   G   A   G   S   H   R   V   E   391
ACT GTC CCA GGT AGC AAT TCC TGG GCG CCA CCC ATG GGG GCT GGA AGC CAC AGA GTT GAA 1206

 G   W   T   V   Y   G   L   A   T   L   L   I   L   T   V   T   A   I   V   A   411
GGA TGG ACA GTC TAT GGT CTG GCA ACT CTC CTC ATC CTC ACA GTC ACA GCC ATT GTA GCA 1266

 K   I   L   L   H   V   T   F   K   S   H   R   V   P   A   S   G   D   L   R   431
AAG ATA CTT CTG CAC GTC ACA TTC AAA TCC CAT CGT GTT CCT GCT TCA GGG GAC CTT AGG 1326

 D   C   H   Q   P   G   T   S   G   E   I   W   S   I   F   Y   K   P   S   T   451
GAT TGT CAT CAA CCA GGG ACT TCG GGG GAA ATC TGG AGC ATT TTT TAC AAG CCT TCC ACT 1386

 S   I   S   I   F   K   K   K   L   K   G   Q   S   Q   Q   D   D   R   N   P   471
TCA ATT TCC ATC TTT AAG AAG AAA CTC AAG GGT CAG AGT CAA CAA GAT GAC CGC AAT CCC 1446

 L   V   S   D   *
CTT GTG AGT GAC TAA
```

Fig. 1C

```
AAACCCCACTGTGCCTAGGACTTGAGGTCCCTCTTTGAGCTCAAGGCTGCCGTGGTCAACCTCTCCTGTGGTTCTTCTC 1540
TGACAGACTCTTCCCTCCTCTCCCTCTGCCTCGGCCTCTTCGGGGAAACCCTCCTCCTACAGACTAGGAAGAGGCACCT 1620
GCTGCCAGGGCAGGCAGAGCCTGGATTCCTCCTGCTT                                           1657
```

Fig. 1D

```
GTCGACCCACGCGTCCGCCCGGCTCCCGGTGCTGCCCCCTCTGCCCCGGGCCGCGCCCGGGGGTCCCGCACTGACGGCC    79

   M   A   P   P   A   A   R   L   A   L   L   S   A   A   A   L   T   L   A      19
C ATG GCG CCG CCC GCC GCC CGT CTC GCG CTG CTC TCC GCC GCT GCG CTC ACT CTG GCG     137

 A   R   P   A   P   G   P   R   S   G   P   E   C   F   T   A   N   G   A   D    39
GCC CGG CCC GCG CCC GGT CCC CGC TCC GGC CCC GAG TGC TTC ACA GCC AAC GGT GCA GAT  197

 Y   R   G   T   Q   S   W   T   A   L   Q   G   G   K   P   C   L   F   W   N    59
TAC AGG GGA ACA CAG AGC TGG ACA GCG CTG CAA GGT GGG AAG CCA TGT CTG TTC TGG AAC  257

 E   T   F   Q   H   P   Y   N   T   L   K   Y   P   N   G   E   G   G   L   G    79
GAG ACT TTC CAG CAT CCG TAC AAC ACG CTG AAG TAC CCC AAC GGG GAA GGA GGA CTG GGC  317

 E   H   N   Y   C   R   N   P   D   G   D   V   S   P   W   C   Y   V   A   E    99
GAG CAC AAT TAT TGC AGA AAT CCA GAT GGA GAC GTG AGC CCT TGG TGC TAC GTG GCC GAG  377
```

Fig.1E

```
 H   E   D   G   V   Y   W   K   Y   C   E   I   P   A   C   Q   M   P   G   N   119
CAT GAG GAC GGA GTC TAC TGG AAG TAC TGT GAA ATT CCT GCC TGC CAG ATG CCT GGA AAC  437

 L   G   C   Y   K   D   H   G   N   P   P   P   L   T   G   T   S   K   T   S   139
CTT GGC TGC TAC AAG GAT CAT GGA AAC CCA CCT CCT CTC ACG GGC ACC AGT AAA ACC TCT  497

 N   K   L   T   I   Q   T   C   I   S   F   C   R   S   Q   R   F   K   F   A   159
AAC AAG CTC ACC ATA CAA ACC TGT ATC AGC TTC TGT CGG AGT CAG AGA TTC AAG TTT GCT  557

 G   M   E   S   G   Y   A   C   F   C   G   N   N   P   D   Y   W   K   H   G   179
GGG ATG GAG TCA GGC TAT GCC TGC TTC TGT GGG AAC AAT CCT GAC TAC TGG AAG CAC GGG  617

 E   A   A   S   T   E   C   N   S   V   C   F   G   D   H   T   Q   P   C   G   199
GAG GCG GCC AGC ACC GAG TGC AAT AGT GTC TGC TTC GGG GAC CAC ACG CAG CCC TGC GGT  677

 G   D   G   R   I   I   L   F   D   T   L   V   G   A   C   G   G   N   Y   S   219
GGG GAC GGC AGG ATT ATC CTC TTT GAC ACT CTC GTG GGC GCC TGC GGT GGG AAC TAC TCA  737

 A   M   A   A   V   V   Y   S   P   D   F   P   D   T   Y   A   T   G   R   V   239
GCC ATG GCA GCC GTG GTG TAC TCC CCT GAC TTC CCT GAC ACC TAC GCC ACT GGC AGA GTC  797

 C   Y   W   T   I   R   V   P   G   A   S   R   I   H   F   N   F   T   L   F   259
TGC TAC TGG ACC ATC CGG GTT CCA GGA GCC TCT CGC ATC CAT TTC AAC TTC ACC CTG TTT  857

 D   I   R   D   S   A   D   M   V   E   L   L   D   G   Y   T   H   R   V   L   279
GAT ATC AGG GAC TCT GCA GAC ATG GTG GAG CTG CTG GAC GGC TAC ACC CAC CGC GTC CTG  917
```

Fig.1F

```
 V   R   L   S   G   R   S   R   P   P   L   S   F   N   V   S   L   D   F   V    299
GTC CGG CTC AGT GGG AGG AGC CGC CCG CCT CTG TCT TTC AAT GTC TCT CTG GAT TTT GTC  977

 I   L   Y   F   F   S   D   R   I   N   Q   A   Q   G   F   A   V   L   Y   Q    319
ATT TTG TAT TTC TTC TCT GAT CGC ATC AAT CAG GCC CAG GGA TTT GCT GTG TTG TAC CAA 1037

 A   T   K   E   E   P   P   Q   E   R   P   A   V   N   Q   T   L   A   E   V    339
GCC ACC AAG GAG GAA CCG CCA CAG GAG AGA CCT GCT GTC AAC CAG ACC CTG GCA GAG GTG 1097

 I   T   E   Q   A   N   L   S   V   S   A   A   H   S   S   K   V   L   Y   V    359
ATC ACC GAG CAA GCC AAC CTC AGT GTC AGC GCT GCC CAC TCC TCC AAA GTC CTC TAT GTC 1157

 I   T   P   S   P   S   H   P   P   Q   T   A   Q   V   A   I   P   G   H   R    379
ATC ACC CCC AGC CCC AGC CAC CCT CCG CAG ACT GCC CAG GTA GCC ATT CCT GGG CAC CGT 1217

 Q   L   G   P   T   A   T   E   W   K   D   G   L   C   T   A   W   R   P   S    399
CAG TTG GGG CCA ACA GCC ACA GAG TGG AAG GAT GGA CTG TGT ACG GCC TGG CGA CCC TCC 1277

 S   S   S   Q   S   Q   Q   L   S   Q   R   F   F   C   M   S   H   L   N   L    419
TCA TCC TCA CAG TCA CAG CAG TTG TCG CAA AGA TTC TTC TGC ATG TCA CAT TTA AAT CTC 1337

 I   E   S   L   H   Q   E   T   L   G   T   V   V   S   L   G   L   L   E   I    439
ATC GAG TCC CTG CAT CAG GAG ACC TTA GGG ACT GTC GTC AGC CTG GGG CTT CTG GAG ATA 1397

 S   G   P   F   S   M   N   L   P   L   Q   S   P   S   L   R   R   S   S   R    459
TCT GGA CCA TTT TCT ATG AAC CTT CCA CTA CAA TCT CCA TCT TTA AGA AGA AGC TCA AGG 1457
```

Fig.1G

```
 V   R   V   N   K   M   T   A   I   P   S   *                                      471
GTC AGA GTC AAC AAG ATG ACC GCA ATC CCC TCG TGA                                    1493

GTGACTGAAGCCCACGCCTGCATGAGAGGCTCCGCTCCAAGCTCGAGTTTGCTCCCCTGAGTTCTCCTCTGATGAGTTC 1572
CCTGCCTTCCCATTCACCACCATCTCTTTTGGGAGCACCCTGCTTTAGAGGCAGCCCAGCCTGGGATCCTCCATCACAT 1651
GTACCAGCCTGGCTGCTCTGCTGGGGATGGTAAGACAGGCCCAGGCTGACAGGACACAGCTGGACCTGACTCCAGAAGA 1730
CTCTTGGGTGGTGGGGAGGTATAGTGTAGGATGAGTTTTCTTGCTTCTTCTCTGTTTTGTCCACATACAGATCGGTTTC 1809
CCCTGTCTTTACAGTTTGCAATAGAGCCAGACTGAAAGAACTGTCAGGTTTTCTAGGCTGGCCTGGTTCCCCACTAAGA 1888
GTGGCATTGGCGCCCTAGAGGCCCAGAGGCCCAGTGTAGGCTTGGAGCTTTCTCTGCTGCCAACTACCATGTGTCATCT 1967
AGTCCGAGGGGACTGAGAGCAGGGCCACACCAGATGTCATCTTTCTAGAGGGTTCTTTTTAGTACCCACTGACCAATGG 2046
GGCAAGCCTGAGGATTGGTCCATCTGTTTGTCCATGGAACAGACACAGTGAACTTCCTGGATACTAGACTTAACTAGCC 2125
TAGCCCTCAAGTAGTTGCCAATCCTGTGGAATCAGAATTCAGCCTGTCTTCCTGTCCTCAGCCCAAGCCTGTAGCCTAG 2204
AGCTGGGGCTGTAGCCTAGAGCTGGGGCTGTAGCCTAGAGCTGGGGCTGTAGCACAGAGCTGGGGCTGTAGCCTAGAGC 2283
TGGGGCTGTAGCACAGAGCTGGGGCTGTAGCCTAGAGCTGGGGCTGTAGCACAGAGCTGGGGCTGTAGCACAGAGCTGG 2362
GGCTGTAGCCTAGAGCTGGGGCTGTAGCACAGAGCTGGGGCTGTAACTCAGCGATCAAGAGCTTGCTTTGTATACATCG 2441
GACCCTAGGTTCTATCCCAGCACTATCAGAAGGTGGGAGAGAAAAAGACTGCACCATAGCATGCGGGCAGCATCTGTGG 2520
TTCCTACGTGAGGTGTCATCATTTTAAAAGCAGATCAAAACTACCGCGAGTTTTGTCCTTTGTCCCTTATCATGGGAGC 2599
AGAGTAGGAGTAAGGGCTCTGGTCTTGCTCATTGTCCCCCAGACAGGGAGGCAGGAAAAGGTCAGGCTTGGGAACTGGA 2678
GATCCTCCCAGGAAAAGCTGCAAGATTGAGAGACCCAGCTGCAGTTGGGAGAGGAAGGGCCATCCCCGACTGAGAAGTC 2757
CTGCAGTCTGGAAGTGGCCTTTGTCAGCAGCAGCTGTGCCCTGAAGGTAGACCTTGGTCACTCTCCTGCCAGCCCTTGA 2836
GCCTCTGCTCTCCTGGGTACCCTCCTGGAACACCATGCTAACCTTCCCCGAGTCTCTCAGTCACTGCCATTGAGGCCTC 2915
TCCTCTAGCTGCTGCTCCCCAGGACTGTCTGGGGCCATCTGGGGATCAGGGAGAGGCAGCAGGAGTACTGACGAGGCAG 2994
TGACCTGAGCTGATGAGTCAACCAGAGGACACCAGAGTCTACAGTGGGCTGGCTGCTGGCTCAGCTCCTATGGGAGGCC 3073
TACAGGGGTACTAAGCTAGGGGGTCATCATCTCATTTGATCTGGGAAAGGCTACAGGCTCCTGGATGTGAAGACAGGCC 3152
CACTACATAAGAAGACCACTGGAAATAGACTGACAGGAGCAGGTTCCACTCTAGGCTGTCCATAGCGTTTGCAGGACTC 3231
```

Fig.1H

CCCTGAGACCAAGTGTTGAGTCACAGAGTGCCATGTGCGTAGTGCATAAAGGATATGGGTTCTTAACCAGGGAAGGCTC 3310
ATAGCAGGCCAGGACATTTTTTCAGCTCAGAGCACTGGCCCCAGGCTTCCTCTAAGCCACCACTCACCTGTCTCTTCCT 3389
ATCTCGGACACAGGAAGCAAGCCCCAGTGTGGTGGCAGCTGCGGCTCAGCATTGGTGTCCCCAGGAAGGGCGGTGGATG 3468
TGCCCACGCTCCTTTTGCTGTGGGCCTGGCACAGCCCAACACTGCAGGGCCCACCTTCTCTCTTGGGGGGTAGGGACAC 3547
ATAAGGAAAACTAACCCACCTCCAACAACAGCAGAGGACAGTGGGAAGGAAGGGCTGTAAATCACCCAGGCCAGACCTC 3626
CAGAAATGACAGGCACAGTCTGTTAGAACCTGTAGGCAGCCAGTCACAGAGGGCCTTTGTGCTGGTAACACCCTGCCTG 3705
GAGCATAGGGGTAAGCCGAGGGAGAAGAGCAGCCCTCAGAGACATCAGCTAAAAACATAGGTGCCCTATGTCCCTCCCT 3784
TCCTGTCACACTGCTTACAAAGCAGAGACAGAGTAGGAAAGAGGTCTTCATCCTCTCCCACATCAGCAAGGATAGGGCT 3863
GCGGCTGCCTAAAGTGAGCAAGGAGAACAGAGCTCTGGACTTCTCTAAATGTGGGCTCTGGCTTCAGACTCCTCAGCCA 3942
AAAGCTCTTGAAGATCAAAGCTCTGGCGGGTACAGCTGTCCTGGCCTGTGGGCCAGCCCATGGGATGTGCCTGGGCCAG 4021
GTGCCACCCCACGGCTCACTGTCATCCCAGGAGGGACCCCACCTGATGCTCCTCATCATCCGCTGGCCTGACACTATCA 4100
GAGCTCGCGCCGGCTGTTGCCAGGGACAGACTGACTACACTTGACCTTCAAGAGCACTTAGAAGTGGATGGCCTCCAGA 4179
CTCTGTCAGCCTCTGCAGGGGCCACACAAGTCTCCCGAGCCAAGTCCACAAGCCTCCATGGTTCCCTGGCTCCTCTCCT 4258
GTGGAGTGTCCTGTTTGATGTCTGAGGTCTGCTTTGGGTACCGCCCTGGGAACTGCTAACCTCCGATTGGTCCCTTTGT 4337
GTCTCTGTTTACTGTCCTCTTCTACCTCCAGGTCACTTAGCTCTGGCTGCTCTGGCTGGGAGTGGGGGTGGGGATGCT 4416
GGCTGCACCCCCACCCTGGTCTGCCAACAGAACCTGGGGGCCTCACACGGGCTCCTGTCTTGCCAAGCTGGAGCTGAGC 4495
ACACTGGCCCAGGCTGAGTGGGGCAGAGCAAACAAGTGGAAGGGGATCTCTCTCCTTAGAGGGAGGTGGCCGAAGGTGT 4574
AGATCCAGCGAGGGAGCTGCCATCCCCGCCACCTTCATAGCAGCAAGACCTTCCCATTTCCAATCTCACCCTCCAGCAG 4653
GGATATGACTTTGGACAACAAGGCTTTATTTGTAAATATGCTCTTAATATGCAACTTTGAGAATAAGATAGAAACATCA 4732
TGTATTTTAAAATATAAAATGAAGTGTGACACACTGTATACAATTTAATATATATTTTTAGGATTTTGTTATTTAAGAA 4811
AATGGAATGTGATGGTACTTAACTTTTACAAAAGAGAGAAAATGTTATTTTTACTGTTTGAAGAAAATAAATATTCTCA 4890
TTGTTGTAGAAAAAAAAAAAAAAAAAAAGGGCGGCCGC 4928

Fig.1I

```
              10        20        30        40        50        60        70
Hum.  MAPPAARLALLSAAALTLAARPAPSPGLGPGPECFTANGADYRGTQNWTALQGGKPCLFWNETFQHPYNT
      ::::::::::::::::::::::::.:   .:::::::::::::::.::::::::::::::::::::::
Mur.  MAPPAARLALLSAAALTLAARPAPGPR--SGPECFTANGADYRGTQSWTALQGGKPCLFWNETFQHPYNT
              10        20          30        40        50        60

              80        90       100       110       120       130       140
Hum.  LKYPNGEGGLGEHNYCRNPDGDVSPWCYVAEHEDGVYWKYCEIPACQMPGNLGCYKDHGNPPPLTGTSKT
      ::::::::::::::::::::::::::::::::::::::::::::::::::::::::::::::::::::::
Mur.  LKYPNGEGGLGEHNYCRNPDGDVSPWCYVAEHEDGVYWKYCEIPACQMPGNLGCYKDHGNPPPLTGTSKT
      70        80        90       100       110       120       130

             150       160       170       180       190       200       210
Hum.  SNKLTIQTCISFCRSQRFKFAGMESGYACFCGNNPDYWKYGEAASTECNSVCFGDHTQPCGGDGRIILFD
      :::::::::::::::::::::::::::::::::::::::: :::::::::::::::::::::::::::::
Mur.  SNKLTIQTCISFCRSQRFKFAGMESGYACFCGNNPDYWKHGEAASTECNSVCFGDHTQPCGGDGRIILFD
     140       150       160       170       180       190       200

             220       230       240       250       260       270       280
Hum.  TLVGACGGNYSAMSSVVYSPDFPDTYATGRVCYWTIRVPGASHIHFSFPLFDIRDSADMVELLDGYTHRV
      :::::::::::::..::::::::::::::::::::::::::.:::.: ::::::::::::::::::::::
Mur.  TLVGACGGNYSAMAAVVYSPDFPDTYATGRVCYWTIRVPGASRIHFNFTLFDIRDSADMVELLDGYTHRV
     210       220       230       240       250       260       270
```

Fig.1J

```
                290       300       310       320       330       340       350
Hum.  LARFHGRSRPPLSFNVSLDFVILYFFSDRINQAQGFAVLYQAVKEELPQERPAVNQTVAEVITEQANLSV
      :.:. :::::::::::::::::::::::::::::::::::::::.::: ::::::::::.:::::::::::::
Mur.  LVRLSGRSRPPLSFNVSLDFVILYFFSDRINQAQGFAVLYQATKEEPPQERPAVNQTLAEVITEQANLSV
      280       290       300       310       320       330       340

                360       370       380       390       400       410       420
Hum.  SAARSSKVLYVITTSPSHPPQTVPGSNSWAPPMGAGSHRVEGWTVYGLATLLILTVTAIVAKILLHVTFK
      :::.::::::::: ::::::::.. .  .   ..:. .    :   :: :    . ..  ..  .   .
Mur.  SAAHSSKVLYVITPSPSHPPQTAQVAIPGHRQLGPTA---TEWKD-GLCTAWRPSSSSQSQQLSQRFFCM
      350       360       370       380          390       400       410

                430       440       450       460       470
Hum.  SHRVPASGDLRDCHQPGTSGEIWSIFYKPSTSISIFKKKLKGQSQ-QDDRNPLVSD
      ::     .  ..     .:  .  :     : ....    :.  :. .  ..   ...
Mur.  SHLNLIESLHQETLGTVVSLGLLEISGPFSMNLPLQSPSLRRSSRVRVNKMTAIPS
         420       430       440       450       460       470
```

Fig.1K

```
                               M   M   L   P   Q   N   S   W   H   I   D   F   G    13
GCGGCCGCTCGCGATCTAGAACTAGTA ATG ATG CTG CCT CAA AAC TCG TGG CAT ATT GAT TTT GGA    66

 R   C   C   C   H   Q   N   L   F   S   A   V   V   T   C   I   L   L   L   N      33
AGA TGC TGC TGT CAT CAG AAC CTT TTC TCT GCT GTG GTA ACT TGC ATC CTG CTC CTG AAT   126

 S   C   F   L   I   S   S   F   N   G   T   D   L   E   L   R   L   V   N   G      53
TCC TGC TTT CTC ATC AGC AGT TTT AAT GGA ACA GAT TTG GAG TTG AGG CTG GTC AAT GGA   186

 D   G   P   C   S   G   T   V   E   V   K   F   Q   G   Q   W   G   T   V   C      73
GAC GGT CCC TGC TCT GGG ACA GTG GAG GTG AAA TTC CAG GGA CAG TGG GGG ACT GTG TGT   246

 D   D   G   W   N   T   T   A   S   T   V   V   C   K   Q   L   G   C   P   F      93
GAT GAT GGG TGG AAC ACT ACT GCC TCA ACT GTC GTG TGC AAA CAG CTT GGA TGT CCA TTT   306

 S   F   A   M   F   R   F   G   Q   A   V   T   R   H   G   K   I   W   L   D     113
TCT TTC GCC ATG TTT CGT TTT GGA CAA GCC GTG ACT AGA CAT GGA AAA ATT TGG CTT GAT   366

 D   V   S   C   Y   G   N   E   S   A   L   W   E   C   Q   H   R   E   W   G     133
GAT GTT TCC TGT TAT GGA AAT GAG TCA GCT CTC TGG GAA TGT CAA CAC CGG GAA TGG GGA   426

 S   H   N   C   Y   H   G   E   D   V   G   V   N   C   Y   G   E   A   N   L     153
AGC CAT AAC TGT TAT CAT GGA GAA GAT GTT GGT GTG AAC TGT TAT GGT GAA GCC AAT CTG   486
```

Fig. 2A

```
G   L   R   L   V   D   G   N   N   S   C   S   G   R   V   E   V   K   F   Q    173
GGT TTG AGG CTA GTG GAT GGA AAC AAC TCC TGT TCA GGG AGA GTG GAG GTG AAA TTC CAA  546

E   R   W   G   T   I   C   D   D   G   W   N   L   N   T   A   A   V   V   C    193
GAA AGG TGG GGG ACT ATA TGT GAT GAT GGG TGG AAC TTG AAT ACT GCT GCC GTG GTG TGC  606

R   Q   L   G   C   P   S   S   F   I   S   S   G   V   V   N   S   P   A   V    213
AGG CAA CTA GGA TGT CCA TCT TCT TTT ATT TCT TCT GGA GTT GTT AAT AGC CCT GCT GTA  666

L   R   P   I   W   L   D   D   I   L   C   Q   G   N   E   L   A   L   W   N    233
TTG CGC CCC ATT TGG CTG GAT GAC ATT TTA TGC CAG GGG AAT GAG TTG GCA CTC TGG AAT  726

C   R   H   R   G   W   G   N   H   D   C   S   H   N   E   D   V   T   L   T    253
TGC AGA CAT CGT GGA TGG GGA AAT CAT GAC TGC AGT CAC AAT GAG GAT GTC ACA TTA ACT  786

C   Y   D   S   S   D   L   E   L   R   L   V   G   G   T   N   R   C   M   G    273
TGT TAT GAT AGT AGT GAT CTT GAA CTA AGG CTT GTA GGT GGA ACT AAC CGC TGT ATG GGG  846

R   V   E   L   K   I   Q   G   R   W   G   T   V   C   H   H   K   W   N   N    293
AGA GTA GAG CTG AAA ATC CAA GGA AGG TGG GGG ACC GTA TGC CAC CAT AAG TGG AAC AAT  906

A   A   A   D   V   V   C   K   Q   L   G   C   G   T   A   L   H   F   A   G    313
GCT GCA GCT GAT GTC GTA TGC AAG CAG TTG GGA TGT GGA ACC GCA CTT CAC TTC GCT GGC  966

L   P   H   L   Q   S   G   S   D   V   V   W   L   D   G   V   S   C   S   G    333
TTG CCT CAT TTG CAG TCA GGG TCT GAT GTT GTA TGG CTT GAT GGT GTC TCC TGC TCC GGT 1026
```

Fig. 2B

```
 N   E   S   F   L   W   D   C   R   H   S   G   T   V   N   F   D   C   L   H    353
AAT GAA TCT TTT CTT TGG GAC TGC AGA CAT TCC GGA ACC GTC AAT TTT GAC TGT CTT CAT 1086

 Q   N   D   V   S   V   I   C   S   D   G   A   D   L   E   L   R   L   A   D    373
CAA AAC GAT GTG TCT GTG ATC TGC TCA GAT GGA GCA GAT TTG GAA CTG CGA CTA GCA GAT 1146

 G   S   N   N   C   S   G   R   V   E   V   R   I   H   E   Q   W   W   T   I    393
GGA AGT AAC AAT TGT TCA GGG AGA GTA GAG GTG AGA ATT CAT GAA CAG TGG TGG ACA ATA 1206

 C   D   Q   N   W   K   N   E   Q   A   L   V   V   C   K   Q   L   G   C   P    413
TGT GAC CAG AAC TGG AAG AAT GAA CAA GCC CTT GTG GTT TGT AAG CAG CTA GGA TGT CCG 1266

 F   S   V   F   G   S   R   R   A   K   P   S   N   E   A   R   D   I   W   I    433
TTC AGC GTC TTT GGC AGT CGT CGT GCT AAA CCT AGT AAT GAA GCT AGA GAC ATT TGG ATA 1326

 N   S   I   S   C   T   G   N   E   S   A   L   W   D   C   T   Y   D   G   K    453
AAC AGC ATA TCT TGC ACT GGG AAT GAG TCA GCT CTC TGG GAC TGC ACA TAT GAT GGA AAA 1386

 A   K   R   T   C   F   R   R   S   D   A   G   V   I   C   S   D   K   A   D    473
GCA AAG CGA ACA TGC TTC CGA AGA TCA GAT GCT GGA GTA ATT TGT TCT GAT AAG GCA GAT 1446

 L   D   L   R   L   V   G   A   H   S   P   C   Y   G   R   L   E   V   K   Y    493
CTG GAC CTA AGG CTT GTC GGG GCT CAT AGC CCC TGT TAT GGG AGA TTG GAG GTG AAA TAC 1506

 Q   G   E   W   G   T   V   C   H   D   R   W   S   T   R   N   A   A   V   V    513
CAA GGA GAG TGG GGG ACT GTG TGT CAT GAC AGA TGG AGC ACA AGG AAT GCA GCT GTT GTG 1566
```

Fig. 2C

```
C   K   Q   L   G   C   G   K   P   M   H   V   F   G   M   T   Y   F   K   E    533
TGT AAA CAA TTG GGA TGT GGA AAG CCT ATG CAT GTG TTT GGT ATG ACC TAT TTT AAA GAA 1626

A   S   G   P   I   W   L   D   D   V   S   C   I   G   N   E   S   N   I   W    553
GCA TCA GGA CCT ATT TGG CTG GAT GAC GTT TCT TGC ATT GGA AAT GAG TCA AAT ATC TGG 1686

D   C   E   H   S   G   W   G   K   H   N   C   V   H   R   E   D   V   I   V    573
GAC TGT GAA CAC AGT GGA TGG GGA AAG CAT AAT TGT GTA CAC AGA GAG GAT GTG ATT GTA 1746

T   C   S   G   D   A   T   W   G   L   R   L   V   G   G   S   N   R   C   S    593
ACC TGC TCA GGT GAT GCA ACA TGG GGC CTG AGG CTG GTG GGC GGC AGC AAC CGC TGC TCG 1806

G   R   L   E   V   Y   F   Q   G   R   W   G   T   V   C   D   D   G   W   N    613
GGA AGA CTG GAG GTG TAC TTT CAA GGA CGG TGG GGC ACA GTG TGT GAT GAC GGC TGG AAC 1866

S   K   A   A   A   V   V   C   S   Q   L   D   C   P   S   S   I   I   G   M    633
AGT AAA GCT GCA GCT GTG GTG TGT AGC CAG CTG GAC TGC CCA TCT TCT ATC ATT GGC ATG 1926

G   L   G   N   A   S   T   G   Y   G   K   I   W   L   D   D   V   S   C   D    653
GGT CTG GGA AAC GCT TCT ACA GGA TAT GGA AAA ATT TGG CTC GAT GAT GTT TCC TGT GAT 1986

G   D   E   S   D   L   W   S   C   R   N   S   G   W   G   N   N   D   C   S    673
GGA GAT GAG TCA GAT CTC TGG TCA TGC AGG AAC AGT GGG TGG GGA AAT AAT GAC TGC AGT 2046

H   S   E   D   V   G   V   I   C   S   D   A   S   D   M   E   L   R   L   V    693
CAC AGT GAA GAT GTT GGA GTG ATC TGT TCT GAT GCA TCG GAT ATG GAG CTG AGG CTT GTG 2106
```

Fig. 2D

```
G   G   S   S   R   C   A   G   K   V   E   V   N   V   Q   G   A   V   G   I    713
GGT GGA AGC AGC AGG TGT GCT GGA AAA GTT GAG GTG AAT GTC CAG GGT GCC GTG GGA ATT 2166

L   C   A   N   G   W   G   M   N   I   A   E   V   V   C   R   Q   L   E   C    733
CTG TGT GCT AAT GGC TGG GGA ATG AAC ATT GCT GAA GTT GTT TGC AGG CAA CTT GAA TGT 2226

G   S   A   I   R   V   S   R   E   P   H   F   T   E   R   T   L   H   I   L    753
GGG TCT GCA ATC AGG GTC TCC AGA GAG CCT CAT TTC ACA GAA AGA ACA TTA CAC ATC TTA 2286

M   S   N   S   G   C   T   G   G   E   A   S   L   W   D   C   I   R   W   E    773
ATG TCG AAT TCT GGC TGC ACT GGA GGG GAA GCC TCT CTC TGG GAT TGT ATA CGA TGG GAG 2346

W   K   Q   T   A   C   H   L   N   M   E   A   S   L   I   C   S   A   H   R    793
TGG AAA CAG ACT GCG TGT CAT TTA AAT ATG GAA GCA AGT TTG ATC TGC TCA GCC CAC AGG 2406

Q   P   R   L   V   G   A   D   M   P   C   S   G   R   V   E   V   K   H   A    813
CAG CCC AGG CTG GTT GGA GCT GAT ATG CCC TGC TCT GGA CGT GTT GAA GTG AAA CAT GCA 2466

D   T   W   R   S   V   C   D   S   D   F   S   L   H   A   A   N   V   L   C    833
GAC ACA TGG CGC TCT GTC TGT GAT TCT GAT TTC TCT CTT CAT GCT GCC AAT GTG CTG TGC 2526

R   E   L   N   C   G   D   A   I   S   L   S   V   G   D   H   F   G   K   G    853
AGA GAA TTA AAT TGT GGA GAT GCC ATA TCT CTT TCT GTG GGA GAT CAC TTT GGA AAA GGG 2586

N   G   L   T   W   A   E   K   F   Q   C   E   G   S   E   T   H   L   A   L    873
AAT GGT CTA ACT TGG GCC GAA AAG TTC CAG TGT GAA GGG AGT GAA ACT CAC CTT GCA TTA 2646
```

Fig. 2E

```
 C   P   I   V   Q   H   P   E   D   T   C   I   H   S   R   E   V   G   V   V   893
TGC CCC ATT GTT CAA CAT CCG GAA GAC ACT TGT ATC CAC AGC AGA GAA GTT GGA GTT GTC 2706

 C   S   R   Y   T   D   V   R   L   V   N   G   K   S   Q   C   D   G   Q   V   913
TGT TCC CGA TAT ACA GAT GTC CGA CTT GTG AAT GGC AAA TCC CAG TGT GAC GGG CAA GTG 2766

 E   I   N   V   L   G   H   W   G   S   L   C   D   T   H   W   D   P   E   D   933
GAG ATC AAC GTG CTT GGA CAC TGG GGC TCA CTG TGT GAC ACC CAC TGG GAC CCA GAA GAT 2826

 A   R   V   L   C   R   Q   L   S   C   G   T   A   L   S   T   T   G   G   K   953
GCC CGT GTT CTA TGC AGA CAG CTC AGC TGT GGG ACT GCT CTC TCA ACC ACA GGA GGA AAA 2886

 Y   I   G   E   R   S   V   R   V   W   G   H   R   F   H   C   L   G   N   E   973
TAT ATT GGA GAA AGA AGT GTT CGT GTG TGG GGA CAC AGG TTT CAT TGC TTA GGG AAT GAG 2946

 S   L   L   D   N   C   Q   M   T   V   L   G   A   P   P   C   I   H   G   N   993
TCA CTT CTG GAT AAC TGT CAA ATG ACA GTT CTT GGA GCA CCT CCC TGT ATC CAT GGA AAT 3006

 T   V   S   V   I   C   T   G   S   L   T   Q   P   L   F   P   C   L   A   N   1013
ACT GTC TCT GTG ATC TGC ACA GGA AGC CTG ACC CAG CCA CTG TTT CCA TGC CTC GCA AAT 3066

 V   S   D   P   Y   L   S   A   V   P   E   G   S   A   L   I   C   L   E   D   1033
GTA TCT GAC CCA TAT TTG TCT GCA GTT CCA GAG GGC AGT GCT TTG ATC TGC TTA GAG GAC 3126

 K   R   L   R   L   V   D   G   D   S   R   C   A   G   R   V   E   I   Y   H   1053
AAA CGG CTC CGC CTA GTG GAT GGG GAC AGC CGC TGT GCC GGG AGA GTA GAG ATC TAT CAC 3186
```

Fig. 2F

```
 D   G   F   W   G   T   I   C   D   D   G   W   D   L   S   D   A   H   V   V  1073
GAC GGC TTC TGG GGC ACC ATC TGT GAT GAC GGC TGG GAC CTG AGC GAT GCC CAC GTG GTG 3246

 C   Q   K   L   G   C   G   V   A   F   N   A   T   V   S   A   H   F   G   E  1093
TGT CAA AAG CTG GGC TGT GGA GTG GCC TTC AAT GCC ACG GTC TCT GCT CAC TTT GGG GAG 3306

 G   S   G   P   I   W   L   D   D   L   N   C   T   G   T   E   S   H   L   W  1113
GGG TCA GGG CCC ATC TGG CTG GAT GAC CTG AAC TGC ACA GGA ACG GAG TCC CAC TTG TGG 3366

 Q   C   P   S   R   G   W   G   Q   H   D   C   R   H   K   E   D   A   G   V  1133
CAG TGC CCT TCC CGC GGC TGG GGG CAG CAC GAC TGC AGG CAC AAG GAG GAC GCA GGG GTC 3426

 I   C   S   E   F   T   A   L   R   L   Y   S   E   T   E   T   E   S   C   A  1153
ATC TGC TCA GAA TTC ACA GCC TTG AGG CTC TAC AGT GAA ACT GAA ACA GAG AGC TGT GCT 3486

 G   R   L   E   V   F   Y   N   G   T   W   G   S   V   G   R   R   N   I   T  1173
GGG AGA TTG GAA GTC TTC TAT AAC GGG ACC TGG GGC AGC GTC GGC AGG AGG AAC ATC ACC 3546

 T   A   I   A   G   I   V   C   R   Q   L   G   C   G   E   N   G   V   V   S  1193
ACA GCC ATA GCA GGC ATT GTG TGC AGG CAG CTG GGC TGT GGG GAG AAT GGA GTT GTC AGC 3606

 L   A   P   L   S   K   T   G   S   G   F   M   W   V   D   D   I   Q   C   P  1213
CTC GCC CCT TTA TCT AAG ACA GGC TCT GGT TTC ATG TGG GTG GAT GAC ATT CAG TGT CCT 3666

 K   T   H   I   S   I   W   Q   C   L   S   A   P   W   E   R   R   I   S   S  1233
AAA ACG CAT ATC TCC ATA TGG CAG TGC CTG TCT GCC CCA TGG GAG CGA AGA ATC TCC AGC 3726
```

Fig. 2G

```
P   A   E   E   T   W   I   T   C   E   D   R   I   R   V   R   G   G   D   T   1253
CCA GCA GAA GAG ACC TGG ATC ACA TGT GAA GAT AGA ATA AGA GTG CGT GGA GGA GAC ACC 3786

E   C   S   G   R   V   E   I   W   H   A   G   S   W   G   T   V   C   D   D   1273
GAG TGC TCT GGG AGA GTG GAG ATC TGG CAC GCA GGC TCC TGG GGC ACA GTG TGT GAT GAC 3846

S   W   D   L   A   E   A   E   V   V   C   Q   Q   L   G   C   G   S   A   L   1293
TCC TGG GAC CTG GCC GAG GCG GAA GTG GTG TGT CAG CAG CTG GGC TGT GGC TCT GCT CTG 3906

A   A   L   R   D   A   S   F   G   Q   G   T   G   T   I   W   L   D   D   M   1313
GCT GCC CTG AGG GAC GCT TCG TTT GGC CAG GGA ACT GGA ACC ATC TGG TTG GAT GAC ATG 3966

R   C   K   G   N   E   S   F   L   W   D   C   H   A   K   P   W   G   Q   S   1333
CGG TGC AAA GGA AAT GAG TCA TTT CTA TGG GAC TGT CAC GCC AAA CCC TGG GGA CAG AGT 4026

D   C   G   H   K   E   D   A   G   V   R   C   S   G   Q   S   L   K   S   L   1353
GAC TGT GGA CAC AAG GAA GAT GCT GGC GTG AGG TGC TCT GGA CAG TCG CTG AAA TCA CTG 4086

N   A   S   S   G   H   L   A   L   I   L   S   S   I   F   G   L   L   L   L   1373
AAT GCC TCC TCA GGT CAT TTA GCA CTT ATT TTA TCC AGT ATC TTT GGG CTC CTT CTC CTG 4146

V   L   F   I   L   F   L   T   W   C   R   V   Q   K   Q   K   H   L   P   L   1393
GTT CTG TTT ATT CTA TTT CTC ACG TGG TGC CGA GTT CAG AAA CAA AAA CAT CTG CCC CTC 4206

R   V   S   T   R   R   R   G   S   L   E   E   N   L   F   H   E   M   E   T   1413
AGA GTT TCA ACC AGA AGG AGG GGT TCT CTC GAG GAG AAT TTA TTC CAT GAG ATG GAG ACC 4266
```

Fig. 2H

```
 C   L   K   R   E   D   P   H   G   T   R   T   S   D   D   T   P   N   H   G  1433
TGC CTC AAG AGA GAG GAC CCA CAT GGG ACA AGA ACC TCA GAT GAC ACC CCC AAC CAT GGT 4326

 C   E   D   A   S   D   T   S   L   L   G   V   L   P   A   S   E   A   T   K  1453
TGT GAA GAT GCT AGC GAC ACA TCG CTG TTG GGA GTT CTT CCT GCC TCT GAA GCC ACA AAA 4386

 *                                                                              1454
TGA                                                                             4389

CTTTAGACTTCCAGGGCTCACCAGATCAACCTCTAAATATCTTTGAAGGAGACAACAACTTTTAAATGAATAAAGAGGA 4468
AGTCAAGTTGCCCTATGGAAAACTTGTCCAAATAACATTTCTTGAACAATAGGAGAACAGCTAAATTGATAAAGACTGG 4547
TGATAATAAAAATTGAATTATGTATATCACTGTTAAAAAAAAAAAAAAAAAAAAAAAAAAAAAACGGACGCGTGGGTCG 4626
AC                                                                              4628
```

Fig. 2I

```
                10        20        30        40        50        60        70
Hum.  MMLPQNSWHIDFGRCCCHQNLFSAVVTCILLLNSCFLISSFNGTDLELRLVNGDGPCSGTVEVKFQGQWG
      : :         ::   : .: .    :.:::..  ...   : .:::::  .:   : : :::: ::.::
WC1   MAL---------GR---HLSLRGL---CVLLLGT--MVG---GQALELRLKDGVHRCEGRVEVKHQGEWG
                       10             20            30        40        50

                80        90       100       110       120           130
Hum.  TVCDDGWNTTASTVVCKQLGCPFSFAMFRFGQAVTR-HGKIWLDDVSCYGNESALWECQH---REWGSHN
      :: .  :.  ...:::.::::  ... :  :       : :::  .:: :.:::.. .:.:   ..  ...
WC1   TVDGYRWTLKDASVVCRQLGCGAAIG-FPGGAYFGPGLGPIWLLYTSCEGTESTVSDCEHSNIKDYRNDG
                60        70         80        90       100       110

         140       150       160       170       180       190       200
Hum.  CYHGEDVGVNCYGEANLGLRLVDGNNSCSGRVEVKFQERWGTICDDGWNLNTAAVVCRQLGCPSSFISSG
       :: :.:: : :     .::..:..:::::::    : :  . :.. .:.:: ..: .:::  .    :
WC1   YNHGRDAGVVCSG----FVRLAGGDGPCSGRVEVHSGEAWIPVSDGNFTLATAQIICAELGCGKAVSVLG
     120       130           140       150       160       170       180

         210       220       230       240       250       260       270
Hum.  VVNSPAVLRPIWLDDILCQGNELALWNCRHRGWGNHDCSHNEDVTLTCYDSSDLELRLVGGTNRCMGRVE
        .   ..: ... :.:.: .:: : .     .  : :. .. ..: . :.. : ...:...: :.::
WC1   HELFRESSAQVWAEEFRCEGEEPELWVCPRVPCPGGTCHHSGSAQVVCSAYSEVRL-MTNGSSQCEGQVE
         190       200       210       220       230       240        250
```

Fig. 2K

```
          280       290       300       310       320       330       340
Hum.  LKIQGRWGTVCHHKWNNAAADVVCKQLGCGTALHFAGLPHLQSGSDVVWLDGVSCSGNESFLWDCRHSGT
      ..: :.: ..:   :. :.:.:.:.:::::.:.  .: :::    .:  .   .   :::.:::::.:  ..
 WC1  MNISGQWRALCASHWSLANANVICRQLGCGVAISTPGGPHLVEEGDQILTARFHCSGAESFLWSCPVTAL
          260       270       280       290       300       310       320

          350       360       370       380       390       400       410
Hum.  VNFDCLHQNDVSVICSDGADLELRLADGSNNCSGRVEVRIHEQWWTICDQNWKNEQALVVCKQLGCPFSV
        . :: : : .::::: :...                                   :.:  :..     ::
 WC1  GGPDCSHGNTASVICS-GNQI---------------------------------QVLPQCND-----SV
          330       340                                           350

          420       430       440       450       460       470       480
Hum.  FGSRRAKPSNEARDIWINSISCTGNESALWDCTYDGKAKRTCFRRSDAGVICSDKADLDLRLVGAHSPCY
              ..:.. :         ....::   :                 :::  .:  :::.. .::
 WC1  -----SQPTGSA----------ASEDSA----PY-----------------CSDSRQL--RLVDGGGPCA
              360                                      370       380

          490       500       510       520       530       540       550
Hum.  GRLEVKYQGEWGTVCHDRWSTRNAAVVCKQLGCGKPMHVFGMTYFKEASGPIWLDDVSCIGNESNIWDCE
      ::.:.  :: :::.:.: :.  .: :::.:::: .... :  .  : ..:::::::...:.:.::..: :
 WC1  GRVEILDQGSWGTICDDGWDLDDARVVCRQLGCGEALNATGSAHFGAGSGPIWLDNLNCTGKESHVWRCP
          390       400       410       420       430       440       450
```

Fig. 2L

```
          560       570       580       590       600       610       620
Hum.  HSGWGKHNCVHREDVIVTCSGDATWGLRLVGGSNRCSGRLEVYFQGRWGTVCDDGWNSKAAAVVCSQLDC
        ::::.::: :..:. :.::   .   .::.:. ...:.:.::::...: ::.:: .  .. .....: ::.:
WC1   SRGWGQHNCRHKQDAGVICS--EFLALRMVSEDQQCAGWLEVFYNGTWGSVCRNPMEDITVSTICRQLGC
          460       470         480       490       500       510       520

          630       640       650       660       670       680       690
Hum.  PSSIIGMGLGNASTGYGKIWLDDVSCDGDESDLWSCRNSGWGNNDCSHSEDVGVICSDASDMELRLVGGS
       .:  .   .   .    :.    :.: . :    ...:: : .. :. :.::  :.. . :.:.    ..:::.:.
WC1   GDSGTLNSSVALREGFRPQWVDRIQCRKTDTSLWQCPSDPWNYNSCSPKEEAYIWCADSR--QIRLVDGG
            530       540       550       560       570       580         590

          700       710       720       730       740       750       760
Hum.  SRCAGKVEVNVQGAVGILCANGWGMNIAEVVCRQLECGSAIRVSREPHFTERTLHILMSNSGCTGGEASL
      .::.:.::.  ::. :..:.. :... : :::.:: :: :. ..  . :    .  :  ... .: : :. .
WC1   GRCSGRVEILDQGSWGTICDDRWDLDDARVVCKQLGCGEALDATVSSFFGTGSGPIWLDEVNCRGEESQV
            600       610       620       630       640       650       660

          770       780       790       800       810       820       830
Hum.  WDCIRWEWKQTACHLNMEASLICSAHRQPRLVGADMPCSGRVEVKHADTWRSVCDSDFSLHAANVLCREL
      : :  : :.: .:. . .:..:::.     ::.:.: ::::::::   ...: .: :..:.: .:.:.: ::
WC1   WRCPSWGWRQHNCNHQEDAGVICSGF--VRLAGGDGPCSGRVEVHSGEAWTPVSDGNFTLPTAQVICAEL
            670       680         690       700       710       720       730
```

Fig. 2M

```
          840       850       860       870       880       890       900
Hum.  NCGDAISLSVGDHFGKGNGLTWAEKFQCEGSETHLALCPIVQHPEDTCIHSREVGVVCSRYTDVRLV-NG
      .:: :.:.      :  ..: .::: :.:.:.:  :  :: :. : .::.:: .. :::: ::.:.:. ::
WC1   GCGKAVSVLGHMPFRESDGQVWAEEFRCDGGEPELWSCPRVPCPGGTCLHSGAAQVVCSVYTEVQLMKNG
                740       750       760       770       780       790       800

          910       920       930       940       950       960       970
Hum.  KSQCDGQVEINVLGHWGSLCDTHWDPEDARVLCRQLSCGTALSTTGGKYIGERSVRVWGHRFHCLGNESL
      :::.:::::... :.: .::..::. ..: :.::::.::.:.::  :  . : . ..  .::: :.::.
WC1   TSQCEGQVEMKISGRWRALCASHWSLANANVVCRQLGCGVAISTPRGPHLVEGGDQISTAQFHCSGAESF
                810       820       830       840       850       860       870

          980       990      1000      1010      1020      1030      1040
Hum.  LDNCQMTVLGAPPCIHGNTVSVICTGSLTQPLFPCLANVSDPYLSAVPEGSALICLEDKRLRLVDGDSRC
      : .:..:.::.: : ::::.::::.:. :: : .: . .:.:  ::..: :.  : ....::::::.. :
WC1   LWSCPVTALGGPDCSHGNTASVICSGNHTQVLPQCNDFLSQPAGSAASEESSPYCSDSRQLRLVDGGGPC
                880       890       900       910       920       930       940

          1050      1060      1070      1080      1090      1100      1110
Hum.  AGRVEIYHDGFWGTICDDGWDLSDAHVVCQKLGCGVAFNATVSAHFGEGSGPIWLDDLNCTGTESHLWQC
      .::::: ..: ::::::.:::.::.:::..:::: :.::: :::::.:::::::::::::: ::::.:.:
WC1   GGRVEILDQGSWGTICDDDWDLDDARVVCRQLGCGEALNATGSAHFGAGSGPIWLDDLNCTGKESHVWRC
                950       960       970       980       990      1000      1010
```

Fig. 2N

```
         1120      1130      1140      1150      1160      1170      1180
Hum.  PSRGWGQHDCRHKEDAGVICSEFTALRLYSETETESCAGRLEVFYNGTWGSVGRRNITTAIAGIVCRQLG
      ::::::.::::::::::::::::: ::::. :: .   :::.:::::::::::: :  .   .....:::::
WC1   PSRGWGRHDCRHKEDAGVICSEFLALRMVSEDQQ--CAGWLEVFYNGTWGSVCRSPMEDITVSVICRQLG
              1020      1030      1040        1050      1060      1070

         1190      1200      1210      1220      1230      1240
Hum.  CGENGVVSLAPLSKTGSGFMWVDDIQCPKTHISIWQCLSAPWERRISSPAEETWITCEDR----------
      ::..: .. .   . ::   ::: ::: : ..:.::: :.::      :: ::. :.::.:
WC1   CGDSGSLNTSVGLREGSRPRWVDLIQCRKMDTSLWQCPSGPWKYSSCSPKEEAYISCEGRRPKSCPTAAA
    1080      1090      1100      1110      1120      1130      1140

               1250      1260      1270      1280      1290      1300
Hum.  ------IRVRGGDTECSGRVEIWHAGSWGTVCDDSWDLAEAEVVCQQLGCGSALAALRDASFGQGTGTIW
            .:.::::.:::::::.::.:::::::::::::.:::::::::::::: ::.:.:.::.:.:.::
WC1   CTDREKLRLRGGDSECSGRVEVWHNGSWGTVCDDSWSLAEAEVVCQQLGCGQALEAVRSAAFGPGNGSIW
    1150      1160      1170      1180      1190      1200      1210

    1310      1320      1330      1340                     1350      1360
Hum.  LDDMRCKGNESFLWDCHAKPWGQSDCGHKEDAGVRCSG---------------QSLKSLNASSGHLALI
      ::...: : :: :::: : ::::::: : :::::::::               .:: .. . .: : ::
WC1   LDEVQCGGRESSLWDCVAEPWGQSDCKHEEDAGVRCSGVRTTLPTTTAGTRTTSNSLPGIFSLPGVLCLI
    1220      1230      1240      1250      1260      1270      1280
```

Fig. 2O

```
           1370      1380            1390             1400              1410
Hum. LSSIFGLLLLVLFILFLTWCRVQK------QKHLPLRVS-------TRRRG--------SLEENLFHEME
     :.:.. :.:..: . .: : :...      .  :.  :        :.. :        .. .. ... :
 WC1 LGSLLFLVLVILVTQLLRW-RAERRALSSYEDALAEAVYEELDYLLTQKEGLGSPDQMTDVPDENYDDAE
   1290      1300       1310      1320      1330      1340      1350

                            1420                1430                  1440
Hum. TC---------------LKREDPHGTRTSD---------DTPNHGCEDAS-------------DTSLLGV
                    .  :  .:.:.:.         ...: :  ..:             :   :..
 WC1 EVPVPGTPSPSQGNEEEVPPEKEDGVRSSQTGSFLNFSREAANPGEGEESFWLLQGKKGDAGYDDVELSA
    1360      1370      1380      1390      1400      1410      1420

      1450
Hum. LPASEAT-K
     : .: .:
 WC1 LGTSPVTFS
    1430
```

Fig. 2P

```
Hum. ATGATGCTGCCTCAAAACTCGTGGCATATTGATTTTGGAAGATGCTGCTGTCATCAGAACCTTTTCTCTG
     :::             .::: :::                      ::.:.::      ::: : : :::
WC1  ATG-------------GCTC-TGG----------------------GCAGACA------CCTCT-CCCTG
                           10                                    20

             80        90       100       110       120       130       140
Hum. CTGTGGTAACTTGCATCCTGCTCCTGAATTCCTGCTTTCTCATCAGCAGTTTTAATGGAACAGATTTGGA
     : : ::. .:: : .:::: :::::      : ::.    :     ::   : ..:::.  :: : ::::
WC1  C-GGGGACTCT-GTGTCCTCCTCCT------CGGCA----C-----CATGGTGGGTGGTCAAGCTCTGGA
       30         40        50                       60        70        80

            150       160       170       180       190       200       210
Hum. GTTGAGGCTGGTCAATGGAGACGGTCCCTGCTCTGGGACAGTGGAGGTGAAATTCCAGGGACAGTGGGGG
     : ::::: ::.. .:::::::.: .:: :::   :::: ::::::::.:::::. .:::.::: :.:::::
WC1  GCTGAGGTTGAAGGATGGAGTCCATCGCTGTGAGGGGAGAGTGGAAGTGAAGCACCAAGGAGAATGGGGC
             90       100       110       120       130       140       150

            220       230       240       250       260       270
Hum. ACTGTGTGTGATGATGGGTGGAACACTACTGCCT-CAACTGTCGTGTGCAAACAGCTTGGATGTCCATTT
     ::.::: .::.: : .:::::: :: :. .:  : ::.:::: :::::::.:::::: ::.:::  :  :
WC1  ACAGTGGATGGTTACAGGTGGA-CATTGAAGGATGCATCTGTAGTGTGCAGACAGCTGGGGTGTGGAGCT
            160       170       180       190       200       210
```

Fig. 2Qi

```
      280       290       300       310         320       330       340
Hum.  TCTTTCGCCATGTTTCGTTTTGGACAAGCCGTGA--CTAGACATGGAAAAATTTGGCTTGATGATGTTTC
       : .: :  .: :: :   . ::.:...   ::.  :..:::.:::    :::::::: .  ::. :::
WC1   GCCATTG--GTTTTCCTGGAGGGGCTTATTTTGGGCCAGGACTTGGCCCCATTTGGCTTTTGTATACTTC
      220        230       240       250        260       270       280
        350       360       370       380       390       400       410
Hum.  CTGTTATGGAAATGAGTCAGCTCTCTGGGAATGTCAACACCGGGAATGGGGAAGCCATAACTGTTATCAT
       ::: :.::.: .:::::::.:: ::.: :: ::: :.::      :::.  .::: : ::.: ::.:: ::
WC1   ATGTGAAGGGACAGAGTCAACTGTCAGTGACTGTGAGCAT-TCTAATATTAAAGAC-TATC-GTAATGAT
        290       300       310       320        330       340        350

        420       430       440       450        460         470       480
Hum.  GGAGAAGATGTTGGTGTGAACTGTTATGGTGAAGCCAA-TCTGGGTTTGAG--GCTAG-TGGATGGAAAC
      ::  :..:: .:::: :.:   :  :::.:.:: :.. ::.::.::::.:   ::.: :::: ::.:.
WC1   GGCTATAATCATGGTCGGGA---TGCTGGAGTAGTCTGCTCAGGATTTGTGCGTCTGGCTGGAGGGGATG
         360       370         380       390       400       410       420

          490       500       510       520       530       540       550
Hum.  AACTCCTGTTCAGGGAGAGTGGAGGTGAAATTCCAAGAAAGGTGGGGACTATATGTGATGATGGGTGGA
      .:: :::: :::::: ::::.::.::: :.:  :..::.:.:   ::..:  ..:::  ::::::::.. .
WC1   GAC-CCTGCTCAGGGCGAGTAGAAGTGCATT--CTGGAGAAGCTTGGATCCCAGTGT-CTGATGGGAACT
             430       440       450          460       470        480
```

Fig. 2Qii

```
           560       570       580       590       600       610       620
Hum.  ACTTGAATACTGCTGCCGTGGTGTGCAGGCAACTAGGATGTCCATCTTCTTTTATTTCTTCTGGAGTTGT
      .:. . .:.: .:::::        :::               :::.::: :       :.:.. : :
WC1   TCACACTTGCCACTGCC--------CAG---------------ATCATCTGT-------GCAGAGTTGGG
      490       500                              510              520

           630       640       650       660       670       680       690
Hum.  TAATAGCCCTGCTGTATTGCGCCCCATTTGGCTGGATGACATTTTATGCCAGGGGAATGAGTTGGCACT-
      :..:.::                    ..:::::  ::.:. :     ::.:::. :::::    :.::
WC1   TTGTGGC--------------------AAGGCTG--TGTCTGT-----CCTGGGACATGAG----CTCTT
      530                           540              550       560

            700       710       720       730       740       750       760
Hum.  CTGGAATTGCAGACATCGTGGATGGGGAAATCATGACTGCAGTCACAATGAGGATGTCACATTAACTTGT
      :.:..: : :::. . :              :: :.:::  : :     :::.:: :::         :
WC1   CAGAGAGTCCAGT-GCC--------------CAGGTCTG--GGC----TGAAGAGTTCA---------GG
       570        580                    590              600

            770       780       790       800       810       820       830
Hum.  TATGATAGTAGTGATCTTGAACTAAGGCTTGTAGGTGGAACTAACCGCTGTATGGGGAGAGTAGAGCTGA
      :.::: .: .. :: : :::.::    ::       ::..::. :: :.:..::            :::
WC1   TGTGAGGGGGAGGAGCCTGAGCT----CT-------GGGTCTGCCC-CAGAGTG----------CCCTG-
       610       620           630              640                 650
```

Fig. 2Qiii

```
              840       850       860       870       880       890       900
Hum.  AAATCCAAGGAAGGTGGGGGACCGTATGCCACCATAAGTGGAACAATGCTGCAGCTGATGTCGTATGCAA
         ::::         :::::  :::.:  ::::: : ::::::.:  :::: ::: : .: :  : .:::.
WC1   ---TCCA--------GGGGGCACGTGT--CACCACA-GTGGATC--TGCT-CAGGTTGTTTGTTCAGCAT
                     660        670       680         690       700

              910       920       930       940       950       960       970
Hum.  GCAGTTGGGATGTGGAACCGCACTTCACTTCGCTGGCTTGCCTCATTTGCAGTCAGGGTCTGATGTTGTA
      .:.        .:..:. : ::.:.: ::.. .: ::::  :::: : .: .:: :.:: :.:.:: .:..
WC1   ACT------CAGAAGTCCGGCTCATGACAA-AC-GGCT--CCTC-TCAG-TGTGAAGGGCAGGTGGAGAT
                710       720       730           740         750       760

              980       990      1000      1010      1020      1030      1040
Hum.  TGGCTTGATGGTGTCTCCTGCTCCGGTAATGAATCTTTTCTTTGGGACTGCAGACATTCCGGAACCGTCA
       ..:.:        :::    .:.  ::..:  . ::: : : :     :::: ::.:.  .:.....::   :
WC1   GAACATT------TCTG-GACAATGGAGAGCGCTCTGTGCCTCCC-ACTGGAGTCTGGCCAATGCC---A
        770              780       790       800         810       820

             1050      1060      1070      1080      1090      1100      1110
Hum.  ATTTTGACTGTCTTCATCAAAACGATGTGTCTGTGATCTGCTCAGATGGAGCAGATTTGGAACTGCGACT
      :: ::..::::: ::: :. ..: .:: .   ::  :::: :.:      ::::         .:: .: :::
WC1   ATGTTATCTGTCGTCAGCTCGGCTGTGGAGTTGCCATCTCCACCCCCGGAG---------GACCAC-ACT
        830       840       850       860       870                  880
```

Fig. 2Qiv

```
            1120      1130      1140      1150      1160       1170      1180
Hum. AGCAGATGGAAGTAACAATTGTTCAGGGAGAGTAGAGGTGAGAATTCA-TGAACAGTGGTGGACAATATG
     .:   .:::::::.:.    ::.::::  :   ::. .:   ::.:::: :: .:.:     :.:.:    ::
 WC1 TG---GTGGAAGAAG---GTGATCAG--ATCCTAACAGCCCGATTTCACTGCTCTG----GGGC----TG
              890           900         910        920        930

             1190      1200      1210      1220      1230      1240      1250
Hum. TGACCAGAACTGGAAGAATGAACAAGCCCTTGTGGTTTGTAAGCAGCTAGGATGTCCGTTCAGCGTCTTT
     .:.::. . ::: .....::.      ::: :::. :     ::  ::.::. ::::  .:.:   : .:
 WC1 AGTCCT-TCCTGTGGAGTTGT------CCT-GTGACT-----GCC-CTGGGTGGTCCTGACTGTTCCCAT
     940        950             960                970        980       990

              1260      1270      1280      1290      1300      1310      1320
Hum. GGCAG-TCGTCGTGCTAAACCTAGTAATGAAGCTAGAGACATTTGGATAAACAGCATATCTTGCACTGGG
     ::::. .:. : :    ..: ::. : : :::.: :::   ::   :: .:   ::: . :.: . :.: :
 WC1 GGCAACACAGCCTCTGTGATCTGCTCAGGAAACCAGATCCAGGTGCTTCCCCAGTGCAACGA-CTCCG--
        1000      1010      1020      1030      1040      1050       1060

              1330      1340      1350      1360      1370      1380      1390
Hum. AATGAGTCAGCTCTCTGGGACTGCACATATGATGGAAAAGCAAAGCGAACATGCTTCCGAAGATCAGATG
       ::. ::::.:  .:.:: .::::            ::      :. :: :.::: ::  ::      :.. ::
 WC1 --TGTCTCAACCTACAGGCTCTGC---------GGC----CTCAGAGGACA-GCGCCC-----CCTACTG
               1070      1080                    1090       1100
```

Fig. 2Qv

```
              1400      1410      1420      1430      1440      1450      1460
Hum.  CTGGAGTAATTTGTTCTGATAAGGCAGATCTGGACCTAAGGCTTGTCGGGGCTCATAGCCCCTGTTATGG
      :: ...          :.:  :::::: :: :  :::.. :  :.:::::  :  .: :::::    ::
WC1   CTCAGA---------CAG--CAGGCAGCTCCG--CCTGGTG---GACGGGG-GC--GGTCCCTGCGCCGG
    1110                 1120      1130           1140         1150     1160

              1470      1480      1490      1500      1510      1520
Hum.  GAGATTGGAGGTGAAATACCAAGGAGAGTGGGGGACTGTGTGTCATGACAGATGGAGCACAAGG-AATGC
      :::: ::::::.:  .. ::::.::    ::::: :: .: ::: ::::::.: :::..: :..:. .::::
WC1   GAGAGTGGAGATCCTTGACCAGGGCTCCTGGGGCACCATCTGTGATGACGGCTGGGAC-CTGGACGATGC
              1170      1180      1190      1200      1210       1220

    1530        1540      1550      1560       1570      1580      1590
Hum.  A-GCTGTTGTGTGTAAACAATTGGGATGTGGA-AAGCCTATGCATGTGTTTGGTATGACCTATTTTAAAG
        :: :: ::::: :..::. :::: :::::: ::::: . . :::   .  :: .  .:  : :: ...:
WC1   CCGC-GTGGTGTGCAGGCAGCTGGGCTGTGGAGAAGCCCTCA-ATGCCACGGGGTCTGCTCACTTCGGGG
    1230        1240      1250      1260       1270      1280      1290

      1600      1610      1620      1630      1640      1650      1660
Hum.  AAGCATCAGGACCTATTTGGCTGGATGACGTTTCTTGCATTGGAAATGAGTCAAATATCTGGACTGTGA
       :: :::::::.:: :: ::: :::: .:: : .  :::: .::::: :::::  : .: :::.. ::
WC1   CAGGATCAGGGCCCATCTGGTTGGACAACTTGAACTGCACAGGAAAGGAGTCCCACGTGTGGAGGTGCCC
      1300      1310      1320      1330      1340      1350      1360
```

Fig. 2Qvi

```
      1670      1680      1690      1700      1710      1720      1730
Hum.  ACACAGTGGATGGGAAAGCATAATTGTGTACACAGAGAGGATGTGATTGTAACCTGCTCAGGTGATGCA
       .  : : :: :::::. :::: :: :: . :::::.. :::: : :.  :: : ::::::::  ..: :
 WC1  TTCCCGGGGCTGGGGGCAGCACAACTGCAGACACAAGCAGGACGCGGGGGTCATCTGCTCAG--AGTTC-
      1370      1380      1390      1400      1410      1420        1430

      1740      1750      1760      1770      1780      1790      1800
Hum.  ACATGGGGCCTGAGGCTGGTGGGCGGCAGCAACCGCTGCTCGGGAAGACTGGAGGTGTACTTTCAAGGAC
        :.  :: ::: ::: :::::.: :. ..: : :. ::   : ::..:.:::::.:: :.::.  :.::.
 WC1  -CT--GGCCCTCAGGATGGTGAGTGAGGACCAGCAGTGTGCTGGGTGGCTGGAAGTTTTCTACAATGGGA
            1440      1450      1460      1470      1480      1490      1500

      1810      1820      1830      1840      1850      1860      1870
Hum.  GGTGGGGCACAGTGTGTGATGACGGCTGGAACAGTAAAGCTGCAGCTGTGGTGTGTAGCCAGCTGGACTG
        ::::::: .:: ::  .:.::  :. :.: .. :. .::: . : . :.: :: :: ::::: :.:::
 WC1  CCTGGGGCAGTGTCTGCCGTAACCCCATGGAAGACATCACTGTGTCCACGATCTGCAGACAGCTTGGCTG
            1510      1520      1530      1540      1550      1560      1570

      1880      1890      1900      1910      1920      1930      1940
Hum.  CCCATCTTCTATCATTGGCATGGGTCTG-GGAAACGCTTCTA-CAGGATATGGAAAAATTTGGCTCGATG
         .   .:..: ...  :. .. :::   :...: :::  :  :::.:.:.:.  : . ::: : :::
 WC1  T--GGGGACAGTGGAACCCTCAACTCTTCTGTTGCTCTTAGAGAAGGTTTTAGGCCACAGTGGGTGGAT-
              1580      1590      1600      1610      1620      1630
```

Fig. 2Qvii

```
          1950      1960      1970      1980      1990      2000        2010
Hum.  ATGTTTCCTGTGATGGAGATGAGTCAGATCTCTGGTCATGCAGGAACAGTGGGTG--GGGAAATAATGAC
        .:..:::.:::. :::.:. .:.::  :::::   :. :::: ..:  :  :.     :.::::.: .::
 WC1  -AGAATCCAGTGTCGGAAAACTGACACCTCTCT---CTGGCAGTGTCCTTCTGACCCTTGGAATTACAAC
        1640      1650      1660      1670          1680      1690      1700

            2020      2030      2040       2050       2060      2070      2080
Hum.  TGCAGTCACAGTGAAGATGTTGGAGTG-ATCTGTTCTGATG-CATCGGATATGGAGCTGAGGCTTGTGGG
      : ::  :.:.  .::::..: ..:  :. ::::: : :: .: :: :.:: :  :: : :   :: ::::.
 WC1  T-CATGCTCTCCAAAGGAGGAAGCCTATATCTGGTGTGCAGACAGCAGACA--GATCCGC--CTGGTGGA
            1710      1720      1730      1740      1750        1760

              2090      2100      2110      2120      2130      2140      2150
Hum.  TGGAAGCAGCAGGTGTGCTGGAAAAGTTGAGGTGAATGTCCAGGGTGCCGTGGAATTCTGTGTGCTAAT
      ::::.: .:  : ::  ::::.:.::: ::::.:  .::.::::::  ::  ::: :   : :::: :.:
 WC1  TGGAGGTGGTCGCTGCTCTGGGAGAGTGGAGATCCTTGACCAGGGCTCCTGGGGCACCATCTGTGATGAC
     1770      1780      1790      1800      1810      1820      1830

              2160      2170      2180      2190      2200      2210      2220
Hum.  GGCTGGGGAATGAACATTGCTGAAGTTGTTTGCAGGCAACTTGAATGTGGGTCTGCAATCAGGTCTCCA
       ::::::.  ::.::..:::   ..:: :: ::::.:::.:: :. :::::.   .::    :  ::.: :::
 WC1  CGCTGGGACCTGGACGATGCCCGTGTGGTGTGCAAGCAGCTGGGCTGTGGAGAAGC---CCTGGACGCCA
     1840      1850      1860      1870      1880      1890          1900
```

Fig. 2Qviii

```
           2230      2240        2250      2260      2270      2280
Hum.  GAGA-GCCTCATTTCACAGAA--AGAACATTACACATCTTAATGTCGAATTCTGGCTGCACTGGAGGGGA
        .:.  : :: ::  .:.:.:  .::.::  .: ::::: . ::   .:.   ..::::: .::::.:::
 WC1  CTGTCTCTTCCTTCTTCGGACGGATCAGGGCCCATCTGGCTGGATGAAGTGAACTGCAGAGGAGAGGA
      1910      1920      1930      1940      1950      1960      1970

   2290      2300      2310      2320        2330      2340      2350
Hum.  AGCCTCTCTCTGGGATTGTATACGATGGGAGTGGAAACAG-ACTGCGTGTCATTTAAATATGGAAGCAAG
      . ::  . : ::::.. ::   .   ::::..::: ..::. ::..: ::  :: .. :....::.::::.:
 WC1  GTCCCAAGTATGGAGGTGCCCTTCCTGGGGATGGCGGCAACACAAC-TGCAATCATCAAGAAGATGCAGG
      1980      1990      2000      2010      2020       2030      2040

    2360      2370      2380      2390      2400      2410      2420
Hum.  TTTGATCTGCTCAGCCCACAGGCAGCCCAGGCTGGTTGGAGCTGATATGCCCTGCTCTGGACGTGTTGAA
      . : ::::::::::   . . ::      : :::: ::::: .:::. .::::::::.::.::.::.:::
 WC1  AGTCATCTGCTCAGGATTTGTGC------GTCTGGCTGGAGGAGATGGACCCTGCTCAGGGCGAGTAGAA
        2050      2060            2070      2080      2090      2100

    2430      2440      2450      2460      2470      2480      2490
Hum.  GTGAAACATGCAGACACATGGCGCTCTGTCTGTGATTCTGATTTCTCTCTTCATGCTGCCAATGT--GCT
      ::: :.  :: ::: .: :::  : :.:: : ::::   ..: :::.:.:: :  .::::: : ::   ::
 WC1  GTGCATTCTGGAGAAGCCTGGACCCCAGTGTCTGATGGAAACTTCACACTCCCCACTGCCCAGGTCATCT
    2110      2120      2130      2140      2150      2160      2170
```

Fig. 2Qix

```
         2500      2510      2520      2530      2540      2550       2560
Hum. GTGCAGAGAATTAAATTGTGGAGATGCCATATCTCTTTCTGTGGAGATCACTTTGGAAAAGGG-AATGG
     ::::::::   :....::::: .: :: .:.:::  : ::: :. : ::  :.:: ..:.::   .::::
WC1  GTGCAGAGC--TGGGATGTGGCAAGGCTGTGTCT-GTCCTGGACACATGCCATTCAGAGAGTCCGATGG
    2180        2190      2200      2210       2220      2230      2240

          2570      2580      2590      2600      2610      2620      2630
Hum. TCTAACTTGGGCCGAAAAGTTCCAGTGTGAAGGGAGTGAAACTCACCTTGCATTATGCCCCATTGTTCAA
      :...  ::::: :::.::::: .::::::.:::.: ::. :: : ::   .:  ::::::: .:: :
WC1  CCAGGTCTGGGCTGAAGAGTTCAGGTGTGATGGGGGGGAGCCTGAGCTCTGGTCCTGCCCCAGAGTGCCC
     2250      2260      2270      2280      2290      2300      2310

          2640      2650      2660      2670      2680      2690      2700
Hum. CATCCGGAAGACACTTGTATCCACAGCAGAGAAGTTGGAGTTGTCTGTTCCCGATATACAGATGTCCGAC
      .:::.:.::.:::.::: ::::::: .::: .: : ..::::::::::   .:: ::::..:::::..:
WC1  TGTCCAGGAGGCACATGTCTCCACAGTGGAGCTGCTCAGGTTGTCTGTTCAGTGTACACAGAAGTCCAGC
     2320      2330      2340      2350      2360      2370      2380

          2710      2720         2730      2740      2750       2760      2770
Hum. TTGTGAATGGCAAATCC---CAGTGTGACGGGCAAGTGGAGATCAACGTGCT-TGGACACTGGGGCTCAC
     ::.:::::...:.. .::   ::.:::::: :::::.::::::::: .: :. :: :::::. ::::.:  :.:
WC1  TTATGAAAAACGGCACCTCTCAATGTGAGGGGCAGGTGGAGAT-GAAGATCTCTGGACGATGGAGAGCGC
     2390      2400      2410      2420       2430      2440      2450
```

Fig. 2Qx

```
            2780      2790      2800      2810      2820      2830      2840
Hum. TGTGTGACACCCACTGGGACCCAGAAGATGCCCGTGTTCTATGCAGACAGCTCAGCTGTGGGACTGCTCT
     : :::: :.:::::::::.. : .:  .::::: .:::: : ::  :.:::::::.::::::::..  ::  :
 WC1 TCTGTGCCTCCCACTGGAGTCTGGCCAATGCCAATGTTGTCTGTCGTCAGCTCGGCTGTGGAGTCGCCAT
       2460      2470      2480      2490      2500      2510      2520

            2850      2860      2870      2880      2890      2900      2910
Hum. CTCAACCACAGGAGGAAAATATATTGGAGAAAGAAGTGTTCGTGTGTGGGGACACAGGTTTCATTGCTTA
     ::: ::: : .:::::  : : .: : .:::.::.:::.::. .: :  .. :  : ..::::: :::: :
 WC1 CTCCACCCCCAGAGGACCACACTTGGTGGAAGGAGGTGATCAGATCTCAACAGCCCAATTTCACTGCTCA
       2530      2540      2550      2560      2570      2580      2590

            2920      2930      2940      2950      2960      2970      2980
Hum. GGGAATGAGTCACTTCTGGATAACTGTCAAATGACAGTTCTTGGAGCACCTCCCTGTATCCATGGAAATA
     :::. ::::::  : ::: . :. :::: ..:::::.:   : ::.: .:::  ::::. :::::: :: :
 WC1 GGGGCTGAGTCCTTCCTGTGGAGTTGTCCTGTGACTGCCTTGGGTGGGCCTGACTGTTCCCATGGCAACA
       2600      2610      2620      2630      2640      2650      2660

            2990      3000      3010      3020      3030      3040      3050
Hum. CTGTCTCTGTGATCTGCACAGGAAGCCTGACCCAGCCACTGTTTCCATGCCTCGCAAATGTATCTGACCC
     :.: ::::::::::::.:::::::.::. ::::::   .:::    : .::: .::   ..   :.::: : ::
 WC1 CAGCCTCTGTGATCTGCTCAGGAAACCACACCCAGGTGCTGCCCCAGTGCAACGACTTCCTGTCTCAACC
       2670      2680      2690      2700      2710      2720      2730
```

Fig. 2Qxi

```
              3060      3070      3080      3090      3100      3110      3120
Hum.  ATATTTGTCTGCAGTTCCAGAGGGCAGTGCTTTGATCTGCTTAGAGGACAAACGGCTCCGCCTAGTGGAT
      .  .    ::::::.:   :::::::. ::: ::   ..::::: ::: ..::..:.:::::::::.:::::
WC1   TGCAGGCTCTGCGGCCTCAGAGGAGAGTTCTCCCTACTGCTCAGACAGCAGGCAGCTCCGCCTGGTGGAC
        2740      2750      2760      2770      2780      2790      2800

              3130      3140      3150      3160      3170      3180      3190
Hum.  GGGGACAGCCGCTGTGCCGGGAGAGTAGAGATCTATCACGACGGCTTCTGGGGCACCATCTGTGATGACG
      ::::.:.: : ::: : ::::::::.::::::: .: :: : :::: ::::::::::::::::::::: :
WC1   GGGGGCGGTCCCTGCGGCGGGAGAGTGGAGATCCTTGACCAGGGCTCCTGGGGCACCATCTGTGATGATG
        2810      2820      2830      2840      2850      2860      2870

              3200      3210      3220      3230      3240      3250      3260
Hum.  GCTGGGACCTGAGCGATGCCCACGTGGTGTGTCAAAAGCTGGGCTGTGGAGTGGCCTTCAATGCCACGGT
      .:::::::::::.::::::::. ::::::::  .. ::::::::::::::::..::: :::::::::::
WC1   ACTGGGACCTGGACGATGCCCGTGTGGTGTGCAGGCAGCTGGGCTGTGGAGAAGCCCTCAATGCCACGGG
        2880      2890      2900      2910      2920      2930      2940

              3270      3280      3290      3300      3310      3320      3330
Hum.  CTCTGCTCACTTTGGGGAGGGGTCAGGGCCCATCTGGCTGGATGACCTGAACTGCACAGGAACGGAGTCC
       ::::::::::: :::: .::.::::::::::::::::::::: ::::::::::::::::::: :::::::
WC1   GTCTGCTCACTTCGGGGCAGGATCAGGGCCCATCTGGCTGGACGACCTGAACTGCACAGGAAAGGAGTCC
        2950      2960      2970      2980      2990      3000      3010
```

Fig. 2Qxii

```
            3340      3350      3360      3370      3380      3390      3400
Hum. CACTTGTGGCAGTGCCCTTCCCGCGGCTGGGGGCAGCACGACTGCAGGCACAAGGAGGACGCAGGGGTCA
     ::: ::::: .:::::::::::: :::::::::.:::::::::::::.::::::::::::: :::::::
 WC1 CACGTGTGGAGGTGCCCTTCCCGGGGCTGGGGGCGGCACGACTGCAGACACAAGGAGGACGCCGGGGTCA
       3020      3030      3040      3050      3060      3070      3080

            3410      3420      3430      3440      3450      3460      3470
Hum. TCTGCTCAGAATTCACAGCCTTGAGGCTCTACAGTGAAACTGAAACAGAGAGCTGTGCTGGGAGATTGGA
     ::::::::::.:::  .::: : ::: :    .::::. : ...:: .. :: ::::::::.:. ::::
 WC1 TCTGCTCAGAGTTCCTGGCCCTCAGGAT----GGTGAG-CGAGGACCAGCAG-TGTGCTGGGTGGCTGGA
       3090      3100      3110          3120      3130       3140

            3480      3490      3500      3510      3520      3530      3540
Hum. AGTCTTCTATAACGGGACCTGGGGCAGCGTCGGCAGGAGGAACATCACCACAGCCATAGCAGGCATTGTG
     .:: ::::: :::::::::::::::: ::: :: : ::   ::: .  . .. :: .: .   :.: .:
 WC1 GGTTTTCTACAACGGGACCTGGGGCAGTGTCTGCCGCAGCCCCATGGAAGATATCACTGTGTCCGTGATC
   3150      3160      3170      3180      3190      3200      3210

            3550      3560      3570      3580      3590         3600
Hum. TGCAGGCAGCTGGGCTGTGGGGAGAATGGAGTTGTCAGCCTCGCCCCTTTA--TCT-AAGACAGGCTCTG
     ::::.:::::: :: :::::::: :.::::  .:::. : .:.:: :: :.  ::: :.:. ::: :::.
 WC1 TGCAGACAGCTTGGATGTGGGGACAGTGGA--AGTCT-CAACACCTCTGTTGGTCTCAGGGAAGGTTCTA
   3220      3230      3240        3250      3260      3270      3280
```

Fig. 2Qxiii

```
        3610      3620      3630      3640      3650      3660      3670
Hum.  GTTTCATGTGGGTGGATGACATTCAGTGTCCTAAAACGCATATCTCCATATGGCAGTGCCTGTCTGCCCC
      :.  :  :::::::.::: . ::::::::::  :::: : ::: :::  : :::::::: :  :::: :::
WC1   GACCCCGGTGGGTAGATTTAATTCAGTGTCGGAAAATGGATACCTCTCTCTGGCAGTGTCCTTCTGGCCC
        3290      3300      3310      3320      3330      3340      3350

        3680      3690      3700      3710      3720      3730          3740
Hum.  ATGGGAGCGAAGAATCTCCAGCCCAGCAGAAGAGACCTGGATCACATGTGAAGATAGAATA----AGAG-
      ::::.:. . ::..  : :.  :::. .::.::..:::. :::.::::::::::.:::: :    ::::
WC1   ATGGAAATACAGTTCATGCTCTCCAAAGGAGGAAGCCTACATCTCATGTGAAGGAAGAAGACCCAAGAGC
        3360      3370      3380      3390      3400      3410      3420

                                                        3750      3760
Hum.  --------TGC-----------------------------------GTGGAGGAGACACCGAGTGCTCTG
              :::                                   : ::::::::::  :::::::::.:
WC1   TGTCCAACTGCTGCCGCCTGCACAGACAGAGAGAAGCTCCGCCTCAGGGGAGGAGACAGCGAGTGCTCAG
        3430      3440      3450      3460      3470      3480      3490

      3770      3780      3790      3800      3810      3820      3830
Hum.  GGAGAGTGGAGATCTGGCACGCAGGCTCCTGGGGCACAGTGTGTGATGACTCCTGGACCTGGCCGAGGC
      :: :.::::::.: ::::::.  ::::::::::::::: ::::: ::::::::::::..:::::: :::::
WC1   GGCGGGTGGAGGTGTGGCACAACGGCTCCTGGGGCACCGTGTGCGATGACTCCTGGAGCCTGGCAGAGGC
        3500      3510      3520      3530      3540      3550      3560
```

Fig. 2Qxiv

```
      3840      3850      3860      3870      3880      3890      3900
Hum.  GGAAGTGGTGTGTCAGCAGCTGGGCTGTGGCTCTGCTCTGGCTGCCCTGAGGGACGCTTCGTTTGGCCAG
        ::.::::::::::::::::::::::::::::::   :: :::: .::: :: ::   ::. :.:::::::
 WC1  TGAGGTGGTGTGTCAGCAGCTGGGCTGTGGCCAGGCCCTGGAAGCCGTGCGGTCTGCAGCATTTGGCCCT
      3570      3580      3590      3600      3610      3620      3630

      3910      3920      3930      3940      3950      3960      3970
Hum.  GGAACTGGAACCATCTGGTTGGATGACATGCGGTGCAAAGGAAATGAGTCATTTCTATGGACTGTCACG
      :::: :::.: ::::::: :::: :: .:::.::::...::  . ::::: :  ::.:::::::::: . :
 WC1  GGAAATGGAGCATCTGGCTGGACGAGGTGCAGTGCGGGGGCCGGGAGTCCTCCCTGTGGACTGTGTTG
      3640      3650      3660      3670      3680      3690      3700

      3980      3990      4000      4010      4020      4030      4040
Hum.  CCAAACCCTGGGGACAGAGTGACTGTGGACACAAGGAAGATGCTGGCGTGAGGTGCTCTGG---ACAGTC
      : .:.::::::::.::::: ::::: ...:::.:::.:::::::: ::::::::::::::   : .:.:
 WC1  CGGAGCCCTGGGGGCAGAGCGACTGCAAGCACGAGGAGGATGCTGGTGTGAGGTGCTCTGGTGTAAGGAC
      3710      3720      3730      3740      3750      3760      3770

                4050      4060                4070          4080      4090
Hum.  G-------CTGAAATCACTGAATG--CCT------CCTCAGGT-CATT---TAGCA-CTTATTTTATCCA
      .       : . .: :::.: : :  ::.       ::::::..: :. :    :.::: ::: :    . ::.
 WC1  AACATTGCCCACGACCACAGCAGGGACCAGAACAACCTCAAATTCTCTCCCTGGCATCTTCTCCCTGCCT
      3780      3790      3800      3810      3820      3830      3840
```

Fig. 2Qxv

```
                4100          4110          4120                4130      4140
Hum. G--------TATCTT----TGGGCTC-CTTCTC---CTGGTTCT---------GTTTATTCTATTTCTCA
     :        :. :::    :::: :: ::::::   ::::: ::         : : : ::.. :.::::
WC1  GGGGTTCTCTGCCTTATCCTGGGGTCGCTTCTTCCTGGTCCTCGTCATCCTGGTGACTCAGCTACTCA
     3850      3860      3870      3880      3890      3900      3910

               4150      4160      4170                   4180
Hum. CGTGGTG--CCGAGTTCAGAAACAAAAACATCT--------GCCC---CT----CAGAGTTT--------
      .:::.:  : :::  ::::. :..:. :: ::        :: :   ::    :.:.::.:
WC1  GATGGAGAGCAGAGCGCAGAGCCTTATCCAGCTATGAAGATGCTCTTGCTGAAGCTGTGTATGAGGAGCT
     3920      3930      3940      3950      3960      3970      3980

               4190           4200          4210          4220
Hum. -------CAAC-----CAGAAGGAGGG---GTTCT-CTCG----AGGAGAATTTATTCCATGA-------
            :..:     :::::::::.::   :  :. : :.    ::..:: : .. ::: :::
WC1  CGATTACCTTCTGACACAGAAGGAAGGTCTGGGCAGCCCAGATCAGATGACTGATGTCCCTGATGAAAAT
     3990      4000      4010      4020      4030      4040      4050

     4230                     4240                              4250
Hum. ---GATGGAG----------------ACCTG------------CCTC-----------AAGAGAGAGGAC
        ::::..:               .::::            ::::           :.:::..:: .:
WC1  TATGATGATGCTGAAGAAGTACCAGTGCCTGGAACTCCTTCTCCCTCTCAGGGGAATGAGGAGGAAGTGC
     4060      4070      4080      4090      4100      4110      4120
```

Fig. 2Qxvi

```
     4260      4270                     4280                   4290
Hum. CCACATGGGACAAGAAC-------------CTCAGA-TGACAC---CC---------CCAA---------
     :: :: .:.: .::.::             :::::: .:.:.:   ::         :::.
 WC1 CCCCAGAGAAGGAGGACGGGGTGAGGTCCTCTCAGACAGGCTCTTTCCTGAACTTCTCCAGAGAGGCAGC
      4130      4140      4150      4160      4170      4180      4190

            4300             4310                      4320      4330
Hum. ----CCATGGTT--GTGAAGA----TGCTAGCGACAC---------------ATCGCTG--TTGGGAGTT
         ::. :: .  :.:::::    : ::.:: .:.:               .. ::::  :. :..:.:
 WC1 TAATCCTGGGGAAGGAGAAGAGAGCTTCTGGCTGCTCCAGGGGAAGAAAGGGGATGCTGGGTATGATGAT
     4200      4210      4220      4230      4240      4250      4260

               4340             4350
Hum. CTT-----------CCTG-------CCTCTGAAGCCACAAAA
      ::           ::::       :: :.:...: .  . .
 WC1 GTTGAACTCAGTGCCCTGGGAACATCCCCAGTGACTTTCTCG
     4270      4280      4290      4300
```

Fig. 2Qxvii

```
                                 M   A   L   P   A   L   G   L   D   P   W   S     12
GTCGACCCACGCGTCCGGTCTGTGGCTGAGC ATG GCC CTC CCA GCC CTG GGC CTG GAC CCC TGG AGC    67

 L   L   G   L   F   L   F   Q   L   L   Q   L   L   L   P   T   T   T   A   G     32
CTC CTG GGC CTT TTC CTC TTC CAA CTG CTT CAG CTG CTG CTG CCG ACG ACG ACC GCG GGG   127

 G   G   G   Q   G   P   M   P   R   V   R   Y   Y   A   G   D   E   R   R   A     52
GGA GGC GGG CAG GGG CCC ATG CCC AGG GTC AGA TAC TAT GCA GGG GAT GAA CGT AGG GCA   187

 L   S   F   F   H   Q   K   G   L   Q   D   F   D   T   L   L   L   S   G   D     72
CTT AGC TTC TTC CAC CAG AAG GGC CTC CAG GAT TTT GAC ACT CTG CTC CTG AGT GGT GAT   247

 G   N   T   L   Y   V   G   A   R   E   A   I   L   A   L   D   I   Q   D   P     92
GGA AAT ACT CTC TAC GTG GGG GCT CGA GAA GCC ATT CTG GCC TTG GAT ATC CAG GAT CCA   307

 G   V   P   R   L   K   N   M   I   P   W   P   A   S   D   R   K   K   S   E    112
GGG GTC CCC AGG CTA AAG AAC ATG ATA CCG TGG CCA GCC AGT GAC AGA AAA AAG AGT GAA   367

 C   A   F   K   K   K   S   N   E   T   Q   C   F   N   F   I   R   V   L   V    132
TGT GCC TTT AAG AAG AAG AGC AAT GAG ACA CAG TGT TTC AAC TTC ATC CGT GTC CTG GTT   427

 S   Y   N   V   T   H   L   Y   T   C   G   T   F   A   F   S   P   A   C   T    152
TCT TAC AAT GTC ACC CAT CTC TAC ACC TGC GGC ACC TTC GCC TTC AGC CCT GCT TGT ACC   487

 F   I   E   L   Q   D   S   Y   L   L   P   I   S   E   D   K   V   M   E   G    172
TTC ATT GAA CTT CAA GAT TCC TAC CTG TTG CCC ATC TCG GAG GAC AAG GTC ATG GAG GGA   547
```

Fig. 3A

```
K   G   Q   S   P   F   D   P   A   H   K   H   T   A   V   L   V   D   G   M    192
AAA GGC CAA AGC CCC TTT GAC CCC GCT CAC AAG CAT ACG GCT GTC TTG GTG GAT GGG ATG  607

L   Y   S   G   T   M   N   N   F   L   G   S   E   P   I   L   M   R   T   L    212
CTC TAT TCT GGT ACT ATG AAC AAC TTC CTG GGC AGT GAG CCC ATC CTG ATG CGC ACA CTG  667

G   S   Q   P   V   L   K   T   D   N   F   L   R   W   L   H   H   D   A   S    232
GGA TCC CAG CCT GTC CTC AAG ACC GAC AAC TTC CTC CGC TGG CTG CAT CAT GAC GCC TCC  727

F   V   A   A   I   P   S   T   Q   V   V   Y   F   F   F   E   E   T   A   S    252
TTT GTG GCA GCC ATC CCT TCG ACC CAG GTC GTC TAC TTC TTC TTC GAG GAG ACA GCC AGC  787

E   F   D   F   F   E   R   L   H   T   S   R   V   A   R   V   C   K   N   D    272
GAG TTT GAC TTC TTT GAG AGG CTC CAC ACA TCG CGG GTG GCT AGA GTC TGC AAG AAT GAC  847

V   G   G   E   K   L   L   Q   K   K   W   T   T   F   L   K   A   Q   L   L    292
GTG GGC GGC GAA AAG CTG CTG CAG AAG AAG TGG ACC ACC TTC CTG AAG GCC CAG CTG CTC  907

C   T   Q   P   G   Q   L   P   F   N   V   I   R   H   A   V   L   L   P   A    312
TGC ACC CAG CCG GGG CAG CTG CCC TTC AAC GTC ATC CGC CAC GCG GTC CTG CTC CCC GCC  967

D   S   P   T   A   P   H   I   Y   A   V   F   T   S   Q   W   Q   V   G   G    332
GAT TCT CCC ACA GCT CCC CAC ATC TAC GCA GTC TTC ACC TCC CAG TGG CAG GTT GGC GGG 1027

T   R   S   S   A   V   C   A   F   S   L   L   D   I   E   R   V   F   K   G    352
ACC AGG AGC TCT GCG GTT TGT GCC TTC TCT CTC TTG GAC ATT GAA CGT GTC TTT AAG GGG 1087
```

Fig. 3B

```
 K   Y   K   E   L   N   K   E   T   S   R   W   T   T   Y   R   G   P   E   T   372
AAA TAC AAA GAG TTG AAC AAA GAA ACT TCA CGC TGG ACT ACT TAT AGG GGC CCT GAG ACC 1147

 N   P   R   P   G   S   C   S   V   G   P   S   S   D   K   A   L   T   F   M   392
AAC CCC CGG CCA GGC AGT TGC TCA GTG GGC CCC TCC TCT GAT AAG GCC CTG ACC TTC ATG 1207

 K   D   H   F   L   M   D   E   Q   V   V   G   T   P   L   L   V   K   S   G   412
AAG GAC CAT TTC CTG ATG GAT GAG CAA GTG GTG GGG ACG CCC CTG CTG GTG AAA TCT GGC 1267

 V   E   Y   T   R   L   A   V   E   T   A   Q   G   L   D   G   H   S   H   L   432
GTG GAG TAT ACA CGG CTT GCA GTG GAG ACA GCC CAG GGC CTT GAT GGG CAC AGC CAT CTT 1327

 V   M   Y   L   G   T   T   T   G   S   L   H   K   A   V   V   S   G   D   S   452
GTC ATG TAC CTG GGA ACC ACC ACA GGG TCG CTC CAC AAG GCT GTG GTA AGT GGG GAC AGC 1387

 S   A   H   L   V   E   E   I   Q   L   F   P   D   P   E   P   V   R   N   L   472
AGT GCT CAT CTG GTG GAA GAG ATT CAG CTG TTC CCT GAC CCT GAA CCT GTT CGC AAC CTG 1447

 Q   L   A   P   T   Q   G   A   V   F   V   G   F   S   G   G   V   W   R   V   492
CAG CTG GCC CCC ACC CAG GGT GCA GTG TTT GTA GGC TTC TCA GGA GGT GTC TGG AGG GTG 1507

 P   R   A   N   C   S   V   Y   E   S   C   V   D   C   V   L   A   R   D   P   512
CCC CGA GCC AAC TGT AGT GTC TAT GAG AGC TGT GTG GAC TGT GTC CTT GCC CGG GAC CCC 1567

 H   C   A   W   D   P   E   S   R   T   C   C   L   L   S   A   P   N   L   N   532
CAC TGT GCC TGG GAC CCT GAG TCC CGA ACC TGT TGC CTC CTG TCT GCC CCC AAC CTG AAC 1627
```

Fig. 3C

```
 S   W   K   Q   D   M   E   R   G   N   P   E   W   A   C   A   S   G   P   M   552
TCC TGG AAG CAG GAC ATG GAG CGG GGG AAC CCA GAG TGG GCA TGT GCC AGT GGC CCC ATG 1687

 S   R   S   L   R   P   Q   S   R   P   Q   I   I   K   E   V   L   A   V   P   572
AGC AGG AGC CTT CGG CCT CAG AGC CGC CCG CAA ATC ATT AAA GAA GTC CTG GCT GTC CCC 1747

 N   S   I   L   E   L   P   C   P   H   L   S   A   L   A   S   Y   Y   W   S   592
AAC TCC ATC CTG GAG CTC CCC TGC CCC CAC CTG TCA GCC TTG GCC TCT TAT TAT TGG AGT 1807

 H   G   P   A   A   V   P   E   A   S   S   T   V   Y   N   G   S   L   L   L   612
CAT GGC CCA GCA GCA GTC CCA GAA GCC TCT TCC ACT GTC TAC AAT GGC TCC CTC TTG CTG 1867

 I   V   Q   D   G   V   G   G   L   Y   Q   C   W   A   T   E   N   G   F   S   632
ATA GTG CAG GAT GGA GTT GGG GGT CTC TAC CAG TGC TGG GCA ACT GAG AAT GGC TTT TCA 1927

 Y   P   V   I   S   Y   W   V   D   S   Q   D   Q   T   L   A   L   D   P   E   652
TAC CCT GTG ATC TCC TAC TGG GTG GAC AGC CAG GAC CAG ACC CTG GCC CTG GAT CCT GAA 1987

 L   A   G   I   P   R   E   H   V   K   V   P   L   T   R   V   S   G   G   A   672
CTG GCA GGC ATC CCC CGG GAG CAT GTG AAG GTC CCG TTG ACC AGG GTC AGT GGT GGG GCC 2047

 A   L   A   A   Q   Q   S   Y   W   P   H   F   V   T   V   T   V   L   F   A   692
GCC CTG GCT GCC CAG CAG TCC TAC TGG CCC CAC TTT GTC ACT GTC ACT GTC CTC TTT GCC 2107

 L   V   L   S   G   A   L   I   I   L   V   A   S   P   L   R   A   L   R   A   712
TTA GTG CTT TCA GGA GCC CTC ATC ATC CTC GTG GCC TCC CCA TTG AGA GCA CTC CGG GCT 2167
```

Fig. 3D

```
 R   G   K   V   Q   G   C   E   T   L   R   P   G   E   K   A   P   L   S   R   732
CGG GGC AAG GTT CAG GGC TGT GAG ACC CTG CGC CCT GGG GAG AAG GCC CCG TTA AGC AGA 2227

 E   Q   H   L   Q   S   P   K   E   C   R   T   S   A   S   D   V   D   A   D   752
GAG CAA CAC CTC CAG TCT CCC AAG GAA TGC AGG ACC TCT GCC AGT GAT GTG GAC GCT GAC 2287

 N   N   C   L   G   T   E   V   A   *                                          762
AAC AAC TGC CTA GGC ACT GAG GTA GCT TAA                                         2317

ACTCTAGGCACAGGCCGGGGCTGCGGTGCAGGCACCTGGCCATGCTGGCTGGGCGGCCCAAGCACAGCCCTGACTAGGA 2396
TGACAGCAGCACAAAAGACCACCTTTCTCCCCTGAGAGGAGCTTCTGCTACTCTGCATCACTGATGACACTCAGCAGGG 2475
TGATGCACAGCAGTCTGCCTCCCCTATGGGACTCCCTTCTACCAAGCACATGAGCTCTCTAACAGGGTGGGGGCTACCC 2554
CCAGACCTGCTCCTACACTGATATTGAAGAACCTGGAGAGGATCCTTCAGTTCTGGCCATTCCAGGGACCCTCCAGAAA 2633
CACAGTGTTTCAAGAGATCCTAAAAAAACCTGCCTGTCCCAGGACCCTATGGTAATGAACACCAAACATCTAAACAATC 2712
ATATGCTAACATGCCACTCCTGGAAACTCCACTCTGAAGCTGCCGCTTTGGACACCAACACTCCCTTCTCCCAGGGTCA 2791
TGCAGGGATCTGCTCCCTCCTGCTTCCCTTACCAGTCGTGCACCGCTGACTCCCAGGAAGTCTTTCCTGAAGTCTGACC 2870
ACCTTTCTTCTTGCTTCAGTTGGGGCAGACTCTGATCCCTTCTGCCCTGGCAGAATGGCAGGGGTAATCTGAGCCTTCT 2949
TCACTCCTTTACCCTAGCTGACCCCTTCACCTCTCCCCCTCCCTTTTCCTTTGTTTTGGGATTCAGAAAACTGCTTGTC 3028
AGAGACTGTTTATTTTTATTAAAAATATAAGGCTTAAAAAAAAAAAAAAAAAAAAAAAAAAAAAAAGGGCGGCCGC    3104
```

Fig. 3E

```
             10        20        30        40        50        60        70
Hum. MALPALGLDPWSLLGLFLFQLLQLLLPTTTAGGGGQGPMPRVRYYAGDERRALSFFHQKGLQDFDTLLLS
     ::::.:: :.:::: .:.:::. :     ..: ::::::::.: ::: .:::::::.::::.::::::::
Mur. MALPSLGQDSWSLLRVFFFQLFLLPSLPPASGTGGQGPMPRVKYHAGDGHRALSFFQQKGLRDFDTLLLS
             10        20        30        40        50        60        70

             80        90       100       110       120       130       140
Hum. GDGNTLYVGAREAILALDIQDPGVPRLKNMIPWPASDRKKSECAFKKKSNETQCFNFIRVLVSYNVTHLY
     .:::::::::::..:::.::.::.::::::::::::.:::.::::::::::::::::::::::::.::::
Mur. DDGNTLYVGARETVLALNIQNPGIPRLKNMIPWPASERKKTECAFKKKSNETQCFNFIRVLVSYNATHLY
             80        90       100       110       120       130       140

            150       160       170       180       190       200       210
Hum. TCGTFAFSPACTFIELQDSYLLPISEDKVMEGKGQSPFDPAHKHTAVLVDGMLYSGTMNNFLGSEPILMR
     .:::::::::::::::::: ::::  ::::.::::::.       :::::::::::::::::::::::::
Mur. ACGTFAFSPACTFIELQDSLLLPILIDKVMDGKGQSPLTLFTSTQAVLVDGMLYSGTMNNFLGSEPILMR
            150       160       170       180       190       200       210

            220       230       240       250       260       270       280
Hum. TLGSQPVLKTDNFLRWLHHDASFVAAIPSTQVVYFFFEETASEFDFFERLHTSRVARVCKNDVGGEKLLQ
     ::::.:::::: :::::: ::::::::::::::::::::::::::::: : .::::.:::::::::::::
Mur. TLGSHPVLKTDIFLRWLHADASFVAAIPSTQVVYFFFEETASEFDFFEELYISRVAQVCKNDVGGEKLLQ
            220       230       240       250       260       270       280
```

Fig. 3F

```
            290       300       310       320       330       340       350
Hum. KKWTTFLKAQLLCTQPGQLPFNVIRHAVLLPADSPTAPHIYAVFTSQWQVGGTRSSAVCAFSLLDIERVF
     :::::::::::::.::::::::.::::::::::::....:::::::::::::::::::::::: ::::::
Mur. KKWTTFLKAQLLCAQPGQLPFNIIRHAVLLPADSPSVSRIYAVFTSQWQVGGTRSSAVCAFSLTDIERVF
            290       300       310       320       330       340       350

            360       370       380       390       400       410       420
Hum. KGKYKELNKETSRWTTYRGPETNPRPGSCSVGPSSDKALTFMKDHFLMDEQVVGTPLLVKSGVEYTRLAV
     :::::::::::::::::::.:..:::::::.:::::::::::::::::::.:::::::::::::::::::
Mur. KGKYKELNKETSRWTTYRGSEVSPRPGSCSMGPSSDKALTFMKDHFLMDEHVVGTPLLVKSGVEYTRLAV
            360       370       380       390       400       410       420

            430       440       450       460       470       480       490
Hum. ETAQGLDGHSHLVMYLGTTTGSLHKAVVSGDSSAHLVEEIQLFPDPEPVRNLQLAPTQGAVFVGFSGGVW
     :.:.:::: ::.::::::.::.::::::. :::: ::::::: ::.::::::::::.:::::.:::::.:
Mur. ESARGLDGSSHVVMYLGTSTGPLHKAVVPQDSSAYLVEEIQLSPDSEPVRNLQLAPAQGAVFAGFSGGIW
            430       440       450       460       470       480       490

            500       510       520       530       540       550       560
Hum. RVPRANCSVYESCVDCVLARDPHCAWDPESRTCCLLSAPNLNSWKQDMERGNPEWACASGPMSRSLRPQS
     ::::::::::::::::::::::::::::::: : :::... ..::::::::::::.:. :::.:: : ::
Mur. RVPRANCSVYESCVDCVLARDPHCAWDPESRLCSLLSGST-KPWKQDMERGNPEWVCTRGPMARSPRRQS
            500       510       520       530        540       550
```

Fig. 3G

```
              570       580       590       600       610       620       630
Hum.  RPQIIKEVLAVPNSILELPCPHLSALASYYWSHGPAAVPEASSTVYNGSLLLIVQDGVGGLYQCWATENG
       ::.:::::.:::::::: :::::::::: :::: : ..:::.::::::::::. :::::::::: :::::
Mur.  PPQLIKEVLTVPNSILELRCPHLSALASYHWSHGRAKISEASATVYNGSLLLLPQDGVGGLYQCVATENG
    560       570       580       590       600       610       620

              640       650       660       670       680       690       700
Hum.  FSYPVISYWVDSQDQTLALDPELAGIPREHVKVPLTRVSGGAALAAQQSYWPHFVTVTVLFALVLSGALI
      .::::.::::::::: :::::::::.:::.:.::::::.:::..:::.::::::.:::::.:.:: :.:.
Mur.  YSYPVVSYWVDSQDQPLALDPELAGVPRERVQVPLTRVGGGASMAAQRSYWPHFLIVTVLLAIVLLGVLT
    630       640       650       660       670       680       690

              710       720       730       740       750       760
Hum.  ILVASPLRALRARGKVQGCETLRPGEKAPLSREQHLQSPKECRTSASDVDADNNCLGTEVA
      .:.:::: ::::::::::  : : :::::::.::::..:. ::::::::::: ::.:::
Mur.  LLLASPLGALRARGKVQGCGMLPPREKAPLSRDQHLQPSKDHRTSASDVDADNNHLGAEVA
    700       710       720       730       740       750       760
```

Fig. 3H

```
                                  10                          20        30
Hum. GTCG-AC-CC----------------ACG----------CGTCCGGT------CTGTGGCTGAGCATGGC
      ::: :: ::                ::           :.:: :::      :: .:::::: ::::::
Mur. CTCGGACGCCTGGGTTAGGGGTCTGTACTGCTGGGGAACCATCTGGTGACCATCTCAGGCTGACCATGGC
              10        20        30        40        50        60        70

       40        50        60        70        80        90        100
Hum. CCTCCCAGCCCTGGCCTGGACCCCTGGAGCCTCCTGGCCTTTTCCTCTTCCAACTGCTTC-AGCTGCT
     ::: ::: :::::::::.:::: : ::::: :::::: :  ::::  :::::::::: :::: .:::::
Mur. CCTACCATCCCTGGGCCAGGACTCATGGAGTCTCCTGCGTGTTTTTTCTTCCAACT-CTTCCTGCTGCC
              80        90        100       110       120       130

       110       120       130       140       150       160       170
Hum. GCTGCCGACGACGACCGCGGGGGAGGCGGGCAGGGGCCCATGCCCAGGGTCAGATACTATGCAGGGGAT
     .   .: : :. : .:  : :::. .:: :: :::::::::::::::::.::::.:::: ::::.::.::
Mur. ATCACTGCCACCTGCTTCTGGGACTGGTGGTCAGGGGCCCATGCCCAGAGTCAAATACCATGCTGGAGAC
   140       150       160       170       180       190       200

       180       190       200       210       220       230       240
Hum. GAACGTAGGGCACTTAGCTTCTTCCACCAGAAGGGCCTCCAGGATTTTGACACTCTGCTCCTGAGTGGTG
     :..:. ::::: :: ::::::::::: ::.::.:::::::..:: :::::::: ::::::::::::. :
Mur. GGGCACAGGGCCCTCAGCTTCTTCCAACAAAAAGGCCTCCGAGACTTTGACACGCTGCTCCTGAGTGACG
   210       220       230       240       250       260       270
```

Fig. 3I

```
          250       260       270       280       290       300       310
Hum. ATGGAAATACTCTCTACGTGGGGGCTCGAGAAGCCATTCTGGCCTTGGATATCCAGGATCCAGGGGTCCC
     :::: :: :::::::: ::::::::::::::..::.: ::::::::.::::::::.: :::::..::::
Mur. ATGGCAACACTCTCTATGTGGGGGCTCGAGAGACCGTCCTGGCCTTGAATATCCAGAACCCAGGAATCCC
      280       290       300       310       320       330       340

          320       330       340       350       360       370       380
Hum. CAGGCTAAAGAACATGATACCGTGGCCAGCCAGTGACAGAAAAAAGAGTGAATGTGCCTTTAAGAAGAAG
      :::::::::::::::::::: :::::::::::::: ::::::::::  ::::::::::::::::::::
Mur. AAGGCTAAAGAACATGATACCCTGGCCAGCCAGTGAGAGAAAAAAGACCGAATGTGCCTTTAAGAAGAAG
      350       360       370       380       390       400       410

          390       400       410       420       430       440       450
Hum. AGCAATGAGACACAGTGTTTCAACTTCATCCGTGTCCTGGTTTCTTACAATGTCACCCATCTCTACACCT
     ::::::::::::::::::::::::::::: ::.:::::::: :::::::::: :: ::.::::: .:::
Mur. AGCAATGAGACACAGTGTTTCAACTTCATTCGAGTCCTGGTCTCTTACAATGCTACTCACCTCTATGCCT
      420       430       440       450       460       470       480

          460       470       480       490       500       510       520
Hum. GCGGCACCTTCGCCTTCAGCCCTGCTTGTACCTTCATTGAACTTCAAGATTCCTACCTGTTGCCCATCTC
     : :: ::::: :::::::::::::: ::::::::::::::::: ::::::::: .::::::::::::::
Mur. GTGGGACCTTTGCCTTCAGCCCTGCCTGTACCTTCATTGAACTCCAAGATTCCCTCCTGTTGCCCATCTT
      490       500       510       520       530       540       550
```

Fig. 3J

```
             530       540       550       560       570       580        590
Hum.  GGAGGACAAGGTCATGGAGGGAAAAGGCCAAAGCCCCTTTGACCCCGCTCACAAGCATACG-GCTGTCTT
      :...:::::::::::::: ::.::.::::::::::: :::::::: : ::::::::: ::. ::::::::
Mur.  GATAGACAAGGTCATGGACGGGAAGGGCCAAAGCCC-TTTGACCCTGTTCACAAGCACACAAGCTGTCTT
    560       570       580       590        600       610       620

              600       610       620       630       640       650       660
Hum.  GGTGGATGGGATGCTCTATTCTGGTACTATGAACAACTTCCTGGGCAGTGAGCCCATCCTGATGCGCACA
      ::: ::::::::::: ::::: :: :: :::::::::::::::::::: ::::::::::::::::: :::
Mur.  GGTCGATGGGATGCTTTATTCCGGCACCATGAACAACTTCCTGGGCAGCGAGCCCATCCTGATGCGGACA
     630       640       650       660       670       680       690

              670       680       690       700       710       720       730
Hum.  CTGGGATCCCAGCCTGTCCTCAAGACCGACAACTTCCTCCGCTGGCTGCATCATGACGCCTCCTTTGTGG
      ::::::::::: ::::: :::::::: ::::.:::: : :::::::::::    :: :::::::: ::::
Mur.  CTGGGATCCCATCCTGTTCTCAAGACTGACATCTTCTTACGCTGGCTGCACGCGGATGCCTCCTTCGTGG
     700       710       720       730       740       750       760

              740       750       760       770       780       790       800
Hum.  CAGCCATCCCTTCGACCCAGGTCGTCTACTTCTTCTTCGAGGAGACAGCCAGCGAGTTTGACTTCTTTGA
      ::::::: ::.:: :::::::::::::: :::::::: ::::::::::::::::::::::::::::::::
Mur.  CAGCCATTCCATCCACCCAGGTCGTCTATTTCTTCTTTGAGGAGACAGCCAGCGAGTTTGACTTCTTTGA
     770       780       790       800       810       820       830
```

Fig. 3K

```
              810       820       830       840       850       860       870
Hum.  GAGGCTCCACACATCGCGGGTGGCTAGAGTCTGCAAGAATGACGTGGGCGGCGAAAAGCTGCTGCAGAAG
      ...:::  : : :::  :::::::: .:::::::::::: ::::::::::: ::::::::::::::::::
Mur.  AGAGCTGTATATATCCAGGGTGGCTCAAGTCTGCAAGAACGACGTGGGCGGTGAAAAGCTGCTGCAGAAG
          840       850       860       870       880       890       900

              880       890       900       910       920       930       940
Hum.  AAGTGGACCACCTTCCTGAAGGCCCAGCTGCTCTGCACCCAGCCGGGGCAGCTGCCCTTCAACGTCATCC
      ::::::::::::::::: ::.:::::: ::::::::.: :::::.::::::::::: ::::::.::::::
Mur.  AAGTGGACCACCTTCCTCAAAGCCCAGTTGCTCTGCGCTCAGCCAGGGCAGCTGCCATTCAACATCATCC
          910       920       930       940       950       960       970

              950       960       970       980       990      1000      1010
Hum.  GCCACGCGGTCCTGCTCCCCGCCGATTCTCCCACAGCTCCCCACATCTACGCAGTCTTCACCTCCCAGTG
      :::::::::::::::: :::::::::::::::.:.: : :::.::::::::::::::: :::::::::::
Mur.  GCCACGCGGTCCTGCTGCCCGCCGATTCTCCCTCTGTTTCCCGCATCTACGCAGTCTTTACCTCCCAGTG
          980       990      1000      1010      1020      1030      1040

             1020      1030      1040      1050      1060      1070      1080
Hum.  GCAGGTTGGCGGGACCAGGAGCTCTGCGGTTTGTGCCTTCTCTCTTGGACATTGAACGTGTCTTTAAG
      ::::::::::::::::::::::::.::.:: :::::::::::::. :::::::::.::.::::::::.
Mur.  GCAGGTTGGCGGGACCAGGAGCTCAGCAGTCTGTGCCTTCTCTCACGGACATTGAGCGAGTCTTTAAA
         1050      1060      1070      1080      1090      1100      1110
```

Fig. 3L

```
           1090      1100      1110      1120      1130      1140      1150
Hum.  GGGAAATACAAAGAGTTGAACAAAGAAACTTCACGCTGGACTACTTATAGGGGCCCTGAGACCAACCCCC
      ::::.:::::.::: ::::::::.::.:: :: :::::::: :::::  ::::: :.:::. ::.:::
Mur.  GGGAAGTACAAGGAGCTGAACAAGGAGACCTCCCGCTGGACCACTTACCGGGGCTCAGAGGTCAGCCCGA
    1120      1130      1140      1150      1160      1170      1180

           1160      1170      1180      1190      1200      1210      1220
Hum.  GGCCAGGCAGTTGCTCAGTGGGCCCCTCCTCTGATAAGGCCCTGACCTTCATGAAGGACCATTTCCTGAT
      :::::::::::::::: .:::::::::::::::: ::.::: :::::::::::::::::::::: :::::
Mur.  GGCCAGGCAGTTGCTCCATGGGCCCCTCCTCTGACAAAGCCTTGACCTTCATGAAGGACCATTTTCTGAT
    1190      1200      1210      1220      1230      1240      1250

           1230      1240      1250      1260      1270      1280      1290
Hum.  GGATGAGCAAGTGGTGGGGACGCCCCTGCTGGTGAAATCTGGCGTGGAGTATACACGGCTTGCAGTGGAG
      ::::::::: :::::.::.::.:::::::::::::::.::::: :::::::: ::::::::::.::::::
Mur.  GGATGAGCACGTGGTAGGAACACCCCTGCTGGTGAAGTCTGGTGTGGAGTACACACGGCTTGCTGTGGAG
    1260      1270      1280      1290      1300      1310      1320

           1300      1310      1320      1330      1340      1350      1360
Hum.  ACAGCCCAGGGCCTTGATGGGCACAGCCATCTTGTCATGTACCTGGGAACCACCACAGGGTCGCTCCACA
      .:::: :.::::::::::::: .::::::: : :::::::: :::::.:::.::::.::  : :: ::::
Mur.  TCAGCTCGGGGCCTTGATGGGAGCAGCCATGTGGTCATGTATCTGGGTACCTCCACGGGTCCCCTGCACA
    1330      1340      1350      1360      1370      1380      1390
```

Fig. 3M

```
          1370      1380      1390      1400      1410      1420      1430
Hum. AGGCTGTGGTAAGTGGGGACAGCAGTGCTCATCTGGTGGAAGAGATTCAGCTGTTCCCTGACCCTGAACC
     ::::::::::.  : .::::::::::::: :::: ::::.:::::::::::::. ::::::: ::::.::
Mur. AGGCTGTGGTGCCTCAGGACAGCAGTGCTTATCTCGTGGAGGAGATTCAGCTGAGCCCTGACTCTGAGCC
      1400      1410      1420      1430      1440      1450      1460

          1440      1450      1460      1470      1480      1490      1500
Hum. TGTTCGCAACCTGCAGCTGGCCCCCACCCAGGGTGCAGTGTTTGTAGGCTTCTCAGGAGGTGTCTGGAGG
     :::::: ::::::::::::::::::.:::::::::::::::::: :::::::::.::::: .:::::::.
Mur. TGTTCGAAACCTGCAGCTGGCCCCCGCCCAGGGTGCAGTGTTTGCAGGCTTCTCTGGAGGCATCTGGAGA
      1470      1480      1490      1500      1510      1520      1530

          1510      1520      1530      1540      1550      1560      1570
Hum. GTGCCCCGAGCCAACTGTAGTGTCTATGAGAGCTGTGTGGACTGTGTCCTTGCCCGGGACCCCCACTGTG
     :: ::: :.::::: :: :::::::: :::::::::::::::::::: :::::: ::::::: :::::::
Mur. GTTCCCAGGGCCAATTGCAGTGTCTACGAGAGCTGTGTGGACTGTGTGCTTGCCAGGGACCCTCACTGTG
      1540      1550      1560      1570      1580      1590      1600

          1580      1590      1600      1610      1620      1630      1640
Hum. CCTGGGACCCTGAGTCCCGAACCTGTTGCCTCCTGTCTGCCCCCAACCTGAACTCCTGGAAGCAGGACAT
     ::::::::::::::.::  ::  ::: .:::: ::::::: : : .::::... ::  ::::::::::::::
Mur. CCTGGGACCCTGAATCAAGACTCTGCAGCCTTCTGTCTGGCTC-TACCAAGCCT--TGGAAGCAGGACAT
      1610      1620      1630      1640      1650      1660       1670
```

Fig. 3N

```
          1650      1660      1670      1680      1690      1700      1710
Hum. GGAGCGGGGAACCCAGAGTGGGCATGTGCCAGTGGCCCCATGAGCAGGAGCCTTCGGCCTCAGAGCCGC
     :::.:: :: :::::.::::::: ::: .:: :::::::::::. ::::::::  :::: :::::::: :
Mur. GGAACGCGGCAACCCGGAGTGGGTATGCACCCGTGGCCCCATGGCCAGGAGCCCCCGGCGTCAGAGCCCC
        1680      1690      1700      1710      1720      1730      1740

          1720      1730      1740      1750      1760      1770      1780
Hum. CCGCAAATCATTAAAGAAGTCCTGGCTGTCCCCAACTCCATCCTGGAGCTCCCCTGCCCCCACCTGTCAG
     :: ::: : :::::::::::::::.:.:::::::::::::::::::::::: : ::::::::::::::::
Mur. CCTCAACTAATTAAAGAAGTCCTGACAGTCCCCAACTCCATCCTGGAGCTGCGCTGCCCCCACCTGTCAG
        1750      1760      1770      1780      1790      1800      1810

          1790      1800      1810      1820      1830      1840      1850
Hum. CCTTGGCCTCTTATTATTGGAGTCATGGCCCAGCAGCAGTCCCAGAAGCCTCTTCCACTGTCTACAATGG
     :  :::::::::  : ::::::::::::: ::: . :.:: :::::::::: : :: :::::::::::
Mur. CACTGGCCTCTTACCACTGGAGTCATGGCCGAGCCAAAATCTCAGAAGCCTCTGCTACCGTCTACAATGG
        1820      1830      1840      1850      1860      1870      1880

          1860      1870      1880      1890      1900      1910      1920
Hum. CTCCCTCTTGCTGATAGTGCAGGATGGAGTTGGGGGTCTCTACCAGTGCTGGGCAACTGAGAATGGCTTT
     ::::::::::::: :.  :::::::::.:: ::::: :::::::::::   :::.:::::::: ::::.
Mur. CTCCCTCTTGCTGCTGCCGCAGGATGGTGTCGGGGGCCTCTACCAGTGTGTGGCGACTGAGAACGGCTAC
        1890      1900      1910      1920      1930      1940      1950
```

Fig. 3O

```
        1930      1940      1950      1960      1970      1980      1990
Hum. TCATACCCTGTGATCTCCTACTGGGTGGACAGCCAGGACCAGACCCTGGCCCTGGATCCTGAACTGGCAG
     :::::::::::::.::::::: :::::.:::::::::::::::: ::::::: ::::: :::::.::::::.:
Mur. TCATACCCTGTGGTCTCCTATTGGGTAGACAGCCAGGACCAGCCCCTGGCGCTGGACCCTGAGCTGGCGG
       1960      1970      1980      1990      2000      2010      2020

        2000      2010      2020      2030      2040      2050      2060
Hum. GCATCCCCCGGGAGCATGTGAAGGTCCCGTTGACCAGGGTCAGTGGTGGGGCCGCCCTGGCTGCCCAGCA
     ::.: ::::: ::::.:::: :::::::: ::::::::::::.:.:: ::.::  :: :::::::::::::.
Mur. GCGTTCCCCGTGAGCGTGTGCAGGTCCCGCTGACCAGGGTCGGAGGCGGAGCTTCCATGGCTGCCCAGCG
       2030      2040      2050      2060      2070      2080      2090

        2070      2080      2090      2100      2110      2120      2130
Hum. GTCCTACTGGCCCCACTTTGTCACTGTCACTGTCCTCTTTGCCTTAGTGCTTTCAGGAGCCCTCATCATC
     :::::::::::::: ::: :::  :: :: :::::: : :::.: :::::   .:::: ::::   ::
Mur. GTCCTACTGGCCCCATTTTCTCATCGTTACCGTCCTCCTGGCCATCGTGCTCCTGGGAGTGCTCACTCTC
       2100      2110      2120      2130      2140      2150      2160

        2140      2150      2160      2170      2180      2190      2200
Hum. CTCGTGGCCTCCCCATTGAGAGCACTCCGGGCTCGGGGCAAGGTTCAGGGCTGTGAGACCCTGCGCCCTG
     ::: : :: :::::: ::.:.::.:: ::::::::::: ::::::::::::::::.::  :::: ::: .
Mur. CTCCTCGCTTCCCCACTGGGGGCGCTGCGGGCTCGGGGTAAGGTTCAGGGCTGTGGGATGCTGCCCCCCA
       2170      2180      2190      2200      2210      2220      2230
```

Fig. 3P

```
          2210      2220      2230      2240      2250      2260      2270
Hum.  GGGAGAAGGCCCCGTTAAGCAGAGAGCAACACCTCCAGTCTCCCAAGGAATGCAGGACCTCTGCCAGTGA
      :::.::::: ::. :.:::::.:: ::.::::::::: :  :::::::  .::::::::::::::::::
Mur.  GGGAAAAGGCTCCACTGAGCAGGGACCAGCACCTCCAGCCCTCCAAGGACCACAGGACCTCTGCCAGTGA
        2240      2250      2260      2270      2280      2290      2300

          2280      2290      2300      2310      2320      2330       2340
Hum.  TGTGGACGCTGACAACAACTGCCTAGGCACTGAGGTAGCTTAAACTCTAGGCACAGG-CCGGGGCTG--C
       ::.:: :: ::::::::: . ::.:::.: ::.::.::::::::.  .:.:::::. ::: .::::  :
Mur.  CGTAGATGCCGACAACAACCATCTGGGCGCCGAAGTGGCTTAAACA-GGGACACAGATCCGCAGCTGAGC
        2310      2320      2330      2340      2350       2360      2370

             2350      2360      2370      2380      2390      2400      2410
Hum.  GGTGCAGGCACCTGGCCATGCTGGCTGGGCGGCCCAAGCACAGCCCTGACTAGGATGACAGCAGCACAAA
      .:.::::.::  :::::.:: :::::. ::    ::.::::::                .:: .:.:.
Mur.  AGAGCAAGCCACTGGCCTTGTTGGCTATGC----CAGGCACAG----------------TGCCACTCT--
         2380      2390      2400          2410                      2420

             2420      2430      2440      2450      2460      2470      2480
Hum.  AGACCACCTTTCTCCCCTGAGAGGAGCTTCTGCTACTCTGCATCACTGATGACACTCAGCAGGGTGATGC
       :::::                :. :::::  :: :: : ::::.. ::  .::.::: :..:::      :
Mur.  -GACCA-----------GGGTAGGAG--GCT-CT-C-CTGCTA-ACGTGTGTCAC-CTACAG-------C
                          2430      2440      2450      2460
```

Fig. 3Q

```
            2490      2500      2510      2520      2530      2540      2550
Hum.  ACAGCAGTCTG-CCTCCCCTATGGGACTCCCTTCTACCAAGCACATGAGCTCTCTAACAGGGTGGGGGCT
      ::  ::::  : ::::::::.:::::::: ::::::.: ::::::::                  :::::
Mur.  ACC-CAGTAGGTCCTCCCCTGTGGGACTCTCTTCTGC-AAGCACATT------------------GGGCT
        2470      2480      2490      2500       2510

             2560      2570       2580      2590      2600      2610
Hum.  ACCCCCAGACCTGCTCCTACACTGATA-TTGAAGAACCTGGAGAGGATCCTTCAGTTCTGGCCATTCCAG
      . : ::: ::::: .: :. .:::. : . ::::::.::.:.  ::::.: ::: ..:: ::.  .. :::.
Mur.  GTCTCCATACCTGTACTTGTGCTGTGACAGGAAGAGCCAGAC-AGGTTTCTTTGATTTTGATTGACCCAA
      2520      2530      2540      2550       2560      2570      2580

   2620       2630       2640      2650      2660      2670      2680
Hum.  GGACCCT-CCAGAAACACA-GTGTTTCAAGAGATCCTAAAAAAACCTGCCTGTCCCAGGACCCTATGGTA
      :..:::: ::.:.:::: : ::: : ::.:::: ::...:::..  :: :::::  .:::  ::.::::.
Mur.  GAGCCCTGCCTGTAACAAACGTGCTCCAGGAGA-CCATGAAAGGTGTGGCTGTCT-GGGATTCTGTGGTG
        2590      2600      2610       2620      2630       2640      2650

    2690      2700      2710      2720             2730      2740      2750
Hum.  ATGAACACCAAACATCTAAACAATCATATGCTAA-CATGC---CAC--TCCTGGAAACT-CCACTCTGAA
      : .::: : ::.:::: .:.::: :. . ::::. : :::   :.:  ::::::.: .::  :::::::..:
Mur.  ACAAAC-CTAAGCATCCGAGCAAGCTGGGGCTATTCCTGCAAACTCCATCCTGAACGCTGTCACTCTAGA
          2660      2670      2680      2690      2700      2710      2720
```

Fig. 3R

```
               2760      2770      2780        2790      2800      2810
Hum. ----GCTGCCGCTTTGGACACCAACACTCCCTTCT-CCCAGG-GTCATGCAGGGATCTGCTCCCTCCTGC
         ::::: :::::::.::::::.: :.:::: :: :::::.: :::.    .::..:  :: ::::  ::
Mur. AGCAGCTGCTGCTTTGAACACCAGCCCACCCTCCTTCCCAAGAGTCTCTATGGAGTTGGC-CCCTTGTGT
         2730      2740      2750      2760       2770      2780       2790

       2820      2830      2840      2850      2860      2870      2880
Hum. TTCCCTTACCAGTCGTGCACCGCTGACTCCCAGGAAGTCTTTCCTGAAGTCTGACCACCTTTCTTCTTGC
     :::: :::::::::: ::   .:::. :   .::::::::.:  ::::::::.::::::::: :::::::
Mur. TTCCTTTACCAGTCGGGCCATACTGTTT---GGGAAGTCATCTCTGAAGTCTAACCACCTTCCTTCTTGG
        2800      2810        2820      2830      2840      2850

       2890      2900      2910         2920      2930      2940      2950
Hum. TTCAGTTGGGGCAGACTCTGATCCCT---TCTGCCCTGGCAGAATGGCAGGGGTAATCTGAGCCTTCTTC
     ::::::: ::.:::: : : ::    :   ::::::::::...:. : .:: .:::::::::::: :::
Mur. TTCAGTTTGGACAGATTGTTATTATTGTCTCTGCCCTGGCTAGAATGGGGGCATAATCTGAGCCTTGTTC
   2860      2870      2880      2890      2900      2910      2920

          2960         2970      2980        2990      3000      3010
Hum. ACTCCTTTACCC---TAGCTGACCCCTTCACCTCTCCC--CCTCCCTTTTCCTTTGTTTTGGATTCAGA
        :::: .::    :.::::::: :: :::::: ::  :::::    : ::::::::::::::::::::
Mur. ---CCTTGTCCAGTGTGGCTGACCC-TTGACCTCTTCCTTCCTCC---TCCCTTTGTTTTGGATTCAGA
      2930      2940      2950       2960          2970      2980      2990
```

Fig. 3S

```
      3020      3030      3040      3050      3060      3070      3080
Hum. AAACTGCTTGTCAGAGACTGTTTATTTTTATTAAAAATATAAGGCTTAAAAAAAAAAAAAAAAAAAAA
     ::::::::::::: ::::..:::::::::::::::::::                        :.:.:.::
Mur. AAACTGCTTGTCACAGACAATTTATTTTTATTAAAAA------------------------AGATATAA
          3000      3010      3020                                3030

      3090      3100
Hum. AAAAAAAAGGGCGGCCGC
     . ...::::
Mur. GCTTTAAAG---------
    3040
```

Fig. 3T

```
GTCGACCCACGCGTCCGCGGACGCGTGGGGACGGCTCCCGGCTGCAGTCTGCCCGCCCGCCCCGCGCGGGGGCCGAGTC  79

                                                     M   R   R   Q   P   A     6
GCGAAGCGCGCCTGCGACCCGGCGTCCGGGCGCGCTGGAGAGGACGCGAGGAGCC ATG AGG CGC CAG CCT GCG   152

 K   V   A   A   L   L   L   G   L   L   L   E   C   T   E   A   K   K   H   C    26
AAG GTG GCG GCG CTG CTG CTC GGG CTG CTC TTG GAG TGC ACA GAA GCC AAA AAG CAT TGC   212

 W   Y   F   E   G   L   Y   P   T   Y   Y   I   C   R   S   Y   E   D   C   C    46
TGG TAT TTC GAA GGA CTC TAT CCA ACC TAT TAT ATA TGC CGC TCC TAC GAG GAC TGC TGT   272

 G   S   R   C   C   V   R   A   L   S   I   Q   R   L   W   Y   F   W   F   L    66
GGC TCC AGG TGC TGT GTG CGG GCC CTC TCC ATA CAG AGG CTG TGG TAC TTC TGG TTC CTT   332

 L   M   M   G   V   L   F   C   C   G   A   G   F   F   I   R   R   R   M   Y    86
CTG ATG ATG GGC GTG CTT TTC TGC TGC GGA GCC GGC TTC TTC ATC CGG AGG CGC ATG TAC   392

 P   P   P   L   I   E   E   P   A   F   N   V   S   Y   T   R   Q   P   P   N   106
CCC CCG CCG CTG ATC GAG GAG CCA GCC TTC AAT GTG TCC TAC ACC AGG CAG CCC CCA AAT   452

 P   G   P   G   A   Q   Q   P   G   P   P   Y   Y   T   D   P   G   G   P   G   126
CCC GGC CCA GGA GCC CAG CAG CCG GGG CCG CCC TAT TAC ACT GAC CCA GGA GGA CCG GGG   512

 M   N   P   V   G   N   S   M   A   M   A   F   Q   V   P   P   N   S   P   Q   146
ATG AAC CCT GTC GGG AAT TCC ATG GCA ATG GCT TTC CAG GTC CCA CCC AAC TCA CCC CAG   572
```

Fig. 4A

```
 G   S   V   A   C   P   P   P   P   A   Y   C   N   T   P   P   P   P   Y   E   166
GGG AGT GTG GCC TGC CCG CCC CCT CCA GCC TAC TGC AAC ACG CCT CCG CCC CCG TAC GAA  632

 Q   V   V   K   A   K   *                                                      173
CAG GTA GTG AAG GCC AAG TAG                                                      653

TGGGGTGCCCACGTGCAAGAGGAGAGACAGGAGAGGGCCTTTCCCTGGCCTTTCTGTCTTCGTTGATGTTCACTTCCAG  732
GAACGGTCTCGTGGGCTGCTAAGGGCAGTTCCTCTGATATCCTCACAGCAAGCACAGCTCTCTTTCAGGCTTTCCATGG  811
AGTACAATATATGAACTCACACTTTGTCTCCTCTGTTGCTTCTGTTTCTGACGCAGTCTGTGCTCTCACATGGTAGTGT  890
GGTGACAGTCCCCGAGGGCTGACGTCCTTACGGTGGCGTGACCAGATCTACAGGAGAGAGACTGAGAGGAAGAAGGCAG  969
TGCTGGAGGTGCAGGTGGCATGTAGAGGGGCCAGGCCGAGCATCCCAGGCAAGCATCCTTCTGCCCGGGTATTAATAGG 1048
AAGCCCCATGCCGGGCGGCTCAGCCGATGAAGCAGCAGCCGACTGAGCTGAGCCCAGCAGGTCATCTGCTCCAGCCTGT 1127
CCTCTCGTCAGCCTTCCTCTTCCAGAAGCTGTTGGAGAGACATTCAGGAGAGAGCAAGCCCCTTGTCATGTTTCTGTCT 1206
CTGTTCATATCCTAAAGATAGACTTCTCCTGCACCGCCAGGGAAGGGTAGCACGTGCAGCTCTCACCGCAGGATGGGGC 1285
CTAGAATCAGGCTTGCCTTGGAGGCCTGACAGTGATCTGACATCCACTAAGCAAATTTATTTAAATTCATGGGAAATCA 1364
CTTCCTGCCCCAAACTGAGACATTGCATTTTGTGAGCTCTTGGTCTGATTTGGAGAAAGGACTGTTACCCATTTTTTTG 1443
GTGTGTTTATGGAAGTGCATGTAGAGCGTCCTGCCCTTTGAAATCAGACTGGGTGTGTGTCTTCCCTGGACATCACTGC 1522
CTCTCCAGGGCATTCTCAGGCCCGGGGGTCTCCTTCCCTCAGGCAGCTCCAGTGGTGGGTTCTGAAGGGTGCTTTCAAA 1601
ACGGGGCACATCTGGCTGGGAAGTCACATGGACTCTTCCAGGGAGAGAGACCAGCTGAGGCGTCTCTCTCTGAGGTTGT 1680
GTTGGGTCTAAGCGGGTGTGTGCTGGGCTCCAAGGAGGAGGAGCTTGCTGGGAAAAGACAGGAGAAGTACTGACTCAAC 1759
TGCACTGACCATGTTGTCATAATTAGAATAAAGAAGAAGTGGTCGGAAATGCACATTCCTGGATAGGAATCACAGCTCA 1838
CCCCAGGATCTCACAGGTAGTCTCCTGAGTAGTTGACGGCTAGCGGGGAGCTAGTTCCGCCGCATAGTTATAGTGTTGA 1917
TGTGTGAACGCTGACCTGTCCTGTGTGCTAAGAGCTATGCAGCTTAGCTGAGGCGCCTAGATTACTAGATGTGCTGTAT 1996
CACGGGGAATGAGGTGGGGGTGCTTATTTTTTAATGAACTAATCAGAGCCTCTTGAGAAATTGTTACTCATTGAACTGG 2075
AGCATCAAGACATCTCATGGAAGTGGATACGGAGTGATTTGGTGTCCATGCTTTTCACTCTGAGGACATTTAATCGGAG 2154
```

Fig. 4B

```
AACCTCCTGGGGAATTTTGTGGGAGACACTTGGGAACAAAACAGACACCCTGGGAATGCAGTTGCAAGCACAGATGCTG 2233
CCACCAGTGTCTCTGACCACCCTGGTGTGACTGCTGACTGCCAGCGTGGTACCTCCCATGCTGCAGGCCTCCATCTAAA 2312
TGAGACAACAAAGCACAATGTTCACTGTTTACAACCAAGACAACTGCGTGGGTCCAAACACTCCTCTTCCTCCAGGTCA 2391
TTTGTTTTGCATTTTTAATGTCTTTATTTTTGTAATGAAAAAGCACACTAAGCTGCCCCTGGAATCGGGTGCAGCTGA 2470
ATAGGCACCCAAAAGTCCGTGACTAAATTTCGTTTGTCTTTTTGATAGCAAATTATGTTAAGAGACAGTGATGGCTAGG 2549
GCTCAACAATTTTGTATTCCCATGTTTGTGTGAGACAGAGTTTGTTTTCCCTTGAACTTGGTTAGAATTGTGCTACTGT 2628
GAACGCTGATCCTGCATATGGAAGTCCCACTTTGGTGACATTTCCTGGCCATTCTTGTTTCCATTGTGTGGATGGTGGG 2707
TTGTGCCCACTTCCTGGAGTGAGACAGCTCCTGGTGTGTAGAATTCCCGGAGCGTCCGTGGTTCAGAGTAAACTTGAAG 2786
CAGATCTGTGCATGCTTTTCCTCTGCAACAATTGGCTCGTTTCTCTTTTTGTTCTCTTTTGATAGGATCCTGTTTCCT 2865
ATGTGTGCAAAATAAAAATAAATTTGGGCAAAAAAAAAAAAAAAAAAAAAAAAAAAAAAAAAAAAAAAAAAAAAAAAAAA 2944
AAAAAAAAAAGGGCGGCCGC                                                            2964
```

Fig. 4C

```
GTCGACCCACGCGTCCGGCCGCGCGTCCTTCTGCCGGCTTCAGCTCGTATCCCCGGAGTCCACCCGCCCGTCCCGGGGT  79

                                                          M   G   R   R   L      5
GCGGACTGGCCCTGAGCTGGCCGTACAGCCCGGCTTCGGACGGTCCTCGCTGGAGCC ATG GGC CGC CGG CTC   151

 G   R   V   A   A   L   L   L   G   L   L   V   E   C   T   E   A   K   K   H   25
GGC AGG GTG GCG GCG CTG CTG CTC GGG CTG CTA GTG GAG TGC ACT GAG GCC AAA AAA CAT 211
```

Fig. 4D

```
 C   W   Y   F   E   G   L   Y   P   T   Y   Y   I   C   R   S   Y   E   D   C   45
TGC TGG TAT TTT GAA GGA CTC TAT CCC ACA TAC TAT ATA TGC CGT TCC TAT GAA GAC TGC 271

 C   G   S   R   C   C   V   R   A   L   S   I   Q   R   L   W   Y   F   W   F   65
TGT GGC TCC AGG TGC TGT GTG AGG GCC CTT TCC ATA CAG AGG CTG TGG TAT TTT TGG TTC 331

 L   L   M   M   G   V   L   F   C   C   G   A   G   F   F   I   R   R   R   M   85
CTG CTG ATG ATG GGT GTG CTG TTC TGC TGT GGT GCC GGT TTC TTC ATT CGC CGG CGC ATG 391

 Y   P   P   P   L   I   E   E   P   T   F   N   V   S   Y   T   R   Q   P   P  105
TAT CCG CCA CCA CTC ATT GAG GAG CCC ACA TTC AAT GTG TCC TAT ACC AGG CAG CCA CCA 451

 N   P   A   P   G   A   Q   Q   M   G   P   P   Y   Y   T   D   P   G   G   P  125
AAT CCT GCT CCA GGA GCA CAG CAA ATG GGA CCG CCA TAT TAC ACC GAC CCT GGA GGA CCC 511

 G   M   N   P   V   G   N   T   M   A   M   A   F   Q   V   Q   P   N   S   P  145
GGG ATG AAT CCT GTT GGC AAT ACC ATG GCT ATG GCT TTC CAG GTC CAG CCC AAT TCA CCT 571

 H   G   G   T   T   Y   P   P   P   P   S   Y   C   N   T   P   P   P   P   Y  165
CAC GGA GGC ACA ACT TAC CCA CCC CCT CCT TCC TAC TGC AAC ACG CCT CCA CCC CCC TAT 631

 E   Q   V   V   K   D   K   *                                                  173
GAA CAG GTG GTG AAG GAC AAG TAG                                                 655

CAAGATGCTACATCAAAGGCAAAGAGGATGGACAGGCCCTTTTGTTTACCTTCCCATCCTCACCGATACTTGCTGATAG 734
```

Fig. 4E

GGTGGTCCAAGGGAAAACTTGGATATTCTCAAAGCAAGCCCAGCTCTCTTTCAAGTCTTTTGTGGAGGACATTTGAATC 813
CACACTGTCTCCTCTGTTGCTTCTGTTTCTGATGTAGTCTGTGCTCTCTGAGAGAGTGTGGCAACAGTCCCTGAGGGTT 892
GATATTCCTAGGGTGTCCAGGGTAGATCCTCGGGAGAGAGGCTAAGGGGAAAGGAAGGCATAGCCTGTGTGTTAGGGGG 971
CAGATAAAGTGGTCAGGCTGAGATAAGACTCACATGATGCAGTAGTTGGCAGTGAACTTCGAAGAGACACTATCCACCA 1050
TCCCAGCCCATTCTCCTAATAGAAGCTGTGGGGCTGTGTTGTTGATGCTCTTTGGTCTCCACTCACATTTTGAAAATAG 1129
GCTTTCCTCTGCAGGAATAGGAAAGACCCAAGTACATATTTGCTTCCACTTAAAAATGAGGGTCAGAACCAGGCCTCAG 1208
TTGGACATCTATAGTTAAATAAAGGCCATTAGAGAGGGGAAATCTTTAAGTTAGGGGAAATTCTCTAAATGGAGACATT 1287
GCGTTTTATGAATCATCGTCTGGCTTTTCTTTTAGTGCATGTATTGAAGTGAGGGTGTCCTTTGAGATCAGATGGGGAG 1366
AGTGAACTCTGCGGGGGGTGGGGTGTCTCTACTCAGAGGGCTCCAACACCCTTTTCTTAGGTAGTTCTGGTGATGGGTT 1445
TTATGGGCACTATAGAGCTGAGGGGCACATTAGGCCGGGTAGTTACATTGACCCTTGGAGAGGAAGAGGACAGCCAAAG 1524
AAACTCAGCAAAGCAAGACCAGCATTGCTGAGTTAGAGCTAGGGTTGTATGTGATCCCAACAGAGATGTGCTGGCCTCA 1603
GAAGAGGGGACGTTTGTGGATAGAGCCGTGAAAACCTACTTAGTTGCACAGATGACATAATCAAAAGTAGAGAAAGAAG 1682
TGTAGTTAGAGATGCCATTTCCCAGGTGAGAATCAGAGCTCATCCATAGATTTACAAGTAGTGGCTGGAGTTAACAGTA 1761
TGGAGTTCTTTTCCCTTGCGTAGTTAGTCACGTTGATGTGTATTTAAACCCAGGTTGAGACCTTGTGTACTAAGAGCAA 1840
GGAAGTATAGCTAAGATGTCTAGATTATTTATATGTAGTATGGTGGGGAGTGGGGCTGCAAGGAAGGGGGCTGACATTG 1919
TAAATGAGAAAATCAGAGCCATTTGATAAACTGTTACTTGTTGGATCAGGCATCCAAAAGTGTCTCTTGAGTGGACATT 1998
GAGTATTCTTTACCACCTACAAGACCAGGAGGCATGGTGTCATTCTCCATTGGGGTATTTATATGAGGTAGAGGTTCAG 2077
GAATCGACAGTAGCTGTGTGGGCTTAGTTTAAGGACTGAAAGCATAGGGACTGGTAGACAGTTTCATAGGAAACTGCGG 2156
GGAAGGAATGGATACCTTTAAAGACAGTTTGTGGATGCAGATGCTGCCACCCATCATTGAGCACCCTTGTGTCTCTGGC 2235
TTCCTGTCACTGGATCCAGTACCCCTCCATGCTTGGGTCCTTGTTTACATAAGACAACAAAGCACAATGTCTGCTGTT 2314
TACAATCAAGACGACTACATGGTCCAAACATTTCTTCTCTCTTCTATCACTTGTGGCTTTAACTTCCATTTCCTCCGTT 2393
CCTTTTTAAAATCAAGAAGCACAGTCAGAGCTGCCCCTGGGATTGCATCAGGGAACGGCTGATCAAGGCATTCAGTGTC 2472
CATGACTAAATCTTATCTTTTTGATAGCAAATCCTTTTAAGAAACTGAACAATTGCTAAGGCTCAGCAATTTTATACTC 2551
CAATGTCTGTGTAAGGTAAATTTTGTTTGCCATTGAGCCCACATTGGAATTCCTTCTGACGTCAACACTGACAATGCCT 2630
ATGGAAATTGCACTTCTGGGTATATGTCCCAGCATCCTTGTTTTCTTATGTTTGGTGAGTAAGGCTCACCCCTTCCAGC 2709

Fig. 4F

```
AGCTCTACTTCTGTGTGCTGAGGTCCTGTAGAGCCGGGGCTTGGGCACAGACATGAGGCAGACTTGTGCATGCTCTTTC 2788
TTGGCAACACTTGGCTCATATTTCTTGTTCTCTTTTGATAGAGTCCTGTTTCCTATGTATTTAAAAAATAATAAAAGTG 2867
AATTTAGTCAAAAAAAAAAAAAAAAAAAAAAAAAAAAAGGGCGGCCGC                                2915
```

Fig. 4G

```
                10        20        30        40        50        60        70
Hum. MRRQPAKVAALLLGLLLECTEAKKHCWYFEGLYPTYYICRSYEDCCGSRCCVRALSIQRLWYFWFLLMMG
     : :. ..::::::::.:::::::::::::::::::::::::::::::::::::::::::::::::::::
Mur. MGRRLGRVAALLLGLLVECTEAKKHCWYFEGLYPTYYICRSYEDCCGSRCCVRALSIQRLWYFWFLLMMG
                10        20        30        40        50        60        70

                80        90       100       110       120       130       140
Hum. VLFCCGAGFFIRRRMYPPPLIEEPAFNVSYTRQPPNPGPGAQQPGPPYYTDPGGPGMNPVGNSMAMAFQV
     ::::::::::::::::::::::::.::::::::::::.::::: ::::::::::::::::::.:::::::
Mur. VLFCCGAGFFIRRRMYPPPLIEEPTFNVSYTRQPPNPAPGAQQMGPPYYTDPGGPGMNPVGNTMAMAFQV
                80        90       100       110       120       130       140

               150       160       170
Hum. PPNSPQGSVACPPPPAYCNTPPPPYEQVVKAK
     .::::.:... ::::.::::::::::::::.:
Mur. QPNSPHGGTTYPPPPSYCNTPPPPYEQVVKDK
               150       160       170
```

Fig. 4H

```
GTCGACCCACGCGTCCGCAGCTTTGGACACTTCCTCTGCTTGAGGACACCTTGACTAACCTCCAAGGGCAACTAAAGGA    79

                                                     M   C   T   K   T   I         6
TCAAGAAAGGCCCAGCACAGCAGAAGATCAGCTGGATCTAGCTCCTGCAGGAG ATG TGT ACA AAG ACA ATC    150

 P   V   L   W   G   C   F   L   L   W   N   L   Y   V   S   S   S   Q   T   I     26
CCA GTC CTC TGG GGA TGT TTC CTC CTG TGG AAT CTC TAT GTC TCA TCC TCT CAG ACC ATT   210

 Y   P   G   I   K   A   R   I   T   Q   R   A   L   D   Y   G   V   Q   A   G     46
TAC CCT GGA ATC AAG GCA AGG ATT ACT CAG AGG GCA CTT GAC TAT GGT GTT CAA GCT GGA   270

 M   K   M   I   E   Q   M   L   K   E   K   K   L   P   D   L   S   G   S   E     66
ATG AAG ATG ATT GAG CAA ATG CTA AAA GAA AAG AAA CTC CCA GAT TTA AGC GGT TCT GAG   330

 S   L   E   F   L   K   V   D   Y   V   N   Y   N   F   S   N   I   K   I   S     86
TCT CTT GAA TTT CTA AAA GTT GAT TAT GTA AAC TAC AAT TTT TCA AAT ATA AAA ATC AGT   390

 A   F   S   F   P   N   T   S   L   A   F   V   P   G   V   G   I   K   A   L    106
GCC TTT TCA TTT CCA AAT ACC TCA TTG GCT TTT GTG CCT GGA GTG GGA ATC AAA GCG CTA   450

 T   N   H   G   T   A   N   I   S   T   D   W   G   F   E   S   P   L   F   V    126
ACC AAC CAT GGC ACT GCC AAC ATC AGC ACA GAC TGG GGG TTC GAG TCT CCA CTT TTT GTT   510

 L   Y   N   S   F   A   E   P   M   E   K   P   I   L   K   N   L   N   E   M    146
CTG TAT AAC TCC TTT GCT GAG CCC ATG GAG AAA CCC ATT TTA AAG AAC TTA AAT GAA ATG   570
```

Fig. 5A

```
L   C   P   I   I   A   S   E   V   K   A   L   N   A   N   L   S   T   L   E    166
CTC TGT CCC ATT ATT GCA AGT GAA GTC AAA GCG CTA AAT GCC AAC CTC AGC ACA CTG GAG  630

V   L   T   K   I   D   N   Y   T   L   L   D   Y   S   L   I   S   S   P   E    186
GTT TTA ACC AAG ATT GAC AAC TAC ACT CTG CTG GAT TAC TCC CTA ATC AGT TCT CCA GAA  690

I   T   E   N   Y   L   D   L   N   L   K   G   V   F   Y   P   L   E   N   L    206
ATT ACT GAG AAC TAC CTT GAC CTG AAC TTG AAG GGT GTA TTC TAC CCA CTG GAA AAC CTC  750

T   D   P   P   F   S   P   V   P   F   V   L   P   E   R   S   N   S   M   L    226
ACC GAC CCC CCC TTC TCA CCA GTT CCT TTT GTG CTC CCA GAA CGC AGC AAC TCC ATG CTC  810

Y   I   G   I   A   E   Y   F   F   K   S   A   S   F   A   H   F   T   A   G    246
TAC ATT GGA ATC GCC GAG TAT TTC TTT AAA TCT GCG TCC TTT GCT CAT TTC ACA GCT GGG  870

V   F   N   L   T   L   S   T   E   E   I   S   N   H   F   V   Q   N   S   Q    266
GTT TTC AAT CTC ACT CTC TCC ACC GAA GAG ATT TCC AAC CAT TTT GTT CAA AAC TCT CAA  930

G   L   G   N   V   L   S   R   I   A   E   I   Y   I   L   S   Q   P   F   M    286
GGC CTT GGC AAC GTG CTC TCC CGG ATT GCA GAG ATC TAC ATC TTG TCC CAG CCC TTC ATG  990

V   R   I   M   A   T   E   P   P   I   I   N   L   Q   P   G   N   F   T   L    306
GTG AGG ATC ATG GCC ACA GAG CCT CCC ATA ATC AAT CTA CAA CCA GGC AAT TTC ACC CTG 1050

D   I   P   A   S   I   M   M   L   T   Q   P   K   N   S   T   V   E   T   I    326
GAC ATC CCT GCC TCC ATC ATG ATG CTC ACC CAA CCC AAG AAC TCC ACA GTT GAA ACC ATC 1110
```

Fig. 5B

```
 V   S   M   D   F   V   A   S   T   S   V   G   L   V   I   L   G   Q   R   L   346
GTT TCC ATG GAC TTC GTT GCT AGT ACC AGT GTT GGC CTG GTT ATT TTG GGA CAA AGA CTG 1170

 V   C   S   L   S   L   N   R   F   R   L   A   L   P   E   S   N   R   S   N   366
GTC TGC TCC TTG TCT CTG AAC AGA TTC CGC CTT GCT TTG CCA GAG TCC AAT CGC AGC AAC 1230

 I   E   V   L   R   F   E   N   I   L   S   S   I   L   H   F   G   V   L   P   386
ATT GAG GTC TTG AGG TTT GAA AAT ATT CTA TCG TCC ATT CTT CAC TTT GGA GTC CTC CCA 1290

 L   A   N   A   K   L   Q   Q   G   F   P   L   P   N   P   H   K   F   L   F   406
CTG GCC AAT GCA AAA TTG CAG CAA GGA TTT CCT CTG CCC AAT CCA CAC AAA TTC TTA TTC 1350

 V   N   S   D   I   E   V   L   E   G   F   L   L   I   S   T   D   L   K   Y   426
GTC AAT TCA GAT ATT GAA GTT CTT GAG GGT TTC CTT TTG ATT TCC ACC GAC CTG AAG TAT 1410

 E   T   S   S   K   Q   Q   P   S   F   H   V   W   E   G   L   N   L   I   S   446
GAA ACA TCC TCA AAG CAG CAG CCA AGT TTC CAC GTA TGG GAA GGT CTG AAC CTG ATA AGC 1470

 R   Q   W   R   G   K   S   A   P   *                                           456
AGA CAG TGG AGG GGG AAG TCA GCC CCT TGA                                         1500

TTGCCGGTTTGCAATTCACCCCAGGAAGTAAATGGTCCTTAATCCTACAACTACTGTAAACCCAGAAGGGAAAGACAGT 1579
ACACACTGGAATTGTAAAGCCCTTGTGAATTGCTTAGGCAGAAAGTTTTCTTTCTTAAGCCTTCAGGAACCCAGAATAA 1658
GGCAGACTCTGTTAAAGGGATAAATAGAGGTGTCTGAATGTGAGTGTATGCATGCTGCGTGTGTCTGTGTTTATGTTTG 1737
TTTGTTTGTTTGGGGCAAGAAAGATTCTAGGACAAGAGCTAGGCATGTACTTCTGACCAGGTGGGTAAGCAACTCTAAG 1816
```

Fig. 5C

```
TCTGTATTTGTATTGGTCATTCTCAGTGGAAATCCCTTAGGCCCTCTAGTGGTTTTCCCCTACCTGCATATTGGTTTTC 1895
ATGTTTTATATTCACTGTTACTATCTTCTGTGTTTAATTAAAATTGTTTTCTATCAAAAAAAAAAAAAAAAAAAAGGGC 1974
GGCCGC                                                                          1980
```

Fig. 5D

```
             10        20        30        40        50        60
286 MCTKT-IPVLWGCFL-LWNLYVSSSQTIYPGIKARITQRALDYGVQAGMKMIEOMLKEKKLPDLSGSESL
    :      .  :  .. : .. .. . .. ::. .::.:..:::. : :   ... ::  :.:: :  .:.
BPI MARGPCNAPRWVSLMVLVAIGTAVTAAVNPGVVVRISQKGLDYASQQGTAALQKELKRIKIPDYS--DSF
            10        20        30        40        50        60

    70        80        90        100       110       120       130
286 EFLKVDYVNYNFSNIKISAFSFPNTSLAFVPGVGIKALTNHGTANISTDWGFESPLFVLYNSFAEPME--
     .  ..  .:.: .. : .: .:.. .. ::.::.:  ..... .::  :  .  .. . ..:. ..:  .
BPI KIKHLGKGHYSFYSMDIREFQLPSSQISMVPNVGLKFSISNANIKISGKWKAQKRFLKMSGNFDLSIEGM
    70        80        90        100       110       120       130

                                                        140        150
286 ---------------KPI-------------------------------------LKN-LNEMLCPIIASE
                   ::.                                    :.: .:  .:  ...
BPI SISADLKLGSNPTSGKPTITCSSCSSHINSVHVHISKSKVGWLIQLFHKKIESALRNKMNSQVCEKVTNS
   140       150       160       170       180       190       200

        160       170       180       190       200       210       220
286 VKA-LNANLSTLEVLTKIDNYTLLDYSLISSPEITENYLDLNLKGVFYPLENLTDPPFSPVPFVLPERSN
    : . :.. . :: :.::::. . ..:.:...:.:..  ::...:: ::. .. . :::.:    .:.  .
BPI VSSKLQPYFQTLPVMTKIDSVAGINYGLVAPPATTAETLDVQMKGEFYSENHHNPPPFAPPVMEFPAAHD
   210       220       230       240       250       260       270
```

Fig. 5F

```
            230       240       250       260         270       280       290
286 SMLYIGIAEYFFKSASFAHFTAGVFNLTLSTEEISNH--FVQNSQGLGNVLSRIAEIYILSQPFMVRIMA
     :.:.:...:::..:...   :::...::  . :..   :  ... .:. :. .:  .  .  . ... :
BPI RMVYLGLSDYFFNTAGLVYQEAGVLKMTLRDDMIPKESKFRLTTKFFGTFLPEVAKKFP-NMKIQIHVSA
     280       290       300       310       320       330        340

              300       310       320       330       340       350       360
286 TEPPIINLQPGNFTLDIPASIMMLTQPKNSTVETIVSMDFVASTSVGLVILGQRLVCSLSLNRFRLALPE
    . :: ...:: ..:.  ....  ..   ::.....  ..  .. :. .   ..:::  : :.:. :.:
BPI STPPHLSVQPTGLTFYPAVDVQAFAVLPNSSLASLFLIGMHTTGSMEVSAESNRLVGELKLDRLLLELKH
    350       360       370       380       390       400       410

              370       380       390       400       410       420       430
286 SNRSNIEVLRFENILSSILHFGVLPLANAKLQQGFPLPNPHKFLFVNSDIEVLEGFLLISTDLKYETSSK
    :: . . :  ...:.. :. . ::: .:.:::.:::::.: .   . :   ..  ..::::...:. :
BPI SNIGPFPVELLQDIMNYIVPILVLPRVNEKLQKGFPLPTPARVQLYNVVLQPHQNFLLFGADVVYK----
    420       430       440       450       460       470       480

              440       450
286 QQPSFHVWEGLNLISRQWRGKSAP

BPI ------------------------
```

Fig. 5G

```
               10        20          30        40        50        60
286  MCTKTIPVLWGCFLLWNLYVSSSQTI--YPGIKARITQRALDYGVQAGMKMIEQMLKEKKLPDLSGSESL
     :  .  .  ..    .::  : .:.....   ::. ::::...:.:..:.:.   ..   :     :::..:   .:
RENP MGALARAL--PSILLALLLTSTPEALGANPGLVARITDKGLQYAAQEGLLALQSELLRITLPDFTG--DL
                 10        20        30        40        50        60

      70        80        90       100       110       120       130
286  EFLKVDYVNYNFSNIKISAFSFPNTSLAFVPGVGIKALTNHGTANISTDWGFESPLFVLYNSFAEPME--
      .  :.    :.: ...: .: .:.. .. ::.::.:    ..... .::  :  .   .. . ..:. ..:
RENP RIPHVGRGRYEFHSLNIHEFQLPSSQISMVPNVGLKFSISNANIKISGKWKAQKRFLKMSGNFDLSIEGM
        70        80        90       100       110       120       130

                                                               140       150
286  ---------------KPI-----------------------------------LKN-LNEMLCPIIASE
                    ::.                                   :.:  .:   .:   ...
RENP SISADLKLGSNPTSGKPTITCSSCSSHINSVHVHISKSKVGWLIQLFHKKIESALRNKMNSQVCEKVTNS
      140       150       160       170       180       190       200

        160       170       180       190       200       210       220
286  VKA-LNANLSTLEVLTKIDNYTLLDYSLISSPEITENYLDLNLKGVFYPLENLTDPPFSPVPFVLPERSN
     :  .  :..  . ::  :.::::.  .  ..:.:...:..:..  ::...:: ::.  .. .  :::.:      .:.  .
RENP VSSKLQPYFQTLPVMTKIDSVAGINYGLVAPPATTAETLDVQMKGEFYSENHHNPPPFAPPVMEFPAAHD
      210       220       230       240       250       260       270
```

Fig. 5H

```
            230       240       250       260         270       280       290
 286 SMLYIGIAEYFFKSASFAHFTAGVFNLTLSTEEISNH--FVQNSQGLGNVLSRIAEIYILSQPFMVRIMA
       :.:.:...:::..:...   ::::...::  . :..    :   ... .:. :. .:  .  .  . ... :
RENP RMVYLGLSDYFFNTAGLVYQEAGVLKMTLRDDMIPKESKFRLTTKFFGTFLPEVAKKFP-NMKIQIHVSA
      280       290       300       310       320       330        340

              300       310       320       330       340       350       360
 286 TEPPIINLQPGNFTLDIPASIMMLTQPKNSTVETIVSMDFVASTSVGLVILGQRLVCSLSLNRFRLALPE
     . :: ...:: ..:.   ....  :.   ::.....  ..   .. :. .   ..:::  : :.:. :.:
RENP STPPHLSVQPTGLTFYPAVDVQALAVLPNSSLASLFLIGMHTTGSMEVSAESNRLVGELKLDRLLLELKH
       350       360       370       380       390       400       410

              370       380       390       400       410       420       430
 286 SNRSNIEVLRFENILSSILHFGVLPLANAKLQQGFPLPNPHKFLFVNSDIEVLEGFLLISTDLKYETSSK
     :: . . :  ...:.. :. . ::: .:.:::.:::::.: .   . :   ..    ..:::...:. :
RENP SNIGPFPVELLQDIMNYIVPILVLPRVNEKLQKGFPLPTPARVQLYNVVLQPHQNFLLFGADVVYK----
       420       430       440       450       460       470       480

              440       450
 286 QQPSFHVWEGLNLISRQWRGKSAP

RENP ------------------------
```

Fig. 5I

```
GTCGACCCACGCGTCCGGGGAATTGCAGCAGGAAAATATGTGAAGAGTTTTTAAACCCACAAATTCTTCTTACTTTAGA   79

                                               M   L   E   T   L   S   R   Q     8
ATTAGTTGTTACATTGGCAGGAAAAAATAAATGCAGATGTTGGACC ATG TTG GAA ACC TTG TCA AGA CAG   149

 W   I   V   S   H   R   M   E   M   W   L   L   I   L   V   A   Y   M   F   Q    28
TGG ATT GTC TCA CAC AGA ATG GAA ATG TGG CTT CTG ATT CTG GTG GCG TAT ATG TTC CAG  209

 R   N   V   N   S   V   H   M   P   T   K   A   V   D   P   E   A   F   M   N    48
AGA AAT GTG AAT TCA GTA CAT ATG CCA ACT AAA GCT GTG GAC CCA GAA GCA TTC ATG AAT  269

 I   S   E   I   I   Q   H   Q   G   Y   P   C   E   E   Y   E   V   A   T   E    68
ATT AGT GAA ATC ATC CAA CAT CAA GGC TAT CCC TGT GAG GAA TAT GAA GTC GCA ACT GAA  329

 D   G   Y   I   L   S   V   N   R   I   P   R   G   L   V   Q   P   K   K   T    88
GAT GGG TAT ATC CTT TCT GTT AAC AGG ATT CCT CGA GGC CTA GTG CAA CCT AAG AAG ACA  389

 G   S   R   P   V   V   L   L   Q   H   G   L   V   G   G   A   S   N   W   I   108
GGT TCC AGG CCT GTG GTG TTA CTG CAG CAT GGC CTA GTT GGA GGT GCT AGC AAC TGG ATT  449

 S   N   L   P   N   N   S   L   G   F   I   L   A   D   A   G   F   D   V   W   128
TCC AAC CTG CCC AAC AAT AGC CTG GGC TTC ATT CTG GCA GAT GCT GGT TTT GAC GTG TGG  509

 M   G   N   S   R   G   N   A   W   S   R   K   H   K   T   L   S   I   D   Q   148
ATG GGG AAC AGC AGG GGA AAC GCC TGG TCT CGA AAA CAC AAG ACA CTC TCC ATA GAC CAA  569
```

Fig. 6A

```
 D   E   F   W   A   F   S   Y   D   E   M   A   R   F   D   L   P   A   V   I   168
GAT GAG TTC TGG GCT TTC AGT TAT GAT GAG ATG GCT AGG TTT GAC CTT CCT GCA GTG ATA  629

 N   F   I   L   Q   K   T   G   Q   E   K   I   Y   Y   V   G   Y   S   Q   G   188
AAC TTT ATT TTG CAG AAA ACG GGC CAG GAA AAG ATC TAT TAT GTC GGC TAT TCA CAG GGC  689

 T   T   M   G   F   I   A   F   S   T   M   P   E   L   A   Q   K   I   K   M   208
ACC ACC ATG GGC TTT ATT GCA TTT TCC ACC ATG CCA GAG CTG GCT CAG AAA ATC AAA ATG  749

 Y   F   A   L   A   P   I   A   T   V   K   H   A   K   S   P   G   T   K   F   228
TAT TTT GCT TTA GCA CCC ATA GCC ACT GTT AAG CAT GCA AAA AGC CCC GGG ACC AAA TTT  809

 L   L   L   P   D   M   M   I   K   G   L   F   G   K   K   E   F   L   Y   Q   248
TTG TTG CTG CCA GAT ATG ATG ATC AAG GGA TTG TTT GGC AAA AAA GAA TTT CTG TAT CAG  869

 T   R   F   L   R   Q   L   V   I   Y   L   C   G   Q   V   I   L   D   Q   I   268
ACC AGA TTT CTC AGA CAA CTT GTT ATT TAC CTT TGT GGC CAG GTG ATT CTT GAT CAG ATT  929

 C   S   N   I   M   L   L   L   G   G   F   N   T   N   N   M   N   M   S   R   288
TGT AGT AAT ATC ATG TTA CTT CTG GGT GGA TTC AAC ACC AAC AAT ATG AAC ATG AGC CGA  989

 A   S   V   Y   A   A   H   T   L   A   G   T   S   V   Q   N   I   L   H   W   308
GCA AGT GTA TAT GCT GCC CAC ACT CTT GCT GGA ACA TCT GTG CAA AAT ATT CTA CAC TGG 1049

 S   Q   A   V   N   S   G   E   L   R   A   F   D   W   G   S   E   T   K   N   328
AGC CAG GCA GTG AAT TCT GGT GAA CTC CGG GCA TTT GAC TGG GGG AGT GAG ACC AAA AAT 1109
```

Fig. 6B

```
 L   E   K   C   N   Q   P   T   P   V   R   Y   R   V   R   D   M   T   V   P   348
CTG GAA AAA TGC AAT CAG CCA ACT CCT GTA AGG TAC AGA GTC AGA GAT ATG ACG GTC CCT 1169

 T   A   M   W   T   G   G   Q   D   W   L   S   N   P   E   D   V   K   M   L   368
ACA GCA ATG TGG ACA GGA GGT CAG GAC TGG CTT TCA AAT CCA GAA GAC GTG AAA ATG CTG 1229

 L   S   E   V   T   N   L   I   Y   H   K   N   I   P   E   W   A   H   V   D   388
CTC TCT GAG GTG ACC AAC CTC ATC TAC CAT AAG AAT ATT CCT GAA TGG GCT CAC GTG GAT 1289

 F   I   W   G   L   D   A   P   H   R   M   Y   N   E   I   I   H   L   M   Q   408
TTC ATC TGG GGT TTG GAT GCT CCT CAC CGT ATG TAC AAT GAA ATC ATC CAT CTG ATG CAG 1349

 Q   E   E   T   N   L   S   Q   G   R   C   E   A   V   L   *                   424
CAG GAG GAG ACC AAC CTT TCC CAG GGA CGG TGT GAG GCC GTA TTG TGA                 1397

AGCATCTGACACTGACGATCTTAGGACAACCTCCTGAGGGATGGGGCTAGGACCCATGAAGGCAGAATTACGGAGAGCA 1476
GAGACCTAGTATACATTTTTCAGATTCCCTGCACTTGGCACTAAATCCGACACTTACATTTACATTTTTTTCTGTAAA 1555
TTAAAGTACTTATTAGGTAAATAGAGGTTTTGTATGCTATTATATATTCTACCATCTTGAAGGGTAGGTTTTACCTGAT 1634
AGCCAGAAAATATCTAGACATTCTCTATATCATTCAGGTAAATCTCTTTAAAACACCTATTGTTTTTCTATAAGCCAT 1713
ATTTTTGGAGCACTAAAGTAAAATGGCAAATTGGGACAGATATTGAGGTCTGGAGTCTGTGGATTATTGTTGACTTTGA 1792
CAAAATAAGCTAGACATTTTCACCTTGTTGCCACAGAGACATAACACTACCTCAGGAAGCTGAGCTGCTTTAAGGACAA 1871
CAACAACAAAATCAGTGTTACAGTATGGATGAAATCTATGTTAAGCATTCTCAGAATAAGGCCAAGTTTTATAGTTGCA 1950
TCTCAGGGAAGAAAATTTTATAGGATGTTTATGAGTTCTCCAATAAATGCATTCTGCATTACATAAAAAAAAAAAAAAA 2029
AAAAAGGGCGGCCGC                                                                2044
```

Fig. 6C

```
                10        20        30        40        50        60        70
294 MLETLSRQWIVSHRMEMWLLILVAYMFQRNVNSVHMPTKAVDPEAFMNISEIIQHQGYPCEEYEVATEDG
    :       :..    . :  :: :      .    . .:      . .::. :::::..:    ::: :::::.::::
HLP M-------WLL---LTMASLISVLGTTHGLFGKLH----PGSPEVTMNISQMITYWGYPNEEYEVVTEDG
                      10        20            30        40        50

                80        90       100       110       120       130       140
294 YILSVNRIPRGLVQPKKTGSRPVVLLQHGLVGGASNWISNLPNNSLGFILADAGFDVWMGNSRGNAWSRK
    ::: ::::: :  .. .:: ::::.:::::...:.:::::::::::.::::::::.:::.:::::::.:.:.
HLP YILEVNRIPYGKKNSGNTGQRPVVFLQHGLLASATNWISNLPNNSLAFILADAGYDVWLGNSRGNTWARR
      60        70        80        90       100       110       120

               150       160       170       180       190       200       210
294 HKTLSIDQDEFWAFSYDEMARFDLPAVINFILQKTGQEKIYYVGYSQGTTMGFIAFSTMPELAQKIKMYF
    .   : :  :::::.::::..::::.:.::..:::: .. ::: :::::.:::::: : ::..:: ..
HLP NLYYSPDSVEFWAFSFDEMAKYDLPATIDFIVKKTGQKQLHYVGHSQGTTIGFIAFSTNPSLAKRIKTFY
     130       140       150       160       170       180       190

               220       230       240       250        260       270
294 ALAPIATVKHAKSPGTKFLLLPDMMIKGLFGKKEFLYQTRFLRQ-LVIYLCGQVILDQICSNIMLLLGGF
    ::::.:::: .::   .:.  ..:. ..: .:: : : :.   :. : :.. .:.. .:. .::: .... ::
HLP ALAPVATVKYTKSLINKLRFVPQSLFKFIFGDKIF-YPHNFFDQFLATEVCSREMLNLLCSNALFIICGF
     200       210       220       230        240       250       260
```

Fig. 6D

```
    280       290       300       310       320       330       340
294 NTNNMNMSRASVYAAHTLAGTSVQNILHWSQAVNSGELRAFDWGSETKNLEKCNQPTPVRYRVRDMTVPT
    ...: : :: .:: .:. ::::::::..::.:::.:: ..:.:::: ..:     .:. :  : : .:.::.
HLP DSKNFNTSRLDVYLSHNPAGTSVQNMFHWTQAVKSGKFQAYDWGSPVQNRMHYDQSQPPYYNVTAMNVPI
        270       280       290       300       310       320       330

    350       360       370       380       390       400       410
294 AMWTGGQDWLSNPEDVKMLLSEVTNLIYHKNIPEWAHVDFIWGLDAPHRMYNEIIHLMQQEETNLSQGRC
    :.:.::.: :..:.:: .::. . :::::::.::  .:.::::::.:::. .::.:. .. ..
HLP AVWNGGKDLLADPQDVGLLLPKLPNLIYHKEIPFYNHLDFIWAMDAPQEVYNDIVSMISEDKK-------
        340       350       360       370       380       390

    420
294 EAVL

HLP ----
```

Fig. 6E

```
            10        20        30          40        50        60
294 MLETLSRQWIVSHRMEMWLLILVAYMFQRNVNSVHMPTK--AVDPEAFMNISEIIQHQGYPCEEYEVATE
    :               :..: ::. .  . ..:     :  :::::. ::.::::   :.: ::: :.::
LAL M--------------KMRFLGLVVCLVLWPLHSEGSGGKLTAVDPETNMNVSEIISYWGFPSEEYLVETE
                          10        20        30        40        50

   70        80        90       100       110       120       130
294 DGYILSVNRIPRGLVQPKKTGSRPVVLLQHGLVGGASNWISNLPNNSLGFILADAGFDVWMGNSRGNAWS
    ::::: .::::.:  .    :..:::.:::::....:::..::.:.:::::::::::::::::::::.::
LAL DGYILCLNRIPHGRKNHSDKGPKPVVFLQHGLLADSSNWVTNLANSSLGFILADAGFDVWMGNSRGNTWS
     60        70        80        90       100       110       120

  140       150       160       170       180       190       200
294 RKHKTLSIDQDEFWAFSYDEMARFDLPAVINFILQKTGQEKIYYVGYSQGTTMGFIAFSTMPELAQKIKM
    :::::::..:::::::::::::..:::: :::::.:::::..:::: :::::.:::::: .::::..:::
LAL RKHKTLSVSQDEFWAFSYDEMAKYDLPASINFILNKTGQEQVYYVGHSQGTTIGFIAFSQIPELAKRIKM
    130       140       150       160       170       180       190

  210       220       230       240       250       260       270
294 YFALAPIATVKHAKSPGTKFLLLPDMMIKGLFGKKEFLYQTRFLRQLVIYLCGQVILDQICSNIMLLLGG
    .:::.:.:.:    :: .:.  ::: .::.::: :::: :. ::. : . .: .::: ..:.:. .:: :
LAL FFALGPVASVAFCTSPMAKLGRLPDHLIKDLFGDKEFLPQSAFLKWLGTHVCTHVILKELCGNLCFLLCG
    200       210       220       230       240       250       260
```

Fig. 6G

```
       280       290       300       310       320       330       340
294 FNTNNMNMSRASVYAAHTLAGTSVQNILHWSQAVNSGELRAFDWGSETKNLEKCNQPTPVRYRVRDMTVP
    ::  :.:::::..:::..:. ::::::::.:::::::.    ..:::::: .::    ::. :  : :.:: ::
LAL FNERNLNMSRVDVYTTHSPAGTSVQNMLHWSQAVKFQKFQAFDWGSSAKNYFHYNQSYPPTYNVKDMLVP
         270       280       290       300       310       320       330

       350       360       370       380       390       400       410
294 TAMWTGGQDWLSNPEDVKMLLSEVTNLIYHKNIPEWAHVDFIWGLDAPHRMYNEIIHLMQQEETNLSQGR
    ::.:.::.:::..  ::..::...:::..: .::::.:.::::::::: :.:: ::.::.. .
LAL TAVWSGGHDWLADVYDVNILLTQITNLVFHESIPEWEHLDFIWGLDAPWRLYNKIINLMRKYQ-------
         340       350       360       370       380       390

       420
294 CEAVL

LAL -----
```

Fig. 6H

```
GTCGACCCACGCGTCCACGGCGAGGGCTCCCGGGGCGCAGCATTGCCCCCCCTGCACCACCTCACCAAG ATG GCT      75

 T   L   G   H   T   F   P   F   Y   A   G   P   K   P   T   F   P   M   D   T      22
ACT TTG GGA CAC ACA TTC CCC TTC TAT GCT GGC CCC AAG CCA ACC TTC CCG ATG GAC ACC    135

 T   L   A   S   I   I   M   I   F   L   T   A   L   A   T   F   I   V   I   L      42
ACT TTG GCC AGC ATC ATC ATG ATC TTT CTG ACT GCA CTG GCC ACG TTC ATC GTC ATC CTG    195

 P   G   I   R   G   K   T   R   L   F   W   L   L   R   V   V   T   S   L   F      62
CCT GGC ATT CGG GGA AAG ACG AGG CTG TTC TGG CTG CTT CGG GTG GTG ACC AGC TTA TTC    255

 I   G   A   A   I   L   A   V   N   F   S   S   E   W   S   V   G   Q   V   S      82
ATC GGG GCT GCA ATC CTG GCT GTG AAT TTC AGT TCT GAG TGG TCT GTG GGC CAG GTC AGC    315

 T   N   T   S   Y   K   A   F   S   S   E   W   I   S   A   D   I   G   L   Q     102
ACC AAC ACA TCA TAC AAG GCC TTC AGT TCT GAG TGG ATC AGC GCT GAT ATT GGG CTG CAG    375

 V   G   L   G   G   V   N   I   T   L   T   G   T   P   V   Q   Q   L   N   E     122
GTC GGG CTG GGT GGA GTC AAC ATC ACA CTC ACA GGG ACC CCC GTG CAG CAG CTG AAT GAG    435

 T   I   N   Y   N   E   E   F   T   W   R   L   G   E   N   Y   A   E   E   C     142
ACC ATC AAT TAC AAC GAG GAG TTC ACC TGG CGC CTG GGT GAG AAC TAT GCT GAG GAG TGT    495

 A   K   A   L   E   K   G   L   P   D   P   V   L   Y   L   A   E   K   F   T     162
GCA AAG GCT CTG GAG AAG GGG CTG CCA GAC CCT GTG TTG TAC CTA GCT GAG AAG TTC ACT    555
```

Fig. 7A

```
 P   R   S   P   C   G   L   Y   R   Q   Y   R   L   A   G   H   Y   T   S   A    182
CCA AGA AGC CCA TGT GGC CTA TAC CGC CAG TAC CGC CTG GCG GGA CAC TAC ACC TCA GCC   615

 M   L   W   V   A   F   L   C   W   L   L   A   N   V   M   L   S   M   P   V    202
ATG CTA TGG GTG GCA TTC CTC TGC TGG CTG CTG GCC AAT GTG ATG CTC TCC ATG CCT GTG   675

 L   V   Y   G   G   Y   M   L   L   A   T   G   I   F   Q   L   L   A   L   L    222
CTG GTA TAT GGT GGC TAC ATG CTA TTG GCC ACG GGC ATC TTC CAG CTG TTG GCT CTG CTC   735

 F   F   S   M   A   T   S   L   T   S   P   C   P   L   H   L   G   A   S   V    242
TTC TTC TCC ATG GCC ACA TCA CTC ACC TCA CCC TGT CCC CTG CAC CTG GGC GCT TCT GTG   795

 L   H   T   H   H   G   P   A   F   W   I   T   L   T   T   G   L   L   C   V    262
CTG CAT ACT CAC CAT GGG CCT GCC TTC TGG ATC ACA TTG ACC ACA GGA CTG CTG TGT GTG   855

 L   L   G   L   A   M   A   V   A   H   R   M   Q   P   H   R   L   K   A   F    282
CTG CTG GGC CTG GCT ATG GCG GTG GCC CAC AGG ATG CAG CCT CAC AGG CTG AAG GCT TTC   915

 F   N   Q   S   V   D   E   D   P   M   L   E   W   S   P   E   E   G   G   L    302
TTC AAC CAG AGT GTG GAT GAA GAC CCC ATG CTG GAG TGG AGT CCT GAG GAA GGT GGA CTC   975

 L   S   P   R   Y   R   S   M   A   D   S   P   K   S   Q   D   I   P   L   S    322
CTG AGC CCC CGC TAC CGG TCC ATG GCT GAC AGT CCC AAG TCC CAG GAC ATT CCC CTG TCA  1035

 E   A   S   S   T   K   A   Y   C   K   E   A   H   P   K   D   P   D   C   A    342
GAG GCT TCC TCC ACC AAG GCA TAC TGT AAG GAG GCA CAC CCC AAA GAT CCT GAT TGT GCT  1095
```

Fig. 7B

```
 L   *                                                                              344
TTA TAA                                                                            1101

CATTCCTCCCCGTGGAGGCCACCTGGACTTCCAGTCTGGCTCCAAACCTCATTGGCGCCCCATAAAACCAGCAGAACTG 1180
CCCTCAGGGTGGCTGTTACCAGACACCCAGCACCAATCTACAGACGGAGTAGAAAAAGGAGGCTCTATATACTGATGTT 1259
AAAAAACAAAACAAAACAAAAAGCCCTAAGGGACTGAAGAGATGCTGGGCCTGTCCATAAAGCCTGTTGCCATGATAAG 1338
GCCAAGCAGGGGCTAGCTTATCTGCACAGCAACCCAGCCTTTCCGTGCTGCCTTGCCTCTTCAAGATGCTATTCACTGA 1417
AACCTAACTTCACCCCCATAACACCAGCAGGGTGGGGTTACATATGATTCTCCTATGGTTTCCTCTCATCCCTCGGCA 1496
CCTCTTGTTTTCCTTTTTCCTGGGTTCCTTTTGTTCTTCCTTTACTTCTCCAGCTTGTGTGGCCTTTTGGTACAATGAA 1575
AGACAGCACTGGAAAGGAGGGGAAACCAAACTTCTCATCCTAGGTCTAACATTAACCAACTATGCCACATTCTCTTTGA 1654
GCTTCAGTTCCCAAATTTGCTACATAAGATTGCAAGACTTGCCAAGAATCTTGGGATTTATCTTTCTATGCCTTGCTGA 1733
CACCTACCTTGGCCCTCAAACACCACCTCACAAGAAGCCAGGTGGGAAGTTAGGGAATCAACTCCAAAACGCTATTCCT 1812
TCCCACCCCACTCAGCTGGGCTAGCTGAGTGGCATCCAGGACGGGGGAGTGGGTGACCTGCCTCATCACTGCCACCTAA 1891
CGTCCCCCTGGGGTGGTTCAGAAAGATGCTAGCTCTGGTAGGGTCCCTCCGGCCTCACTAGAGGGCGCCCCTATTACTC 1970
TGGAGTCGACGCAGAGAATCAGGTTTCACAGCACTGCGGAGAGTGTACTAGGCTGTCTCCAGCCCAGCGAAGCTCATGA 2049
GGACGTGCGACCCCGGCGCGGAGAAGCCATGAAAATTAATGGAAAAACAGTTTTTAAAAAAAAAAAAAAAAAAGGGCG 2128
GCCGC                                                                              2133
```

Fig. 7C

```
                10        20        30        40        50        60.       70
296 MATLGHTFPFYAGPKPTFPMDTTLASIIMIFLTALATFIVILPGIRGKTRLFWLLRVVTSLFIGAAILAV
    :  ..:     :... ..        ::. .::..: ..:.:::::: . :.    .  :  : .:.:..:
CRP M-RIAH-----ASSRGNI-------SIFSVFLIPLIAYILILPGVR-RKRVVTTVTYVLMLAVGGALIAS
                   10                20        30         40        50

                80        90        100       110              120         130
296 NFSSEWSVGQVSTNTSYKAFSSEWISADIGLQVGLGGVNITL------TGTPVQQLNETIN--YNEEFTW
     . . :. :    . : ... :.:.: : ::...::    ::.::        ... : . .. ..  ::: :
CRP LIYPCWASGSQMIYTQFRGHSNERILAKIGVEIGLQKVNVTLKFERLLSSNDVLPGSDMTELYYNEGFDI
      60        70        80        90        100       110       120

             140       150       160        170       180       190        200
296 RLGENYAEECAKALEKGLPDPVLYLAEKFT-PRSPCGLYRQYRLAGHYTSAMLWVAFLCWLLANV-MLSM
        . ::.   .::.::: :.: . : :.   ... .   :.::.::::: : .: :: :: :. : :: .
CRP SGISSMAEALHHGLENGLPYPMLSVLEYFSLNQDSFDWGRHYRVAGHYTHAAIWFAFACWCLSVVLMLFL
     130       140       150       160       170       180       190

               210       220       230          240       250           260
296 PVLVYGGYMLLATGIFQLLALLFFSMATSLTSPCPLHL---GASVLHTHHGPAF----WITLTTGLLCVL
    :  .: .  .::::: :.: : .      : ::: :..   :..  ...  ..:      .....:.:::
CRP PHNAYKS--ILATGISCLIACLVYL----LLSPCELRIAFTGENFERVDLTATFSFCFYLIFAIGILCVL
     200        210          220       230       240       250       260
```

Fig. 7E

```
          270       280       290             300         310       320
296 LGLAMAVAHRMQPHRLKAFFNQSVDEDPMLEW------SPEEGGLLSPRY--RSMADSPKSQDIPLSEAS
     ::....  . .   : .:.. :.::.    :      .:.  :.    :   . ..:   .::. . ..
CRP CGLGLGICEHWRIYTLSTFLDASLDEHVGPKWKKLPTGGPALQGVQIGAYGTNTTNSSRDKNDISSDKTA
             270       280       290       300       310       320       330

        330                          340
296 STKAY------CK--------------EAHPKDPD------------CA---L
    .. ..      :.              :.   ...            :.
CRP GSSGFQSRTSTCQSSASSASLRSQSSIETVHDEAELERTHVHFLQEPCSSSST
             340       350       360       370       380
```

Fig. 7F

SEQUENCE LISTING

```
<160> NUMBER OF SEQ ID NOS:  79
<210> SEQ ID NO 1
<211> LENGTH: 1656
<212> TYPE: DNA
<213> ORGANISM: Homo sapiens

<400> SEQUENCE: 1

gtcgacccac gcgtccgccc acgcgtccgg cccatggcgc cgcccgccgc ccgcctcgcc     60

ctgctctccg ccgcggcgct cacgctggcg gcccggcccg cgcctagccc cggcctcggc    120

cccggacccg agtgtttcac agccaatggt gcggattata ggggaacaca gaactggaca    180

gcactacaag gcgggaagcc atgtctgttt tggaacgaga ctttccagca tccatacaac    240

actctgaaat accccaacgg ggagggggc ctgggtgagc acaactattg cagaaatcca    300

gatggagacg tgagcccctg gtgctatgtg gcagagcacg aggatggtgt ctactggaag    360

tactgtgaga tacctgcttg ccagatgcct ggaaaccttg gctgctacaa ggatcatgga    420

aacccacctc ctctaactgg caccagtaaa acgtccaaca aactcaccat acaaacttgc    480

atcagttttt gtcggagtca gaggttcaag tttgctggga tggagtcagg ctatgcttgc    540

ttctgtggaa acaatcctga ttactggaag tacggggagg cagccagtac cgaatgcaac    600
```

-continued agcgtctgct tcggggatca cacccaaccc tgtggtggcg atggcaggat catcctcttt 660
gatactctcg tgggcgcctg cggtgggaac tactcagcca tgtcttctgt ggtctattcc 720
cctgacttcc ccgacaccta tgccacgggg agggtctgct actggaccat ccgggttccg 780
ggggcctccc acatccactt cagcttcccc ctatttgaca tcagggactc ggcggacatg 840
gtggagcttc tggatggcta cacccaccgt gtcctagccc gcttccacgg gaggagccgc 900
ccacctctgt ccttcaacgt ctctctggac ttcgtcatct tgtatttctt ctctgatcgc 960
atcaatcagg cccagggatt tgctgtttta taccaagccg tcaaggaaga actgccacag 1020
gagaggcccg ctgtcaacca gacggtggcc gaggtgatca cggagcaggc caacctcagt 1080
gtcagcgctg cccggtcctc caaagtcctc tatgtcatca ccaccagccc cagccaccca 1140
cctcagactg tcccaggtag caattcctgg gcgccaccca tgggggctgg aagccacaga 1200
gttgaaggat ggacagtcta tggtctggca actctcctca tcctcacagt cacagccatt 1260
gtagcaaaga tacttctgca cgtcacattc aaatcccatc gtgttcctgc ttcaggggac 1320
cttagggatt gtcatcaacc agggacttcg ggggaaatct ggagcatttt ttacaagcct 1380
tccacttcaa tttccatctt taagaagaaa ctcaagggtc agagtcaaca agatgaccgc 1440
aatccccttg tgagtgacta aaaaccccac tgtgcctagg acttgaggtc cctctttgag 1500
ctcaaggctg ccgtggtcaa cctctcctgt ggttcttctc tgacagactc ttccctcctc 1560
tccctctgcc tcggcctctt cggggaaacc ctcctcctac agactaggaa gaggcacctg 1620
ctgccagggc aggcagagcc tggattcctc ctgctt 1656

<210> SEQ ID NO 2
<211> LENGTH: 1425
<212> TYPE: DNA
<213> ORGANISM: Homo sapiens

<400> SEQUENCE: 2
atggcgccgc ccgccgcccg cctcgccctg ctctccgccg cggcgctcac gctggcggcc 60
cggcccgcgc ctagccccgg cctcggcccc ggacccgagt gtttcacagc caatggtgcg 120
gattataggg gaacacagaa ctggacagca ctacaaggcg ggaagccatg tctgttttgg 180
aacgagactt tccagcatcc atacaacact ctgaaatacc ccaacgggga gggggggcctg 240 ggtgagcaca actattgcag aaatccagat ggagacgtga gcccctggtg ctatgtggca 300
gagcacgagg atggtgtcta ctggaagtac tgtgagatac ctgcttgcca gatgcctgga 360
aaccttggct gctacaagga tcatggaaac ccacctcctc taactggcac cagtaaaacg 420
tccaacaaac tcaccataca aacttgcatc agtttttgtc ggagtcagag gttcaagttt 480
gctgggatgg agtcaggcta tgcttgcttc tgtggaaaca atcctgatta ctggaagtac 540
ggggaggcag ccagtaccga atgcaacagc gtctgcttcg gggatcacac ccaaccctgt 600
ggtggcgatg gcaggatcat cctctttgat actctcgtgg gcgcctgcgg tgggaactac 660
tcagccatgt cttctgtggt ctattcccct gacttccccg acacctatgc cacggggagg 720
gtctgctact ggaccatccg ggttccgggg gcctcccaca tccacttcag cttcccccta 780
tttgacatca gggactcggc ggacatggtg gagcttctgg atggctacac ccaccgtgtc 840
ctagcccgct tccacgggag gagccgccca cctctgtcct tcaacgtctc tctggacttc 900
gtcatcttgt atttcttctc tgatcgcatc aatcaggccc agggatttgc tgttttatac 960
caagccgtca aggaagaact gccacaggag aggcccgctg tcaaccagac ggtggccgag 1020

-continued

```
gtgatcacgg agcaggccaa cctcagtgtc agcgctgccc ggtcctccaa agtcctctat   1080

gtcatcacca ccagccccag ccacccacct cagactgtcc caggtagcaa ttcctgggcg   1140

ccacccatgg gggctggaag ccacagagtt gaaggatgga cagtctatgg tctggcaact   1200

ctcctcatcc tcacagtcac agccattgta gcaaagatac ttctgcacgt cacattcaaa   1260

tcccatcgtg ttcctgcttc aggggacctt agggattgtc atcaaccagg gacttcgggg   1320

gaaatctgga gcattttttta caagccttcc acttcaattt ccatctttaa gaagaaactc   1380

aagggtcaga gtcaacaaga tgaccgcaat ccccttgtga gtgac                    1425
```

```
<210> SEQ ID NO 3
<211> LENGTH: 475
<212> TYPE: PRT
<213> ORGANISM: Homo sapiens

<400> SEQUENCE: 3

Met Ala Pro Pro Ala Ala Arg Leu Ala Leu Leu Ser Ala Ala Ala Leu
  1               5                  10                  15

Thr Leu Ala Ala Arg Pro Ala Pro Ser Pro Gly Leu Gly Pro Gly Pro
             20                  25                  30

Glu Cys Phe Thr Ala Asn Gly Ala Asp Tyr Arg Gly Thr Gln Asn Trp
         35                  40                  45

Thr Ala Leu Gln Gly Gly Lys Pro Cys Leu Phe Trp Asn Glu Thr Phe
     50                  55                  60

Gln His Pro Tyr Asn Thr Leu Lys Tyr Pro Asn Gly Glu Gly Gly Leu
 65                  70                  75                  80

Gly Glu His Asn Tyr Cys Arg Asn Pro Asp Gly Asp Val Ser Pro Trp
                 85                  90                  95

Cys Tyr Val Ala Glu His Glu Asp Gly Val Tyr Trp Lys Tyr Cys Glu
            100                 105                 110

Ile Pro Ala Cys Gln Met Pro Gly Asn Leu Gly Cys Tyr Lys Asp His
        115                 120                 125

Gly Asn Pro Pro Pro Leu Thr Gly Thr Ser Lys Thr Ser Asn Lys Leu
    130                 135                 140

Thr Ile Gln Thr Cys Ile Ser Phe Cys Arg Ser Gln Arg Phe Lys Phe
145                 150                 155                 160

Ala Gly Met Glu Ser Gly Tyr Ala Cys Phe Cys Gly Asn Asn Pro Asp
                165                 170                 175

Tyr Trp Lys Tyr Gly Glu Ala Ala Ser Thr Glu Cys Asn Ser Val Cys
            180                 185                 190

Phe Gly Asp His Thr Gln Pro Cys Gly Gly Asp Gly Arg Ile Ile Leu
        195                 200                 205

Phe Asp Thr Leu Val Gly Ala Cys Gly Gly Asn Tyr Ser Ala Met Ser
    210                 215                 220

Ser Val Val Tyr Ser Pro Asp Phe Pro Asp Thr Tyr Ala Thr Gly Arg
225                 230                 235                 240

Val Cys Tyr Trp Thr Ile Arg Val Pro Gly Ala Ser His Ile His Phe
                245                 250                 255

Ser Phe Pro Leu Phe Asp Ile Arg Asp Ser Ala Asp Met Val Glu Leu
            260                 265                 270

Leu Asp Gly Tyr Thr His Arg Val Leu Ala Arg Phe His Gly Arg Ser
        275                 280                 285

Arg Pro Pro Leu Ser Phe Asn Val Ser Leu Asp Phe Val Ile Leu Tyr
    290                 295                 300
```

-continued

```
Phe Phe Ser Asp Arg Ile Asn Gln Ala Gln Gly Phe Ala Val Leu Tyr
305                 310                 315                 320

Gln Ala Val Lys Glu Glu Leu Pro Gln Glu Arg Pro Ala Val Asn Gln
                325                 330                 335

Thr Val Ala Glu Val Ile Thr Glu Gln Ala Asn Leu Ser Val Ser Ala
            340                 345                 350

Ala Arg Ser Ser Lys Val Leu Tyr Val Ile Thr Thr Ser Pro Ser His
        355                 360                 365

Pro Pro Gln Thr Val Pro Gly Ser Asn Ser Trp Ala Pro Pro Met Gly
    370                 375                 380

Ala Gly Ser His Arg Val Glu Gly Trp Thr Val Tyr Gly Leu Ala Thr
385                 390                 395                 400

Leu Leu Ile Leu Thr Val Thr Ala Ile Val Ala Lys Ile Leu Leu His
                405                 410                 415

Val Thr Phe Lys Ser His Arg Val Pro Ala Ser Gly Asp Leu Arg Asp
            420                 425                 430

Cys His Gln Pro Gly Thr Ser Gly Glu Ile Trp Ser Ile Phe Tyr Lys
        435                 440                 445

Pro Ser Thr Ser Ile Ser Ile Phe Lys Lys Lys Leu Lys Gly Gln Ser
    450                 455                 460

Gln Gln Asp Asp Arg Asn Pro Leu Val Ser Asp
465                 470                 475


<210> SEQ ID NO 4
<211> LENGTH: 19
<212> TYPE: PRT
<213> ORGANISM: Homo sapiens

<400> SEQUENCE: 4

Met Ala Pro Pro Ala Ala Arg Leu Ala Leu Leu Ser Ala Ala Ala Leu
  1               5                  10                  15

Thr Leu Ala


<210> SEQ ID NO 5
<211> LENGTH: 456
<212> TYPE: PRT
<213> ORGANISM: Homo sapiens

<400> SEQUENCE: 5

Ala Arg Pro Ala Pro Ser Pro Gly Leu Gly Pro Gly Pro Glu Cys Phe
  1               5                  10                  15

Thr Ala Asn Gly Ala Asp Tyr Arg Gly Thr Gln Asn Trp Thr Ala Leu
             20                  25                  30

Gln Gly Gly Lys Pro Cys Leu Phe Trp Asn Glu Thr Phe Gln His Pro
         35                  40                  45

Tyr Asn Thr Leu Lys Tyr Pro Asn Gly Glu Gly Gly Leu Gly Glu His
     50                  55                  60

Asn Tyr Cys Arg Asn Pro Asp Gly Asp Val Ser Pro Trp Cys Tyr Val
 65                  70                  75                  80

Ala Glu His Glu Asp Gly Val Tyr Trp Lys Tyr Cys Glu Ile Pro Ala
                 85                  90                  95

Cys Gln Met Pro Gly Asn Leu Gly Cys Tyr Lys Asp His Gly Asn Pro
            100                 105                 110

Pro Pro Leu Thr Gly Thr Ser Lys Thr Ser Asn Lys Leu Thr Ile Gln
        115                 120                 125

Thr Cys Ile Ser Phe Cys Arg Ser Gln Arg Phe Lys Phe Ala Gly Met
```

-continued

```
    130                 135                 140

Glu Ser Gly Tyr Ala Cys Phe Cys Gly Asn Asn Pro Asp Tyr Trp Lys
145                 150                 155                 160

Tyr Gly Glu Ala Ala Ser Thr Glu Cys Asn Ser Val Cys Phe Gly Asp
                165                 170                 175

His Thr Gln Pro Cys Gly Gly Asp Gly Arg Ile Ile Leu Phe Asp Thr
            180                 185                 190

Leu Val Gly Ala Cys Gly Gly Asn Tyr Ser Ala Met Ser Ser Val Val
        195                 200                 205

Tyr Ser Pro Asp Phe Pro Asp Thr Tyr Ala Thr Gly Arg Val Cys Tyr
    210                 215                 220

Trp Thr Ile Arg Val Pro Gly Ala Ser His Ile His Phe Ser Phe Pro
225                 230                 235                 240

Leu Phe Asp Ile Arg Asp Ser Ala Asp Met Val Glu Leu Leu Asp Gly
                245                 250                 255

Tyr Thr His Arg Val Leu Ala Arg Phe His Gly Arg Ser Arg Pro Pro
            260                 265                 270

Leu Ser Phe Asn Val Ser Leu Asp Phe Val Ile Leu Tyr Phe Phe Ser
        275                 280                 285

Asp Arg Ile Asn Gln Ala Gln Gly Phe Ala Val Leu Tyr Gln Ala Val
    290                 295                 300

Lys Glu Glu Leu Pro Gln Glu Arg Pro Ala Val Asn Gln Thr Val Ala
305                 310                 315                 320

Glu Val Ile Thr Glu Gln Ala Asn Leu Ser Val Ser Ala Ala Arg Ser
                325                 330                 335

Ser Lys Val Leu Tyr Val Ile Thr Thr Ser Pro Ser His Pro Pro Gln
            340                 345                 350

Thr Val Pro Gly Ser Asn Ser Trp Ala Pro Pro Met Gly Ala Gly Ser
        355                 360                 365

His Arg Val Glu Gly Trp Thr Val Tyr Gly Leu Ala Thr Leu Leu Ile
    370                 375                 380

Leu Thr Val Thr Ala Ile Val Ala Lys Ile Leu Leu His Val Thr Phe
385                 390                 395                 400

Lys Ser His Arg Val Pro Ala Ser Gly Asp Leu Arg Asp Cys His Gln
                405                 410                 415

Pro Gly Thr Ser Gly Glu Ile Trp Ser Ile Phe Tyr Lys Pro Ser Thr
            420                 425                 430

Ser Ile Ser Ile Phe Lys Lys Lys Leu Lys Gly Gln Ser Gln Gln Asp
        435                 440                 445

Asp Arg Asn Pro Leu Val Ser Asp
    450                 455


<210> SEQ ID NO 6
<211> LENGTH: 373
<212> TYPE: PRT
<213> ORGANISM: Homo sapiens

<400> SEQUENCE: 6

Ala Arg Pro Ala Pro Ser Pro Gly Leu Gly Pro Gly Pro Glu Cys Phe
  1               5                  10                  15

Thr Ala Asn Gly Ala Asp Tyr Arg Gly Thr Gln Asn Trp Thr Ala Leu
            20                  25                  30

Gln Gly Gly Lys Pro Cys Leu Phe Trp Asn Glu Thr Phe Gln His Pro
        35                  40                  45
```

-continued

```
Tyr Asn Thr Leu Lys Tyr Pro Asn Gly Glu Gly Gly Leu Gly Glu His
     50                  55                  60

Asn Tyr Cys Arg Asn Pro Asp Gly Asp Val Ser Pro Trp Cys Tyr Val
 65                  70                  75                  80

Ala Glu His Glu Asp Gly Val Tyr Trp Lys Tyr Cys Glu Ile Pro Ala
                 85                  90                  95

Cys Gln Met Pro Gly Asn Leu Gly Cys Tyr Lys Asp His Gly Asn Pro
            100                 105                 110

Pro Pro Leu Thr Gly Thr Ser Lys Thr Ser Asn Lys Leu Thr Ile Gln
        115                 120                 125

Thr Cys Ile Ser Phe Cys Arg Ser Gln Arg Phe Lys Phe Ala Gly Met
    130                 135                 140

Glu Ser Gly Tyr Ala Cys Phe Cys Gly Asn Asn Pro Asp Tyr Trp Lys
145                 150                 155                 160

Tyr Gly Glu Ala Ala Ser Thr Glu Cys Asn Ser Val Cys Phe Gly Asp
                165                 170                 175

His Thr Gln Pro Cys Gly Gly Asp Gly Arg Ile Ile Leu Phe Asp Thr
            180                 185                 190

Leu Val Gly Ala Cys Gly Gly Asn Tyr Ser Ala Met Ser Ser Val Val
        195                 200                 205

Tyr Ser Pro Asp Phe Pro Asp Thr Tyr Ala Thr Gly Arg Val Cys Tyr
    210                 215                 220

Trp Thr Ile Arg Val Pro Gly Ala Ser His Ile His Phe Ser Phe Pro
225                 230                 235                 240

Leu Phe Asp Ile Arg Asp Ser Ala Asp Met Val Glu Leu Leu Asp Gly
                245                 250                 255

Tyr Thr His Arg Val Leu Ala Arg Phe His Gly Arg Ser Arg Pro Pro
            260                 265                 270

Leu Ser Phe Asn Val Ser Leu Asp Phe Val Ile Leu Tyr Phe Phe Ser
        275                 280                 285

Asp Arg Ile Asn Gln Ala Gln Gly Phe Ala Val Leu Tyr Gln Ala Val
    290                 295                 300

Lys Glu Glu Leu Pro Gln Glu Arg Pro Ala Val Asn Gln Thr Val Ala
305                 310                 315                 320

Glu Val Ile Thr Glu Gln Ala Asn Leu Ser Val Ser Ala Ala Arg Ser
                325                 330                 335

Ser Lys Val Leu Tyr Val Ile Thr Thr Ser Pro Ser His Pro Pro Gln
            340                 345                 350

Thr Val Pro Gly Ser Asn Ser Trp Ala Pro Pro Met Gly Ala Gly Ser
        355                 360                 365

His Arg Val Glu Gly
    370


<210> SEQ ID NO 7
<211> LENGTH: 23
<212> TYPE: PRT
<213> ORGANISM: Homo sapiens

<400> SEQUENCE: 7

Trp Thr Val Tyr Gly Leu Ala Thr Leu Leu Ile Leu Thr Val Thr Ala
  1               5                  10                  15

Ile Val Ala Lys Ile Leu Leu
            20


<210> SEQ ID NO 8
```

-continued

<211> LENGTH: 60
<212> TYPE: PRT
<213> ORGANISM: Homo sapiens

<400> SEQUENCE: 8

His Val Thr Phe Lys Ser His Arg Val Pro Ala Ser Gly Asp Leu Arg
1 5 10 15

Asp Cys His Gln Pro Gly Thr Ser Gly Glu Ile Trp Ser Ile Phe Tyr
20 25 30

Lys Pro Ser Thr Ser Ile Ser Ile Phe Lys Lys Lys Leu Lys Gly Gln
35 40 45

Ser Gln Gln Asp Asp Arg Asn Pro Leu Val Ser Asp
50 55 60

<210> SEQ ID NO 9
<211> LENGTH: 4628
<212> TYPE: DNA
<213> ORGANISM: Homo sapiens

<400> SEQUENCE: 9
gcggccgctc gcgatctaga actagtaatg atgctgcctc aaaactcgtg gcatattgat 60
tttggaagat gctgctgtca tcagaacctt ttctctgctg tggtaacttg catcctgctc 120
ctgaattcct gctttctcat cagcagtttt aatggaacag atttggagtt gaggctggtc 180
aatggagacg gtccctgctc tgggacagtg gaggtgaaat tccagggaca gtgggggact 240
gtgtgtgatg atgggtggaa cactactgcc tcaactgtcg tgtgcaaaca gcttggatgt 300
ccattttctt tcgccatgtt tcgttttgga caagccgtga ctagacatgg aaaaatttgg 360
cttgatgatg tttcctgtta tggaaatgag tcagctctct gggaatgtca acaccgggaa 420
tggggaagcc ataactgtta tcatggagaa gatgttggtg tgaactgtta tggtgaagcc 480
aatctgggtt tgaggctagt ggatggaaac aactcctgtt cagggagagt ggaggtgaaa 540
ttccaagaaa ggtgggggac tatatgtgat gatgggtgga acttgaatac tgctgccgtg 600
gtgtgcaggc aactaggatg tccatcttct tttatttctt ctggagttgt taatagccct 660
gctgtattgc gccccatttg gctggatgac attttatgcc aggggaatga gttggcactc 720
tggaattgca gacatcgtgg atggggaaat catgactgca gtcacaatga ggatgtcaca 780
ttaacttgtt atgatagtag tgatcttgaa ctaaggcttg taggtggaac taaccgctgt 840
atggggagag tagagctgaa aatccaagga aggtggggga ccgtatgcca ccataagtgg 900
aacaatgctg cagctgatgt cgtatgcaag cagttgggat gtggaaccgc acttcacttc 960
gctggcttgc ctcatttgca gtcagggtct gatgttgtat ggcttgatgg tgtctcctgc 1020
tccggtaatg aatcttttct ttgggactgc agacattccg gaaccgtcaa ttttgactgt 1080
cttcatcaaa acgatgtgtc tgtgatctgc tcagatggag cagatttgga actgcgacta 1140
gcagatggaa gtaacaattg ttcagggaga gtagaggtga gaattcatga acagtggtgg 1200
acaatatgtg accagaactg gaagaatgaa caagcccttg tggtttgtaa gcagctagga 1260
tgtccgttca gcgtctttgg cagtcgtcgt gctaaaccta gtaatgaagc tagagacatt 1320
tggataaaca gcatatcttg cactgggaat gagtcagctc tctgggactg cacatatgat 1380
ggaaaagcaa agcgaacatg cttccgaaga tcagatgctg gagtaatttg ttctgataag 1440
gcagatctgg acctaaggct tgtcggggct catagcccct gttatgggag attggaggtg 1500
aaataccaag gagagtgggg gactgtgtgt catgacagat ggagcacaag gaatgcagct 1560
gttgtgtgta aacaattggg atgtggaaag cctatgcatg tgtttggtat gacctatttt 1620

-continued

```
aaagaagcat caggacctat ttggctggat gacgtttctt gcattggaaa tgagtcaaat   1680
atctgggact gtgaacacag tggatgggga aagcataatt gtgtacacag agaggatgtg   1740
attgtaacct gctcaggtga tgcaacatgg ggcctgaggc tggtgggcgg cagcaaccgc   1800
tgctcgggaa gactggaggt gtactttcaa ggacggtggg gcacagtgtg tgatgacggc   1860
tggaacagta aagctgcagc tgtggtgtgt agccagctgg actgcccatc ttctatcatt   1920
ggcatgggtc tgggaaacgc ttctacagga tatggaaaaa tttggctcga tgatgtttcc   1980
tgtgatggag atgagtcaga tctctggtca tgcaggaaca gtgggtgggg aaataatgac   2040
tgcagtcaca gtgaagatgt tggagtgatc tgttctgatg catcggatat ggagctgagg   2100
cttgtgggtg gaagcagcag gtgtgctgga aaagttgagg tgaatgtcca gggtgccgtg   2160
ggaattctgt gtgctaatgg ctggggaatg aacattgctg aagttgtttg caggcaactt   2220
gaatgtgggt ctgcaatcag ggtctccaga gagcctcatt tcacagaaag aacattacac   2280
atcttaatgt cgaattctgg ctgcactgga ggggaagcct ctctctggga ttgtatacga   2340
tgggagtgga aacagactgc gtgtcattta aatatggaag caagtttgat ctgctcagcc   2400
cacaggcagc ccaggctggt tggagctgat atgccctgct ctggacgtgt tgaagtgaaa   2460
catgcagaca catggcgctc tgtctgtgat tctgatttct ctcttcatgc tgccaatgtg   2520
ctgtgcagag aattaaattg tggagatgcc atatctcttt ctgtgggaga tcactttgga   2580
aaagggaatg gtctaacttg ggccgaaaag ttccagtgtg aagggagtga aactcacctt   2640
gcattatgcc ccattgttca acatccggaa gacacttgta tccacagcag agaagttgga   2700
gttgtctgtt cccgatatac agatgtccga cttgtgaatg gcaaatccca gtgtgacggg   2760
caagtggaga tcaacgtgct tggacactgg ggctcactgt gtgacaccca ctgggaccca   2820
gaagatgccc gtgttctatg cagacagctc agctgtggga ctgctctctc aaccacagga   2880
ggaaaatata ttggagaaag aagtgttcgt gtgtggggac acaggtttca ttgcttaggg   2940
aatgagtcac ttctggataa ctgtcaaatg acagttcttg gagcacctcc ctgtatccat   3000
ggaaatactg tctctgtgat ctgcacagga agcctgaccc agccactgtt tccatgcctc   3060
gcaaatgtat ctgacccata tttgtctgca gttccagagg gcagtgcttt gatctgctta   3120
gaggacaaac ggctccgcct agtggatggg gacagccgct gtgccgggag agtagagatc   3180
tatcacgacg gcttctgggg caccatctgt gatgacggct gggacctgag cgatgcccac   3240
gtggtgtgtc aaaagctggg ctgtggagtg gccttcaatg ccacggtctc tgctcacttt   3300
ggggaggggt cagggcccat ctggctggat gacctgaact gcacaggaac ggagtcccac   3360
ttgtggcagt gcccttcccg cggctggggg cagcacgact gcaggcacaa ggaggacgca   3420
ggggtcatct gctcagaatt cacagccttg aggctctaca gtgaaactga aacagagagc   3480
tgtgctggga gattggaagt cttctataac gggacctggg gcagcgtcgg caggaggaac   3540
atcaccacag ccatagcagg cattgtgtgc aggcagctgg gctgtgggga gaatggagtt   3600
gtcagcctcg cccctttatc taagacaggc tctggtttca tgtgggtgga tgacattcag   3660
tgtcctaaaa cgcatatctc catatggcag tgcctgtctg ccccatggga gcgaagaatc   3720
tccagcccag cagaagagac ctggatcaca tgtgaagata gaataagagt gcgtggagga   3780
gacaccgagt gctctgggag agtggagatc tggcacgcag gctcctgggg cacagtgtgt   3840
gatgactcct gggacctggc cgaggcggaa gtggtgtgtc agcagctggg ctgtggctct   3900
gctctggctg ccctgaggga cgcttcgttt ggccagggaa ctggaaccat ctggttggat   3960
```

-continued

```
gacatgcggt gcaaaggaaa tgagtcattt ctatgggact gtcacgccaa accctgggga   4020

cagagtgact gtggacacaa ggaagatgct ggcgtgaggt gctctggaca gtcgctgaaa   4080

tcactgaatg cctcctcagg tcatttagca cttattttat ccagtatctt tgggctcctt   4140

ctcctggttc tgtttattct atttctcacg tggtgccgag ttcagaaaca aaaacatctg   4200

cccctcagag tttcaaccag aaggaggggt tctctcgagg agaatttatt ccatgagatg   4260

gagacctgcc tcaagagaga ggacccacat gggacaagaa cctcagatga cacccccaac   4320

catggttgtg aagatgctag cgacacatcg ctgttgggag ttcttcctgc ctctgaagcc   4380

acaaaatgac tttagacttc cagggctcac cagatcaacc tctaaatatc tttgaaggag   4440

acaacaactt ttaaatgaat aaagaggaag tcaagttgcc ctatggaaaa cttgtccaaa   4500

taacatttct tgaacaatag gagaacagct aaattgataa agactggtga taataaaaat   4560

tgaattatgt atatcactgt taaaaaaaaa aaaaaaaaaa aaaaaaaaaa acggacgcgt   4620

gggtcgac                                                            4628
```

<210> SEQ ID NO 10
<211> LENGTH: 4359
<212> TYPE: DNA
<213> ORGANISM: Homo sapiens

<400> SEQUENCE: 10

```
atgatgctgc ctcaaaactc gtggcatatt gattttggaa gatgctgctg tcatcagaac     60

cttttctctg ctgtggtaac ttgcatcctg ctcctgaatt cctgctttct catcagcagt    120

tttaatggaa cagatttgga gttgaggctg gtcaatggag acggtccctg ctctgggaca    180

gtggaggtga aattccaggg acagtggggg actgtgtgtg atgatgggtg gaacactact    240

gcctcaactg tcgtgtgcaa acagcttgga tgtccatttt ctttcgccat gtttcgtttt    300

ggacaagccg tgactagaca tggaaaaatt tggcttgatg atgtttcctg ttatggaaat    360

gagtcagctc tctgggaatg tcaacaccgg gaatggggaa gccataactg ttatcatgga    420

gaagatgttg gtgtgaactg ttatggtgaa gccaatctgg gtttgaggct agtggatgga    480

aacaactcct gttcagggag agtggaggtg aaattccaag aaaggtgggg gactatatgt    540

gatgatgggt ggaacttgaa tactgctgcc gtggtgtgca ggcaactagg atgtccatct    600

tcttttattt cttctggagt tgttaatagc cctgctgtat tgcgccccat ttggctggat    660

gacattttat gccaggggaa tgagttggca ctctggaatt gcagacatcg tggatgggga    720

aatcatgact gcagtcacaa tgaggatgtc acattaactt gttatgatag tagtgatctt    780

gaactaaggc ttgtaggtgg aactaaccgc tgtatgggga gagtagagct gaaaatccaa    840

ggaaggtggg ggaccgtatg ccaccataag tggaacaatg ctgcagctga tgtcgtatgc    900

aagcagttgg gatgtggaac cgcacttcac ttcgctggct tgcctcattt gcagtcaggg    960

tctgatgttg tatggcttga tggtgtctcc tgctccggta atgaatcttt tctttgggac   1020

tgcagacatt ccggaaccgt caattttgac tgtcttcatc aaaacgatgt gtctgtgatc   1080

tgctcagatg gagcagattt ggaactgcga ctagcagatg gaagtaacaa ttgttcaggg   1140

agagtagagg tgagaattca tgaacagtgg tggacaatat gtgaccagaa ctggaagaat   1200

gaacaagccc ttgtggtttg taagcagcta ggatgtccgt tcagcgtctt tggcagtcgt   1260

cgtgctaaac ctagtaatga agctagagac atttggataa acagcatatc ttgcactggg   1320

aatgagtcag ctctctggga ctgcacatat gatggaaaag caaagcgaac atgcttccga   1380

agatcagatg ctggagtaat ttgttctgat aaggcagatc tggacctaag gcttgtcggg   1440
```

-continued

```
gctcatagcc cctgttatgg gagattggag gtgaaatacc aaggagagtg ggggactgtg   1500
tgtcatgaca gatggagcac aaggaatgca gctgttgtgt gtaaacaatt gggatgtgga   1560
aagcctatgc atgtgtttgg tatgacctat tttaaagaag catcaggacc tatttggctg   1620
gatgacgttt cttgcattgg aaatgagtca aatatctggg actgtgaaca cagtggatgg   1680
ggaaagcata attgtgtaca cagagaggat gtgattgtaa cctgctcagg tgatgcaaca   1740
tggggcctga ggctggtggg cggcagcaac cgctgctcgg gaagactgga ggtgtacttt   1800
caaggacggt ggggcacagt gtgtgatgac ggctggaaca gtaaagctgc agctgtggtg   1860
tgtagccagc tggactgccc atcttctatc attggcatgg gtctgggaaa cgcttctaca   1920
ggatatggaa aaatttggct cgatgatgtt tcctgtgatg gagatgagtc agatctctgg   1980
tcatgcagga acagtgggtg gggaaataat gactgcagtc acagtgaaga tgttggagtg   2040
atctgttctg atgcatcgga tatggagctg aggcttgtgg gtggaagcag caggtgtgct   2100
ggaaaagttg aggtgaatgt ccagggtgcc gtgggaattc tgtgtgctaa tggctgggga   2160
atgaacattg ctgaagttgt ttgcaggcaa cttgaatgtg ggtctgcaat cagggtctcc   2220
agagagcctc atttcacaga aagaacatta cacatcttaa tgtcgaattc tggctgcact   2280
ggaggggaag cctctctctg ggattgtata cgatgggagt ggaaacagac tgcgtgtcat   2340
ttaaatatgg aagcaagttt gatctgctca gcccacaggc agcccaggct ggttggagct   2400
gatatgccct gctctggacg tgttgaagtg aaacatgcag acacatggcg ctctgtctgt   2460
gattctgatt tctctcttca tgctgccaat gtgctgtgca gagaattaaa ttgtggagat   2520
gccatatctc tttctgtggg agatcacttt ggaaaaggga atggtctaac ttgggccgaa   2580
aagttccagt gtgaagggag tgaaactcac cttgcattat gccccattgt tcaacatccg   2640
gaagacactt gtatccacag cagagaagtt ggagttgtct gttcccgata tacagatgtc   2700
cgacttgtga atggcaaatc ccagtgtgac gggcaagtgg agatcaacgt gcttggacac   2760
tggggctcac tgtgtgacac ccactgggac ccagaagatg cccgtgttct atgcagacag   2820
ctcagctgtg ggactgctct ctcaaccaca ggaggaaaat atattggaga aagaagtgtt   2880
cgtgtgtggg gacacaggtt tcattgctta gggaatgagt cacttctgga taactgtcaa   2940
atgacagttc ttggagcacc tccctgtatc catggaaata ctgtctctgt gatctgcaca   3000
ggaagcctga cccagccact gtttccatgc ctcgcaaatg tatctgaccc atatttgtct   3060
gcagttccag agggcagtgc tttgatctgc ttagaggaca aacggctccg cctagtggat   3120
ggggacagcc gctgtgccgg gagagtagag atctatcacg acggcttctg ggcaccatc    3180
tgtgatgacg gctgggacct gagcgatgcc cacgtggtgt gtcaaaagct gggctgtgga   3240
gtggccttca atgccacggt ctctgctcac tttggggagg ggtcagggcc catctggctg   3300
gatgacctga actgcacagg aacggagtcc cacttgtggc agtgcccttc ccgcggctgg   3360
gggcagcacg actgcaggca caaggaggac gcaggggtca tctgctcaga attcacagcc   3420
ttgaggctct acagtgaaac tgaaacagag agctgtgctg ggagattgga agtcttctat   3480
aacgggacct ggggcagcgt cggcaggagg aacatcacca cagccatagc aggcattgtg   3540
tgcaggcagc tgggctgtgg ggagaatgga gttgtcagcc tcgccccttt atctaagaca   3600
ggctctggtt tcatgtgggt ggatgacatt cagtgtccta aaacgcatat ctccatatgg   3660
cagtgcctgt ctgccccatg ggagcgaaga atctccagcc cagcagaaga gacctggatc   3720
acatgtgaag atagaataag agtgcgtgga ggagacaccg agtgctctgg gagagtggag   3780
```

-continued

```
atctggcacg caggctcctg gggcacagtg tgtgatgact cctgggacct ggccgaggcg   3840

gaagtggtgt gtcagcagct gggctgtggc tctgctctgg ctgccctgag ggacgcttcg   3900

tttggccagg gaactggaac catctggttg gatgacatgc ggtgcaaagg aaatgagtca   3960

tttctatggg actgtcacgc caaaccctgg ggacagagtg actgtggaca caaggaagat   4020

gctggcgtga ggtgctctgg acagtcgctg aaatcactga atgcctcctc aggtcattta   4080

gcacttattt tatccagtat ctttgggctc cttctcctgg ttctgtttat tctatttctc   4140

acgtggtgcc gagttcagaa acaaaaacat ctgcccctca gagtttcaac cagaaggagg   4200

ggttctctcg aggagaattt attccatgag atggagacct gcctcaagag agaggaccca   4260

catgggacaa gaacctcaga tgacaccccc aaccatggtt gtgaagatgc tagcgacaca   4320

tcgctgttgg gagttcttcc tgcctctgaa gccacaaaa                         4359
```

```
<210> SEQ ID NO 11
<211> LENGTH: 1453
<212> TYPE: PRT
<213> ORGANISM: Homo sapiens

<400> SEQUENCE: 11

Met Met Leu Pro Gln Asn Ser Trp His Ile Asp Phe Gly Arg Cys Cys
 1               5                  10                  15

Cys His Gln Asn Leu Phe Ser Ala Val Val Thr Cys Ile Leu Leu Leu
            20                  25                  30

Asn Ser Cys Phe Leu Ile Ser Ser Phe Asn Gly Thr Asp Leu Glu Leu
        35                  40                  45

Arg Leu Val Asn Gly Asp Gly Pro Cys Ser Gly Thr Val Glu Val Lys
    50                  55                  60

Phe Gln Gly Gln Trp Gly Thr Val Cys Asp Asp Gly Trp Asn Thr Thr
65                  70                  75                  80

Ala Ser Thr Val Val Cys Lys Gln Leu Gly Cys Pro Phe Ser Phe Ala
                85                  90                  95

Met Phe Arg Phe Gly Gln Ala Val Thr Arg His Gly Lys Ile Trp Leu
            100                 105                 110

Asp Asp Val Ser Cys Tyr Gly Asn Glu Ser Ala Leu Trp Glu Cys Gln
        115                 120                 125

His Arg Glu Trp Gly Ser His Asn Cys Tyr His Gly Glu Asp Val Gly
    130                 135                 140

Val Asn Cys Tyr Gly Glu Ala Asn Leu Gly Leu Arg Leu Val Asp Gly
145                 150                 155                 160

Asn Asn Ser Cys Ser Gly Arg Val Glu Val Lys Phe Gln Glu Arg Trp
                165                 170                 175

Gly Thr Ile Cys Asp Asp Gly Trp Asn Leu Asn Thr Ala Ala Val Val
            180                 185                 190

Cys Arg Gln Leu Gly Cys Pro Ser Ser Phe Ile Ser Ser Gly Val Val
        195                 200                 205

Asn Ser Pro Ala Val Leu Arg Pro Ile Trp Leu Asp Asp Ile Leu Cys
    210                 215                 220

Gln Gly Asn Glu Leu Ala Leu Trp Asn Cys Arg His Arg Gly Trp Gly
225                 230                 235                 240

Asn His Asp Cys Ser His Asn Glu Asp Val Thr Leu Thr Cys Tyr Asp
                245                 250                 255

Ser Ser Asp Leu Glu Leu Arg Leu Val Gly Gly Thr Asn Arg Cys Met
            260                 265                 270
```

-continued

```
Gly Arg Val Glu Leu Lys Ile Gln Gly Arg Trp Gly Thr Val Cys His
        275                 280                 285

His Lys Trp Asn Asn Ala Ala Ala Asp Val Val Cys Lys Gln Leu Gly
    290                 295                 300

Cys Gly Thr Ala Leu His Phe Ala Gly Leu Pro His Leu Gln Ser Gly
305                 310                 315                 320

Ser Asp Val Val Trp Leu Asp Gly Val Ser Cys Ser Gly Asn Glu Ser
                325                 330                 335

Phe Leu Trp Asp Cys Arg His Ser Gly Thr Val Asn Phe Asp Cys Leu
            340                 345                 350

His Gln Asn Asp Val Ser Val Ile Cys Ser Asp Gly Ala Asp Leu Glu
        355                 360                 365

Leu Arg Leu Ala Asp Gly Ser Asn Asn Cys Ser Gly Arg Val Glu Val
    370                 375                 380

Arg Ile His Glu Gln Trp Trp Thr Ile Cys Asp Gln Asn Trp Lys Asn
385                 390                 395                 400

Glu Gln Ala Leu Val Val Cys Lys Gln Leu Gly Cys Pro Phe Ser Val
                405                 410                 415

Phe Gly Ser Arg Arg Ala Lys Pro Ser Asn Glu Ala Arg Asp Ile Trp
            420                 425                 430

Ile Asn Ser Ile Ser Cys Thr Gly Asn Glu Ser Ala Leu Trp Asp Cys
        435                 440                 445

Thr Tyr Asp Gly Lys Ala Lys Arg Thr Cys Phe Arg Arg Ser Asp Ala
    450                 455                 460

Gly Val Ile Cys Ser Asp Lys Ala Asp Leu Asp Leu Arg Leu Val Gly
465                 470                 475                 480

Ala His Ser Pro Cys Tyr Gly Arg Leu Glu Val Lys Tyr Gln Gly Glu
                485                 490                 495

Trp Gly Thr Val Cys His Asp Arg Trp Ser Thr Arg Asn Ala Ala Val
            500                 505                 510

Val Cys Lys Gln Leu Gly Cys Gly Lys Pro Met His Val Phe Gly Met
        515                 520                 525

Thr Tyr Phe Lys Glu Ala Ser Gly Pro Ile Trp Leu Asp Asp Val Ser
    530                 535                 540

Cys Ile Gly Asn Glu Ser Asn Ile Trp Asp Cys Glu His Ser Gly Trp
545                 550                 555                 560

Gly Lys His Asn Cys Val His Arg Glu Asp Val Ile Val Thr Cys Ser
                565                 570                 575

Gly Asp Ala Thr Trp Gly Leu Arg Leu Val Gly Gly Ser Asn Arg Cys
            580                 585                 590

Ser Gly Arg Leu Glu Val Tyr Phe Gln Gly Arg Trp Gly Thr Val Cys
        595                 600                 605

Asp Asp Gly Trp Asn Ser Lys Ala Ala Ala Val Val Cys Ser Gln Leu
    610                 615                 620

Asp Cys Pro Ser Ser Ile Ile Gly Met Gly Leu Gly Asn Ala Ser Thr
625                 630                 635                 640

Gly Tyr Gly Lys Ile Trp Leu Asp Asp Val Ser Cys Asp Gly Asp Glu
                645                 650                 655

Ser Asp Leu Trp Ser Cys Arg Asn Ser Gly Trp Gly Asn Asn Asp Cys
            660                 665                 670

Ser His Ser Glu Asp Val Gly Val Ile Cys Ser Asp Ala Ser Asp Met
        675                 680                 685

Glu Leu Arg Leu Val Gly Gly Ser Ser Arg Cys Ala Gly Lys Val Glu
```

-continued

```
    690                 695                 700

Val Asn Val Gln Gly Ala Val Gly Ile Leu Cys Ala Asn Gly Trp Gly
705                 710                 715                 720

Met Asn Ile Ala Glu Val Val Cys Arg Gln Leu Glu Cys Gly Ser Ala
                725                 730                 735

Ile Arg Val Ser Arg Glu Pro His Phe Thr Glu Arg Thr Leu His Ile
            740                 745                 750

Leu Met Ser Asn Ser Gly Cys Thr Gly Gly Glu Ala Ser Leu Trp Asp
        755                 760                 765

Cys Ile Arg Trp Glu Trp Lys Gln Thr Ala Cys His Leu Asn Met Glu
    770                 775                 780

Ala Ser Leu Ile Cys Ser Ala His Arg Gln Pro Arg Leu Val Gly Ala
785                 790                 795                 800

Asp Met Pro Cys Ser Gly Arg Val Glu Val Lys His Ala Asp Thr Trp
                805                 810                 815

Arg Ser Val Cys Asp Ser Asp Phe Ser Leu His Ala Ala Asn Val Leu
            820                 825                 830

Cys Arg Glu Leu Asn Cys Gly Asp Ala Ile Ser Leu Ser Val Gly Asp
        835                 840                 845

His Phe Gly Lys Gly Asn Gly Leu Thr Trp Ala Glu Lys Phe Gln Cys
    850                 855                 860

Glu Gly Ser Glu Thr His Leu Ala Leu Cys Pro Ile Val Gln His Pro
865                 870                 875                 880

Glu Asp Thr Cys Ile His Ser Arg Glu Val Gly Val Val Cys Ser Arg
                885                 890                 895

Tyr Thr Asp Val Arg Leu Val Asn Gly Lys Ser Gln Cys Asp Gly Gln
            900                 905                 910

Val Glu Ile Asn Val Leu Gly His Trp Gly Ser Leu Cys Asp Thr His
        915                 920                 925

Trp Asp Pro Glu Asp Ala Arg Val Leu Cys Arg Gln Leu Ser Cys Gly
    930                 935                 940

Thr Ala Leu Ser Thr Thr Gly Gly Lys Tyr Ile Gly Glu Arg Ser Val
945                 950                 955                 960

Arg Val Trp Gly His Arg Phe His Cys Leu Gly Asn Glu Ser Leu Leu
                965                 970                 975

Asp Asn Cys Gln Met Thr Val Leu Gly Ala Pro Pro Cys Ile His Gly
            980                 985                 990

Asn Thr Val Ser Val Ile Cys Thr Gly Ser Leu Thr Gln Pro Leu Phe
        995                 1000                1005

Pro Cys Leu Ala Asn Val Ser Asp Pro Tyr Leu Ser Ala Val Pro Glu
   1010                 1015                1020

Gly Ser Ala Leu Ile Cys Leu Glu Asp Lys Arg Leu Arg Leu Val Asp
1025                1030                1035                1040

Gly Asp Ser Arg Cys Ala Gly Arg Val Glu Ile Tyr His Asp Gly Phe
               1045                1050                1055

Trp Gly Thr Ile Cys Asp Asp Gly Trp Asp Leu Ser Asp Ala His Val
           1060                1065                1070

Val Cys Gln Lys Leu Gly Cys Gly Val Ala Phe Asn Ala Thr Val Ser
       1075                1080                1085

Ala His Phe Gly Glu Gly Ser Gly Pro Ile Trp Leu Asp Asp Leu Asn
   1090                1095                1100

Cys Thr Gly Thr Glu Ser His Leu Trp Gln Cys Pro Ser Arg Gly Trp
1105                1110                1115                1120
```

-continued

```
Gly Gln His Asp Cys Arg His Lys Glu Asp Ala Gly Val Ile Cys Ser
                1125                1130                1135

Glu Phe Thr Ala Leu Arg Leu Tyr Ser Glu Thr Glu Thr Glu Ser Cys
            1140                1145                1150

Ala Gly Arg Leu Glu Val Phe Tyr Asn Gly Thr Trp Gly Ser Val Gly
        1155                1160                1165

Arg Arg Asn Ile Thr Thr Ala Ile Ala Gly Ile Val Cys Arg Gln Leu
    1170                1175                1180

Gly Cys Gly Glu Asn Gly Val Val Ser Leu Ala Pro Leu Ser Lys Thr
1185                1190                1195                1200

Gly Ser Gly Phe Met Trp Val Asp Asp Ile Gln Cys Pro Lys Thr His
                1205                1210                1215

Ile Ser Ile Trp Gln Cys Leu Ser Ala Pro Trp Glu Arg Arg Ile Ser
            1220                1225                1230

Ser Pro Ala Glu Glu Thr Trp Ile Thr Cys Glu Asp Arg Ile Arg Val
        1235                1240                1245

Arg Gly Gly Asp Thr Glu Cys Ser Gly Arg Val Glu Ile Trp His Ala
    1250                1255                1260

Gly Ser Trp Gly Thr Val Cys Asp Asp Ser Trp Asp Leu Ala Glu Ala
1265                1270                1275                1280

Glu Val Val Cys Gln Gln Leu Gly Cys Gly Ser Ala Leu Ala Ala Leu
                1285                1290                1295

Arg Asp Ala Ser Phe Gly Gln Gly Thr Gly Thr Ile Trp Leu Asp Asp
            1300                1305                1310

Met Arg Cys Lys Gly Asn Glu Ser Phe Leu Trp Asp Cys His Ala Lys
        1315                1320                1325

Pro Trp Gly Gln Ser Asp Cys Gly His Lys Glu Asp Ala Gly Val Arg
    1330                1335                1340

Cys Ser Gly Gln Ser Leu Lys Ser Leu Asn Ala Ser Ser Gly His Leu
1345                1350                1355                1360

Ala Leu Ile Leu Ser Ser Ile Phe Gly Leu Leu Leu Leu Val Leu Phe
                1365                1370                1375

Ile Leu Phe Leu Thr Trp Cys Arg Val Gln Lys Gln Lys His Leu Pro
            1380                1385                1390

Leu Arg Val Ser Thr Arg Arg Arg Gly Ser Leu Glu Glu Asn Leu Phe
        1395                1400                1405

His Glu Met Glu Thr Cys Leu Lys Arg Glu Asp Pro His Gly Thr Arg
    1410                1415                1420

Thr Ser Asp Asp Thr Pro Asn His Gly Cys Glu Asp Ala Ser Asp Thr
1425                1430                1435                1440

Ser Leu Leu Gly Val Leu Pro Ala Ser Glu Ala Thr Lys
                1445                1450


<210> SEQ ID NO 12
<211> LENGTH: 40
<212> TYPE: PRT
<213> ORGANISM: Homo sapiens

<400> SEQUENCE: 12

Met Met Leu Pro Gln Asn Ser Trp His Ile Asp Phe Gly Arg Cys Cys
  1               5                  10                  15

Cys His Gln Asn Leu Phe Ser Ala Val Val Thr Cys Ile Leu Leu Leu
             20                  25                  30

Asn Ser Cys Phe Leu Ile Ser Ser
```

-continued

```
        35                  40


<210> SEQ ID NO 13
<211> LENGTH: 1413
<212> TYPE: PRT
<213> ORGANISM: Homo sapiens

<400> SEQUENCE: 13

Phe Asn Gly Thr Asp Leu Glu Leu Arg Leu Val Asn Gly Asp Gly Pro
  1               5                  10                  15

Cys Ser Gly Thr Val Glu Val Lys Phe Gln Gly Gln Trp Gly Thr Val
             20                  25                  30

Cys Asp Asp Gly Trp Asn Thr Thr Ala Ser Thr Val Val Cys Lys Gln
         35                  40                  45

Leu Gly Cys Pro Phe Ser Phe Ala Met Phe Arg Phe Gly Gln Ala Val
     50                  55                  60

Thr Arg His Gly Lys Ile Trp Leu Asp Asp Val Ser Cys Tyr Gly Asn
 65                  70                  75                  80

Glu Ser Ala Leu Trp Glu Cys Gln His Arg Glu Trp Gly Ser His Asn
                 85                  90                  95

Cys Tyr His Gly Glu Asp Val Gly Val Asn Cys Tyr Gly Glu Ala Asn
            100                 105                 110

Leu Gly Leu Arg Leu Val Asp Gly Asn Asn Ser Cys Ser Gly Arg Val
        115                 120                 125

Glu Val Lys Phe Gln Glu Arg Trp Gly Thr Ile Cys Asp Asp Gly Trp
    130                 135                 140

Asn Leu Asn Thr Ala Ala Val Val Cys Arg Gln Leu Gly Cys Pro Ser
145                 150                 155                 160

Ser Phe Ile Ser Ser Gly Val Val Asn Ser Pro Ala Val Leu Arg Pro
                165                 170                 175

Ile Trp Leu Asp Asp Ile Leu Cys Gln Gly Asn Glu Leu Ala Leu Trp
            180                 185                 190

Asn Cys Arg His Arg Gly Trp Gly Asn His Asp Cys Ser His Asn Glu
        195                 200                 205

Asp Val Thr Leu Thr Cys Tyr Asp Ser Ser Asp Leu Glu Leu Arg Leu
    210                 215                 220

Val Gly Gly Thr Asn Arg Cys Met Gly Arg Val Glu Leu Lys Ile Gln
225                 230                 235                 240

Gly Arg Trp Gly Thr Val Cys His His Lys Trp Asn Asn Ala Ala Ala
                245                 250                 255

Asp Val Val Cys Lys Gln Leu Gly Cys Gly Thr Ala Leu His Phe Ala
            260                 265                 270

Gly Leu Pro His Leu Gln Ser Gly Ser Asp Val Val Trp Leu Asp Gly
        275                 280                 285

Val Ser Cys Ser Gly Asn Glu Ser Phe Leu Trp Asp Cys Arg His Ser
    290                 295                 300

Gly Thr Val Asn Phe Asp Cys Leu His Gln Asn Asp Val Ser Val Ile
305                 310                 315                 320

Cys Ser Asp Gly Ala Asp Leu Glu Leu Arg Leu Ala Asp Gly Ser Asn
                325                 330                 335

Asn Cys Ser Gly Arg Val Glu Val Arg Ile His Glu Gln Trp Trp Thr
            340                 345                 350

Ile Cys Asp Gln Asn Trp Lys Asn Glu Gln Ala Leu Val Val Cys Lys
        355                 360                 365
```

-continued

```
Gln Leu Gly Cys Pro Phe Ser Val Phe Gly Ser Arg Arg Ala Lys Pro
    370                 375                 380

Ser Asn Glu Ala Arg Asp Ile Trp Ile Asn Ser Ile Ser Cys Thr Gly
385                 390                 395                 400

Asn Glu Ser Ala Leu Trp Asp Cys Thr Tyr Asp Gly Lys Ala Lys Arg
                405                 410                 415

Thr Cys Phe Arg Arg Ser Asp Ala Gly Val Ile Cys Ser Asp Lys Ala
            420                 425                 430

Asp Leu Asp Leu Arg Leu Val Gly Ala His Ser Pro Cys Tyr Gly Arg
        435                 440                 445

Leu Glu Val Lys Tyr Gln Gly Glu Trp Gly Thr Val Cys His Asp Arg
    450                 455                 460

Trp Ser Thr Arg Asn Ala Ala Val Val Cys Lys Gln Leu Gly Cys Gly
465                 470                 475                 480

Lys Pro Met His Val Phe Gly Met Thr Tyr Phe Lys Glu Ala Ser Gly
                485                 490                 495

Pro Ile Trp Leu Asp Asp Val Ser Cys Ile Gly Asn Glu Ser Asn Ile
            500                 505                 510

Trp Asp Cys Glu His Ser Gly Trp Gly Lys His Asn Cys Val His Arg
        515                 520                 525

Glu Asp Val Ile Val Thr Cys Ser Gly Asp Ala Thr Trp Gly Leu Arg
    530                 535                 540

Leu Val Gly Gly Ser Asn Arg Cys Ser Gly Arg Leu Glu Val Tyr Phe
545                 550                 555                 560

Gln Gly Arg Trp Gly Thr Val Cys Asp Asp Gly Trp Asn Ser Lys Ala
                565                 570                 575

Ala Ala Val Val Cys Ser Gln Leu Asp Cys Pro Ser Ser Ile Ile Gly
            580                 585                 590

Met Gly Leu Gly Asn Ala Ser Thr Gly Tyr Gly Lys Ile Trp Leu Asp
        595                 600                 605

Asp Val Ser Cys Asp Gly Asp Glu Ser Asp Leu Trp Ser Cys Arg Asn
    610                 615                 620

Ser Gly Trp Gly Asn Asn Asp Cys Ser His Ser Glu Asp Val Gly Val
625                 630                 635                 640

Ile Cys Ser Asp Ala Ser Asp Met Glu Leu Arg Leu Val Gly Gly Ser
                645                 650                 655

Ser Arg Cys Ala Gly Lys Val Glu Val Asn Val Gln Gly Ala Val Gly
            660                 665                 670

Ile Leu Cys Ala Asn Gly Trp Gly Met Asn Ile Ala Glu Val Val Cys
        675                 680                 685

Arg Gln Leu Glu Cys Gly Ser Ala Ile Arg Val Ser Arg Glu Pro His
    690                 695                 700

Phe Thr Glu Arg Thr Leu His Ile Leu Met Ser Asn Ser Gly Cys Thr
705                 710                 715                 720

Gly Gly Glu Ala Ser Leu Trp Asp Cys Ile Arg Trp Glu Trp Lys Gln
                725                 730                 735

Thr Ala Cys His Leu Asn Met Glu Ala Ser Leu Ile Cys Ser Ala His
            740                 745                 750

Arg Gln Pro Arg Leu Val Gly Ala Asp Met Pro Cys Ser Gly Arg Val
        755                 760                 765

Glu Val Lys His Ala Asp Thr Trp Arg Ser Val Cys Asp Ser Asp Phe
    770                 775                 780

Ser Leu His Ala Ala Asn Val Leu Cys Arg Glu Leu Asn Cys Gly Asp
```

-continued 785 790 795 800

Ala Ile Ser Leu Ser Val Gly Asp His Phe Gly Lys Gly Asn Gly Leu
805 810 815

Thr Trp Ala Glu Lys Phe Gln Cys Glu Gly Ser Glu Thr His Leu Ala
820 825 830

Leu Cys Pro Ile Val Gln His Pro Glu Asp Thr Cys Ile His Ser Arg
835 840 845

Glu Val Gly Val Val Cys Ser Arg Tyr Thr Asp Val Arg Leu Val Asn
850 855 860

Gly Lys Ser Gln Cys Asp Gly Gln Val Glu Ile Asn Val Leu Gly His
865 870 875 880

Trp Gly Ser Leu Cys Asp Thr His Trp Asp Pro Glu Asp Ala Arg Val
885 890 895

Leu Cys Arg Gln Leu Ser Cys Gly Thr Ala Leu Ser Thr Thr Gly Gly
900 905 910

Lys Tyr Ile Gly Glu Arg Ser Val Arg Val Trp Gly His Arg Phe His
915 920 925

Cys Leu Gly Asn Glu Ser Leu Leu Asp Asn Cys Gln Met Thr Val Leu
930 935 940

Gly Ala Pro Pro Cys Ile His Gly Asn Thr Val Ser Val Ile Cys Thr
945 950 955 960

Gly Ser Leu Thr Gln Pro Leu Phe Pro Cys Leu Ala Asn Val Ser Asp
965 970 975

Pro Tyr Leu Ser Ala Val Pro Glu Gly Ser Ala Leu Ile Cys Leu Glu
980 985 990

Asp Lys Arg Leu Arg Leu Val Asp Gly Asp Ser Arg Cys Ala Gly Arg
995 1000 1005

Val Glu Ile Tyr His Asp Gly Phe Trp Gly Thr Ile Cys Asp Asp Gly
1010 1015 1020

Trp Asp Leu Ser Asp Ala His Val Val Cys Gln Lys Leu Gly Cys Gly
1025 1030 1035 1040

Val Ala Phe Asn Ala Thr Val Ser Ala His Phe Gly Glu Gly Ser Gly
1045 1050 1055

Pro Ile Trp Leu Asp Asp Leu Asn Cys Thr Gly Thr Glu Ser His Leu
1060 1065 1070

Trp Gln Cys Pro Ser Arg Gly Trp Gly Gln His Asp Cys Arg His Lys
1075 1080 1085

Glu Asp Ala Gly Val Ile Cys Ser Glu Phe Thr Ala Leu Arg Leu Tyr
1090 1095 1100

Ser Glu Thr Glu Thr Glu Ser Cys Ala Gly Arg Leu Glu Val Phe Tyr
1105 1110 1115 1120

Asn Gly Thr Trp Gly Ser Val Gly Arg Arg Asn Ile Thr Thr Ala Ile
1125 1130 1135

Ala Gly Ile Val Cys Arg Gln Leu Gly Cys Gly Glu Asn Gly Val Val
1140 1145 1150

Ser Leu Ala Pro Leu Ser Lys Thr Gly Ser Gly Phe Met Trp Val Asp
1155 1160 1165

Asp Ile Gln Cys Pro Lys Thr His Ile Ser Ile Trp Gln Cys Leu Ser
1170 1175 1180

Ala Pro Trp Glu Arg Arg Ile Ser Ser Pro Ala Glu Glu Thr Trp Ile
1185 1190 1195 1200

Thr Cys Glu Asp Arg Ile Arg Val Arg Gly Gly Asp Thr Glu Cys Ser
1205 1210 1215

-continued

```
Gly Arg Val Glu Ile Trp His Ala Gly Ser Trp Gly Thr Val Cys Asp
          1220                1225                1230

Asp Ser Trp Asp Leu Ala Glu Ala Glu Val Val Cys Gln Gln Leu Gly
      1235                1240                1245

Cys Gly Ser Ala Leu Ala Ala Leu Arg Asp Ala Ser Phe Gly Gln Gly
   1250                1255                1260

Thr Gly Thr Ile Trp Leu Asp Asp Met Arg Cys Lys Gly Asn Glu Ser
1265                1270                1275                1280

Phe Leu Trp Asp Cys His Ala Lys Pro Trp Gly Gln Ser Asp Cys Gly
              1285                1290                1295

His Lys Glu Asp Ala Gly Val Arg Cys Ser Gly Gln Ser Leu Lys Ser
          1300                1305                1310

Leu Asn Ala Ser Ser Gly His Leu Ala Leu Ile Leu Ser Ser Ile Phe
      1315                1320                1325

Gly Leu Leu Leu Leu Val Leu Phe Ile Leu Phe Leu Thr Trp Cys Arg
   1330                1335                1340

Val Gln Lys Gln Lys His Leu Pro Leu Arg Val Ser Thr Arg Arg Arg
1345                1350                1355                1360

Gly Ser Leu Glu Glu Asn Leu Phe His Glu Met Glu Thr Cys Leu Lys
              1365                1370                1375

Arg Glu Asp Pro His Gly Thr Arg Thr Ser Asp Asp Thr Pro Asn His
          1380                1385                1390

Gly Cys Glu Asp Ala Ser Asp Thr Ser Leu Leu Gly Val Leu Pro Ala
      1395                1400                1405

Ser Glu Ala Thr Lys
   1410


<210> SEQ ID NO 14
<211> LENGTH: 1319
<212> TYPE: PRT
<213> ORGANISM: Homo sapiens

<400> SEQUENCE: 14

Phe Asn Gly Thr Asp Leu Glu Leu Arg Leu Val Asn Gly Asp Gly Pro
  1               5                  10                  15

Cys Ser Gly Thr Val Glu Val Lys Phe Gln Gly Gln Trp Gly Thr Val
             20                  25                  30

Cys Asp Asp Gly Trp Asn Thr Thr Ala Ser Thr Val Val Cys Lys Gln
         35                  40                  45

Leu Gly Cys Pro Phe Ser Phe Ala Met Phe Arg Phe Gly Gln Ala Val
     50                  55                  60

Thr Arg His Gly Lys Ile Trp Leu Asp Asp Val Ser Cys Tyr Gly Asn
 65                  70                  75                  80

Glu Ser Ala Leu Trp Glu Cys Gln His Arg Glu Trp Gly Ser His Asn
                 85                  90                  95

Cys Tyr His Gly Glu Asp Val Gly Val Asn Cys Tyr Gly Glu Ala Asn
            100                 105                 110

Leu Gly Leu Arg Leu Val Asp Gly Asn Asn Ser Cys Ser Gly Arg Val
        115                 120                 125

Glu Val Lys Phe Gln Glu Arg Trp Gly Thr Ile Cys Asp Asp Gly Trp
    130                 135                 140

Asn Leu Asn Thr Ala Ala Val Val Cys Arg Gln Leu Gly Cys Pro Ser
145                 150                 155                 160

Ser Phe Ile Ser Ser Gly Val Val Asn Ser Pro Ala Val Leu Arg Pro
```

-continued

```
                165                 170                 175

Ile Trp Leu Asp Asp Ile Leu Cys Gln Gly Asn Glu Leu Ala Leu Trp
            180                 185                 190

Asn Cys Arg His Arg Gly Trp Gly Asn His Asp Cys Ser His Asn Glu
        195                 200                 205

Asp Val Thr Leu Thr Cys Tyr Asp Ser Ser Asp Leu Glu Leu Arg Leu
    210                 215                 220

Val Gly Gly Thr Asn Arg Cys Met Gly Arg Val Glu Leu Lys Ile Gln
225                 230                 235                 240

Gly Arg Trp Gly Thr Val Cys His His Lys Trp Asn Asn Ala Ala Ala
                245                 250                 255

Asp Val Val Cys Lys Gln Leu Gly Cys Gly Thr Ala Leu His Phe Ala
            260                 265                 270

Gly Leu Pro His Leu Gln Ser Gly Ser Asp Val Val Trp Leu Asp Gly
        275                 280                 285

Val Ser Cys Ser Gly Asn Glu Ser Phe Leu Trp Asp Cys Arg His Ser
    290                 295                 300

Gly Thr Val Asn Phe Asp Cys Leu His Gln Asn Asp Val Ser Val Ile
305                 310                 315                 320

Cys Ser Asp Gly Ala Asp Leu Glu Leu Arg Leu Ala Asp Gly Ser Asn
                325                 330                 335

Asn Cys Ser Gly Arg Val Glu Val Arg Ile His Glu Gln Trp Trp Thr
            340                 345                 350

Ile Cys Asp Gln Asn Trp Lys Asn Glu Gln Ala Leu Val Val Cys Lys
        355                 360                 365

Gln Leu Gly Cys Pro Phe Ser Val Phe Gly Ser Arg Arg Ala Lys Pro
    370                 375                 380

Ser Asn Glu Ala Arg Asp Ile Trp Ile Asn Ser Ile Ser Cys Thr Gly
385                 390                 395                 400

Asn Glu Ser Ala Leu Trp Asp Cys Thr Tyr Asp Gly Lys Ala Lys Arg
                405                 410                 415

Thr Cys Phe Arg Arg Ser Asp Ala Gly Val Ile Cys Ser Asp Lys Ala
            420                 425                 430

Asp Leu Asp Leu Arg Leu Val Gly Ala His Ser Pro Cys Tyr Gly Arg
        435                 440                 445

Leu Glu Val Lys Tyr Gln Gly Glu Trp Gly Thr Val Cys His Asp Arg
    450                 455                 460

Trp Ser Thr Arg Asn Ala Ala Val Val Cys Lys Gln Leu Gly Cys Gly
465                 470                 475                 480

Lys Pro Met His Val Phe Gly Met Thr Tyr Phe Lys Glu Ala Ser Gly
                485                 490                 495

Pro Ile Trp Leu Asp Asp Val Ser Cys Ile Gly Asn Glu Ser Asn Ile
            500                 505                 510

Trp Asp Cys Glu His Ser Gly Trp Gly Lys His Asn Cys Val His Arg
        515                 520                 525

Glu Asp Val Ile Val Thr Cys Ser Gly Asp Ala Thr Trp Gly Leu Arg
    530                 535                 540

Leu Val Gly Gly Ser Asn Arg Cys Ser Gly Arg Leu Glu Val Tyr Phe
545                 550                 555                 560

Gln Gly Arg Trp Gly Thr Val Cys Asp Asp Gly Trp Asn Ser Lys Ala
                565                 570                 575

Ala Ala Val Val Cys Ser Gln Leu Asp Cys Pro Ser Ser Ile Ile Gly
            580                 585                 590
```

-continued

```
Met Gly Leu Gly Asn Ala Ser Thr Gly Tyr Gly Lys Ile Trp Leu Asp
        595                 600                 605

Asp Val Ser Cys Asp Gly Asp Glu Ser Asp Leu Trp Ser Cys Arg Asn
    610                 615                 620

Ser Gly Trp Gly Asn Asn Asp Cys Ser His Ser Glu Asp Val Gly Val
625                 630                 635                 640

Ile Cys Ser Asp Ala Ser Asp Met Glu Leu Arg Leu Val Gly Gly Ser
                645                 650                 655

Ser Arg Cys Ala Gly Lys Val Glu Val Asn Val Gln Gly Ala Val Gly
            660                 665                 670

Ile Leu Cys Ala Asn Gly Trp Gly Met Asn Ile Ala Glu Val Val Cys
        675                 680                 685

Arg Gln Leu Glu Cys Gly Ser Ala Ile Arg Val Ser Arg Glu Pro His
    690                 695                 700

Phe Thr Glu Arg Thr Leu His Ile Leu Met Ser Asn Ser Gly Cys Thr
705                 710                 715                 720

Gly Gly Glu Ala Ser Leu Trp Asp Cys Ile Arg Trp Glu Trp Lys Gln
                725                 730                 735

Thr Ala Cys His Leu Asn Met Glu Ala Ser Leu Ile Cys Ser Ala His
            740                 745                 750

Arg Gln Pro Arg Leu Val Gly Ala Asp Met Pro Cys Ser Gly Arg Val
        755                 760                 765

Glu Val Lys His Ala Asp Thr Trp Arg Ser Val Cys Asp Ser Asp Phe
    770                 775                 780

Ser Leu His Ala Ala Asn Val Leu Cys Arg Glu Leu Asn Cys Gly Asp
785                 790                 795                 800

Ala Ile Ser Leu Ser Val Gly Asp His Phe Gly Lys Gly Asn Gly Leu
                805                 810                 815

Thr Trp Ala Glu Lys Phe Gln Cys Glu Gly Ser Glu Thr His Leu Ala
            820                 825                 830

Leu Cys Pro Ile Val Gln His Pro Glu Asp Thr Cys Ile His Ser Arg
        835                 840                 845

Glu Val Gly Val Val Cys Ser Arg Tyr Thr Asp Val Arg Leu Val Asn
    850                 855                 860

Gly Lys Ser Gln Cys Asp Gly Gln Val Glu Ile Asn Val Leu Gly His
865                 870                 875                 880

Trp Gly Ser Leu Cys Asp Thr His Trp Asp Pro Glu Asp Ala Arg Val
                885                 890                 895

Leu Cys Arg Gln Leu Ser Cys Gly Thr Ala Leu Ser Thr Thr Gly Gly
            900                 905                 910

Lys Tyr Ile Gly Glu Arg Ser Val Arg Val Trp Gly His Arg Phe His
        915                 920                 925

Cys Leu Gly Asn Glu Ser Leu Leu Asp Asn Cys Gln Met Thr Val Leu
    930                 935                 940

Gly Ala Pro Pro Cys Ile His Gly Asn Thr Val Ser Val Ile Cys Thr
945                 950                 955                 960

Gly Ser Leu Thr Gln Pro Leu Phe Pro Cys Leu Ala Asn Val Ser Asp
                965                 970                 975

Pro Tyr Leu Ser Ala Val Pro Glu Gly Ser Ala Leu Ile Cys Leu Glu
            980                 985                 990

Asp Lys Arg Leu Arg Leu Val Asp Gly Asp Ser Arg Cys Ala Gly Arg
        995                1000                1005
```

-continued

```
Val Glu Ile Tyr His Asp Gly Phe Trp Gly Thr Ile Cys Asp Asp Gly
   1010                1015                1020

Trp Asp Leu Ser Asp Ala His Val Val Cys Gln Lys Leu Gly Cys Gly
1025                1030                1035                1040

Val Ala Phe Asn Ala Thr Val Ser Ala His Phe Gly Glu Gly Ser Gly
                1045                1050                1055

Pro Ile Trp Leu Asp Asp Leu Asn Cys Thr Gly Thr Glu Ser His Leu
            1060                1065                1070

Trp Gln Cys Pro Ser Arg Gly Trp Gly Gln His Asp Cys Arg His Lys
        1075                1080                1085

Glu Asp Ala Gly Val Ile Cys Ser Glu Phe Thr Ala Leu Arg Leu Tyr
   1090                1095                1100

Ser Glu Thr Glu Thr Glu Ser Cys Ala Gly Arg Leu Glu Val Phe Tyr
1105                1110                1115                1120

Asn Gly Thr Trp Gly Ser Val Gly Arg Arg Asn Ile Thr Thr Ala Ile
                1125                1130                1135

Ala Gly Ile Val Cys Arg Gln Leu Gly Cys Gly Glu Asn Gly Val Val
            1140                1145                1150

Ser Leu Ala Pro Leu Ser Lys Thr Gly Ser Gly Phe Met Trp Val Asp
        1155                1160                1165

Asp Ile Gln Cys Pro Lys Thr His Ile Ser Ile Trp Gln Cys Leu Ser
   1170                1175                1180

Ala Pro Trp Glu Arg Arg Ile Ser Ser Pro Ala Glu Glu Thr Trp Ile
1185                1190                1195                1200

Thr Cys Glu Asp Arg Ile Arg Val Arg Gly Gly Asp Thr Glu Cys Ser
                1205                1210                1215

Gly Arg Val Glu Ile Trp His Ala Gly Ser Trp Gly Thr Val Cys Asp
            1220                1225                1230

Asp Ser Trp Asp Leu Ala Glu Ala Glu Val Val Cys Gln Gln Leu Gly
        1235                1240                1245

Cys Gly Ser Ala Leu Ala Ala Leu Arg Asp Ala Ser Phe Gly Gln Gly
   1250                1255                1260

Thr Gly Thr Ile Trp Leu Asp Asp Met Arg Cys Lys Gly Asn Glu Ser
1265                1270                1275                1280

Phe Leu Trp Asp Cys His Ala Lys Pro Trp Gly Gln Ser Asp Cys Gly
                1285                1290                1295

His Lys Glu Asp Ala Gly Val Arg Cys Ser Gly Gln Ser Leu Lys Ser
            1300                1305                1310

Leu Asn Ala Ser Ser Gly His
        1315


<210> SEQ ID NO 15
<211> LENGTH: 24
<212> TYPE: PRT
<213> ORGANISM: Homo sapiens

<400> SEQUENCE: 15

Leu Ala Leu Ile Leu Ser Ser Ile Phe Gly Leu Leu Leu Leu Val Leu
  1               5                  10                  15

Phe Ile Leu Phe Leu Thr Trp Cys
             20


<210> SEQ ID NO 16
<211> LENGTH: 70
<212> TYPE: PRT
<213> ORGANISM: Homo sapiens
```

-continued

<400> SEQUENCE: 16

```
Arg Val Gln Lys Gln Lys His Leu Pro Leu Arg Val Ser Thr Arg Arg
  1               5                  10                  15

Arg Gly Ser Leu Glu Glu Asn Leu Phe His Glu Met Glu Thr Cys Leu
             20                  25                  30

Lys Arg Glu Asp Pro His Gly Thr Arg Thr Ser Asp Asp Thr Pro Asn
         35                  40                  45

His Gly Cys Glu Asp Ala Ser Asp Thr Ser Leu Leu Gly Val Leu Pro
     50                  55                  60

Ala Ser Glu Ala Thr Lys
 65                  70
```

<210> SEQ ID NO 17
<211> LENGTH: 3104
<212> TYPE: DNA
<213> ORGANISM: Homo sapiens

<400> SEQUENCE: 17

```
gtcgacccac gcgtccggtc tgtggctgag catggccctc ccagccctgg gcctggaccc     60
ctggagcctc ctgggccttt tcctcttcca actgcttcag ctgctgctgc cgacgacgac    120
cgcgggggga ggcgggcagg ggcccatgcc caggtcaga tactatgcag gggatgaacg    180
tagggcactt agcttcttcc accagaaggg cctccaggat tttgacactc tgctcctgag    240
tggtgatgga aatactctct acgtgggggc tcgagaagcc attctggcct tggatatcca    300
ggatccaggg gtccccaggc taaagaacat gataccgtgg ccagccagtg acagaaaaaa    360
gagtgaatgt gcctttaaga agaagagcaa tgagacacag tgtttcaact tcatccgtgt    420
cctggtttct tacaatgtca cccatctcta cacctgcggc accttcgcct tcagccctgc    480
ttgtaccttc attgaacttc aagattccta cctgttgccc atctcggagg acaaggtcat    540
ggagggaaaa ggccaaagcc cctttgaccc cgctcacaag catacggctg tcttggtgga    600
tgggatgctc tattctggta ctatgaacaa cttcctgggc agtgagccca tcctgatgcg    660
cacactggga tcccagcctg tcctcaagac cgacaacttc ctccgctggc tgcatcatga    720
cgcctccttt gtggcagcca tcccttcgac ccaggtcgtc tacttcttct tcgaggagac    780
agccagcgag tttgacttct ttgagaggct ccacacatcg cgggtggcta gagtctgcaa    840
gaatgacgtg ggcggcgaaa agctgctgca gaagaagtgg accaccttcc tgaaggccca    900
gctgctctgc acccagccgg ggcagctgcc cttcaacgtc atccgccacg cggtcctgct    960
ccccgccgat tctcccacag ctccccacat ctacgcagtc ttcacctccc agtggcaggt   1020
tggcgggacc aggagctctg cggtttgtgc cttctctctc ttggacattg aacgtgtctt   1080
taaggggaaa tacaaagagt tgaacaaaga aacttcacgc tggactactt ataggggccc   1140
tgagaccaac ccccggccag gcagttgctc agtgggcccc tcctctgata aggccctgac   1200
cttcatgaag gaccatttcc tgatggatga gcaagtggtg gggacgcccc tgctggtgaa   1260
atctggcgtg gagtatacac ggcttgcagt ggagacagcc cagggccttg atgggcacag   1320
ccatcttgtc atgtacctgg gaaccaccac agggtcgctc cacaaggctg tggtaagtgg   1380
ggacagcagt gctcatctgg tggaagagat tcagctgttc cctgaccctg aacctgttcg   1440
caacctgcag ctggccccca cccagggtgc agtgtttgta ggcttctcag gaggtgtctg   1500
gagggtgccc cgagccaact gtagtgtcta tgagagctgt gtggactgtg tccttgcccg   1560
ggacccccac tgtgcctggg accctgagtc ccgaacctgt tgcctcctgt ctgcccccaa   1620
```

-continued

```
cctgaactcc tggaagcagg acatggagcg ggggaaccca gagtgggcat gtgccagtgg   1680
ccccatgagc aggagccttc ggcctcagag ccgcccgcaa atcattaaag aagtcctggc   1740
tgtccccaac tccatcctgg agctcccctg cccccacctg tcagccttgg cctcttatta   1800
ttggagtcat ggcccagcag cagtcccaga agcctcttcc actgtctaca atggctccct   1860
cttgctgata gtgcaggatg gagttggggg tctctaccag tgctgggcaa ctgagaatgg   1920
cttttcatac cctgtgatct cctactgggt ggacagccag gaccagaccc tggccctgga   1980
tcctgaactg gcaggcatcc cccgggagca tgtgaaggtc ccgttgacca gggtcagtgg   2040
tggggccgcc ctggctgccc agcagtccta ctggccccac tttgtcactg tcactgtcct   2100
ctttgcctta gtgctttcag gagccctcat catcctcgtg gcctccccat tgagagcact   2160
ccgggctcgg ggcaaggttc agggctgtga gaccctgcgc cctggggaga aggccccgtt   2220
aagcagagag caacacctcc agtctcccaa ggaatgcagg acctctgcca gtgatgtgga   2280
cgctgacaac aactgcctag gcactgaggt agcttaaact ctaggcacag gccggggctg   2340
cggtgcaggc acctggccat gctggctggg cggcccaagc acagccctga ctaggatgac   2400
agcagcacaa aagaccacct ttctcccctg agaggagctt ctgctactct gcatcactga   2460
tgacactcag cagggtgatg cacagcagtc tgcctcccct atgggactcc cttctaccaa   2520
gcacatgagc tctctaacag ggtgggggct acccccagac ctgctcctac actgatattg   2580
aagaacctgg agaggatcct tcagttctgg ccattccagg gaccctccag aaacacagtg   2640
tttcaagaga tcctaaaaaa acctgcctgt cccaggaccc tatggtaatg aacaccaaac   2700
atctaaacaa tcatatgcta acatgccact cctggaaact ccactctgaa gctgccgctt   2760
tggacaccaa cactcccttc tcccagggtc atgcagggat ctgctccctc ctgcttccct   2820
taccagtcgt gcaccgctga ctcccaggaa gtctttcctg aagtctgacc acctttcttc   2880
ttgcttcagt tggggcagac tctgatccct tctgccctgg cagaatggca ggggtaatct   2940
gagccttctt cactccttta ccctagctga ccccttcacc tctcccctc cttttcctt   3000
tgttttggga ttcagaaaac tgcttgtcag agactgttta ttttttatta aaaatataag   3060
gcttaaaaaa aaaaaaaaaa aaaaaaaaaa aaaagggcgg ccgc                   3104
```

<210> SEQ ID NO 18
<211> LENGTH: 2283
<212> TYPE: DNA
<213> ORGANISM: Homo sapiens

<400> SEQUENCE: 18

```
atggccctcc cagccctggg cctggacccc tggagcctcc tgggcctttt cctcttccaa     60
ctgcttcagc tgctgctgcc gacgacgacc gcgggggggag gcgggcaggg gcccatgccc   120
agggtcagat actatgcagg ggatgaacgt agggcactta gcttcttcca ccagaagggc   180
ctccaggatt ttgacactct gctcctgagt ggtgatggaa atactctcta cgtgggggct   240
cgagaagcca ttctggcctt ggatatccag gatccagggg tccccaggct aaagaacatg   300
ataccgtggc cagccagtga cagaaaaaag agtgaatgtg cctttaagaa gaagagcaat   360
gagacacagt gtttcaactt catccgtgtc ctggtttctt acaatgtcac ccatctctac   420
acctgcggca ccttcgcctt cagccctgct tgtaccttca ttgaacttca agattcctac   480
ctgttgccca tctcggagga caaggtcatg gagggaaaag gccaaagccc ctttgacccc   540
gctcacaagc atacggctgt cttggtggat gggatgctct attctggtac tatgaacaac   600
```

-continued

```
ttcctgggca gtgagcccat cctgatgcgc acactgggat cccagcctgt cctcaagacc    660

gacaacttcc tccgctggct gcatcatgac gcctcctttg tggcagccat cccttcgacc    720

caggtcgtct acttcttctt cgaggagaca gccagcgagt ttgacttctt tgagaggctc    780

cacacatcgc gggtggctag agtctgcaag aatgacgtgg gcggcgaaaa gctgctgcag    840

aagaagtgga ccaccttcct gaaggcccag ctgctctgca cccagccggg gcagctgccc    900

ttcaacgtca tccgccacgc ggtcctgctc cccgccgatt ctcccacagc tccccacatc    960

tacgcagtct tcacctccca gtggcaggtt ggcgggacca ggagctctgc ggtttgtgcc   1020

ttctctctct tggacattga acgtgtcttt aaggggaaat acaaagagtt gaacaaagaa   1080

acttcacgct ggactactta taggggccct gagaccaacc cccggccagg cagttgctca   1140

gtgggcccct cctctgataa ggccctgacc ttcatgaagg accatttcct gatggatgag   1200

caagtggtgg ggacgcccct gctggtgaaa tctggcgtgg agtatacacg gcttgcagtg   1260

gagacagccc agggccttga tgggcacagc catcttgtca tgtacctggg aaccaccaca   1320

gggtcgctcc acaaggctgt ggtaagtggg gacagcagtg ctcatctggt ggaagagatt   1380

cagctgttcc ctgaccctga acctgttcgc aacctgcagc tggcccccac ccagggtgca   1440

gtgtttgtag gcttctcagg aggtgtctgg agggtgcccc gagccaactg tagtgtctat   1500

gagagctgtg tggactgtgt ccttgcccgg gacccccact gtgcctggga ccctgagtcc   1560

cgaacctgtt gcctcctgtc tgccccccaac ctgaactcct ggaagcagga catggagcgg   1620

gggaacccag agtgggcatg tgccagtggc cccatgagca ggagccttcg gcctcagagc   1680

cgcccgcaaa tcattaaaga agtcctggct gtccccaact ccatcctgga gctcccctgc   1740

ccccacctgt cagccttggc ctcttattat tggagtcatg gcccagcagc agtcccagaa   1800

gcctcttcca ctgtctacaa tggctccctc ttgctgatag tgcaggatgg agttgggggt   1860

ctctaccagt gctgggcaac tgagaatggc ttttcatacc ctgtgatctc ctactgggtg   1920

gacagccagg accagaccct ggccctggat cctgaactgg caggcatccc ccgggagcat   1980

gtgaaggtcc cgttgaccag ggtcagtggt ggggccgccc tggctgccca gcagtcctac   2040

tggccccact ttgtcactgt cactgtcctc tttgccttag tgctttcagg agccctcatc   2100

atcctcgtgg cctccccatt gagagcactc cgggctcggg gcaaggttca gggctgtgag   2160

accctgcgcc ctggggagaa ggccccgtta agcagagagc aacacctcca gtctcccaag   2220

gaatgcagga cctctgccag tgatgtggac gctgacaaca actgcctagg cactgaggta   2280

gct                                                                 2283
```

<210> SEQ ID NO 19
<211> LENGTH: 761
<212> TYPE: PRT
<213> ORGANISM: Homo sapiens

<400> SEQUENCE: 19

```
Met Ala Leu Pro Ala Leu Gly Leu Asp Pro Trp Ser Leu Leu Gly Leu
  1               5                  10                  15

Phe Leu Phe Gln Leu Leu Gln Leu Leu Leu Pro Thr Thr Thr Ala Gly
             20                  25                  30

Gly Gly Gly Gln Gly Pro Met Pro Arg Val Arg Tyr Tyr Ala Gly Asp
         35                  40                  45

Glu Arg Arg Ala Leu Ser Phe Phe His Gln Lys Gly Leu Gln Asp Phe
     50                  55                  60

Asp Thr Leu Leu Leu Ser Gly Asp Gly Asn Thr Leu Tyr Val Gly Ala
```

-continued

```
65                  70                  75                  80

Arg Glu Ala Ile Leu Ala Leu Asp Ile Gln Asp Pro Gly Val Pro Arg
                85                  90                  95

Leu Lys Asn Met Ile Pro Trp Pro Ala Ser Asp Arg Lys Lys Ser Glu
            100                 105                 110

Cys Ala Phe Lys Lys Lys Ser Asn Glu Thr Gln Cys Phe Asn Phe Ile
        115                 120                 125

Arg Val Leu Val Ser Tyr Asn Val Thr His Leu Tyr Thr Cys Gly Thr
    130                 135                 140

Phe Ala Phe Ser Pro Ala Cys Thr Phe Ile Glu Leu Gln Asp Ser Tyr
145                 150                 155                 160

Leu Leu Pro Ile Ser Glu Asp Lys Val Met Glu Gly Lys Gly Gln Ser
                165                 170                 175

Pro Phe Asp Pro Ala His Lys His Thr Ala Val Leu Val Asp Gly Met
            180                 185                 190

Leu Tyr Ser Gly Thr Met Asn Asn Phe Leu Gly Ser Glu Pro Ile Leu
        195                 200                 205

Met Arg Thr Leu Gly Ser Gln Pro Val Leu Lys Thr Asp Asn Phe Leu
    210                 215                 220

Arg Trp Leu His His Asp Ala Ser Phe Val Ala Ala Ile Pro Ser Thr
225                 230                 235                 240

Gln Val Val Tyr Phe Phe Phe Glu Glu Thr Ala Ser Glu Phe Asp Phe
                245                 250                 255

Phe Glu Arg Leu His Thr Ser Arg Val Ala Arg Val Cys Lys Asn Asp
            260                 265                 270

Val Gly Gly Glu Lys Leu Leu Gln Lys Lys Trp Thr Thr Phe Leu Lys
        275                 280                 285

Ala Gln Leu Leu Cys Thr Gln Pro Gly Gln Leu Pro Phe Asn Val Ile
    290                 295                 300

Arg His Ala Val Leu Leu Pro Ala Asp Ser Pro Thr Ala Pro His Ile
305                 310                 315                 320

Tyr Ala Val Phe Thr Ser Gln Trp Gln Val Gly Gly Thr Arg Ser Ser
                325                 330                 335

Ala Val Cys Ala Phe Ser Leu Leu Asp Ile Glu Arg Val Phe Lys Gly
            340                 345                 350

Lys Tyr Lys Glu Leu Asn Lys Glu Thr Ser Arg Trp Thr Thr Tyr Arg
        355                 360                 365

Gly Pro Glu Thr Asn Pro Arg Pro Gly Ser Cys Ser Val Gly Pro Ser
    370                 375                 380

Ser Asp Lys Ala Leu Thr Phe Met Lys Asp His Phe Leu Met Asp Glu
385                 390                 395                 400

Gln Val Val Gly Thr Pro Leu Leu Val Lys Ser Gly Val Glu Tyr Thr
                405                 410                 415

Arg Leu Ala Val Glu Thr Ala Gln Gly Leu Asp Gly His Ser His Leu
            420                 425                 430

Val Met Tyr Leu Gly Thr Thr Thr Gly Ser Leu His Lys Ala Val Val
        435                 440                 445

Ser Gly Asp Ser Ser Ala His Leu Val Glu Glu Ile Gln Leu Phe Pro
    450                 455                 460

Asp Pro Glu Pro Val Arg Asn Leu Gln Leu Ala Pro Thr Gln Gly Ala
465                 470                 475                 480

Val Phe Val Gly Phe Ser Gly Gly Val Trp Arg Val Pro Arg Ala Asn
                485                 490                 495
```

-continued

```
Cys Ser Val Tyr Glu Ser Cys Val Asp Cys Val Leu Ala Arg Asp Pro
            500                 505                 510

His Cys Ala Trp Asp Pro Glu Ser Arg Thr Cys Cys Leu Leu Ser Ala
        515                 520                 525

Pro Asn Leu Asn Ser Trp Lys Gln Asp Met Glu Arg Gly Asn Pro Glu
    530                 535                 540

Trp Ala Cys Ala Ser Gly Pro Met Ser Arg Ser Leu Arg Pro Gln Ser
545                 550                 555                 560

Arg Pro Gln Ile Ile Lys Glu Val Leu Ala Val Pro Asn Ser Ile Leu
                565                 570                 575

Glu Leu Pro Cys Pro His Leu Ser Ala Leu Ala Ser Tyr Tyr Trp Ser
            580                 585                 590

His Gly Pro Ala Ala Val Pro Glu Ala Ser Ser Thr Val Tyr Asn Gly
        595                 600                 605

Ser Leu Leu Leu Ile Val Gln Asp Gly Val Gly Gly Leu Tyr Gln Cys
    610                 615                 620

Trp Ala Thr Glu Asn Gly Phe Ser Tyr Pro Val Ile Ser Tyr Trp Val
625                 630                 635                 640

Asp Ser Gln Asp Gln Thr Leu Ala Leu Asp Pro Glu Leu Ala Gly Ile
                645                 650                 655

Pro Arg Glu His Val Lys Val Pro Leu Thr Arg Val Ser Gly Gly Ala
            660                 665                 670

Ala Leu Ala Ala Gln Gln Ser Tyr Trp Pro His Phe Val Thr Val Thr
        675                 680                 685

Val Leu Phe Ala Leu Val Leu Ser Gly Ala Leu Ile Ile Leu Val Ala
    690                 695                 700

Ser Pro Leu Arg Ala Leu Arg Ala Arg Gly Lys Val Gln Gly Cys Glu
705                 710                 715                 720

Thr Leu Arg Pro Gly Glu Lys Ala Pro Leu Ser Arg Glu Gln His Leu
                725                 730                 735

Gln Ser Pro Lys Glu Cys Arg Thr Ser Ala Ser Asp Val Asp Ala Asp
            740                 745                 750

Asn Asn Cys Leu Gly Thr Glu Val Ala
        755                 760


<210> SEQ ID NO 20
<211> LENGTH: 31
<212> TYPE: PRT
<213> ORGANISM: Homo sapiens

<400> SEQUENCE: 20

Met Ala Leu Pro Ala Leu Gly Leu Asp Pro Trp Ser Leu Leu Gly Leu
  1               5                  10                  15

Phe Leu Phe Gln Leu Leu Gln Leu Leu Leu Pro Thr Thr Thr Ala
             20                  25                  30


<210> SEQ ID NO 21
<211> LENGTH: 730
<212> TYPE: PRT
<213> ORGANISM: Homo sapiens

<400> SEQUENCE: 21

Gly Gly Gly Gly Gln Gly Pro Met Pro Arg Val Arg Tyr Tyr Ala Gly
  1               5                  10                  15

Asp Glu Arg Arg Ala Leu Ser Phe Phe His Gln Lys Gly Leu Gln Asp
             20                  25                  30
```

-continued

```
Phe Asp Thr Leu Leu Leu Ser Gly Asp Gly Asn Thr Leu Tyr Val Gly
        35                  40                  45

Ala Arg Glu Ala Ile Leu Ala Leu Asp Ile Gln Asp Pro Gly Val Pro
    50                  55                  60

Arg Leu Lys Asn Met Ile Pro Trp Pro Ala Ser Asp Arg Lys Lys Ser
65                  70                  75                  80

Glu Cys Ala Phe Lys Lys Lys Ser Asn Glu Thr Gln Cys Phe Asn Phe
                85                  90                  95

Ile Arg Val Leu Val Ser Tyr Asn Val Thr His Leu Tyr Thr Cys Gly
            100                 105                 110

Thr Phe Ala Phe Ser Pro Ala Cys Thr Phe Ile Glu Leu Gln Asp Ser
        115                 120                 125

Tyr Leu Leu Pro Ile Ser Glu Asp Lys Val Met Glu Gly Lys Gly Gln
    130                 135                 140

Ser Pro Phe Asp Pro Ala His Lys His Thr Ala Val Leu Val Asp Gly
145                 150                 155                 160

Met Leu Tyr Ser Gly Thr Met Asn Asn Phe Leu Gly Ser Glu Pro Ile
                165                 170                 175

Leu Met Arg Thr Leu Gly Ser Gln Pro Val Leu Lys Thr Asp Asn Phe
            180                 185                 190

Leu Arg Trp Leu His His Asp Ala Ser Phe Val Ala Ala Ile Pro Ser
        195                 200                 205

Thr Gln Val Val Tyr Phe Phe Phe Glu Glu Thr Ala Ser Glu Phe Asp
    210                 215                 220

Phe Phe Glu Arg Leu His Thr Ser Arg Val Ala Arg Val Cys Lys Asn
225                 230                 235                 240

Asp Val Gly Gly Glu Lys Leu Leu Gln Lys Lys Trp Thr Thr Phe Leu
                245                 250                 255

Lys Ala Gln Leu Leu Cys Thr Gln Pro Gly Gln Leu Pro Phe Asn Val
            260                 265                 270

Ile Arg His Ala Val Leu Leu Pro Ala Asp Ser Pro Thr Ala Pro His
        275                 280                 285

Ile Tyr Ala Val Phe Thr Ser Gln Trp Gln Val Gly Gly Thr Arg Ser
    290                 295                 300

Ser Ala Val Cys Ala Phe Ser Leu Leu Asp Ile Glu Arg Val Phe Lys
305                 310                 315                 320

Gly Lys Tyr Lys Glu Leu Asn Lys Glu Thr Ser Arg Trp Thr Thr Tyr
                325                 330                 335

Arg Gly Pro Glu Thr Asn Pro Arg Pro Gly Ser Cys Ser Val Gly Pro
            340                 345                 350

Ser Ser Asp Lys Ala Leu Thr Phe Met Lys Asp His Phe Leu Met Asp
        355                 360                 365

Glu Gln Val Val Gly Thr Pro Leu Leu Val Lys Ser Gly Val Glu Tyr
    370                 375                 380

Thr Arg Leu Ala Val Glu Thr Ala Gln Gly Leu Asp Gly His Ser His
385                 390                 395                 400

Leu Val Met Tyr Leu Gly Thr Thr Thr Gly Ser Leu His Lys Ala Val
                405                 410                 415

Val Ser Gly Asp Ser Ser Ala His Leu Val Glu Glu Ile Gln Leu Phe
            420                 425                 430

Pro Asp Pro Glu Pro Val Arg Asn Leu Gln Leu Ala Pro Thr Gln Gly
        435                 440                 445
```

-continued

```
Ala Val Phe Val Gly Phe Ser Gly Gly Val Trp Arg Val Pro Arg Ala
    450                 455                 460

Asn Cys Ser Val Tyr Glu Ser Cys Val Asp Cys Val Leu Ala Arg Asp
465                 470                 475                 480

Pro His Cys Ala Trp Asp Pro Glu Ser Arg Thr Cys Cys Leu Leu Ser
                485                 490                 495

Ala Pro Asn Leu Asn Ser Trp Lys Gln Asp Met Glu Arg Gly Asn Pro
            500                 505                 510

Glu Trp Ala Cys Ala Ser Gly Pro Met Ser Arg Ser Leu Arg Pro Gln
        515                 520                 525

Ser Arg Pro Gln Ile Ile Lys Glu Val Leu Ala Val Pro Asn Ser Ile
    530                 535                 540

Leu Glu Leu Pro Cys Pro His Leu Ser Ala Leu Ala Ser Tyr Tyr Trp
545                 550                 555                 560

Ser His Gly Pro Ala Ala Val Pro Glu Ala Ser Ser Thr Val Tyr Asn
                565                 570                 575

Gly Ser Leu Leu Leu Ile Val Gln Asp Gly Val Gly Gly Leu Tyr Gln
            580                 585                 590

Cys Trp Ala Thr Glu Asn Gly Phe Ser Tyr Pro Val Ile Ser Tyr Trp
        595                 600                 605

Val Asp Ser Gln Asp Gln Thr Leu Ala Leu Asp Pro Glu Leu Ala Gly
    610                 615                 620

Ile Pro Arg Glu His Val Lys Val Pro Leu Thr Arg Val Ser Gly Gly
625                 630                 635                 640

Ala Ala Leu Ala Ala Gln Gln Ser Tyr Trp Pro His Phe Val Thr Val
                645                 650                 655

Thr Val Leu Phe Ala Leu Val Leu Ser Gly Ala Leu Ile Ile Leu Val
            660                 665                 670

Ala Ser Pro Leu Arg Ala Leu Arg Ala Arg Gly Lys Val Gln Gly Cys
        675                 680                 685

Glu Thr Leu Arg Pro Gly Glu Lys Ala Pro Leu Ser Arg Glu Gln His
    690                 695                 700

Leu Gln Ser Pro Lys Glu Cys Arg Thr Ser Ala Ser Asp Val Asp Ala
705                 710                 715                 720

Asp Asn Asn Cys Leu Gly Thr Glu Val Ala
                725                 730


<210> SEQ ID NO 22
<211> LENGTH: 652
<212> TYPE: PRT
<213> ORGANISM: Homo sapiens

<400> SEQUENCE: 22

Gly Gly Gly Gly Gln Gly Pro Met Pro Arg Val Arg Tyr Tyr Ala Gly
  1               5                  10                  15

Asp Glu Arg Arg Ala Leu Ser Phe Phe His Gln Lys Gly Leu Gln Asp
             20                  25                  30

Phe Asp Thr Leu Leu Leu Ser Gly Asp Gly Asn Thr Leu Tyr Val Gly
         35                  40                  45

Ala Arg Glu Ala Ile Leu Ala Leu Asp Ile Gln Asp Pro Gly Val Pro
     50                  55                  60

Arg Leu Lys Asn Met Ile Pro Trp Pro Ala Ser Asp Arg Lys Lys Ser
 65                  70                  75                  80

Glu Cys Ala Phe Lys Lys Lys Ser Asn Glu Thr Gln Cys Phe Asn Phe
                 85                  90                  95
```

-continued

```
Ile Arg Val Leu Val Ser Tyr Asn Val Thr His Leu Tyr Thr Cys Gly
            100                 105                 110

Thr Phe Ala Phe Ser Pro Ala Cys Thr Phe Ile Glu Leu Gln Asp Ser
        115                 120                 125

Tyr Leu Leu Pro Ile Ser Glu Asp Lys Val Met Glu Gly Lys Gly Gln
    130                 135                 140

Ser Pro Phe Asp Pro Ala His Lys His Thr Ala Val Leu Val Asp Gly
145                 150                 155                 160

Met Leu Tyr Ser Gly Thr Met Asn Asn Phe Leu Gly Ser Glu Pro Ile
                165                 170                 175

Leu Met Arg Thr Leu Gly Ser Gln Pro Val Leu Lys Thr Asp Asn Phe
            180                 185                 190

Leu Arg Trp Leu His His Asp Ala Ser Phe Val Ala Ala Ile Pro Ser
        195                 200                 205

Thr Gln Val Val Tyr Phe Phe Phe Glu Glu Thr Ala Ser Glu Phe Asp
    210                 215                 220

Phe Phe Glu Arg Leu His Thr Ser Arg Val Ala Arg Val Cys Lys Asn
225                 230                 235                 240

Asp Val Gly Gly Glu Lys Leu Leu Gln Lys Lys Trp Thr Thr Phe Leu
                245                 250                 255

Lys Ala Gln Leu Leu Cys Thr Gln Pro Gly Gln Leu Pro Phe Asn Val
            260                 265                 270

Ile Arg His Ala Val Leu Leu Pro Ala Asp Ser Pro Thr Ala Pro His
        275                 280                 285

Ile Tyr Ala Val Phe Thr Ser Gln Trp Gln Val Gly Gly Thr Arg Ser
    290                 295                 300

Ser Ala Val Cys Ala Phe Ser Leu Leu Asp Ile Glu Arg Val Phe Lys
305                 310                 315                 320

Gly Lys Tyr Lys Glu Leu Asn Lys Glu Thr Ser Arg Trp Thr Thr Tyr
                325                 330                 335

Arg Gly Pro Glu Thr Asn Pro Arg Pro Gly Ser Cys Ser Val Gly Pro
            340                 345                 350

Ser Ser Asp Lys Ala Leu Thr Phe Met Lys Asp His Phe Leu Met Asp
        355                 360                 365

Glu Gln Val Val Gly Thr Pro Leu Leu Val Lys Ser Gly Val Glu Tyr
    370                 375                 380

Thr Arg Leu Ala Val Glu Thr Ala Gln Gly Leu Asp Gly His Ser His
385                 390                 395                 400

Leu Val Met Tyr Leu Gly Thr Thr Thr Gly Ser Leu His Lys Ala Val
                405                 410                 415

Val Ser Gly Asp Ser Ser Ala His Leu Val Glu Glu Ile Gln Leu Phe
            420                 425                 430

Pro Asp Pro Glu Pro Val Arg Asn Leu Gln Leu Ala Pro Thr Gln Gly
        435                 440                 445

Ala Val Phe Val Gly Phe Ser Gly Gly Val Trp Arg Val Pro Arg Ala
    450                 455                 460

Asn Cys Ser Val Tyr Glu Ser Cys Val Asp Cys Val Leu Ala Arg Asp
465                 470                 475                 480

Pro His Cys Ala Trp Asp Pro Glu Ser Arg Thr Cys Cys Leu Leu Ser
                485                 490                 495

Ala Pro Asn Leu Asn Ser Trp Lys Gln Asp Met Glu Arg Gly Asn Pro
            500                 505                 510
```

-continued

```
Glu Trp Ala Cys Ala Ser Gly Pro Met Ser Arg Ser Leu Arg Pro Gln
        515                 520                 525

Ser Arg Pro Gln Ile Ile Lys Glu Val Leu Ala Val Pro Asn Ser Ile
    530                 535                 540

Leu Glu Leu Pro Cys Pro His Leu Ser Ala Leu Ala Ser Tyr Tyr Trp
545                 550                 555                 560

Ser His Gly Pro Ala Ala Val Pro Glu Ala Ser Ser Thr Val Tyr Asn
                565                 570                 575

Gly Ser Leu Leu Leu Ile Val Gln Asp Gly Val Gly Gly Leu Tyr Gln
            580                 585                 590

Cys Trp Ala Thr Glu Asn Gly Phe Ser Tyr Pro Val Ile Ser Tyr Trp
        595                 600                 605

Val Asp Ser Gln Asp Gln Thr Leu Ala Leu Asp Pro Glu Leu Ala Gly
    610                 615                 620

Ile Pro Arg Glu His Val Lys Val Pro Leu Thr Arg Val Ser Gly Gly
625                 630                 635                 640

Ala Ala Leu Ala Ala Gln Gln Ser Tyr Trp Pro His
                645                 650


<210> SEQ ID NO 23
<211> LENGTH: 21
<212> TYPE: PRT
<213> ORGANISM: Homo sapiens

<400> SEQUENCE: 23

Phe Val Thr Val Thr Val Leu Phe Ala Leu Val Leu Ser Gly Ala Leu
  1               5                  10                  15

Ile Ile Leu Val Ala
             20


<210> SEQ ID NO 24
<211> LENGTH: 57
<212> TYPE: PRT
<213> ORGANISM: Homo sapiens

<400> SEQUENCE: 24

Ser Pro Leu Arg Ala Leu Arg Ala Arg Gly Lys Val Gln Gly Cys Glu
  1               5                  10                  15

Thr Leu Arg Pro Gly Glu Lys Ala Pro Leu Ser Arg Glu Gln His Leu
             20                  25                  30

Gln Ser Pro Lys Glu Cys Arg Thr Ser Ala Ser Asp Val Asp Ala Asp
         35                  40                  45

Asn Asn Cys Leu Gly Thr Glu Val Ala
     50                  55


<210> SEQ ID NO 25
<211> LENGTH: 2964
<212> TYPE: DNA
<213> ORGANISM: Homo sapiens

<400> SEQUENCE: 25

gtcgacccac gcgtccgcgg acgcgtgggg acggctcccg gctgcagtct gcccgcccgc      60

cccgcgcggg ggccgagtcg cgaagcgcgc ctgcgacccg gcgtccgggc gcgctggaga     120

ggacgcgagg agccatgagg cgccagcctg cgaaggtggc ggcgctgctg ctcgggctgc     180

tcttggagtg cacagaagcc aaaaagcatt gctggtattt cgaaggactc tatccaacct     240

attatatatg ccgctcctac gaggactgct gtggctccag gtgctgtgtg cgggccctct     300
```

-continued

```
ccatacagag gctgtggtac ttctggttcc ttctgatgat gggcgtgctt ttctgctgcg    360
gagccggctt cttcatccgg aggcgcatgt accccccgcc gctgatcgag gagccagcct    420
tcaatgtgtc ctacaccagg cagcccccaa atcccggccc aggagcccag cagccggggc    480
cgccctatta cactgaccca ggaggaccgg ggatgaaccc tgtcgggaat tccatggcaa    540
tggctttcca ggtcccaccc aactcacccc aggggagtgt ggcctgcccg ccccctccag    600
cctactgcaa cacgcctccg cccccgtacg aacaggtagt gaaggccaag tagtggggtg    660
cccacgtgca agaggagaga caggagaggg cctttccctg gcctttctgt cttcgttgat    720
gttcacttcc aggaacggtc tcgtgggctg ctaagggcag ttcctctgat atcctcacag    780
caagcacagc tctctttcag gctttccatg gagtacaata tatgaactca cactttgtct    840
cctctgttgc ttctgtttct gacgcagtct gtgctctcac atggtagtgt ggtgacagtc    900
cccgagggct gacgtcctta cggtggcgtg accagatcta caggagagag actgagagga    960
agaaggcagt gctggaggtg caggtggcat gtagaggggc caggccgagc atcccaggca   1020
agcatccttc tgcccgggta ttaataggaa gccccatgcc gggcggctca gccgatgaag   1080
cagcagccga ctgagctgag cccagcaggt catctgctcc agcctgtcct ctcgtcagcc   1140
ttcctcttcc agaagctgtt ggagagacat tcaggagaga gcaagcccct tgtcatgttt   1200
ctgtctctgt tcatatccta aagatagact tctcctgcac cgccagggaa gggtagcacg   1260
tgcagctctc accgcaggat ggggcctaga atcaggcttg ccttggaggc ctgacagtga   1320
tctgacatcc actaagcaaa tttatttaaa ttcatgggaa atcacttcct gccccaaact   1380
gagacattgc attttgtgag ctcttggtct gatttggaga aaggactgtt acccattttt   1440
ttggtgtgtt tatggaagtg catgtagagc gtcctgccct ttgaaatcag actgggtgtg   1500
tgtcttccct ggacatcact gcctctccag ggcattctca ggcccggggg tctccttccc   1560
tcaggcagct ccagtggtgg gttctgaagg gtgctttcaa aacggggcac atctggctgg   1620
gaagtcacat ggactcttcc agggagagag accagctgag gcgtctctct ctgaggttgt   1680
gttgggtcta agcgggtgtg tgctgggctc caaggaggag gagcttgctg ggaaaagaca   1740
ggagaagtac tgactcaact gcactgacca tgttgtcata attagaataa agaagaagtg   1800
gtcggaaatg cacattcctg gataggaatc acagctcacc ccaggatctc acaggtagtc   1860
tcctgagtag ttgacggcta gcggggagct agttccgccg catagttata gtgttgatgt   1920
gtgaacgctg acctgtcctg tgtgctaaga gctatgcagc ttagctgagg cgcctagatt   1980
actagatgtg ctgtatcacg gggaatgagg tgggggtgct tattttttaa tgaactaatc   2040
agagcctctt gagaaattgt tactcattga actggagcat caagacatct catggaagtg   2100
gatacggagt gatttggtgt ccatgctttt cactctgagg acatttaatc ggagaacctc   2160
ctggggaatt ttgtgggaga cacttgggaa caaaacagac accctgggaa tgcagttgca   2220
agcacagatg ctgccaccag tgtctctgac caccctggtg tgactgctga ctgccagcgt   2280
ggtacctccc atgctgcagg cctccatcta aatgagacaa caaagcacaa tgttcactgt   2340
ttacaaccaa gacaactgcg tgggtccaaa cactcctctt cctccaggtc atttgttttg   2400
catttttaat gtctttattt tttgtaatga aaaagcacac taagctgccc ctggaatcgg   2460
gtgcagctga ataggcaccc aaaagtccgt gactaaattt cgtttgtctt tttgatagca   2520
aattatgtta agagacagtg atggctaggg ctcaacaatt ttgtattccc atgtttgtgt   2580
gagacagagt ttgttttccc ttgaacttgg ttagaattgt gctactgtga acgctgatcc   2640
tgcatatgga agtcccactt tggtgacatt tcctggccat tcttgtttcc attgtgtgga   2700
```

-continued

```
tggtgggttg tgcccacttc ctggagtgag acagctcctg gtgtgtagaa ttcccggagc   2760

gtccgtggtt cagagtaaac ttgaagcaga tctgtgcatg cttttcctct gcaacaattg   2820

gctcgtttct ctttttgtt ctcttttgat aggatcctgt ttcctatgtg tgcaaaataa   2880

aaataaattt gggcaaaaaa aaaaaaaaaa aaaaaaaaaa aaaaaaaaaa aaaaaaaaaa   2940

aaaaaaaaaa aaaagggcgg ccgc                                          2964
```

<210> SEQ ID NO 26
<211> LENGTH: 516
<212> TYPE: DNA
<213> ORGANISM: Homo sapiens

<400> SEQUENCE: 26

```
atgaggcgcc agcctgcgaa ggtggcggcg ctgctgctcg ggctgctctt ggagtgcaca     60

gaagccaaaa agcattgctg gtatttcgaa ggactctatc caacctatta tatatgccgc    120

tcctacgagg actgctgtgg ctccaggtgc tgtgtgcggg ccctctccat acagaggctg    180

tggtacttct ggttccttct gatgatgggc gtgcttttct gctgcggagc cggcttcttc    240

atccggaggc gcatgtaccc cccgccgctg atcgaggagc cagccttcaa tgtgtcctac    300

accaggcagc cccaaatcc cggcccagga gcccagcagc cggggccgcc ctattacact     360

gacccaggag gaccggggat gaaccctgtc gggaattcca tggcaatggc tttccaggtc    420

ccacccaact caccccaggg gagtgtggcc tgcccgcccc ctccagccta ctgcaacacg    480

cctccgcccc cgtacgaaca ggtagtgaag gccaag                              516
```

<210> SEQ ID NO 27
<211> LENGTH: 172
<212> TYPE: PRT
<213> ORGANISM: Homo sapiens

<400> SEQUENCE: 27

```
Met Arg Arg Gln Pro Ala Lys Val Ala Ala Leu Leu Leu Gly Leu Leu
1               5                   10                  15

Leu Glu Cys Thr Glu Ala Lys Lys His Cys Trp Tyr Phe Glu Gly Leu
            20                  25                  30

Tyr Pro Thr Tyr Tyr Ile Cys Arg Ser Tyr Glu Asp Cys Cys Gly Ser
        35                  40                  45

Arg Cys Cys Val Arg Ala Leu Ser Ile Gln Arg Leu Trp Tyr Phe Trp
    50                  55                  60

Phe Leu Leu Met Met Gly Val Leu Phe Cys Cys Gly Ala Gly Phe Phe
65                  70                  75                  80

Ile Arg Arg Arg Met Tyr Pro Pro Pro Leu Ile Glu Glu Pro Ala Phe
                85                  90                  95

Asn Val Ser Tyr Thr Arg Gln Pro Pro Asn Pro Gly Pro Gly Ala Gln
            100                 105                 110

Gln Pro Gly Pro Pro Tyr Tyr Thr Asp Pro Gly Gly Pro Gly Met Asn
        115                 120                 125

Pro Val Gly Asn Ser Met Ala Met Ala Phe Gln Val Pro Pro Asn Ser
    130                 135                 140

Pro Gln Gly Ser Val Ala Cys Pro Pro Pro Pro Ala Tyr Cys Asn Thr
145                 150                 155                 160

Pro Pro Pro Pro Tyr Glu Gln Val Val Lys Ala Lys
                165                 170
```

-continued

<210> SEQ ID NO 28
<211> LENGTH: 22
<212> TYPE: PRT
<213> ORGANISM: Homo sapiens

<400> SEQUENCE: 28

```
Met Arg Arg Gln Pro Ala Lys Val Ala Ala Leu Leu Leu Gly Leu Leu
  1               5                  10                  15

Leu Glu Cys Thr Glu Ala
             20
```

<210> SEQ ID NO 29
<211> LENGTH: 150
<212> TYPE: PRT
<213> ORGANISM: Homo sapiens

<400> SEQUENCE: 29

```
Lys Lys His Cys Trp Tyr Phe Glu Gly Leu Tyr Pro Thr Tyr Tyr Ile
  1               5                  10                  15

Cys Arg Ser Tyr Glu Asp Cys Cys Gly Ser Arg Cys Cys Val Arg Ala
             20                  25                  30

Leu Ser Ile Gln Arg Leu Trp Tyr Phe Trp Phe Leu Leu Met Met Gly
         35                  40                  45

Val Leu Phe Cys Cys Gly Ala Gly Phe Phe Ile Arg Arg Arg Met Tyr
     50                  55                  60

Pro Pro Pro Leu Ile Glu Glu Pro Ala Phe Asn Val Ser Tyr Thr Arg
 65                  70                  75                  80

Gln Pro Pro Asn Pro Gly Pro Gly Ala Gln Gln Pro Gly Pro Pro Tyr
                 85                  90                  95

Tyr Thr Asp Pro Gly Gly Pro Gly Met Asn Pro Val Gly Asn Ser Met
            100                 105                 110

Ala Met Ala Phe Gln Val Pro Pro Asn Ser Pro Gln Gly Ser Val Ala
        115                 120                 125

Cys Pro Pro Pro Pro Ala Tyr Cys Asn Thr Pro Pro Pro Pro Tyr Glu
    130                 135                 140

Gln Val Val Lys Ala Lys
145                 150
```

<210> SEQ ID NO 30
<211> LENGTH: 38
<212> TYPE: PRT
<213> ORGANISM: Homo sapiens

<400> SEQUENCE: 30

```
Lys Lys His Cys Trp Tyr Phe Glu Gly Leu Tyr Pro Thr Tyr Tyr Ile
  1               5                  10                  15

Cys Arg Ser Tyr Glu Asp Cys Cys Gly Ser Arg Cys Cys Val Arg Ala
             20                  25                  30

Leu Ser Ile Gln Arg Leu
         35
```

<210> SEQ ID NO 31
<211> LENGTH: 21
<212> TYPE: PRT
<213> ORGANISM: Homo sapiens

<400> SEQUENCE: 31

```
Trp Tyr Phe Trp Phe Leu Leu Met Met Gly Val Leu Phe Cys Cys Gly
  1               5                  10                  15
```

-continued

```
Ala Gly Phe Phe Ile
            20


<210> SEQ ID NO 32
<211> LENGTH: 91
<212> TYPE: PRT
<213> ORGANISM: Homo sapiens

<400> SEQUENCE: 32

Arg Arg Arg Met Tyr Pro Pro Pro Leu Ile Glu Glu Pro Ala Phe Asn
  1               5                  10                  15

Val Ser Tyr Thr Arg Gln Pro Pro Asn Pro Gly Pro Gly Ala Gln Gln
            20                  25                  30

Pro Gly Pro Pro Tyr Tyr Thr Asp Pro Gly Gly Pro Gly Met Asn Pro
        35                  40                  45

Val Gly Asn Ser Met Ala Met Ala Phe Gln Val Pro Pro Asn Ser Pro
     50                  55                  60

Gln Gly Ser Val Ala Cys Pro Pro Pro Pro Ala Tyr Cys Asn Thr Pro
 65                  70                  75                  80

Pro Pro Pro Tyr Glu Gln Val Val Lys Ala Lys
                 85                  90


<210> SEQ ID NO 33
<211> LENGTH: 1980
<212> TYPE: DNA
<213> ORGANISM: Homo sapiens

<400> SEQUENCE: 33

gtcgacccac gcgtccgcag ctttggacac ttcctctgct tgaggacacc ttgactaacc     60

tccaagggca actaaaggat caagaaaggc ccagcacagc agaagatcag ctggatctag    120

ctcctgcagg agatgtgtac aaagacaatc ccagtcctct ggggatgttt cctcctgtgg    180

aatctctatg tctcatcctc tcagaccatt taccctggaa tcaaggcaag gattactcag    240

agggcacttg actatggtgt tcaagctgga atgaagatga ttgagcaaat gctaaaagaa    300

aagaaactcc cagatttaag cggttctgag tctcttgaat ttctaaaagt tgattatgta    360

aactacaatt tttcaaatat aaaaatcagt gccttttcat ttccaaatac ctcattggct    420

tttgtgcctg gagtgggaat caaagcgcta accaaccatg gcactgccaa catcagcaca    480

gactgggggt tcgagtctcc actttttgtt ctgtataact cctttgctga gcccatggag    540

aaacccattt taaagaactt aaatgaaatg ctctgtccca ttattgcaag tgaagtcaaa    600

gcgctaaatg ccaacctcag cacactggag gttttaacca agattgacaa ctacactctg    660

ctggattact ccctaatcag ttctccagaa attactgaga actaccttga cctgaacttg    720

aagggtgtat tctacccact ggaaaacctc accgaccccc ccttctcacc agttcctttt    780

gtgctcccag aacgcagcaa ctccatgctc tacattggaa tcgccgagta tttctttaaa    840

tctgcgtcct ttgctcattt cacagctggg gttttcaatc tcactctctc caccgaagag    900

atttccaacc attttgttca aaactctcaa ggccttggca acgtgctctc ccggattgca    960

gagatctaca tcttgtccca gcccttcatg gtgaggatca tggccacaga gcctcccata   1020

atcaatctac aaccaggcaa tttcaccctg gacatccctg cctccatcat gatgctcacc   1080

caacccaaga actccacagt tgaaaccatc gtttccatgg acttcgttgc tagtaccagt   1140

gttggcctgg ttattttggg acaaagactg gtctgctcct tgtctctgaa cagattccgc   1200

cttgctttgc cagagtccaa tcgcagcaac attgaggtct tgaggtttga aaatattcta   1260
```

-continued

```
tcgtccattc ttcactttgg agtcctccca ctggccaatg caaaattgca gcaaggattt   1320
cctctgccca atccacacaa attcttattc gtcaattcag atattgaagt tcttgagggt   1380
ttccttttga tttccaccga cctgaagtat gaaacatcct caaagcagca gccaagtttc   1440
cacgtatggg aaggtctgaa cctgataagc agacagtgga gggggaagtc agccccttga   1500
ttgccggttt gcaattcacc ccaggaagta aatggtcctt aatcctacaa ctactgtaaa   1560
cccagaaggg aaagacagta cacactggaa ttgtaaagcc cttgtgaatt gcttaggcag   1620
aaagttttct ttcttaagcc ttcaggaacc cagaataagg cagactctgt taaagggata   1680
aatagaggtg tctgaatgtg agtgtatgca tgctgcgtgt gtctgtgttt atgtttgttt   1740
gtttgtttgg ggcaagaaag attctaggac aagagctagg catgtacttc tgaccaggtg   1800
ggtaagcaac tctaagtctg tatttgtatt ggtcattctc agtggaaatc ccttaggccc   1860
tctagtggtt ttcccctacc tgcatattgg ttttcatgtt ttatattcac tgttactatc   1920
ttctgtgttt aattaaaatt gttttctatc aaaaaaaaaa aaaaaaaaaa gggcggccgc   1980
```

<210> SEQ ID NO 34
<211> LENGTH: 1365
<212> TYPE: DNA
<213> ORGANISM: Homo sapiens

<400> SEQUENCE: 34

```
atgtgtacaa agacaatccc agtcctctgg ggatgtttcc tcctgtggaa tctctatgtc     60
tcatcctctc agaccattta ccctggaatc aaggcaagga ttactcagag ggcacttgac    120
tatggtgttc aagctggaat gaagatgatt gagcaaatgc taaaagaaaa gaaactccca    180
gatttaagcg gttctgagtc tcttgaattt ctaaaagttg attatgtaaa ctacaatttt    240
tcaaatataa aaatcagtgc cttttcattt ccaaatacct cattggcttt tgtgcctgga    300
gtgggaatca aagcgctaac caaccatggc actgccaaca tcagcacaga ctgggggttc    360
gagtctccac tttttgttct gtataactcc tttgctgagc ccatggagaa acccatttta    420
aagaacttaa atgaaatgct ctgtcccatt attgcaagtg aagtcaaagc gctaaatgcc    480
aacctcagca cactggaggt tttaaccaag attgacaact acactctgct ggattactcc    540
ctaatcagtt ctccagaaat tactgagaac taccttgacc tgaacttgaa gggtgtattc    600
tacccactgg aaaacctcac cgaccccccc ttctcaccag ttccttttgt gctcccagaa    660
cgcagcaact ccatgctcta cattggaatc gccgagtatt tctttaaatc tgcgtccttt    720
gctcatttca cagctggggt tttcaatctc actctctcca ccgaagagat ttccaaccat    780
tttgttcaaa actctcaagg ccttggcaac gtgctctccc ggattgcaga gatctacatc    840
ttgtcccagc ccttcatggt gaggatcatg gccacagagc ctcccataat caatctacaa    900
ccaggcaatt tcaccctgga catccctgcc tccatcatga tgctcaccca acccaagaac    960
tccacagttg aaaccatcgt ttccatggac ttcgttgcta gtaccagtgt tggcctggtt   1020
attttgggac aaagactggt ctgctccttg tctctgaaca gattccgcct tgctttgcca   1080
gagtccaatc gcagcaacat tgaggtcttg aggtttgaaa atattctatc gtccattctt   1140
cactttggag tcctcccact ggccaatgca aaattgcagc aaggatttcc tctgcccaat   1200
ccacacaaat tcttattcgt caattcagat attgaagttc ttgagggttt ccttttgatt   1260
tccaccgacc tgaagtatga aacatcctca aagcagcagc caagtttcca cgtatgggaa   1320
ggtctgaacc tgataagcag acagtggagg gggaagtcag cccct                    1365
```

-continued

<210> SEQ ID NO 35
<211> LENGTH: 455
<212> TYPE: PRT
<213> ORGANISM: Homo sapiens

<400> SEQUENCE: 35

```
Met Cys Thr Lys Thr Ile Pro Val Leu Trp Gly Cys Phe Leu Leu Trp
  1               5                  10                  15

Asn Leu Tyr Val Ser Ser Ser Gln Thr Ile Tyr Pro Gly Ile Lys Ala
             20                  25                  30

Arg Ile Thr Gln Arg Ala Leu Asp Tyr Gly Val Gln Ala Gly Met Lys
         35                  40                  45

Met Ile Glu Gln Met Leu Lys Glu Lys Lys Leu Pro Asp Leu Ser Gly
     50                  55                  60

Ser Glu Ser Leu Glu Phe Leu Lys Val Asp Tyr Val Asn Tyr Asn Phe
 65                  70                  75                  80

Ser Asn Ile Lys Ile Ser Ala Phe Ser Phe Pro Asn Thr Ser Leu Ala
                 85                  90                  95

Phe Val Pro Gly Val Gly Ile Lys Ala Leu Thr Asn His Gly Thr Ala
            100                 105                 110

Asn Ile Ser Thr Asp Trp Gly Phe Glu Ser Pro Leu Phe Val Leu Tyr
        115                 120                 125

Asn Ser Phe Ala Glu Pro Met Glu Lys Pro Ile Leu Lys Asn Leu Asn
    130                 135                 140

Glu Met Leu Cys Pro Ile Ile Ala Ser Glu Val Lys Ala Leu Asn Ala
145                 150                 155                 160

Asn Leu Ser Thr Leu Glu Val Leu Thr Lys Ile Asp Asn Tyr Thr Leu
                165                 170                 175

Leu Asp Tyr Ser Leu Ile Ser Ser Pro Glu Ile Thr Glu Asn Tyr Leu
            180                 185                 190

Asp Leu Asn Leu Lys Gly Val Phe Tyr Pro Leu Glu Asn Leu Thr Asp
        195                 200                 205

Pro Pro Phe Ser Pro Val Pro Phe Val Leu Pro Glu Arg Ser Asn Ser
    210                 215                 220

Met Leu Tyr Ile Gly Ile Ala Glu Tyr Phe Phe Lys Ser Ala Ser Phe
225                 230                 235                 240

Ala His Phe Thr Ala Gly Val Phe Asn Leu Thr Leu Ser Thr Glu Glu
                245                 250                 255

Ile Ser Asn His Phe Val Gln Asn Ser Gln Gly Leu Gly Asn Val Leu
            260                 265                 270

Ser Arg Ile Ala Glu Ile Tyr Ile Leu Ser Gln Pro Phe Met Val Arg
        275                 280                 285

Ile Met Ala Thr Glu Pro Pro Ile Ile Asn Leu Gln Pro Gly Asn Phe
    290                 295                 300

Thr Leu Asp Ile Pro Ala Ser Ile Met Met Leu Thr Gln Pro Lys Asn
305                 310                 315                 320

Ser Thr Val Glu Thr Ile Val Ser Met Asp Phe Val Ala Ser Thr Ser
                325                 330                 335

Val Gly Leu Val Ile Leu Gly Gln Arg Leu Val Cys Ser Leu Ser Leu
            340                 345                 350

Asn Arg Phe Arg Leu Ala Leu Pro Glu Ser Asn Arg Ser Asn Ile Glu
        355                 360                 365

Val Leu Arg Phe Glu Asn Ile Leu Ser Ser Ile Leu His Phe Gly Val
    370                 375                 380
```

-continued

```
Leu Pro Leu Ala Asn Ala Lys Leu Gln Gln Gly Phe Pro Leu Pro Asn
385                 390                 395                 400

Pro His Lys Phe Leu Phe Val Asn Ser Asp Ile Glu Val Leu Glu Gly
                405                 410                 415

Phe Leu Leu Ile Ser Thr Asp Leu Lys Tyr Glu Thr Ser Ser Lys Gln
            420                 425                 430

Gln Pro Ser Phe His Val Trp Glu Gly Leu Asn Leu Ile Ser Arg Gln
        435                 440                 445

Trp Arg Gly Lys Ser Ala Pro
    450                 455


<210> SEQ ID NO 36
<211> LENGTH: 23
<212> TYPE: PRT
<213> ORGANISM: Homo sapiens

<400> SEQUENCE: 36

Met Cys Thr Lys Thr Ile Pro Val Leu Trp Gly Cys Phe Leu Leu Trp
  1               5                  10                  15

Asn Leu Tyr Val Ser Ser Ser
            20


<210> SEQ ID NO 37
<211> LENGTH: 432
<212> TYPE: PRT
<213> ORGANISM: Homo sapiens

<400> SEQUENCE: 37

Gln Thr Ile Tyr Pro Gly Ile Lys Ala Arg Ile Thr Gln Arg Ala Leu
  1               5                  10                  15

Asp Tyr Gly Val Gln Ala Gly Met Lys Met Ile Glu Gln Met Leu Lys
             20                  25                  30

Glu Lys Lys Leu Pro Asp Leu Ser Gly Ser Glu Ser Leu Glu Phe Leu
         35                  40                  45

Lys Val Asp Tyr Val Asn Tyr Asn Phe Ser Asn Ile Lys Ile Ser Ala
     50                  55                  60

Phe Ser Phe Pro Asn Thr Ser Leu Ala Phe Val Pro Gly Val Gly Ile
 65                  70                  75                  80

Lys Ala Leu Thr Asn His Gly Thr Ala Asn Ile Ser Thr Asp Trp Gly
                 85                  90                  95

Phe Glu Ser Pro Leu Phe Val Leu Tyr Asn Ser Phe Ala Glu Pro Met
            100                 105                 110

Glu Lys Pro Ile Leu Lys Asn Leu Asn Glu Met Leu Cys Pro Ile Ile
        115                 120                 125

Ala Ser Glu Val Lys Ala Leu Asn Ala Asn Leu Ser Thr Leu Glu Val
    130                 135                 140

Leu Thr Lys Ile Asp Asn Tyr Thr Leu Leu Asp Tyr Ser Leu Ile Ser
145                 150                 155                 160

Ser Pro Glu Ile Thr Glu Asn Tyr Leu Asp Leu Asn Leu Lys Gly Val
                165                 170                 175

Phe Tyr Pro Leu Glu Asn Leu Thr Asp Pro Pro Phe Ser Pro Val Pro
            180                 185                 190

Phe Val Leu Pro Glu Arg Ser Asn Ser Met Leu Tyr Ile Gly Ile Ala
        195                 200                 205

Glu Tyr Phe Phe Lys Ser Ala Ser Phe Ala His Phe Thr Ala Gly Val
    210                 215                 220
```

-continued

Phe Asn Leu Thr Leu Ser Thr Glu Glu Ile Ser Asn His Phe Val Gln
225 230 235 240

Asn Ser Gln Gly Leu Gly Asn Val Leu Ser Arg Ile Ala Glu Ile Tyr
245 250 255

Ile Leu Ser Gln Pro Phe Met Val Arg Ile Met Ala Thr Glu Pro Pro
260 265 270

Ile Ile Asn Leu Gln Pro Gly Asn Phe Thr Leu Asp Ile Pro Ala Ser
275 280 285

Ile Met Met Leu Thr Gln Pro Lys Asn Ser Thr Val Glu Thr Ile Val
290 295 300

Ser Met Asp Phe Val Ala Ser Thr Ser Val Gly Leu Val Ile Leu Gly
305 310 315 320

Gln Arg Leu Val Cys Ser Leu Ser Leu Asn Arg Phe Arg Leu Ala Leu
325 330 335

Pro Glu Ser Asn Arg Ser Asn Ile Glu Val Leu Arg Phe Glu Asn Ile
340 345 350

Leu Ser Ser Ile Leu His Phe Gly Val Leu Pro Leu Ala Asn Ala Lys
355 360 365

Leu Gln Gln Gly Phe Pro Leu Pro Asn Pro His Lys Phe Leu Phe Val
370 375 380

Asn Ser Asp Ile Glu Val Leu Glu Gly Phe Leu Leu Ile Ser Thr Asp
385 390 395 400

Leu Lys Tyr Glu Thr Ser Ser Lys Gln Gln Pro Ser Phe His Val Trp
405 410 415

Glu Gly Leu Asn Leu Ile Ser Arg Gln Trp Arg Gly Lys Ser Ala Pro
420 425 430

<210> SEQ ID NO 38
<211> LENGTH: 483
<212> TYPE: PRT
<213> ORGANISM: Homo sapiens

<400> SEQUENCE: 38

Met Ala Arg Gly Pro Cys Asn Ala Pro Arg Trp Val Ser Leu Met Val
1 5 10 15

Leu Val Ala Ile Gly Thr Ala Val Thr Ala Ala Val Asn Pro Gly Val
20 25 30

Val Val Arg Ile Ser Gln Lys Gly Leu Asp Tyr Ala Ser Gln Gln Gly
35 40 45

Thr Ala Ala Leu Gln Lys Glu Leu Lys Arg Ile Lys Ile Pro Asp Tyr
50 55 60

Ser Asp Ser Phe Lys Ile Lys His Leu Gly Lys Gly His Tyr Ser Phe
65 70 75 80

Tyr Ser Met Asp Ile Arg Glu Phe Gln Leu Pro Ser Ser Gln Ile Ser
85 90 95

Met Val Pro Asn Val Gly Leu Lys Phe Ser Ile Ser Asn Ala Asn Ile
100 105 110

Lys Ile Ser Gly Lys Trp Lys Ala Gln Lys Arg Phe Leu Lys Met Ser
115 120 125

Gly Asn Phe Asp Leu Ser Ile Glu Gly Met Ser Ile Ser Ala Asp Leu
130 135 140

Lys Leu Gly Ser Asn Pro Thr Ser Gly Lys Pro Thr Ile Thr Cys Ser
145 150 155 160

Ser Cys Ser Ser His Ile Asn Ser Val His Val His Ile Ser Lys Ser
165 170 175

-continued

```
Lys Val Gly Trp Leu Ile Gln Leu Phe His Lys Lys Ile Glu Ser Ala
            180                 185                 190

Leu Arg Asn Lys Met Asn Ser Gln Val Cys Glu Lys Val Thr Asn Ser
        195                 200                 205

Val Ser Ser Lys Leu Gln Pro Tyr Phe Gln Thr Leu Pro Val Met Thr
    210                 215                 220

Lys Ile Asp Ser Val Ala Gly Ile Asn Tyr Gly Leu Val Ala Pro Pro
225                 230                 235                 240

Ala Thr Thr Ala Glu Thr Leu Asp Val Gln Met Lys Gly Glu Phe Tyr
                245                 250                 255

Ser Glu Asn His His Asn Pro Pro Pro Phe Ala Pro Pro Val Met Glu
            260                 265                 270

Phe Pro Ala Ala His Asp Arg Met Val Tyr Leu Gly Leu Ser Asp Tyr
        275                 280                 285

Phe Phe Asn Thr Ala Gly Leu Val Tyr Gln Glu Ala Gly Val Leu Lys
    290                 295                 300

Met Thr Leu Arg Asp Asp Met Ile Pro Lys Glu Ser Lys Phe Arg Leu
305                 310                 315                 320

Thr Thr Lys Phe Phe Gly Thr Phe Leu Pro Glu Val Ala Lys Lys Phe
                325                 330                 335

Pro Asn Met Lys Ile Gln Ile His Val Ser Ala Ser Thr Pro Pro His
            340                 345                 350

Leu Ser Val Gln Pro Thr Gly Leu Thr Phe Tyr Pro Ala Val Asp Val
        355                 360                 365

Gln Ala Phe Ala Val Leu Pro Asn Ser Ser Leu Ala Ser Leu Phe Leu
    370                 375                 380

Ile Gly Met His Thr Thr Gly Ser Met Glu Val Ser Ala Glu Ser Asn
385                 390                 395                 400

Arg Leu Val Gly Glu Leu Lys Leu Asp Arg Leu Leu Leu Glu Leu Lys
                405                 410                 415

His Ser Asn Ile Gly Pro Phe Pro Val Glu Leu Leu Gln Asp Ile Met
            420                 425                 430

Asn Tyr Ile Val Pro Ile Leu Val Leu Pro Arg Val Asn Glu Lys Leu
        435                 440                 445

Gln Lys Gly Phe Pro Leu Pro Thr Pro Ala Arg Val Gln Leu Tyr Asn
    450                 455                 460

Val Val Leu Gln Pro His Gln Asn Phe Leu Leu Phe Gly Ala Asp Val
465                 470                 475                 480

Val Tyr Lys


<210> SEQ ID NO 39
<211> LENGTH: 481
<212> TYPE: PRT
<213> ORGANISM: Homo sapiens

<400> SEQUENCE: 39

Met Gly Ala Leu Ala Arg Ala Leu Pro Ser Ile Leu Leu Ala Leu Leu
  1               5                  10                  15

Leu Thr Ser Thr Pro Glu Ala Leu Gly Ala Asn Pro Gly Leu Val Ala
             20                  25                  30

Arg Ile Thr Asp Lys Gly Leu Gln Tyr Ala Ala Gln Glu Gly Leu Leu
         35                  40                  45

Ala Leu Gln Ser Glu Leu Leu Arg Ile Thr Leu Pro Asp Phe Thr Gly
     50                  55                  60
```

-continued

```
Asp Leu Arg Ile Pro His Val Gly Arg Gly Arg Tyr Glu Phe His Ser
 65                  70                  75                  80

Leu Asn Ile His Glu Phe Gln Leu Pro Ser Ser Gln Ile Ser Met Val
                 85                  90                  95

Pro Asn Val Gly Leu Lys Phe Ser Ile Ser Asn Ala Asn Ile Lys Ile
            100                 105                 110

Ser Gly Lys Trp Lys Ala Gln Lys Arg Phe Leu Lys Met Ser Gly Asn
        115                 120                 125

Phe Asp Leu Ser Ile Glu Gly Met Ser Ile Ser Ala Asp Leu Lys Leu
    130                 135                 140

Gly Ser Asn Pro Thr Ser Gly Lys Pro Thr Ile Thr Cys Ser Ser Cys
145                 150                 155                 160

Ser Ser His Ile Asn Ser Val His Val His Ile Ser Lys Ser Lys Val
                165                 170                 175

Gly Trp Leu Ile Gln Leu Phe His Lys Lys Ile Glu Ser Ala Leu Arg
            180                 185                 190

Asn Lys Met Asn Ser Gln Val Cys Glu Lys Val Thr Asn Ser Val Ser
        195                 200                 205

Ser Lys Leu Gln Pro Tyr Phe Gln Thr Leu Pro Val Met Thr Lys Ile
    210                 215                 220

Asp Ser Val Ala Gly Ile Asn Tyr Gly Leu Val Ala Pro Pro Ala Thr
225                 230                 235                 240

Thr Ala Glu Thr Leu Asp Val Gln Met Lys Gly Glu Phe Tyr Ser Glu
                245                 250                 255

Asn His His Asn Pro Pro Pro Phe Ala Pro Pro Val Met Glu Phe Pro
            260                 265                 270

Ala Ala His Asp Arg Met Val Tyr Leu Gly Leu Ser Asp Tyr Phe Phe
        275                 280                 285

Asn Thr Ala Gly Leu Val Tyr Gln Glu Ala Gly Val Leu Lys Met Thr
    290                 295                 300

Leu Arg Asp Asp Met Ile Pro Lys Glu Ser Lys Phe Arg Leu Thr Thr
305                 310                 315                 320

Lys Phe Phe Gly Thr Phe Leu Pro Glu Val Ala Lys Lys Phe Pro Asn
                325                 330                 335

Met Lys Ile Gln Ile His Val Ser Ala Ser Thr Pro Pro His Leu Ser
            340                 345                 350

Val Gln Pro Thr Gly Leu Thr Phe Tyr Pro Ala Val Asp Val Gln Ala
        355                 360                 365

Leu Ala Val Leu Pro Asn Ser Ser Leu Ala Ser Leu Phe Leu Ile Gly
    370                 375                 380

Met His Thr Thr Gly Ser Met Glu Val Ser Ala Glu Ser Asn Arg Leu
385                 390                 395                 400

Val Gly Glu Leu Lys Leu Asp Arg Leu Leu Leu Glu Leu Lys His Ser
                405                 410                 415

Asn Ile Gly Pro Phe Pro Val Glu Leu Leu Gln Asp Ile Met Asn Tyr
            420                 425                 430

Ile Val Pro Ile Leu Val Leu Pro Arg Val Asn Glu Lys Leu Gln Lys
        435                 440                 445

Gly Phe Pro Leu Pro Thr Pro Ala Arg Val Gln Leu Tyr Asn Val Val
    450                 455                 460

Leu Gln Pro His Gln Asn Phe Leu Leu Phe Gly Ala Asp Val Val Tyr
465                 470                 475                 480
```

-continued

Lys

<210> SEQ ID NO 40
<211> LENGTH: 383
<212> TYPE: PRT
<213> ORGANISM: Caenorhabditis elegans

<400> SEQUENCE: 40

```
Met Arg Ile Ala His Ala Ser Ser Arg Gly Asn Ile Ser Ile Phe Ser
  1               5                  10                  15

Val Phe Leu Ile Pro Leu Ile Ala Tyr Ile Leu Ile Leu Pro Gly Val
             20                  25                  30

Arg Arg Lys Arg Val Val Thr Thr Val Thr Tyr Val Leu Met Leu Ala
         35                  40                  45

Val Gly Gly Ala Leu Ile Ala Ser Leu Ile Tyr Pro Cys Trp Ala Ser
     50                  55                  60

Gly Ser Gln Met Ile Tyr Thr Gln Phe Arg Gly His Ser Asn Glu Arg
 65                  70                  75                  80

Ile Leu Ala Lys Ile Gly Val Glu Ile Gly Leu Gln Lys Val Asn Val
                 85                  90                  95

Thr Leu Lys Phe Glu Arg Leu Leu Ser Ser Asn Asp Val Leu Pro Gly
            100                 105                 110

Ser Asp Met Thr Glu Leu Tyr Tyr Asn Glu Gly Phe Asp Ile Ser Gly
        115                 120                 125

Ile Ser Ser Met Ala Glu Ala Leu His His Gly Leu Glu Asn Gly Leu
    130                 135                 140

Pro Tyr Pro Met Leu Ser Val Leu Glu Tyr Phe Ser Leu Asn Gln Asp
145                 150                 155                 160

Ser Phe Asp Trp Gly Arg His Tyr Arg Val Ala Gly His Tyr Thr His
                165                 170                 175

Ala Ala Ile Trp Phe Ala Phe Ala Cys Trp Cys Leu Ser Val Val Leu
            180                 185                 190

Met Leu Phe Leu Pro His Asn Ala Tyr Lys Ser Ile Leu Ala Thr Gly
        195                 200                 205

Ile Ser Cys Leu Ile Ala Cys Leu Val Tyr Leu Leu Leu Ser Pro Cys
    210                 215                 220

Glu Leu Arg Ile Ala Phe Thr Gly Glu Asn Phe Glu Arg Val Asp Leu
225                 230                 235                 240

Thr Ala Thr Phe Ser Phe Cys Phe Tyr Leu Ile Phe Ala Ile Gly Ile
                245                 250                 255

Leu Cys Val Leu Cys Gly Leu Gly Leu Gly Ile Cys Glu His Trp Arg
            260                 265                 270

Ile Tyr Thr Leu Ser Thr Phe Leu Asp Ala Ser Leu Asp Glu His Val
        275                 280                 285

Gly Pro Lys Trp Lys Lys Leu Pro Thr Gly Gly Pro Ala Leu Gln Gly
    290                 295                 300

Val Gln Ile Gly Ala Tyr Gly Thr Asn Thr Thr Asn Ser Ser Arg Asp
305                 310                 315                 320

Lys Asn Asp Ile Ser Ser Asp Lys Thr Ala Gly Ser Ser Gly Phe Gln
                325                 330                 335

Ser Arg Thr Ser Thr Cys Gln Ser Ser Ala Ser Ser Ala Ser Leu Arg
            340                 345                 350

Ser Gln Ser Ser Ile Glu Thr Val His Asp Glu Ala Glu Leu Glu Arg
        355                 360                 365
```

-continued

```
Thr His Val His Phe Leu Gln Glu Pro Cys Ser Ser Ser Ser Thr
    370                 375                 380


<210> SEQ ID NO 41
<211> LENGTH: 399
<212> TYPE: PRT
<213> ORGANISM: Homo sapiens

<400> SEQUENCE: 41

Met Lys Met Arg Phe Leu Gly Leu Val Val Cys Leu Val Leu Trp Pro
  1               5                  10                  15

Leu His Ser Glu Gly Ser Gly Gly Lys Leu Thr Ala Val Asp Pro Glu
             20                  25                  30

Thr Asn Met Asn Val Ser Glu Ile Ile Ser Tyr Trp Gly Phe Pro Ser
         35                  40                  45

Glu Glu Tyr Leu Val Glu Thr Glu Asp Gly Tyr Ile Leu Cys Leu Asn
     50                  55                  60

Arg Ile Pro His Gly Arg Lys Asn His Ser Asp Lys Gly Pro Lys Pro
 65                  70                  75                  80

Val Val Phe Leu Gln His Gly Leu Leu Ala Asp Ser Ser Asn Trp Val
                 85                  90                  95

Thr Asn Leu Ala Asn Ser Ser Leu Gly Phe Ile Leu Ala Asp Ala Gly
            100                 105                 110

Phe Asp Val Trp Met Gly Asn Ser Arg Gly Asn Thr Trp Ser Arg Lys
        115                 120                 125

His Lys Thr Leu Ser Val Ser Gln Asp Glu Phe Trp Ala Phe Ser Tyr
    130                 135                 140

Asp Glu Met Ala Lys Tyr Asp Leu Pro Ala Ser Ile Asn Phe Ile Leu
145                 150                 155                 160

Asn Lys Thr Gly Gln Glu Gln Val Tyr Tyr Val Gly His Ser Gln Gly
                165                 170                 175

Thr Thr Ile Gly Phe Ile Ala Phe Ser Gln Ile Pro Glu Leu Ala Lys
            180                 185                 190

Arg Ile Lys Met Phe Phe Ala Leu Gly Pro Val Ala Ser Val Ala Phe
        195                 200                 205

Cys Thr Ser Pro Met Ala Lys Leu Gly Arg Leu Pro Asp His Leu Ile
    210                 215                 220

Lys Asp Leu Phe Gly Asp Lys Glu Phe Leu Pro Gln Ser Ala Phe Leu
225                 230                 235                 240

Lys Trp Leu Gly Thr His Val Cys Thr His Val Ile Leu Lys Glu Leu
                245                 250                 255

Cys Gly Asn Leu Cys Phe Leu Leu Cys Gly Phe Asn Glu Arg Asn Leu
            260                 265                 270

Asn Met Ser Arg Val Asp Val Tyr Thr Thr His Ser Pro Ala Gly Thr
        275                 280                 285

Ser Val Gln Asn Met Leu His Trp Ser Gln Ala Val Lys Phe Gln Lys
    290                 295                 300

Phe Gln Ala Phe Asp Trp Gly Ser Ser Ala Lys Asn Tyr Phe His Tyr
305                 310                 315                 320

Asn Gln Ser Tyr Pro Pro Thr Tyr Asn Val Lys Asp Met Leu Val Pro
                325                 330                 335

Thr Ala Val Trp Ser Gly Gly His Asp Trp Leu Ala Asp Val Tyr Asp
            340                 345                 350

Val Asn Ile Leu Leu Thr Gln Ile Thr Asn Leu Val Phe His Glu Ser
        355                 360                 365
```

-continued

```
Ile Pro Glu Trp Glu His Leu Asp Phe Ile Trp Gly Leu Asp Ala Pro
    370                 375                 380

Trp Arg Leu Tyr Asn Lys Ile Ile Asn Leu Met Arg Lys Tyr Gln
385                 390                 395


<210> SEQ ID NO 42
<211> LENGTH: 19
<212> TYPE: PRT
<213> ORGANISM: Mus sp.

<400> SEQUENCE: 42

Met Ala Pro Pro Ala Ala Arg Leu Ala Leu Leu Ser Ala Ala Ala Leu
  1               5                  10                  15

Thr Leu Ala


<210> SEQ ID NO 43
<211> LENGTH: 451
<212> TYPE: PRT
<213> ORGANISM: Mus sp.

<400> SEQUENCE: 43

Ala Arg Pro Ala Pro Gly Pro Arg Ser Gly Pro Glu Cys Phe Thr Ala
  1               5                  10                  15

Asn Gly Ala Asp Tyr Arg Gly Thr Gln Ser Trp Thr Ala Leu Gln Gly
            20                  25                  30

Gly Lys Pro Cys Leu Phe Trp Asn Glu Thr Phe Gln His Pro Tyr Asn
        35                  40                  45

Thr Leu Lys Tyr Pro Asn Gly Glu Gly Gly Leu Gly Glu His Asn Tyr
     50                  55                  60

Cys Arg Asn Pro Asp Gly Asp Val Ser Pro Trp Cys Tyr Val Ala Glu
 65                  70                  75                  80

His Glu Asp Gly Val Tyr Trp Lys Tyr Cys Glu Ile Pro Ala Cys Gln
                 85                  90                  95

Met Pro Gly Asn Leu Gly Cys Tyr Lys Asp His Gly Asn Pro Pro Pro
            100                 105                 110

Leu Thr Gly Thr Ser Lys Thr Ser Asn Lys Leu Thr Ile Gln Thr Cys
        115                 120                 125

Ile Ser Phe Cys Arg Ser Gln Arg Phe Lys Phe Ala Gly Met Glu Ser
    130                 135                 140

Gly Tyr Ala Cys Phe Cys Gly Asn Asn Pro Asp Tyr Trp Lys His Gly
145                 150                 155                 160

Glu Ala Ala Ser Thr Glu Cys Asn Ser Val Cys Phe Gly Asp His Thr
                165                 170                 175

Gln Pro Cys Gly Gly Asp Gly Arg Ile Ile Leu Phe Asp Thr Leu Val
            180                 185                 190

Gly Ala Cys Gly Gly Asn Tyr Ser Ala Met Ala Ala Val Val Tyr Ser
        195                 200                 205

Pro Asp Phe Pro Asp Thr Tyr Ala Thr Gly Arg Val Cys Tyr Trp Thr
    210                 215                 220

Ile Arg Val Pro Gly Ala Ser Arg Ile His Phe Asn Phe Thr Leu Phe
225                 230                 235                 240

Asp Ile Arg Asp Ser Ala Asp Met Val Glu Leu Leu Asp Gly Tyr Thr
                245                 250                 255

His Arg Val Leu Val Arg Leu Ser Gly Arg Ser Arg Pro Pro Leu Ser
            260                 265                 270
```

-continued

```
Phe Asn Val Ser Leu Asp Phe Val Ile Leu Tyr Phe Phe Ser Asp Arg
        275                 280                 285

Ile Asn Gln Ala Gln Gly Phe Ala Val Leu Tyr Gln Ala Thr Lys Glu
    290                 295                 300

Glu Pro Pro Gln Glu Arg Pro Ala Val Asn Gln Thr Leu Ala Glu Val
305                 310                 315                 320

Ile Thr Glu Gln Ala Asn Leu Ser Val Ser Ala Ala His Ser Ser Lys
                325                 330                 335

Val Leu Tyr Val Ile Thr Pro Ser Pro Ser His Pro Pro Gln Thr Ala
            340                 345                 350

Gln Val Ala Ile Pro Gly His Arg Gln Leu Gly Pro Thr Ala Thr Glu
        355                 360                 365

Trp Lys Asp Gly Leu Cys Thr Ala Trp Arg Pro Ser Ser Ser Ser Gln
    370                 375                 380

Ser Gln Gln Leu Ser Gln Arg Phe Phe Cys Met Ser His Leu Asn Leu
385                 390                 395                 400

Ile Glu Ser Leu His Gln Glu Thr Leu Gly Thr Val Val Ser Leu Gly
                405                 410                 415

Leu Leu Glu Ile Ser Gly Pro Phe Ser Met Asn Leu Pro Leu Gln Ser
            420                 425                 430

Pro Ser Leu Arg Arg Ser Ser Arg Val Arg Val Asn Lys Met Thr Ala
        435                 440                 445

Ile Pro Ser
    450
```

<210> SEQ ID NO 44
<211> LENGTH: 150
<212> TYPE: PRT
<213> ORGANISM: Mus sp.

<400> SEQUENCE: 44

```
Lys Lys His Cys Trp Tyr Phe Glu Gly Leu Tyr Pro Thr Tyr Tyr Ile
  1               5                  10                  15

Cys Arg Ser Tyr Glu Asp Cys Cys Gly Ser Arg Cys Cys Val Arg Ala
             20                  25                  30

Leu Ser Ile Gln Arg Leu Trp Tyr Phe Trp Phe Leu Leu Met Met Gly
         35                  40                  45

Val Leu Phe Cys Cys Gly Ala Gly Phe Phe Ile Arg Arg Arg Met Tyr
     50                  55                  60

Pro Pro Pro Leu Ile Glu Glu Pro Thr Phe Asn Val Ser Tyr Thr Arg
 65                  70                  75                  80

Gln Pro Pro Asn Pro Ala Pro Gly Ala Gln Gln Met Gly Pro Pro Tyr
                 85                  90                  95

Tyr Thr Asp Pro Gly Gly Pro Gly Met Asn Pro Val Gly Asn Thr Met
            100                 105                 110

Ala Met Ala Phe Gln Val Gln Pro Asn Ser Pro His Gly Gly Thr Thr
        115                 120                 125

Tyr Pro Pro Pro Pro Ser Tyr Cys Asn Thr Pro Pro Pro Pro Tyr Glu
    130                 135                 140

Gln Val Val Lys Asp Lys
145                 150
```

<210> SEQ ID NO 45
<211> LENGTH: 2044
<212> TYPE: DNA
<213> ORGANISM: Homo sapiens -continued

<400> SEQUENCE: 45

```
gtcgacccac gcgtccgggg aattgcagca ggaaaatatg tgaagagttt ttaaacccac     60
aaattcttct tactttagaa ttagttgtta cattggcagg aaaaaataaa tgcagatgtt    120
ggaccatgtt ggaaaccttg tcaagacagt ggattgtctc acacagaatg gaaatgtggc    180
ttctgattct ggtggcgtat atgttccaga gaaatgtgaa ttcagtacat atgccaacta    240
aagctgtgga cccagaagca ttcatgaata ttagtgaaat catccaacat caaggctatc    300
cctgtgagga atatgaagtc gcaactgaag atgggtatat cctttctgtt aacaggattc    360
ctcgaggcct agtgcaacct aagaagacag gttccaggcc tgtggtgtta ctgcagcatg    420
gcctagttgg aggtgctagc aactggattt ccaacctgcc caacaatagc ctgggcttca    480
ttctggcaga tgctggtttt gacgtgtgga tggggaacag caggggaaac gcctggtctc    540
gaaaacacaa gacactctcc atagaccaag atgagttctg ggctttcagt tatgatgaga    600
tggctaggtt tgaccttcct gcagtgataa actttatttt gcagaaaacg ggccaggaaa    660
agatctatta tgtcggctat tcacagggca ccaccatggg ctttattgca ttttccacca    720
tgccagagct ggctcagaaa atcaaaatgt attttgcttt agcacccata gccactgtta    780
agcatgcaaa aagccccggg accaaatttt tgttgctgcc agatatgatg atcaagggat    840
tgtttggcaa aaaagaattt ctgtatcaga ccagatttct cagacaactt gttatttacc    900
tttgtggcca ggtgattctt gatcagattt gtagtaatat catgttactt ctgggtggat    960
tcaacaccaa caatatgaac atgagccgag caagtgtata tgctgcccac actcttgctg   1020
gaacatctgt gcaaaatatt ctacactgga gccaggcagt gaattctggt gaactccggg   1080
catttgactg gggggagtgag accaaaaatc tggaaaaatg caatcagcca actcctgtaa  1140
ggtacagagt cagagatatg acggtcccta cagcaatgtg gacaggaggt caggactggc   1200
tttcaaatcc agaagacgtg aaaatgctgc tctctgaggt gaccaacctc atctaccata   1260
agaatattcc tgaatgggct cacgtggatt tcatctgggg tttggatgct cctcaccgta   1320
tgtacaatga aatcatccat ctgatgcagc aggaggagac caacctttcc cagggacggt   1380
gtgaggccgt attgtgaagc atctgacact gacgatctta ggacaacctc ctgagggatg   1440
gggctaggac ccatgaaggc agaattacgg agagcagaga cctagtatac atttttcaga   1500
ttccctgcac ttggcactaa atccgacact tacatttaca tttttttct gtaaattaaa    1560
gtacttatta ggtaaataga ggttttgtat gctattatat attctaccat cttgaagggt   1620
aggttttacc tgatagccag aaaatatcta gacattctct atatcattca ggtaaatctc   1680
tttaaaacac ctattgtttt ttctataagc catatttttg gagcactaaa gtaaaatggc   1740
aaattgggac agatattgag gtctggagtc tgtggattat tgttgacttt gacaaaataa   1800
gctagacatt ttcaccttgt tgccacagag acataacact acctcaggaa gctgagctgc   1860
tttaaggaca acaacaacaa aatcagtgtt acagtatgga tgaaatctat gttaagcatt   1920
ctcagaataa ggccaagttt tatagttgca tctcagggaa gaaaatttta taggatgttt   1980
atgagttctc caataaatgc attctgcatt acataaaaaa aaaaaaaaaa aaaagggcgg   2040
ccgc                                                                2044
```

<210> SEQ ID NO 46
<211> LENGTH: 1269
<212> TYPE: DNA
<213> ORGANISM: Homo sapiens -continued

<400> SEQUENCE: 46
atgttggaaa ccttgtcaag acagtggatt gtctcacaca gaatggaaat gtggcttctg 60
attctggtgg cgtatatgtt ccagagaaat gtgaattcag tacatatgcc aactaaagct 120
gtggacccag aagcattcat gaatattagt gaaatcatcc aacatcaagg ctatccctgt 180
gaggaatatg aagtcgcaac tgaagatggg tatatccttt ctgttaacag gattcctcga 240
ggcctagtgc aacctaagaa gacaggttcc aggcctgtgg tgttactgca gcatggccta 300
gttggaggtg ctagcaactg gatttccaac ctgcccaaca atagcctggg cttcattctg 360
gcagatgctg gttttgacgt gtggatgggg aacagcaggg gaaacgcctg gtctcgaaaa 420
cacaagacac tctccataga ccaagatgag ttctgggctt tcagttatga tgagatggct 480
aggtttgacc ttcctgcagt gataaacttt attttgcaga aaacgggcca ggaaaagatc 540
tattatgtcg gctattcaca gggcaccacc atgggcttta ttgcattttc caccatgcca 600
gagctggctc agaaaatcaa aatgtatttt gctttagcac ccatagccac tgttaagcat 660
gcaaaaagcc ccgggaccaa atttttgttg ctgccagata tgatgatcaa gggattgttt 720
ggcaaaaaag aatttctgta tcagaccaga tttctcagac aacttgttat ttacctttgt 780
ggccaggtga ttcttgatca gatttgtagt aatatcatgt tacttctggg tggattcaac 840
accaacaata tgaacatgag ccgagcaagt gtatatgctg cccacactct tgctggaaca 900
tctgtgcaaa atattctaca ctggagccag gcagtgaatt ctggtgaact ccgggcattt 960
gactggggga gtgagaccaa aaatctggaa aaatgcaatc agccaactcc tgtaaggtac 1020
agagtcagag atatgacggt ccctacagca atgtggacag gaggtcagga ctggctttca 1080
aatccagaag acgtgaaaat gctgctctct gaggtgacca acctcatcta ccataagaat 1140
attcctgaat gggctcacgt ggatttcatc tggggtttgg atgctcctca ccgtatgtac 1200
aatgaaatca tccatctgat gcagcaggag gagaccaacc tttcccaggg acggtgtgag 1260
gccgtattg 1269

<210> SEQ ID NO 47
<211> LENGTH: 423
<212> TYPE: PRT
<213> ORGANISM: Homo sapiens

<400> SEQUENCE: 47

Met Leu Glu Thr Leu Ser Arg Gln Trp Ile Val Ser His Arg Met Glu
1 5 10 15

Met Trp Leu Leu Ile Leu Val Ala Tyr Met Phe Gln Arg Asn Val Asn
20 25 30

Ser Val His Met Pro Thr Lys Ala Val Asp Pro Glu Ala Phe Met Asn
35 40 45

Ile Ser Glu Ile Ile Gln His Gln Gly Tyr Pro Cys Glu Glu Tyr Glu
50 55 60

Val Ala Thr Glu Asp Gly Tyr Ile Leu Ser Val Asn Arg Ile Pro Arg
65 70 75 80

Gly Leu Val Gln Pro Lys Lys Thr Gly Ser Arg Pro Val Val Leu Leu
85 90 95

Gln His Gly Leu Val Gly Gly Ala Ser Asn Trp Ile Ser Asn Leu Pro
100 105 110

Asn Asn Ser Leu Gly Phe Ile Leu Ala Asp Ala Gly Phe Asp Val Trp
115 120 125

Met Gly Asn Ser Arg Gly Asn Ala Trp Ser Arg Lys His Lys Thr Leu

-continued

```
    130                 135                 140

Ser Ile Asp Gln Asp Glu Phe Trp Ala Phe Ser Tyr Asp Glu Met Ala
145                 150                 155                 160

Arg Phe Asp Leu Pro Ala Val Ile Asn Phe Ile Leu Gln Lys Thr Gly
                165                 170                 175

Gln Glu Lys Ile Tyr Tyr Val Gly Tyr Ser Gln Gly Thr Thr Met Gly
            180                 185                 190

Phe Ile Ala Phe Ser Thr Met Pro Glu Leu Ala Gln Lys Ile Lys Met
        195                 200                 205

Tyr Phe Ala Leu Ala Pro Ile Ala Thr Val Lys His Ala Lys Ser Pro
    210                 215                 220

Gly Thr Lys Phe Leu Leu Leu Pro Asp Met Met Ile Lys Gly Leu Phe
225                 230                 235                 240

Gly Lys Lys Glu Phe Leu Tyr Gln Thr Arg Phe Leu Arg Gln Leu Val
                245                 250                 255

Ile Tyr Leu Cys Gly Gln Val Ile Leu Asp Gln Ile Cys Ser Asn Ile
            260                 265                 270

Met Leu Leu Leu Gly Gly Phe Asn Thr Asn Asn Met Asn Met Ser Arg
        275                 280                 285

Ala Ser Val Tyr Ala Ala His Thr Leu Ala Gly Thr Ser Val Gln Asn
    290                 295                 300

Ile Leu His Trp Ser Gln Ala Val Asn Ser Gly Glu Leu Arg Ala Phe
305                 310                 315                 320

Asp Trp Gly Ser Glu Thr Lys Asn Leu Glu Lys Cys Asn Gln Pro Thr
                325                 330                 335

Pro Val Arg Tyr Arg Val Arg Asp Met Thr Val Pro Thr Ala Met Trp
            340                 345                 350

Thr Gly Gly Gln Asp Trp Leu Ser Asn Pro Glu Asp Val Lys Met Leu
        355                 360                 365

Leu Ser Glu Val Thr Asn Leu Ile Tyr His Lys Asn Ile Pro Glu Trp
    370                 375                 380

Ala His Val Asp Phe Ile Trp Gly Leu Asp Ala Pro His Arg Met Tyr
385                 390                 395                 400

Asn Glu Ile Ile His Leu Met Gln Gln Glu Glu Thr Asn Leu Ser Gln
                405                 410                 415

Gly Arg Cys Glu Ala Val Leu
            420


<210> SEQ ID NO 48
<211> LENGTH: 33
<212> TYPE: PRT
<213> ORGANISM: Homo sapiens

<400> SEQUENCE: 48

Met Leu Glu Thr Leu Ser Arg Gln Trp Ile Val Ser His Arg Met Glu
  1               5                  10                  15

Met Trp Leu Leu Ile Leu Val Ala Tyr Met Phe Gln Arg Asn Val Asn
             20                  25                  30

Ser


<210> SEQ ID NO 49
<211> LENGTH: 390
<212> TYPE: PRT
<213> ORGANISM: Homo sapiens

<400> SEQUENCE: 49
```

-continued

```
Val His Met Pro Thr Lys Ala Val Asp Pro Glu Ala Phe Met Asn Ile
  1               5                  10                  15

Ser Glu Ile Ile Gln His Gln Gly Tyr Pro Cys Glu Glu Tyr Glu Val
             20                  25                  30

Ala Thr Glu Asp Gly Tyr Ile Leu Ser Val Asn Arg Ile Pro Arg Gly
         35                  40                  45

Leu Val Gln Pro Lys Lys Thr Gly Ser Arg Pro Val Val Leu Leu Gln
     50                  55                  60

His Gly Leu Val Gly Gly Ala Ser Asn Trp Ile Ser Asn Leu Pro Asn
 65                  70                  75                  80

Asn Ser Leu Gly Phe Ile Leu Ala Asp Ala Gly Phe Asp Val Trp Met
                 85                  90                  95

Gly Asn Ser Arg Gly Asn Ala Trp Ser Arg Lys His Lys Thr Leu Ser
            100                 105                 110

Ile Asp Gln Asp Glu Phe Trp Ala Phe Ser Tyr Asp Glu Met Ala Arg
        115                 120                 125

Phe Asp Leu Pro Ala Val Ile Asn Phe Ile Leu Gln Lys Thr Gly Gln
    130                 135                 140

Glu Lys Ile Tyr Tyr Val Gly Tyr Ser Gln Gly Thr Thr Met Gly Phe
145                 150                 155                 160

Ile Ala Phe Ser Thr Met Pro Glu Leu Ala Gln Lys Ile Lys Met Tyr
                165                 170                 175

Phe Ala Leu Ala Pro Ile Ala Thr Val Lys His Ala Lys Ser Pro Gly
            180                 185                 190

Thr Lys Phe Leu Leu Leu Pro Asp Met Met Ile Lys Gly Leu Phe Gly
        195                 200                 205

Lys Lys Glu Phe Leu Tyr Gln Thr Arg Phe Leu Arg Gln Leu Val Ile
    210                 215                 220

Tyr Leu Cys Gly Gln Val Ile Leu Asp Gln Ile Cys Ser Asn Ile Met
225                 230                 235                 240

Leu Leu Leu Gly Gly Phe Asn Thr Asn Asn Met Asn Met Ser Arg Ala
                245                 250                 255

Ser Val Tyr Ala Ala His Thr Leu Ala Gly Thr Ser Val Gln Asn Ile
            260                 265                 270

Leu His Trp Ser Gln Ala Val Asn Ser Gly Glu Leu Arg Ala Phe Asp
        275                 280                 285

Trp Gly Ser Glu Thr Lys Asn Leu Glu Lys Cys Asn Gln Pro Thr Pro
    290                 295                 300

Val Arg Tyr Arg Val Arg Asp Met Thr Val Pro Thr Ala Met Trp Thr
305                 310                 315                 320

Gly Gly Gln Asp Trp Leu Ser Asn Pro Glu Asp Val Lys Met Leu Leu
                325                 330                 335

Ser Glu Val Thr Asn Leu Ile Tyr His Lys Asn Ile Pro Glu Trp Ala
            340                 345                 350

His Val Asp Phe Ile Trp Gly Leu Asp Ala Pro His Arg Met Tyr Asn
        355                 360                 365

Glu Ile Ile His Leu Met Gln Gln Glu Glu Thr Asn Leu Ser Gln Gly
    370                 375                 380

Arg Cys Glu Ala Val Leu
385                 390
```

<210> SEQ ID NO 50
<211> LENGTH: 221

-continued

<212> TYPE: PRT
<213> ORGANISM: Homo sapiens

<400> SEQUENCE: 50

Val His Met Pro Thr Lys Ala Val Asp Pro Glu Ala Phe Met Asn Ile
1 5 10 15

Ser Glu Ile Ile Gln His Gln Gly Tyr Pro Cys Glu Glu Tyr Glu Val
20 25 30

Ala Thr Glu Asp Gly Tyr Ile Leu Ser Val Asn Arg Ile Pro Arg Gly
35 40 45

Leu Val Gln Pro Lys Lys Thr Gly Ser Arg Pro Val Val Leu Leu Gln
50 55 60

His Gly Leu Val Gly Gly Ala Ser Asn Trp Ile Ser Asn Leu Pro Asn
65 70 75 80

Asn Ser Leu Gly Phe Ile Leu Ala Asp Ala Gly Phe Asp Val Trp Met
85 90 95

Gly Asn Ser Arg Gly Asn Ala Trp Ser Arg Lys His Lys Thr Leu Ser
100 105 110

Ile Asp Gln Asp Glu Phe Trp Ala Phe Ser Tyr Asp Glu Met Ala Arg
115 120 125

Phe Asp Leu Pro Ala Val Ile Asn Phe Ile Leu Gln Lys Thr Gly Gln
130 135 140

Glu Lys Ile Tyr Tyr Val Gly Tyr Ser Gln Gly Thr Thr Met Gly Phe
145 150 155 160

Ile Ala Phe Ser Thr Met Pro Glu Leu Ala Gln Lys Ile Lys Met Tyr
165 170 175

Phe Ala Leu Ala Pro Ile Ala Thr Val Lys His Ala Lys Ser Pro Gly
180 185 190

Thr Lys Phe Leu Leu Leu Pro Asp Met Met Ile Lys Gly Leu Phe Gly
195 200 205

Lys Lys Glu Phe Leu Tyr Gln Thr Arg Phe Leu Arg Gln
210 215 220

<210> SEQ ID NO 51
<211> LENGTH: 25
<212> TYPE: PRT
<213> ORGANISM: Homo sapiens

<400> SEQUENCE: 51

Leu Val Ile Tyr Leu Cys Gly Gln Val Ile Leu Asp Gln Ile Cys Ser
1 5 10 15

Asn Ile Met Leu Leu Leu Gly Gly Phe
20 25

<210> SEQ ID NO 52
<211> LENGTH: 144
<212> TYPE: PRT
<213> ORGANISM: Homo sapiens

<400> SEQUENCE: 52

Asn Thr Asn Asn Met Asn Met Ser Arg Ala Ser Val Tyr Ala Ala His
1 5 10 15

Thr Leu Ala Gly Thr Ser Val Gln Asn Ile Leu His Trp Ser Gln Ala
20 25 30

Val Asn Ser Gly Glu Leu Arg Ala Phe Asp Trp Gly Ser Glu Thr Lys
35 40 45

Asn Leu Glu Lys Cys Asn Gln Pro Thr Pro Val Arg Tyr Arg Val Arg

-continued

```
                50                  55                  60

Asp Met Thr Val Pro Thr Ala Met Trp Thr Gly Gly Gln Asp Trp Leu
 65                  70                  75                  80

Ser Asn Pro Glu Asp Val Lys Met Leu Leu Ser Glu Val Thr Asn Leu
                 85                  90                  95

Ile Tyr His Lys Asn Ile Pro Glu Trp Ala His Val Asp Phe Ile Trp
            100                 105                 110

Gly Leu Asp Ala Pro His Arg Met Tyr Asn Glu Ile Ile His Leu Met
        115                 120                 125

Gln Gln Glu Glu Thr Asn Leu Ser Gln Gly Arg Cys Glu Ala Val Leu
    130                 135                 140
```

<210> SEQ ID NO 53
<211> LENGTH: 2133
<212> TYPE: DNA
<213> ORGANISM: Homo sapiens

<400> SEQUENCE: 53

```
gtcgacccac gcgtccacgg cgagggctcc cggggcgcag cattgccccc cctgcaccac     60
ctcaccaaga tggctacttt gggacacaca ttccccttct atgctggccc caagccaacc    120
ttcccgatgg acaccacttt ggccagcatc atcatgatct ttctgactgc actggccacg    180
ttcatcgtca tcctgcctgg cattcgggga aagacgaggc tgttctggct gcttcgggtg    240
gtgaccagct tattcatcgg ggctgcaatc ctggctgtga atttcagttc tgagtggtct    300
gtgggccagg tcagcaccaa cacatcatac aaggccttca gttctgagtg gatcagcgct    360
gatattgggc tgcaggtcgg gctgggtgga gtcaacatca cactcacagg gacccccgtg    420
cagcagctga atgagaccat caattacaac gaggagttca cctggcgcct gggtgagaac    480
tatgctgagg agtgtgcaaa ggctctggag aaggggctgc cagaccctgt gttgtaccta    540
gctgagaagt tcactccaag aagcccatgt ggcctatacc gccagtaccg cctggcggga    600
cactacacct cagccatgct atgggtggca ttcctctgct ggctgctggc caatgtgatg    660
ctctccatgc ctgtgctggt atatggtggc tacatgctat tggccacggg catcttccag    720
ctgttggctc tgctcttctt ctccatggcc acatcactca cctcaccctg tcccctgcac    780
ctgggcgctt ctgtgctgca tactcaccat gggcctgcct tctggatcac attgaccaca    840
ggactgctgt gtgtgctgct gggcctggct atggcggtgg cccacaggat gcagcctcac    900
aggctgaagg ctttcttcaa ccagagtgtg gatgaagacc ccatgctgga gtggagtcct    960
gaggaaggtg gactcctgag cccccgctac cggtccatgg ctgacagtcc caagtcccag   1020
gacattcccc tgtcagaggc ttcctccacc aaggcatact gtaaggaggc acaccccaaa   1080
gatcctgatt gtgctttata acattcctcc ccgtggaggc cacctggact tccagtctgg   1140
ctccaaacct cattggcgcc ccataaaacc agcagaactg ccctcagggt ggctgttacc   1200
agacacccag caccaatcta cagacggagt agaaaaagga ggctctatat actgatgtta   1260
aaaaacaaaa caaaacaaaa agccctaagg gactgaagag atgctgggcc tgtccataaa   1320
gcctgttgcc atgataaggc caagcagggg ctagcttatc tgcacagcaa cccagccttt   1380
ccgtgctgcc ttgcctcttc aagatgctat tcactgaaac ctaacttcac ccccataaca   1440
ccagcagggt gggggttaca tatgattctc ctatggtttc ctctcatccc tcggcacctc   1500
ttgttttcct ttttcctggg ttccttttgt tcttccttta cttctccagc ttgtgtggcc   1560
ttttggtaca atgaaagaca gcactggaaa ggaggggaaa ccaaacttct catcctaggt   1620
```

-continued

```
ctaacattaa ccaactatgc cacattctct ttgagcttca gttcccaaat ttgctacata   1680

agattgcaag acttgccaag aatcttggga tttatctttc tatgccttgc tgacacctac   1740

cttggccctc aaacaccacc tcacaagaag ccaggtggga agttagggaa tcaactccaa   1800

aacgctattc cttcccaccc cactcagctg ggctagctga gtggcatcca ggacggggga   1860

gtgggtgacc tgcctcatca ctgccaccta acgtccccct ggggtggttc agaaagatgc   1920

tagctctggt agggtccctc cggcctcact agagggcgcc cctattactc tggagtcgac   1980

gcagagaatc aggtttcaca gcactgcgga gagtgtacta ggctgtctcc agcccagcga   2040

agctcatgag gacgtgcgac cccggcgcgg agaagccatg aaaattaatg ggaaaaacag   2100

tttttaaaaa aaaaaaaaaa aaagggcggc cgc                                 2133
```

<210> SEQ ID NO 54
<211> LENGTH: 1029
<212> TYPE: DNA
<213> ORGANISM: Homo sapiens

<400> SEQUENCE: 54

```
atggctactt tgggacacac attccccttc tatgctggcc ccaagccaac cttcccgatg     60

gacaccactt tggccagcat catcatgatc tttctgactg cactggccac gttcatcgtc    120

atcctgcctg gcattcgggg aaagacgagg ctgttctggc tgcttcgggt ggtgaccagc    180

ttattcatcg ggctgcaat cctggctgtg aatttcagtt ctgagtggtc tgtgggccag    240

gtcagcacca acacatcata caaggccttc agttctgagt ggatcagcgc tgatattggg    300

ctgcaggtcg ggctgggtgg agtcaacatc acactcacag ggacccccgt gcagcagctg    360

aatgagacca tcaattacaa cgaggagttc acctggcgcc tgggtgagaa ctatgctgag    420

gagtgtgcaa aggctctgga gaaggggctg ccagaccctg tgttgtacct agctgagaag    480

ttcactccaa gaagcccatg tggcctatac cgccagtacc gcctggcggg acactacacc    540

tcagccatgc tatgggtggc attcctctgc tggctgctgg ccaatgtgat gctctccatg    600

cctgtgctgg tatatggtgg ctacatgcta ttggccacgg gcatcttcca gctgttggct    660

ctgctcttct tctccatggc cacatcactc acctcaccct gtcccctgca cctgggcgct    720

tctgtgctgc atactcacca tgggcctgcc ttctggatca cattgaccac aggactgctg    780

tgtgtgctgc tgggcctggc tatggcggtg gcccacagga tgcagcctca caggctgaag    840

gctttcttca accagagtgt ggatgaagac ccccatgctgg agtggagtcc tgaggaaggt    900

ggactcctga gcccccgcta ccggtccatg gctgacagtc ccaagtccca ggacattccc    960

ctgtcagagg cttcctccac caaggcatac tgtaaggagg cacaccccaa agatcctgat   1020

tgtgctttta                                                           1029
```

<210> SEQ ID NO 55
<211> LENGTH: 343
<212> TYPE: PRT
<213> ORGANISM: Homo sapiens

<400> SEQUENCE: 55

```
Met Ala Thr Leu Gly His Thr Phe Pro Phe Tyr Ala Gly Pro Lys Pro
  1               5                  10                  15

Thr Phe Pro Met Asp Thr Thr Leu Ala Ser Ile Ile Met Ile Phe Leu
             20                  25                  30

Thr Ala Leu Ala Thr Phe Ile Val Ile Leu Pro Gly Ile Arg Gly Lys
         35                  40                  45
```

-continued

```
Thr Arg Leu Phe Trp Leu Leu Arg Val Val Thr Ser Leu Phe Ile Gly
     50                  55                  60

Ala Ala Ile Leu Ala Val Asn Phe Ser Ser Glu Trp Ser Val Gly Gln
 65                  70                  75                  80

Val Ser Thr Asn Thr Ser Tyr Lys Ala Phe Ser Ser Glu Trp Ile Ser
                 85                  90                  95

Ala Asp Ile Gly Leu Gln Val Gly Leu Gly Gly Val Asn Ile Thr Leu
            100                 105                 110

Thr Gly Thr Pro Val Gln Gln Leu Asn Glu Thr Ile Asn Tyr Asn Glu
        115                 120                 125

Glu Phe Thr Trp Arg Leu Gly Glu Asn Tyr Ala Glu Glu Cys Ala Lys
    130                 135                 140

Ala Leu Glu Lys Gly Leu Pro Asp Pro Val Leu Tyr Leu Ala Glu Lys
145                 150                 155                 160

Phe Thr Pro Arg Ser Pro Cys Gly Leu Tyr Arg Gln Tyr Arg Leu Ala
                165                 170                 175

Gly His Tyr Thr Ser Ala Met Leu Trp Val Ala Phe Leu Cys Trp Leu
            180                 185                 190

Leu Ala Asn Val Met Leu Ser Met Pro Val Leu Val Tyr Gly Gly Tyr
        195                 200                 205

Met Leu Leu Ala Thr Gly Ile Phe Gln Leu Leu Ala Leu Leu Phe Phe
    210                 215                 220

Ser Met Ala Thr Ser Leu Thr Ser Pro Cys Pro Leu His Leu Gly Ala
225                 230                 235                 240

Ser Val Leu His Thr His His Gly Pro Ala Phe Trp Ile Thr Leu Thr
                245                 250                 255

Thr Gly Leu Leu Cys Val Leu Leu Gly Leu Ala Met Ala Val Ala His
            260                 265                 270

Arg Met Gln Pro His Arg Leu Lys Ala Phe Phe Asn Gln Ser Val Asp
        275                 280                 285

Glu Asp Pro Met Leu Glu Trp Ser Pro Glu Glu Gly Gly Leu Leu Ser
    290                 295                 300

Pro Arg Tyr Arg Ser Met Ala Asp Ser Pro Lys Ser Gln Asp Ile Pro
305                 310                 315                 320

Leu Ser Glu Ala Ser Ser Thr Lys Ala Tyr Cys Lys Glu Ala His Pro
                325                 330                 335

Lys Asp Pro Asp Cys Ala Leu
            340


<210> SEQ ID NO 56
<211> LENGTH: 23
<212> TYPE: PRT
<213> ORGANISM: Homo sapiens

<400> SEQUENCE: 56

Met Ala Thr Leu Gly His Thr Phe Pro Phe Tyr Ala Gly Pro Lys Pro
  1               5                  10                  15

Thr Phe Pro Met Asp Thr Thr
             20


<210> SEQ ID NO 57
<211> LENGTH: 112
<212> TYPE: PRT
<213> ORGANISM: Homo sapiens

<400> SEQUENCE: 57
```

-continued

```
Asn Phe Ser Ser Glu Trp Ser Val Gly Gln Val Ser Thr Asn Thr Ser
  1               5                  10                  15

Tyr Lys Ala Phe Ser Ser Glu Trp Ile Ser Ala Asp Ile Gly Leu Gln
             20                  25                  30

Val Gly Leu Gly Gly Val Asn Ile Thr Leu Thr Gly Thr Pro Val Gln
         35                  40                  45

Gln Leu Asn Glu Thr Ile Asn Tyr Asn Glu Glu Phe Thr Trp Arg Leu
     50                  55                  60

Gly Glu Asn Tyr Ala Glu Glu Cys Ala Lys Ala Leu Glu Lys Gly Leu
 65                  70                  75                  80

Pro Asp Pro Val Leu Tyr Leu Ala Glu Lys Phe Thr Pro Arg Ser Pro
                 85                  90                  95

Cys Gly Leu Tyr Arg Gln Tyr Arg Leu Ala Gly His Tyr Thr Ser Ala
            100                 105                 110


<210> SEQ ID NO 58
<211> LENGTH: 22
<212> TYPE: PRT
<213> ORGANISM: Homo sapiens

<400> SEQUENCE: 58

Thr Ser Leu Thr Ser Pro Cys Pro Leu His Leu Gly Ala Ser Val Leu
  1               5                  10                  15

His Thr His His Gly Pro
             20


<210> SEQ ID NO 59
<211> LENGTH: 19
<212> TYPE: PRT
<213> ORGANISM: Homo sapiens

<400> SEQUENCE: 59

Leu Ala Ser Ile Ile Met Ile Phe Leu Thr Ala Leu Ala Thr Phe Ile
  1               5                  10                  15

Val Ile Leu


<210> SEQ ID NO 60
<211> LENGTH: 20
<212> TYPE: PRT
<213> ORGANISM: Homo sapiens

<400> SEQUENCE: 60

Leu Phe Trp Leu Leu Arg Val Val Thr Ser Leu Phe Ile Gly Ala Ala
  1               5                  10                  15

Ile Leu Ala Val
             20


<210> SEQ ID NO 61
<211> LENGTH: 22
<212> TYPE: PRT
<213> ORGANISM: Homo sapiens

<400> SEQUENCE: 61

Met Leu Trp Val Ala Phe Leu Cys Trp Leu Leu Ala Asn Val Met Leu
  1               5                  10                  15

Ser Met Pro Val Leu Val
             20


<210> SEQ ID NO 62
<211> LENGTH: 17
```

-continued

<212> TYPE: PRT
<213> ORGANISM: Homo sapiens

<400> SEQUENCE: 62

Leu Ala Thr Gly Ile Phe Gln Leu Leu Ala Leu Leu Phe Phe Ser Met
1 5 10 15

Ala

<210> SEQ ID NO 63
<211> LENGTH: 22
<212> TYPE: PRT
<213> ORGANISM: Homo sapiens

<400> SEQUENCE: 63

Ala Phe Trp Ile Thr Leu Thr Thr Gly Leu Leu Cys Val Leu Leu Gly
1 5 10 15

Leu Ala Met Ala Val Ala
20

<210> SEQ ID NO 64
<211> LENGTH: 8
<212> TYPE: PRT
<213> ORGANISM: Homo sapiens

<400> SEQUENCE: 64

Pro Gly Ile Arg Gly Lys Thr Arg
1 5

<210> SEQ ID NO 65
<211> LENGTH: 6
<212> TYPE: PRT
<213> ORGANISM: Homo sapiens

<400> SEQUENCE: 65

Tyr Gly Gly Tyr Met Leu
1 5

<210> SEQ ID NO 66
<211> LENGTH: 72
<212> TYPE: PRT
<213> ORGANISM: Homo sapiens

<400> SEQUENCE: 66

His Arg Met Gln Pro His Arg Leu Lys Ala Phe Phe Asn Gln Ser Val
1 5 10 15

Asp Glu Asp Pro Met Leu Glu Trp Ser Pro Glu Glu Gly Gly Leu Leu
20 25 30

Ser Pro Arg Tyr Arg Ser Met Ala Asp Ser Pro Lys Ser Gln Asp Ile
35 40 45

Pro Leu Ser Glu Ala Ser Ser Thr Lys Ala Tyr Cys Lys Glu Ala His
50 55 60

Pro Lys Asp Pro Asp Cys Ala Leu
65 70

<210> SEQ ID NO 67
<211> LENGTH: 4928
<212> TYPE: DNA
<213> ORGANISM: Mus sp.

<400> SEQUENCE: 67
gtcgacccac gcgtccgccc ggctcccggt gctgccccct ctgccccggg ccgcgcccgg 60

-continued

```
gggtcccgca ctgacggccc atggcgccgc ccgccgcccg tctcgcgctg ctctccgccg    120
ctgcgctcac tctggcggcc cggcccgcgc ccggtccccg ctccggcccc gagtgcttca    180
cagccaacgg tgcagattac aggggaacac agagctggac agcgctgcaa ggtgggaagc    240
catgtctgtt ctggaacgag actttccagc atccgtacaa cacgctgaag taccccaacg    300
gggaaggagg actgggcgag cacaattatt gcagaaatcc agatggagac gtgagccctt    360
ggtgctacgt ggccgagcat gaggacggag tctactggaa gtactgtgaa attcctgcct    420
gccagatgcc tggaaacctt ggctgctaca aggatcatgg aaacccacct cctctcacgg    480
gcaccagtaa aacctctaac aagctcacca tacaaacctg tatcagcttc tgtcggagtc    540
agagattcaa gtttgctggg atggagtcag gctatgcctg cttctgtggg aacaatcctg    600
actactggaa gcacggggag gcggccagca ccgagtgcaa tagtgtctgc ttcggggacc    660
acacgcagcc ctgcggtggg gacggcagga ttatcctctt tgacactctc gtgggcgcct    720
gcggtgggaa ctactcagcc atggcagccg tggtgtactc ccctgacttc cctgacacct    780
acgccactgg cagagtctgc tactggacca tccgggttcc aggagcctct cgcatccatt    840
tcaacttcac cctgtttgat atcagggact ctgcagacat ggtggagctg ctggacggct    900
acacccaccg cgtcctggtc cggctcagtg ggaggagccg cccgcctctg tctttcaatg    960
tctctctgga ttttgtcatt ttgtatttct tctctgatcg catcaatcag gcccagggat   1020
ttgctgtgtt gtaccaagcc accaaggagg aaccgccaca ggagagacct gctgtcaacc   1080
agaccctggc agaggtgatc accgagcaag ccaacctcag tgtcagcgct gcccactcct   1140
ccaaagtcct ctatgtcatc acccccagcc ccagccaccc tccgcagact gcccaggtag   1200
ccattcctgg gcaccgtcag ttggggccaa cagccacaga gtggaaggat ggactgtgta   1260
cggcctggcg accctcctca tcctcacagt cacagcagtt gtcgcaaaga ttcttctgca   1320
tgtcacattt aaatctcatc gagtccctgc atcaggagac cttagggact gtcgtcagcc   1380
tggggcttct ggagatatct ggaccatttt ctatgaacct tccactacaa tctccatctt   1440
taagaagaag ctcaagggtc agagtcaaca agatgaccgc aatcccctcg tgagtgactg   1500
aagcccacgc ctgcatgaga ggctccgctc caagctcgag tttgctcccc tgagttctcc   1560
tctgatgagt tccctgcctt cccattcacc accatctctt ttgggagcac cctgctttag   1620
aggcagccca gcctgggatc ctccatcaca tgtaccagcc tggctgctct gctggggatg   1680
gtaagacagg cccaggctga caggacacag ctggacctga ctccagaaga ctcttgggtg   1740
gtggggaggt atagtgtagg atgagttttc ttgcttcttc tctgttttgt ccacatacag   1800
atcggtttcc cctgtcttta cagtttgcaa tagagccaga ctgaaagaac tgtcaggttt   1860
tctaggctgg cctggttccc cactaagagt ggcattggcg ccctagaggc ccagaggccc   1920
agtgtaggct tggagctttc tctgctgcca actaccatgt gtcatctagt ccgaggggac   1980
tgagagcagg gccacaccag atgtcatctt tctagagggt tctttttagt acccactgac   2040
caatggggca agcctgagga ttggtccatc tgtttgtcca tggaacagac acagtgaact   2100
tcctggatac tagacttaac tagcctagcc ctcaagtagt tgccaatcct gtggaatcag   2160
aattcagcct gtcttcctgt cctcagccca agcctgtagc ctagagctgg ggctgtagcc   2220
tagagctggg gctgtagcct agagctgggg ctgtagcaca gagctggggc tgtagcctag   2280
agctggggct gtagcacaga gctggggctg tagcctagag ctggggctgt agcacagagc   2340
tggggctgta gcacagagct ggggctgtag cctagagctg gggctgtagc acagagctgg   2400
ggctgtaact cagcgatcaa gagcttgctt tgtatacatc ggaccctagg ttctatccca   2460
```

-continued

```
gcactatcag aaggtgggag agaaaaagac tgcaccatag catgcgggca gcatctgtgg   2520
ttcctacgtg aggtgtcatc attttaaaag cagatcaaaa ctaccgcgag ttttgtcctt   2580
tgtcccttat catgggagca gagtaggagt aagggctctg gtcttgctca ttgtccccca   2640
gacagggagg caggaaaagg tcaggcttgg gaactggaga tcctcccagg aaaagctgca   2700
agattgagag acccagctgc agttgggaga ggaagggcca tccccgactg agaagtcctg   2760
cagtctggaa gtggcctttg tcagcagcag ctgtgccctg aaggtagacc ttggtcactc   2820
tcctgccagc ccttgagcct ctgctctcct gggtaccctc ctggaacacc atgctaacct   2880
tccccgagtc tctcagtcac tgccattgag gcctctcctc tagctgctgc tccccaggac   2940
tgtctggggc catctgggga tcagggagag gcagcaggag tactgacgag gcagtgacct   3000
gagctgatga gtcaaccaga ggacaccaga gtctacagtg ggctggctgc tggctcagct   3060
cctatgggag gcctacaggg gtactaagct agggggtcat catctcattt gatctgggaa   3120
aggctacagg ctcctggatg tgaagacagg cccactacat aagaagacca ctggaaatag   3180
actgacagga gcaggttcca ctctaggctg tccatagcgt ttgcaggact cccctgagac   3240
caagtgttga gtcacagagt gccatgtgcg tagtgcataa aggatatggg ttcttaacca   3300
gggaaggctc atagcaggcc aggacatttt ttcagctcag agcactggcc ccaggcttcc   3360
tctaagccac cactcacctg tctcttccta tctcggacac aggaagcaag ccccagtgtg   3420
gtggcagctg cggctcagca ttggtgtccc caggaagggc ggtggatgtg cccacgctcc   3480
ttttgctgtg ggcctggcac agcccaacac tgcagggccc accttctctc ttgggggta   3540
gggacacata aggaaaacta acccacctcc aacaacagca gaggacagtg ggaaggaagg   3600
gctgtaaatc acccaggcca gacctccaga aatgacaggc acagtctgtt agaacctgta   3660
ggcagccagt cacagagggc ctttgtgctg gtaacaccct gcctggagca taggggtaag   3720
ccgagggaga agagcagccc tcagagacat cagctaaaaa cataggtgcc ctatgtccct   3780
cccttcctgt cacactgctt acaaagcaga gacagagtag gaaagaggtc ttcatcctct   3840
cccacatcag caaggatagg gctgcggctg cctaaagtga gcaaggagaa cagagctctg   3900
gacttctcta aatgtgggct ctggcttcag actcctcagc caaaagctct tgaagatcaa   3960
agctctggcg ggtacagctg tcctggcctg tgggccagcc catgggatgt gcctgggcca   4020
ggtgccaccc cacggctcac tgtcatccca ggagggaccc cacctgatgc tcctcatcat   4080
ccgctggcct gacactatca gagctcgcgc cggctgttgc cagggacaga ctgactacac   4140
ttgaccttca agagcactta gaagtggatg gcctccagac tctgtcagcc tctgcagggg   4200
ccacacaagt ctcccgagcc aagtccacaa gcctccatgg ttccctggct cctctcctgt   4260
ggagtgtcct gtttgatgtc tgaggtctgc tttgggtacc gccctgggaa ctgctaacct   4320
ccgattggtc cctttgtgtc tctgtttact gtcctcttct acctccaggt cacttagctc   4380
tggctgctct ggctgggagt gggggtggg gatgctggct gcaccccac cctggtctgc   4440
caacagaacc tgggggcctc acacgggctc ctgtcttgcc aagctggagc tgagcacact   4500
ggcccaggct gagtggggca gagcaaacaa gtggaagggg atctctctcc ttagagggag   4560
gtggccgaag gtgtagatcc agcgagggag ctgccatccc cgccaccttc atagcagcaa   4620
gaccttccca tttccaatct caccctccag cagggatatg actttggaca acaaggcttt   4680
atttgtaaat atgctcttaa tatgcaactt tgagaataag atagaaacat catgtatttt   4740
aaaatataaa atgaagtgtg acacactgta tacaatttaa tatatatttt taggattttg   4800
```

-continued

```
ttatttaaga aaatggaatg tgatggtact taacttttac aaaagagaga aaatgttatt   4860

tttactgttt gaagaaaata aatattctca ttgttgtaga aaaaaaaaaa aaaaaaaagg   4920

gcggccgc                                                            4928
```

<210> SEQ ID NO 68
<211> LENGTH: 1410
<212> TYPE: DNA
<213> ORGANISM: Mus sp.

<400> SEQUENCE: 68

```
atggcgccgc ccgccgcccg tctcgcgctg ctctccgccg ctgcgctcac tctggcggcc     60

cggcccgcgc ccggtccccg ctccggcccc gagtgcttca cagccaacgg tgcagattac    120

aggggaacac agagctggac agcgctgcaa ggtgggaagc catgtctgtt ctggaacgag    180

actttccagc atccgtacaa cacgctgaag taccccaacg gggaaggagg actgggcgag    240

cacaattatt gcagaaatcc agatggagac gtgagccctt ggtgctacgt ggccgagcat    300

gaggacggag tctactggaa gtactgtgaa attcctgcct gccagatgcc tggaaacctt    360

ggctgctaca aggatcatgg aaacccacct cctctcacgg gcaccagtaa aacctctaac    420

aagctcacca tacaaacctg tatcagcttc tgtcggagtc agagattcaa gtttgctggg    480

atggagtcag gctatgcctg cttctgtggg aacaatcctg actactggaa gcacggggag    540

gcggccagca ccgagtgcaa tagtgtctgc ttcggggacc acacgcagcc ctgcggtggg    600

gacggcagga ttatcctctt tgacactctc gtgggcgcct gcggtgggaa ctactcagcc    660

atggcagccg tggtgtactc ccctgacttc cctgacacct acgccactgg cagagtctgc    720

tactggacca tccgggttcc aggagcctct cgcatccatt tcaacttcac cctgtttgat    780

atcagggact ctgcagacat ggtggagctg ctggacggct acacccaccg cgtcctggtc    840

cggctcagtg ggaggagccg cccgcctctg tctttcaatg tctctctgga ttttgtcatt    900

ttgtatttct tctctgatcg catcaatcag gcccagggat ttgctgtgtt gtaccaagcc    960

accaaggagg aaccgccaca ggagagacct gctgtcaacc agaccctggc agaggtgatc   1020

accgagcaag ccaacctcag tgtcagcgct gcccactcct ccaaagtcct ctatgtcatc   1080

acccccagcc ccagccaccc tccgcagact gcccaggtag ccattcctgg gcaccgtcag   1140

ttggggccaa cagccacaga gtggaaggat ggactgtgta cggcctggcg accctcctca   1200

tcctcacagt cacagcagtt gtcgcaaaga ttcttctgca tgtcacattt aaatctcatc   1260

gagtccctgc atcaggagac cttagggact gtcgtcagcc tggggcttct ggagatatct   1320

ggaccatttt ctatgaacct tccactacaa tctccatctt taagaagaag ctcaagggtc   1380

agagtcaaca agatgaccgc aatcccctcg                                    1410
```

<210> SEQ ID NO 69
<211> LENGTH: 470
<212> TYPE: PRT
<213> ORGANISM: Mus sp.

<400> SEQUENCE: 69

```
Met Ala Pro Pro Ala Ala Arg Leu Ala Leu Leu Ser Ala Ala Ala Leu
  1               5                  10                  15

Thr Leu Ala Ala Arg Pro Ala Pro Gly Pro Arg Ser Gly Pro Glu Cys
             20                  25                  30

Phe Thr Ala Asn Gly Ala Asp Tyr Arg Gly Thr Gln Ser Trp Thr Ala
         35                  40                  45
```

-continued

```
Leu Gln Gly Gly Lys Pro Cys Leu Phe Trp Asn Glu Thr Phe Gln His
     50                  55                  60

Pro Tyr Asn Thr Leu Lys Tyr Pro Asn Gly Glu Gly Gly Leu Gly Glu
 65                  70                  75                  80

His Asn Tyr Cys Arg Asn Pro Asp Gly Asp Val Ser Pro Trp Cys Tyr
                 85                  90                  95

Val Ala Glu His Glu Asp Gly Val Tyr Trp Lys Tyr Cys Glu Ile Pro
            100                 105                 110

Ala Cys Gln Met Pro Gly Asn Leu Gly Cys Tyr Lys Asp His Gly Asn
        115                 120                 125

Pro Pro Pro Leu Thr Gly Thr Ser Lys Thr Ser Asn Lys Leu Thr Ile
    130                 135                 140

Gln Thr Cys Ile Ser Phe Cys Arg Ser Gln Arg Phe Lys Phe Ala Gly
145                 150                 155                 160

Met Glu Ser Gly Tyr Ala Cys Phe Cys Gly Asn Asn Pro Asp Tyr Trp
                165                 170                 175

Lys His Gly Glu Ala Ala Ser Thr Glu Cys Asn Ser Val Cys Phe Gly
            180                 185                 190

Asp His Thr Gln Pro Cys Gly Gly Asp Gly Arg Ile Ile Leu Phe Asp
        195                 200                 205

Thr Leu Val Gly Ala Cys Gly Gly Asn Tyr Ser Ala Met Ala Ala Val
    210                 215                 220

Val Tyr Ser Pro Asp Phe Pro Asp Thr Tyr Ala Thr Gly Arg Val Cys
225                 230                 235                 240

Tyr Trp Thr Ile Arg Val Pro Gly Ala Ser Arg Ile His Phe Asn Phe
                245                 250                 255

Thr Leu Phe Asp Ile Arg Asp Ser Ala Asp Met Val Glu Leu Leu Asp
            260                 265                 270

Gly Tyr Thr His Arg Val Leu Val Arg Leu Ser Gly Arg Ser Arg Pro
        275                 280                 285

Pro Leu Ser Phe Asn Val Ser Leu Asp Phe Val Ile Leu Tyr Phe Phe
    290                 295                 300

Ser Asp Arg Ile Asn Gln Ala Gln Gly Phe Ala Val Leu Tyr Gln Ala
305                 310                 315                 320

Thr Lys Glu Glu Pro Pro Gln Glu Arg Pro Ala Val Asn Gln Thr Leu
                325                 330                 335

Ala Glu Val Ile Thr Glu Gln Ala Asn Leu Ser Val Ser Ala Ala His
            340                 345                 350

Ser Ser Lys Val Leu Tyr Val Ile Thr Pro Ser Pro Ser His Pro Pro
        355                 360                 365

Gln Thr Ala Gln Val Ala Ile Pro Gly His Arg Gln Leu Gly Pro Thr
    370                 375                 380

Ala Thr Glu Trp Lys Asp Gly Leu Cys Thr Ala Trp Arg Pro Ser Ser
385                 390                 395                 400

Ser Ser Gln Ser Gln Gln Leu Ser Gln Arg Phe Phe Cys Met Ser His
                405                 410                 415

Leu Asn Leu Ile Glu Ser Leu His Gln Glu Thr Leu Gly Thr Val Val
            420                 425                 430

Ser Leu Gly Leu Leu Glu Ile Ser Gly Pro Phe Ser Met Asn Leu Pro
        435                 440                 445

Leu Gln Ser Pro Ser Leu Arg Arg Ser Ser Arg Val Arg Val Asn Lys
    450                 455                 460

Met Thr Ala Ile Pro Ser
```

-continued 465 470

<210> SEQ ID NO 70
<211> LENGTH: 760
<212> TYPE: PRT
<213> ORGANISM: Mus sp.

<400> SEQUENCE: 70

```
Met Ala Leu Pro Ser Leu Gly Gln Asp Ser Trp Ser Leu Leu Arg Val
  1               5                  10                  15

Phe Phe Phe Gln Leu Phe Leu Leu Pro Ser Leu Pro Pro Ala Ser Gly
             20                  25                  30

Thr Gly Gly Gln Gly Pro Met Pro Arg Val Lys Tyr His Ala Gly Asp
         35                  40                  45

Gly His Arg Ala Leu Ser Phe Phe Gln Gln Lys Gly Leu Arg Asp Phe
     50                  55                  60

Asp Thr Leu Leu Leu Ser Asp Asp Gly Asn Thr Leu Tyr Val Gly Ala
 65                  70                  75                  80

Arg Glu Thr Val Leu Ala Leu Asn Ile Gln Asn Pro Gly Ile Pro Arg
                 85                  90                  95

Leu Lys Asn Met Ile Pro Trp Pro Ala Ser Glu Arg Lys Lys Thr Glu
            100                 105                 110

Cys Ala Phe Lys Lys Lys Ser Asn Glu Thr Gln Cys Phe Asn Phe Ile
        115                 120                 125

Arg Val Leu Val Ser Tyr Asn Ala Thr His Leu Tyr Ala Cys Gly Thr
    130                 135                 140

Phe Ala Phe Ser Pro Ala Cys Thr Phe Ile Glu Leu Gln Asp Ser Leu
145                 150                 155                 160

Leu Leu Pro Ile Leu Ile Asp Lys Val Met Asp Gly Lys Gly Gln Ser
                165                 170                 175

Pro Leu Thr Leu Phe Thr Ser Thr Gln Ala Val Leu Val Asp Gly Met
            180                 185                 190

Leu Tyr Ser Gly Thr Met Asn Asn Phe Leu Gly Ser Glu Pro Ile Leu
        195                 200                 205

Met Arg Thr Leu Gly Ser His Pro Val Leu Lys Thr Asp Ile Phe Leu
    210                 215                 220

Arg Trp Leu His Ala Asp Ala Ser Phe Val Ala Ala Ile Pro Ser Thr
225                 230                 235                 240

Gln Val Val Tyr Phe Phe Phe Glu Glu Thr Ala Ser Glu Phe Asp Phe
                245                 250                 255

Phe Glu Glu Leu Tyr Ile Ser Arg Val Ala Gln Val Cys Lys Asn Asp
            260                 265                 270

Val Gly Gly Glu Lys Leu Leu Gln Lys Lys Trp Thr Thr Phe Leu Lys
        275                 280                 285

Ala Gln Leu Leu Cys Ala Gln Pro Gly Gln Leu Pro Phe Asn Ile Ile
    290                 295                 300

Arg His Ala Val Leu Leu Pro Ala Asp Ser Pro Ser Val Ser Arg Ile
305                 310                 315                 320

Tyr Ala Val Phe Thr Ser Gln Trp Gln Val Gly Gly Thr Arg Ser Ser
                325                 330                 335

Ala Val Cys Ala Phe Ser Leu Thr Asp Ile Glu Arg Val Phe Lys Gly
            340                 345                 350

Lys Tyr Lys Glu Leu Asn Lys Glu Thr Ser Arg Trp Thr Thr Tyr Arg
        355                 360                 365
```

-continued

```
Gly Ser Glu Val Ser Pro Arg Pro Gly Ser Cys Ser Met Gly Pro Ser
    370                 375                 380

Ser Asp Lys Ala Leu Thr Phe Met Lys Asp His Phe Leu Met Asp Glu
385                 390                 395                 400

His Val Val Gly Thr Pro Leu Leu Val Lys Ser Gly Val Glu Tyr Thr
                405                 410                 415

Arg Leu Ala Val Glu Ser Ala Arg Gly Leu Asp Gly Ser Ser His Val
            420                 425                 430

Val Met Tyr Leu Gly Thr Ser Thr Gly Pro Leu His Lys Ala Val Val
        435                 440                 445

Pro Gln Asp Ser Ser Ala Tyr Leu Val Glu Glu Ile Gln Leu Ser Pro
    450                 455                 460

Asp Ser Glu Pro Val Arg Asn Leu Gln Leu Ala Pro Ala Gln Gly Ala
465                 470                 475                 480

Val Phe Ala Gly Phe Ser Gly Gly Ile Trp Arg Val Pro Arg Ala Asn
                485                 490                 495

Cys Ser Val Tyr Glu Ser Cys Val Asp Cys Val Leu Ala Arg Asp Pro
            500                 505                 510

His Cys Ala Trp Asp Pro Glu Ser Arg Leu Cys Ser Leu Leu Ser Gly
        515                 520                 525

Ser Thr Lys Pro Trp Lys Gln Asp Met Glu Arg Gly Asn Pro Glu Trp
    530                 535                 540

Val Cys Thr Arg Gly Pro Met Ala Arg Ser Pro Arg Arg Gln Ser Pro
545                 550                 555                 560

Pro Gln Leu Ile Lys Glu Val Leu Thr Val Pro Asn Ser Ile Leu Glu
                565                 570                 575

Leu Arg Cys Pro His Leu Ser Ala Leu Ala Ser Tyr His Trp Ser His
            580                 585                 590

Gly Arg Ala Lys Ile Ser Glu Ala Ser Ala Thr Val Tyr Asn Gly Ser
        595                 600                 605

Leu Leu Leu Leu Pro Gln Asp Gly Val Gly Gly Leu Tyr Gln Cys Val
    610                 615                 620

Ala Thr Glu Asn Gly Tyr Ser Tyr Pro Val Val Ser Tyr Trp Val Asp
625                 630                 635                 640

Ser Gln Asp Gln Pro Leu Ala Leu Asp Pro Glu Leu Ala Gly Val Pro
                645                 650                 655

Arg Glu Arg Val Gln Val Pro Leu Thr Arg Val Gly Gly Gly Ala Ser
            660                 665                 670

Met Ala Ala Gln Arg Ser Tyr Trp Pro His Phe Leu Ile Val Thr Val
        675                 680                 685

Leu Leu Ala Ile Val Leu Leu Gly Val Leu Thr Leu Leu Leu Ala Ser
    690                 695                 700

Pro Leu Gly Ala Leu Arg Ala Arg Gly Lys Val Gln Gly Cys Gly Met
705                 710                 715                 720

Leu Pro Pro Arg Glu Lys Ala Pro Leu Ser Arg Asp Gln His Leu Gln
                725                 730                 735

Pro Ser Lys Asp His Arg Thr Ser Ala Ser Asp Val Asp Ala Asp Asn
            740                 745                 750

Asn His Leu Gly Ala Glu Val Ala
        755                 760
```

<210> SEQ ID NO 71
<211> LENGTH: 3046
<212> TYPE: DNA

-continued

<213> ORGANISM: Mus sp.

<400> SEQUENCE: 71
ctcggacgcc tgggttaggg gtctgtactg ctggggaacc atctggtgac catctcaggc 60
tgaccatggc cctaccatcc ctgggccagg actcatggag tctcctgcgt gttttttttct 120
tccaactctt cctgctgcca tcactgccac ctgcttctgg gactggtggt caggggccca 180
tgcccagagt caaataccat gctggagacg ggcacagggc cctcagcttc ttccaacaaa 240
aaggcctccg agactttgac acgctgctcc tgagtgacga tggcaacact ctctatgtgg 300
gggctcgaga gaccgtcctg gccttgaata tccagaaccc aggaatccca aggctaaaga 360
acatgatacc ctggccagcc agtgagagaa aaaagaccga atgtgccttt aagaagaaga 420
gcaatgagac acagtgtttc aacttcattc gagtcctggt ctcttacaat gctactcacc 480
tctatgcctg tgggaccttt gccttcagcc ctgcctgtac cttcattgaa ctccaagatt 540
ccctcctgtt gcccatcttg atagacaagg tcatggacgg gaagggccaa agccctttga 600
ccctgttcac aagcacacaa gctgtcttgg tcgatgggat gctttattcc ggcaccatga 660
acaacttcct gggcagcgag cccatcctga tgcggacact gggatcccat cctgttctca 720
agactgacat cttcttacgc tggctgcacg cggatgcctc cttcgtggca gccattccat 780
ccacccaggt cgtctatttc ttctttgagg agacagccag cgagtttgac ttctttgaag 840
agctgtatat atccagggtg gctcaagtct gcaagaacga cgtgggcggt gaaaagctgc 900
tgcagaagaa gtggaccacc ttcctcaaag cccagttgct ctgcgctcag ccagggcagc 960
tgccattcaa catcatccgc cacgcggtcc tgctgcccgc cgattctccc tctgtttccc 1020
gcatctacgc agtctttacc tcccagtggc aggttggcgg gaccaggagc tcagcagtct 1080
gtgccttctc tctcacggac attgagcgag tctttaaagg gaagtacaag gagctgaaca 1140
aggagacctc ccgctggacc acttaccggg gctcagaggt cagcccgagg ccaggcagtt 1200
gctccatggg cccctcctct gacaaagcct tgaccttcat gaaggaccat tttctgatgg 1260
atgagcacgt ggtaggaaca cccctgctgg tgaagtctgg tgtggagtac acacggcttg 1320
ctgtggagtc agctcggggc cttgatggga gcagccatgt ggtcatgtat ctgggtacct 1380
ccacgggtcc cctgcacaag gctgtggtgc ctcaggacag cagtgcttat ctcgtggagg 1440
agattcagct gagccctgac tctgagcctg ttcgaaacct gcagctggcc cccgcccagg 1500
gtgcagtgtt tgcaggcttc tctggaggca tctggagagt tcccagggcc aattgcagtg 1560
tctacgagag ctgtgtggac tgtgtgcttg ccagggaccc tcactgtgcc tgggaccctg 1620
aatcaagact ctgcagcctt ctgtctggct ctaccaagcc ttggaagcag gacatggaac 1680
gcggcaaccc ggagtgggta tgcacccgtg gccccatggc caggagcccc cggcgtcaga 1740
gcccccctca actaattaaa gaagtcctga cagtccccaa ctccatcctg gagctgcgct 1800
gcccccacct gtcagcactg gcctcttacc actggagtca tggccgagcc aaaatctcag 1860
aagcctctgc taccgtctac aatggctccc tcttgctgct gccgcaggat ggtgtcgggg 1920
gcctctacca gtgtgtggcg actgagaacg gctactcata ccctgtggtc tcctattggg 1980
tagacagcca ggaccagccc ctggcgctgg accctgagct ggcgggcgtt ccccgtgagc 2040
gtgtgcaggt cccgctgacc agggtcggag gcggagcttc catggctgcc cagcggtcct 2100
actggcccca ttttctcatc gttaccgtcc tcctggccat cgtgctcctg ggagtgctca 2160
ctctcctcct cgcttcccca ctgggggcgc tgcgggctcg gggtaaggtt cagggctgtg 2220
ggatgctgcc ccccagggaa aaggctccac tgagcaggga ccagcacctc cagccctcca 2280

-continued

```
aggaccacag gacctctgcc agtgacgtag atgccgacaa caaccatctg ggcgccgaag   2340
tggcttaaac agggacacag atccgcagct gagcagagca agccactggc cttgttggct   2400
atgccaggca cagtgccact ctgaccaggg taggaggctc tcctgctaac gtgtgtcacc   2460
tacagcaccc agtaggtcct cccctgtggg actctcttct gcaagcacat tgggctgtct   2520
ccatacctgt acttgtgctg tgacaggaag agccagacag gtttctttga ttttgattga   2580
cccaagagcc ctgcctgtaa caaacgtgct ccaggagacc atgaaaggtg tggctgtctg   2640
ggattctgtg gtgacaaacc taagcatccg agcaagctgg ggctattcct gcaaactcca   2700
tcctgaacgc tgtcactcta gaagcagctg ctgctttgaa caccagccca ccctccttcc   2760
caagagtctc tatggagttg gccccttgtg tttcctttac cagtcgggcc atactgtttg   2820
ggaagtcatc tctgaagtct aaccaccttc cttcttggtt cagtttggac agattgttat   2880
tattgtctct gccctggcta gaatgggggc ataatctgag ccttgttccc ttgtccagtg   2940
tggctgaccc ttgacctctt ccttcctcct ccctttgttt tgggattcag aaaactgctt   3000
gtcacagaca atttattttt tattaaaaaa gatataagct ttaaag                 3046
```

<210> SEQ ID NO 72
<211> LENGTH: 2915
<212> TYPE: DNA
<213> ORGANISM: Mus sp.

<400> SEQUENCE: 72

```
gtcgacccac gcgtccggcc gcgcgtcctt ctgccggctt cagctcgtat ccccggagtc     60
cacccgcccg tcccggggtg cggactggcc ctgagctggc cgtacagccc ggcttcggac    120
ggtcctcgct ggagccatgg gccgccggct cggcagggtg gcggcgctgc tgctcgggct    180
gctagtggag tgcactgagg ccaaaaaaca ttgctggtat tttgaaggac tctatcccac    240
atactatata tgccgttcct atgaagactg ctgtggctcc aggtgctgtg tgagggccct    300
ttccatacag aggctgtggt atttttggtt cctgctgatg atgggtgtgc tgttctgctg    360
tggtgccggt ttcttcattc gccggcgcat gtatccgcca ccactcattg aggagcccac    420
attcaatgtg tcctatacca ggcagccacc aaatcctgct ccaggagcac agcaaatggg    480
accgccatat tacaccgacc ctggaggacc cgggatgaat cctgttggca ataccatggc    540
tatggctttc caggtccagc ccaattcacc tcacggaggc acaacttacc caccccctcc    600
ttcctactgc aacacgcctc caccccccta tgaacaggtg gtgaaggaca agtagcaaga    660
tgctacatca aaggcaaaga ggatggacag gccctttttgt ttaccttccc atcctcaccg    720
atacttgctg atagggtggt ccaagggaaa acttggatat tctcaaagca agcccagctc    780
tctttcaagt cttttgtgga ggacatttga atccacactg tctcctctgt tgcttctgtt    840
tctgatgtag tctgtgctct ctgagagagt gtggcaacag tccctgaggg ttgatattcc    900
tagggtgtcc agggtagatc ctcgggagag aggctaaggg gaaaggaagg catagcctgt    960
gtgttagggg gcagataaag tggtcaggct gagataagac tcacatgatg cagtagttgg   1020
cagtgaactt cgaagagaca ctatccacca tcccagccca ttctcctaat agaagctgtg   1080
gggctgtgtt gttgatgctc tttggtctcc actcacattt tgaaaatagg ctttcctctg   1140
caggaatagg aaagacccaa gtacatattt gcttccactt aaaaatgagg gtcagaacca   1200
ggcctcagtt ggacatctat agttaaataa aggccattag agaggggaaa tctttaagtt   1260
aggggaaatt ctctaaatgg agacattgcg ttttatgaat catcgtctgg cttttctttt   1320
```

-continued

```
agtgcatgta ttgaagtgag ggtgtccttt gagatcagat ggggagagtg aactctgcgg   1380

ggggtggggt gtctctactc agagggctcc aacacccttt tcttaggtag ttctggtgat   1440

gggttttatg ggcactatag agctgagggg cacattaggc cgggtagtta cattgaccct   1500

tggagaggaa gaggacagcc aaagaaactc agcaaagcaa gaccagcatt gctgagttag   1560

agctagggtt gtatgtgatc ccaacagaga tgtgctggcc tcagaagagg ggacgtttgt   1620

ggatagagcc gtgaaaacct acttagttgc acagatgaca taatcaaaag tagagaaaga   1680

agtgtagtta gagatgccat ttcccaggtg agaatcagag ctcatccata gatttacaag   1740

tagtggctgg agttaacagt atggagttct tttcccttgc gtagttagtc acgttgatgt   1800

gtatttaaac ccaggttgag accttgtgta ctaagagcaa ggaagtatag ctaagatgtc   1860

tagattattt atatgtagta tggtggggag tggggctgca aggaaggggg ctgacattgt   1920

aaatgagaaa atcagagcca tttgataaac tgttacttgt tggatcaggc atccaaaagt   1980

gtctcttgag tggacattga gtattcttta ccacctacaa gaccaggagg catggtgtca   2040

ttctccattg ggtatttat atgaggtaga ggttcaggaa tcgacagtag ctgtgtgggc   2100

ttagtttaag gactgaaagc atagggactg gtagacagtt tcataggaaa ctgcggggaa   2160

ggaatggata cctttaaaga cagtttgtgg atgcagatgc tgccacccat cattgagcac   2220

ccttgtgtct ctggcttcct gtcactggat ccagtacccc tccatgcttg ggtccttgtt   2280

ttacataaga caacaaagca caatgtctgc tgtttacaat caagacgact acatggtcca   2340

aacatttctt ctctcttcta tcacttgtgg ctttaacttc catttcctcc gttccttttt   2400

aaaatcaaga agcacagtca gagctgcccc tgggattgca tcagggaacg gctgatcaag   2460

gcattcagtg tccatgacta aatcttatct ttttgatagc aaatcctttt aagaaactga   2520

acaattgcta aggctcagca attttatact ccaatgtctg tgtaaggtaa attttgtttg   2580

ccattgagcc cacattggaa ttccttctga cgtcaacact gacaatgcct atggaaattg   2640

cacttctggg tatatgtccc agcatccttg ttttcttatg tttggtgagt aaggctcacc   2700

ccttccagca gctctacttc tgtgtgctga ggtcctgtag agccggggct tgggcacaga   2760

catgaggcag acttgtgcat gctctttctt ggcaacactt ggctcatatt tcttgttctc   2820

ttttgataga gtcctgtttc ctatgtattt aaaaaataat aaaagtgaat ttagtcaaaa   2880

aaaaaaaaaa aaaaaaaaaa aaaaagggcg gccgc                              2915
```

<210> SEQ ID NO 73
<211> LENGTH: 516
<212> TYPE: DNA
<213> ORGANISM: Mus sp.

<400> SEQUENCE: 73

```
atgggccgcc ggctcggcag ggtggcggcg ctgctgctcg ggctgctagt ggagtgcact     60

gaggccaaaa aacattgctg gtattttgaa ggactctatc ccacatacta tatatgccgt    120

tcctatgaag actgctgtgg ctccaggtgc tgtgtgaggg ccctttccat acagaggctg    180

tggtattttt ggttcctgct gatgatgggt gtgctgttct gctgtggtgc cggtttcttc    240

attcgccggc gcatgtatcc gccaccactc attgaggagc ccacattcaa tgtgtcctat    300

accaggcagc caccaaatcc tgctccagga gcacagcaaa tgggaccgcc atattacacc    360

gaccctggag gacccgggat gaatcctgtt ggcaatacca tggctatggc tttccaggtc    420

cagcccaatt cacctcacgg aggcacaact tacccacccc ctccttccta ctgcaacacg    480

cctccacccc cctatgaaca ggtggtgaag gacaag                              516
```

<210> SEQ ID NO 74
<211> LENGTH: 172
<212> TYPE: PRT
<213> ORGANISM: Mus sp.

<400> SEQUENCE: 74

```
Met Gly Arg Arg Leu Gly Arg Val Ala Ala Leu Leu Leu Gly Leu Leu
  1               5                  10                  15

Val Glu Cys Thr Glu Ala Lys Lys His Cys Trp Tyr Phe Glu Gly Leu
             20                  25                  30

Tyr Pro Thr Tyr Tyr Ile Cys Arg Ser Tyr Glu Asp Cys Cys Gly Ser
         35                  40                  45

Arg Cys Cys Val Arg Ala Leu Ser Ile Gln Arg Leu Trp Tyr Phe Trp
     50                  55                  60

Phe Leu Leu Met Met Gly Val Leu Phe Cys Cys Gly Ala Gly Phe Phe
 65                  70                  75                  80

Ile Arg Arg Arg Met Tyr Pro Pro Pro Leu Ile Glu Glu Pro Thr Phe
                 85                  90                  95

Asn Val Ser Tyr Thr Arg Gln Pro Pro Asn Pro Ala Pro Gly Ala Gln
            100                 105                 110

Gln Met Gly Pro Pro Tyr Tyr Thr Asp Pro Gly Gly Pro Gly Met Asn
        115                 120                 125

Pro Val Gly Asn Thr Met Ala Met Ala Phe Gln Val Gln Pro Asn Ser
    130                 135                 140

Pro His Gly Gly Thr Thr Tyr Pro Pro Pro Pro Ser Tyr Cys Asn Thr
145                 150                 155                 160

Pro Pro Pro Pro Tyr Glu Gln Val Val Lys Asp Lys
                165                 170
```

<210> SEQ ID NO 75
<211> LENGTH: 398
<212> TYPE: PRT
<213> ORGANISM: Homo sapiens

<400> SEQUENCE: 75

```
Met Trp Leu Leu Leu Thr Met Ala Ser Leu Ile Ser Val Leu Gly Thr
  1               5                  10                  15

Thr His Gly Leu Phe Gly Lys Leu His Pro Gly Ser Pro Glu Val Thr
             20                  25                  30

Met Asn Ile Ser Gln Met Ile Thr Tyr Trp Gly Tyr Pro Asn Glu Glu
         35                  40                  45

Tyr Glu Val Val Thr Glu Asp Gly Tyr Ile Leu Glu Val Asn Arg Ile
     50                  55                  60

Pro Tyr Gly Lys Lys Asn Ser Gly Asn Thr Gly Gln Arg Pro Val Val
 65                  70                  75                  80

Phe Leu Gln His Gly Leu Leu Ala Ser Ala Thr Asn Trp Ile Ser Asn
                 85                  90                  95

Leu Pro Asn Asn Ser Leu Ala Phe Ile Leu Ala Asp Ala Gly Tyr Asp
            100                 105                 110

Val Trp Leu Gly Asn Ser Arg Gly Asn Thr Trp Ala Arg Arg Asn Leu
        115                 120                 125

Tyr Tyr Ser Pro Asp Ser Val Glu Phe Trp Ala Phe Ser Phe Asp Glu
    130                 135                 140

Met Ala Lys Tyr Asp Leu Pro Ala Thr Ile Asp Phe Ile Val Lys Lys
145                 150                 155                 160
```

-continued

```
Thr Gly Gln Lys Gln Leu His Tyr Val Gly His Ser Gln Gly Thr Thr
                165                 170                 175

Ile Gly Phe Ile Ala Phe Ser Thr Asn Pro Ser Leu Ala Lys Arg Ile
            180                 185                 190

Lys Thr Phe Tyr Ala Leu Ala Pro Val Ala Thr Val Lys Tyr Thr Lys
        195                 200                 205

Ser Leu Ile Asn Lys Leu Arg Phe Val Pro Gln Ser Leu Phe Lys Phe
    210                 215                 220

Ile Phe Gly Asp Lys Ile Phe Tyr Pro His Asn Phe Phe Asp Gln Phe
225                 230                 235                 240

Leu Ala Thr Glu Val Cys Ser Arg Glu Met Leu Asn Leu Leu Cys Ser
                245                 250                 255

Asn Ala Leu Phe Ile Ile Cys Gly Phe Asp Ser Lys Asn Phe Asn Thr
            260                 265                 270

Ser Arg Leu Asp Val Tyr Leu Ser His Asn Pro Ala Gly Thr Ser Val
        275                 280                 285

Gln Asn Met Phe His Trp Thr Gln Ala Val Lys Ser Gly Lys Phe Gln
    290                 295                 300

Ala Tyr Asp Trp Gly Ser Pro Val Gln Asn Arg Met His Tyr Asp Gln
305                 310                 315                 320

Ser Gln Pro Pro Tyr Tyr Asn Val Thr Ala Met Asn Val Pro Ile Ala
                325                 330                 335

Val Trp Asn Gly Gly Lys Asp Leu Leu Ala Asp Pro Gln Asp Val Gly
            340                 345                 350

Leu Leu Leu Pro Lys Leu Pro Asn Leu Ile Tyr His Lys Glu Ile Pro
        355                 360                 365

Phe Tyr Asn His Leu Asp Phe Ile Trp Ala Met Asp Ala Pro Gln Glu
    370                 375                 380

Val Tyr Asn Asp Ile Val Ser Met Ile Ser Glu Asp Lys Lys
385                 390                 395


<210> SEQ ID NO 76
<211> LENGTH: 760
<212> TYPE: PRT
<213> ORGANISM: Mus sp.

<400> SEQUENCE: 76

Met Ala Leu Pro Ser Leu Gly Gln Asp Ser Trp Ser Leu Leu Arg Val
  1               5                  10                  15

Phe Phe Phe Gln Leu Phe Leu Leu Pro Ser Leu Pro Pro Ala Ser Gly
             20                  25                  30

Thr Gly Gly Gln Gly Pro Met Pro Arg Val Lys Tyr His Ala Gly Asp
         35                  40                  45

Gly His Arg Ala Leu Ser Phe Phe Gln Gln Lys Gly Leu Arg Asp Phe
     50                  55                  60

Asp Thr Leu Leu Leu Ser Asp Asp Gly Asn Thr Leu Tyr Val Gly Ala
 65                  70                  75                  80

Arg Glu Thr Val Leu Ala Leu Asn Ile Gln Asn Pro Gly Ile Pro Arg
                 85                  90                  95

Leu Lys Asn Met Ile Pro Trp Pro Ala Ser Glu Arg Lys Lys Thr Glu
            100                 105                 110

Cys Ala Phe Lys Lys Lys Ser Asn Glu Thr Gln Cys Phe Asn Phe Ile
        115                 120                 125

Arg Val Leu Val Ser Tyr Asn Ala Thr His Leu Tyr Ala Cys Gly Thr
```

-continued

```
    130                 135                 140

Phe Ala Phe Ser Pro Ala Cys Thr Phe Ile Glu Leu Gln Asp Ser Leu
145                 150                 155                 160

Leu Leu Pro Ile Leu Ile Asp Lys Val Met Asp Gly Lys Gly Gln Ser
                165                 170                 175

Pro Leu Thr Leu Phe Thr Ser Thr Gln Ala Val Leu Val Asp Gly Met
            180                 185                 190

Leu Tyr Ser Gly Thr Met Asn Asn Phe Leu Gly Ser Glu Pro Ile Leu
        195                 200                 205

Met Arg Thr Leu Gly Ser His Pro Val Leu Lys Thr Asp Ile Phe Leu
    210                 215                 220

Arg Trp Leu His Ala Asp Ala Ser Phe Val Ala Ala Ile Pro Ser Thr
225                 230                 235                 240

Gln Val Val Tyr Phe Phe Phe Glu Glu Thr Ala Ser Glu Phe Asp Phe
                245                 250                 255

Phe Glu Glu Leu Tyr Ile Ser Arg Val Ala Gln Val Cys Lys Asn Asp
            260                 265                 270

Val Gly Gly Glu Lys Leu Leu Gln Lys Lys Trp Thr Thr Phe Leu Lys
        275                 280                 285

Ala Gln Leu Leu Cys Ala Gln Pro Gly Gln Leu Pro Phe Asn Ile Ile
    290                 295                 300

Arg His Ala Val Leu Leu Pro Ala Asp Ser Pro Ser Val Ser Arg Ile
305                 310                 315                 320

Tyr Ala Val Phe Thr Ser Gln Trp Gln Val Gly Gly Thr Arg Ser Ser
                325                 330                 335

Ala Val Cys Ala Phe Ser Leu Thr Asp Ile Glu Arg Val Phe Lys Gly
            340                 345                 350

Lys Tyr Lys Glu Leu Asn Lys Glu Thr Ser Arg Trp Thr Thr Tyr Arg
        355                 360                 365

Gly Ser Glu Val Ser Pro Arg Pro Gly Ser Cys Ser Met Gly Pro Ser
    370                 375                 380

Ser Asp Lys Ala Leu Thr Phe Met Lys Asp His Phe Leu Met Asp Glu
385                 390                 395                 400

His Val Val Gly Thr Pro Leu Leu Val Lys Ser Gly Val Glu Tyr Thr
                405                 410                 415

Arg Leu Ala Val Glu Ser Ala Arg Gly Leu Asp Gly Ser Ser His Val
            420                 425                 430

Val Met Tyr Leu Gly Thr Ser Thr Gly Pro Leu His Lys Ala Val Val
        435                 440                 445

Pro Gln Asp Ser Ser Ala Tyr Leu Val Glu Glu Ile Gln Leu Ser Pro
    450                 455                 460

Asp Ser Glu Pro Val Arg Asn Leu Gln Leu Ala Pro Ala Gln Gly Ala
465                 470                 475                 480

Val Phe Ala Gly Phe Ser Gly Gly Ile Trp Arg Val Pro Arg Ala Asn
                485                 490                 495

Cys Ser Val Tyr Glu Ser Cys Val Asp Cys Val Leu Ala Arg Asp Pro
            500                 505                 510

His Cys Ala Trp Asp Pro Glu Ser Arg Leu Cys Ser Leu Leu Ser Gly
        515                 520                 525

Ser Thr Lys Pro Trp Lys Gln Asp Met Glu Arg Gly Asn Pro Glu Trp
    530                 535                 540

Val Cys Thr Arg Gly Pro Met Ala Arg Ser Pro Arg Arg Gln Ser Pro
545                 550                 555                 560
```

-continued

```
Pro Gln Leu Ile Lys Glu Val Leu Thr Val Pro Asn Ser Ile Leu Glu
                565                 570                 575

Leu Arg Cys Pro His Leu Ser Ala Leu Ala Ser Tyr His Trp Ser His
            580                 585                 590

Gly Arg Ala Lys Ile Ser Glu Ala Ser Ala Thr Val Tyr Asn Gly Ser
        595                 600                 605

Leu Leu Leu Leu Pro Gln Asp Gly Val Gly Gly Leu Tyr Gln Cys Val
    610                 615                 620

Ala Thr Glu Asn Gly Tyr Ser Tyr Pro Val Val Ser Tyr Trp Val Asp
625                 630                 635                 640

Ser Gln Asp Gln Pro Leu Ala Leu Asp Pro Glu Leu Ala Gly Val Pro
                645                 650                 655

Arg Glu Arg Val Gln Val Pro Leu Thr Arg Val Gly Gly Gly Ala Ser
            660                 665                 670

Met Ala Ala Gln Arg Ser Tyr Trp Pro His Phe Leu Ile Val Thr Val
        675                 680                 685

Leu Leu Ala Ile Val Leu Leu Gly Val Leu Thr Leu Leu Leu Ala Ser
    690                 695                 700

Pro Leu Gly Ala Leu Arg Ala Arg Gly Lys Val Gln Gly Cys Gly Met
705                 710                 715                 720

Leu Pro Pro Arg Glu Lys Ala Pro Leu Ser Arg Asp Gln His Leu Gln
                725                 730                 735

Pro Ser Lys Asp His Arg Thr Ser Ala Ser Asp Val Asp Ala Asp Asn
            740                 745                 750

Asn His Leu Gly Ala Glu Val Ala
        755                 760
```

<210> SEQ ID NO 77
<211> LENGTH: 3046
<212> TYPE: DNA
<213> ORGANISM: Mus sp.

<400> SEQUENCE: 77

```
ctcggacgcc tgggttaggg gtctgtactg ctggggaacc atctggtgac catctcaggc     60

tgaccatggc cctaccatcc ctgggccagg actcatggag tctcctgcgt gtttttttct    120

tccaactctt cctgctgcca tcactgccac ctgcttctgg gactggtggt caggggccca    180

tgcccagagt caaataccat gctggagacg ggcacagggc cctcagcttc ttccaacaaa    240

aaggcctccg agactttgac acgctgctcc tgagtgacga tggcaacact ctctatgtgg    300

gggctcgaga gaccgtcctg gccttgaata tccagaaccc aggaatccca aggctaaaga    360

acatgatacc ctggccagcc agtgagagaa aaaagaccga atgtgccttt aagaagaaga    420

gcaatgagac acagtgtttc aacttcattc gagtcctggt ctcttacaat gctactcacc    480

tctatgcctg tgggaccttt gccttcagcc ctgcctgtac cttcattgaa ctccaagatt    540

ccctcctgtt gcccatcttg atagacaagg tcatggacgg gaagggccaa agccctttga    600

ccctgttcac aagcacacaa gctgtcttgg tcgatgggat gctttattcc ggcaccatga    660

acaacttcct gggcagcgag cccatcctga tgcggacact gggatcccat cctgttctca    720

agactgacat cttcttacgc tggctgcacg cggatgcctc cttcgtggca gccattccat    780

ccacccaggt cgtctatttc ttctttgagg agacagccag cgagtttgac ttctttgaag    840

agctgtatat atccagggtg gctcaagtct gcaagaacga cgtgggcggt gaaaagctgc    900

tgcagaagaa gtggaccacc ttcctcaaag cccagttgct ctgcgctcag ccagggcagc    960
```

-continued

```
tgccattcaa catcatccgc cacgcggtcc tgctgcccgc cgattctccc tctgtttccc   1020
gcatctacgc agtctttacc tcccagtggc aggttggcgg gaccaggagc tcagcagtct   1080
gtgccttctc tctcacggac attgagcgag tctttaaagg gaagtacaag gagctgaaca   1140
aggagacctc ccgctggacc acttaccggg gctcagaggt cagcccgagg ccaggcagtt   1200
gctccatggg cccctcctct gacaaagcct tgaccttcat gaaggaccat tttctgatgg   1260
atgagcacgt ggtaggaaca cccctgctgg tgaagtctgg tgtggagtac acacggcttg   1320
ctgtggagtc agctcggggc cttgatggga gcagccatgt ggtcatgtat ctgggtacct   1380
ccacgggtcc cctgcacaag gctgtggtgc ctcaggacag cagtgcttat ctcgtggagg   1440
agattcagct gagccctgac tctgagcctg ttcgaaacct gcagctggcc cccgcccagg   1500
gtgcagtgtt tgcaggcttc tctggaggca tctggagagt tcccagggcc aattgcagtg   1560
tctacgagag ctgtgtggac tgtgtgcttg ccagggaccc tcactgtgcc tgggaccctg   1620
aatcaagact ctgcagcctt ctgtctggct ctaccaagcc ttggaagcag gacatggaac   1680
gcggcaaccc ggagtgggta tgcacccgtg gccccatggc caggagcccc cggcgtcaga   1740
gcccccctca actaattaaa gaagtcctga cagtccccaa ctccatcctg gagctgcgct   1800
gcccccacct gtcagcactg gcctcttacc actggagtca tggccgagcc aaaatctcag   1860
aagcctctgc taccgtctac aatggctccc tcttgctgct gccgcaggat ggtgtcgggg   1920
gcctctacca gtgtgtggcg actgagaacg gctactcata ccctgtggtc tcctattggg   1980
tagacagcca ggaccagccc ctggcgctgg accctgagct ggcgggcgtt ccccgtgagc   2040
gtgtgcaggt cccgctgacc agggtcggag gcggagcttc catggctgcc cagcggtcct   2100
actggcccca ttttctcatc gttaccgtcc tcctggccat cgtgctcctg ggagtgctca   2160
ctctcctcct cgcttcccca ctgggggcgc tgcgggctcg ggtaaggtt cagggctgtg   2220
ggatgctgcc ccccagggaa aaggctccac tgagcaggga ccagcacctc cagccctcca   2280
aggaccacag gacctctgcc agtgacgtag atgccgacaa caaccatctg ggcgccgaag   2340
tggcttaaac agggacacag atccgcagct gagcagagca agccactggc cttgttggct   2400
atgccaggca cagtgccact ctgaccaggg taggaggctc tcctgctaac gtgtgtcacc   2460
tacagcaccc agtaggtcct cccctgtggg actctcttct gcaagcacat tgggctgtct   2520
ccatacctgt acttgtgctg tgacaggaag agccagacag gtttctttga ttttgattga   2580
cccaagagcc ctgcctgtaa caaacgtgct ccaggagacc atgaaaggtg tggctgtctg   2640
ggattctgtg gtgacaaacc taagcatccg agcaagctgg ggctattcct gcaaactcca   2700
tcctgaacgc tgtcactcta gaagcagctg ctgctttgaa caccagccca ccctccttcc   2760
caagagtctc tatggagttg gcccccttgtg tttcctttac cagtcgggcc atactgtttg   2820
ggaagtcatc tctgaagtct aaccaccttc cttcttggtt cagtttggac agattgttat   2880
tattgtctct gccctggcta gaatgggggc ataatctgag ccttgttccc ttgtccagtg   2940
tggctgaccc ttgacctctt ccttcctcct ccctttgttt tgggattcag aaaactgctt   3000
gtcacagaca atttattttt tattaaaaaa gatataagct ttaaag                 3046
```

<210> SEQ ID NO 78
<211> LENGTH: 1436
<212> TYPE: PRT
<213> ORGANISM: Bos sp.

<400> SEQUENCE: 78

-continued

```
Met Ala Leu Gly Arg His Leu Ser Leu Arg Gly Leu Cys Val Leu Leu
  1               5                  10                  15

Leu Gly Thr Met Val Gly Gly Gln Ala Leu Glu Leu Arg Leu Lys Asp
             20                  25                  30

Gly Val His Arg Cys Glu Gly Arg Val Glu Val Lys His Gln Gly Glu
         35                  40                  45

Trp Gly Thr Val Asp Gly Tyr Arg Trp Thr Leu Lys Asp Ala Ser Val
     50                  55                  60

Val Cys Arg Gln Leu Gly Cys Gly Ala Ala Ile Gly Phe Pro Gly Gly
 65                  70                  75                  80

Ala Tyr Phe Gly Pro Gly Leu Gly Pro Ile Trp Leu Leu Tyr Thr Ser
                 85                  90                  95

Cys Glu Gly Thr Glu Ser Thr Val Ser Asp Cys Glu His Ser Asn Ile
            100                 105                 110

Lys Asp Tyr Arg Asn Asp Gly Tyr Asn His Gly Arg Asp Ala Gly Val
        115                 120                 125

Val Cys Ser Gly Phe Val Arg Leu Ala Gly Gly Asp Gly Pro Cys Ser
    130                 135                 140

Gly Arg Val Glu Val His Ser Gly Glu Ala Trp Ile Pro Val Ser Asp
145                 150                 155                 160

Gly Asn Phe Thr Leu Ala Thr Ala Gln Ile Ile Cys Ala Glu Leu Gly
                165                 170                 175

Cys Gly Lys Ala Val Ser Val Leu Gly His Glu Leu Phe Arg Glu Ser
            180                 185                 190

Ser Ala Gln Val Trp Ala Glu Glu Phe Arg Cys Glu Gly Glu Glu Pro
        195                 200                 205

Glu Leu Trp Val Cys Pro Arg Val Pro Cys Pro Gly Gly Thr Cys His
    210                 215                 220

His Ser Gly Ser Ala Gln Val Val Cys Ser Ala Tyr Ser Glu Val Arg
225                 230                 235                 240

Leu Met Thr Asn Gly Ser Ser Gln Cys Glu Gly Gln Val Glu Met Asn
                245                 250                 255

Ile Ser Gly Gln Trp Arg Ala Leu Cys Ala Ser His Trp Ser Leu Ala
            260                 265                 270

Asn Ala Asn Val Ile Cys Arg Gln Leu Gly Cys Gly Val Ala Ile Ser
        275                 280                 285

Thr Pro Gly Gly Pro His Leu Val Glu Glu Gly Asp Gln Ile Leu Thr
    290                 295                 300

Ala Arg Phe His Cys Ser Gly Ala Glu Ser Phe Leu Trp Ser Cys Pro
305                 310                 315                 320

Val Thr Ala Leu Gly Gly Pro Asp Cys Ser His Gly Asn Thr Ala Ser
                325                 330                 335

Val Ile Cys Ser Gly Asn Gln Ile Gln Val Leu Pro Gln Cys Asn Asp
            340                 345                 350

Ser Val Ser Gln Pro Thr Gly Ser Ala Ala Ser Glu Asp Ser Ala Pro
        355                 360                 365

Tyr Cys Ser Asp Ser Arg Gln Leu Arg Leu Val Asp Gly Gly Gly Pro
    370                 375                 380

Cys Ala Gly Arg Val Glu Ile Leu Asp Gln Gly Ser Trp Gly Thr Ile
385                 390                 395                 400

Cys Asp Asp Gly Trp Asp Leu Asp Asp Ala Arg Val Val Cys Arg Gln
                405                 410                 415

Leu Gly Cys Gly Glu Ala Leu Asn Ala Thr Gly Ser Ala His Phe Gly
```

-continued

```
            420                 425                 430

Ala Gly Ser Gly Pro Ile Trp Leu Asp Asn Leu Asn Cys Thr Gly Lys
        435                 440                 445

Glu Ser His Val Trp Arg Cys Pro Ser Arg Gly Trp Gly Gln His Asn
    450                 455                 460

Cys Arg His Lys Gln Asp Ala Gly Val Ile Cys Ser Glu Phe Leu Ala
465                 470                 475                 480

Leu Arg Met Val Ser Glu Asp Gln Gln Cys Ala Gly Trp Leu Glu Val
                485                 490                 495

Phe Tyr Asn Gly Thr Trp Gly Ser Val Cys Arg Asn Pro Met Glu Asp
            500                 505                 510

Ile Thr Val Ser Thr Ile Cys Arg Gln Leu Gly Cys Gly Asp Ser Gly
        515                 520                 525

Thr Leu Asn Ser Ser Val Ala Leu Arg Glu Gly Phe Arg Pro Gln Trp
    530                 535                 540

Val Asp Arg Ile Gln Cys Arg Lys Thr Asp Thr Ser Leu Trp Gln Cys
545                 550                 555                 560

Pro Ser Asp Pro Trp Asn Tyr Asn Ser Cys Ser Pro Lys Glu Glu Ala
                565                 570                 575

Tyr Ile Trp Cys Ala Asp Ser Arg Gln Ile Arg Leu Val Asp Gly Gly
            580                 585                 590

Gly Arg Cys Ser Gly Arg Val Glu Ile Leu Asp Gln Gly Ser Trp Gly
        595                 600                 605

Thr Ile Cys Asp Asp Arg Trp Asp Leu Asp Asp Ala Arg Val Val Cys
    610                 615                 620

Lys Gln Leu Gly Cys Gly Glu Ala Leu Asp Ala Thr Val Ser Ser Phe
625                 630                 635                 640

Phe Gly Thr Gly Ser Gly Pro Ile Trp Leu Asp Glu Val Asn Cys Arg
                645                 650                 655

Gly Glu Glu Ser Gln Val Trp Arg Cys Pro Ser Trp Gly Trp Arg Gln
            660                 665                 670

His Asn Cys Asn His Gln Glu Asp Ala Gly Val Ile Cys Ser Gly Phe
        675                 680                 685

Val Arg Leu Ala Gly Gly Asp Gly Pro Cys Ser Gly Arg Val Glu Val
    690                 695                 700

His Ser Gly Glu Ala Trp Thr Pro Val Ser Asp Gly Asn Phe Thr Leu
705                 710                 715                 720

Pro Thr Ala Gln Val Ile Cys Ala Glu Leu Gly Cys Gly Lys Ala Val
                725                 730                 735

Ser Val Leu Gly His Met Pro Phe Arg Glu Ser Asp Gly Gln Val Trp
            740                 745                 750

Ala Glu Glu Phe Arg Cys Asp Gly Gly Glu Pro Glu Leu Trp Ser Cys
        755                 760                 765

Pro Arg Val Pro Cys Pro Gly Gly Thr Cys Leu His Ser Gly Ala Ala
    770                 775                 780

Gln Val Val Cys Ser Val Tyr Thr Glu Val Gln Leu Met Lys Asn Gly
785                 790                 795                 800

Thr Ser Gln Cys Glu Gly Gln Val Glu Met Lys Ile Ser Gly Arg Trp
                805                 810                 815

Arg Ala Leu Cys Ala Ser His Trp Ser Leu Ala Asn Ala Asn Val Val
            820                 825                 830

Cys Arg Gln Leu Gly Cys Gly Val Ala Ile Ser Thr Pro Arg Gly Pro
        835                 840                 845
```

-continued

```
His Leu Val Glu Gly Gly Asp Gln Ile Ser Thr Ala Gln Phe His Cys
    850                 855                 860

Ser Gly Ala Glu Ser Phe Leu Trp Ser Cys Pro Val Thr Ala Leu Gly
865                 870                 875                 880

Gly Pro Asp Cys Ser His Gly Asn Thr Ala Ser Val Ile Cys Ser Gly
                885                 890                 895

Asn His Thr Gln Val Leu Pro Gln Cys Asn Asp Phe Leu Ser Gln Pro
            900                 905                 910

Ala Gly Ser Ala Ala Ser Glu Glu Ser Ser Pro Tyr Cys Ser Asp Ser
        915                 920                 925

Arg Gln Leu Arg Leu Val Asp Gly Gly Gly Pro Cys Gly Gly Arg Val
    930                 935                 940

Glu Ile Leu Asp Gln Gly Ser Trp Gly Thr Ile Cys Asp Asp Asp Trp
945                 950                 955                 960

Asp Leu Asp Asp Ala Arg Val Val Cys Arg Gln Leu Gly Cys Gly Glu
                965                 970                 975

Ala Leu Asn Ala Thr Gly Ser Ala His Phe Gly Ala Gly Ser Gly Pro
            980                 985                 990

Ile Trp Leu Asp Asp Leu Asn Cys Thr Gly Lys Glu Ser His Val Trp
        995                 1000                1005

Arg Cys Pro Ser Arg Gly Trp Gly Arg His Asp Cys Arg His Lys Glu
   1010                 1015                1020

Asp Ala Gly Val Ile Cys Ser Glu Phe Leu Ala Leu Arg Met Val Ser
1025                1030                1035                1040

Glu Asp Gln Gln Cys Ala Gly Trp Leu Glu Val Phe Tyr Asn Gly Thr
               1045                1050                1055

Trp Gly Ser Val Cys Arg Ser Pro Met Glu Asp Ile Thr Val Ser Val
           1060                1065                1070

Ile Cys Arg Gln Leu Gly Cys Gly Asp Ser Gly Ser Leu Asn Thr Ser
       1075                1080                1085

Val Gly Leu Arg Glu Gly Ser Arg Pro Arg Trp Val Asp Leu Ile Gln
   1090                1095                1100

Cys Arg Lys Met Asp Thr Ser Leu Trp Gln Cys Pro Ser Gly Pro Trp
1105                1110                1115                1120

Lys Tyr Ser Ser Cys Ser Pro Lys Glu Glu Ala Tyr Ile Ser Cys Glu
               1125                1130                1135

Gly Arg Arg Pro Lys Ser Cys Pro Thr Ala Ala Ala Cys Thr Asp Arg
           1140                1145                1150

Glu Lys Leu Arg Leu Arg Gly Gly Asp Ser Glu Cys Ser Gly Arg Val
       1155                1160                1165

Glu Val Trp His Asn Gly Ser Trp Gly Thr Val Cys Asp Asp Ser Trp
   1170                1175                1180

Ser Leu Ala Glu Ala Glu Val Val Cys Gln Gln Leu Gly Cys Gly Gln
1185                1190                1195                1200

Ala Leu Glu Ala Val Arg Ser Ala Ala Phe Gly Pro Gly Asn Gly Ser
               1205                1210                1215

Ile Trp Leu Asp Glu Val Gln Cys Gly Gly Arg Glu Ser Ser Leu Trp
           1220                1225                1230

Asp Cys Val Ala Glu Pro Trp Gly Gln Ser Asp Cys Lys His Glu Glu
       1235                1240                1245

Asp Ala Gly Val Arg Cys Ser Gly Val Arg Thr Thr Leu Pro Thr Thr
   1250                1255                1260
```

-continued

```
Thr Ala Gly Thr Arg Thr Thr Ser Asn Ser Leu Pro Gly Ile Phe Ser
1265                1270                1275                1280

Leu Pro Gly Val Leu Cys Leu Ile Leu Gly Ser Leu Leu Phe Leu Val
                1285                1290                1295

Leu Val Ile Leu Val Thr Gln Leu Leu Arg Trp Arg Ala Glu Arg Arg
            1300                1305                1310

Ala Leu Ser Ser Tyr Glu Asp Ala Leu Ala Glu Ala Val Tyr Glu Glu
        1315                1320                1325

Leu Asp Tyr Leu Leu Thr Gln Lys Glu Gly Leu Gly Ser Pro Asp Gln
    1330                1335                1340

Met Thr Asp Val Pro Asp Glu Asn Tyr Asp Asp Ala Glu Glu Val Pro
1345                1350                1355                1360

Val Pro Gly Thr Pro Ser Pro Ser Gln Gly Asn Glu Glu Glu Val Pro
                1365                1370                1375

Pro Glu Lys Glu Asp Gly Val Arg Ser Ser Gln Thr Gly Ser Phe Leu
            1380                1385                1390

Asn Phe Ser Arg Glu Ala Ala Asn Pro Gly Glu Gly Glu Glu Ser Phe
        1395                1400                1405

Trp Leu Leu Gln Gly Lys Lys Gly Asp Ala Gly Tyr Asp Asp Val Glu
    1410                1415                1420

Leu Ser Ala Leu Gly Thr Ser Pro Val Thr Phe Ser
1425                1430                1435
```

<210> SEQ ID NO 79
<211> LENGTH: 4308
<212> TYPE: DNA
<213> ORGANISM: Bos sp.

<400> SEQUENCE: 79

```
atggctctgg gcagacacct ctccctgcgg ggactctgtg tcctcctcct cggcaccatg     60

gtgggtggtc aagctctgga gctgaggttg aaggatggag tccatcgctg tgaggggaga    120

gtggaagtga agcaccaagg agaatggggc acagtggatg gttacaggtg gacattgaag    180

gatgcatctg tagtgtgcag acagctgggg tgtggagctg ccattggttt tcctggaggg    240

gcttattttg ggccaggact tggccccatt tggcttttgt atacttcatg tgaagggaca    300

gagtcaactg tcagtgactg tgagcattct aatattaaag actatcgtaa tgatggctat    360

aatcatggtc gggatgctgg agtagtctgc tcaggatttg tgcgtctggc tggaggggat    420

ggaccctgct cagggcgagt agaagtgcat tctggagaag cttggatccc agtgtctgat    480

gggaacttca cacttgccac tgcccagatc atctgtgcag agttgggttg tggcaaggct    540

gtgtctgtcc tgggacatga gctcttcaga gagtccagtg cccaggtctg ggctgaagag    600

ttcaggtgtg agggggagga gcctgagctc tgggtctgcc ccagagtgcc ctgtccaggg    660

ggcacgtgtc accacagtgg atctgctcag gttgtttgtt cagcatactc agaagtccgg    720

ctcatgacaa acggctcctc tcagtgtgaa gggcaggtgg agatgaacat ttctggacaa    780

tggagagcgc tctgtgcctc ccactggagt ctggccaatg ccaatgttat ctgtcgtcag    840

ctcggctgtg gagttgccat ctccaccccc ggaggaccac acttggtgga agaaggtgat    900

cagatcctaa cagcccgatt tcactgctct ggggctgagt ccttcctgtg gagttgtcct    960

gtgactgccc tgggtggtcc tgactgttcc catggcaaca cagcctctgt gatctgctca   1020

ggaaaccaga tccaggtgct tccccagtgc aacgactccg tgtctcaacc tacaggctct   1080

gcggcctcag aggacagcgc cccctactgc tcagacagca ggcagctccg cctggtggac   1140
```

-continued

```
gggggcggtc cctgcgccgg gagagtggag atccttgacc agggctcctg gggcaccatc   1200
tgtgatgacg gctgggacct ggacgatgcc cgcgtggtgt gcaggcagct gggctgtgga   1260
gaagccctca atgccacggg gtctgctcac ttcggggcag gatcagggcc catctggttg   1320
gacaacttga actgcacagg aaaggagtcc cacgtgtgga ggtgcccttc ccggggctgg   1380
gggcagcaca actgcagaca caagcaggac gcgggggtca tctgctcaga gttcctggcc   1440
ctcaggatgg tgagtgagga ccagcagtgt gctgggtggc tggaagtttt ctacaatggg   1500
acctggggca gtgtctgccg taaccccatg gaagacatca ctgtgtccac gatctgcaga   1560
cagcttggct gtggggacag tggaaccctc aactcttctg ttgctcttag agaaggtttt   1620
aggccacagt gggtggatag aatccagtgt cggaaaactg acacctctct ctggcagtgt   1680
ccttctgacc cttggaatta caactcatgc tctccaaagg aggaagccta tatctggtgt   1740
gcagacagca gacagatccg cctggtggat ggaggtggtc gctgctctgg gagagtggag   1800
atccttgacc agggctcctg gggcaccatc tgtgatgacc gctgggacct ggacgatgcc   1860
cgtgtggtgt gcaagcagct gggctgtgga gaagccctgg acgccactgt ctcttccttc   1920
ttcgggacgg gatcagggcc catctggctg gatgaagtga actgcagagg agaggagtcc   1980
caagtatgga ggtgcccttc ctggggatgg cggcaacaca actgcaatca tcaagaagat   2040
gcaggagtca tctgctcagg atttgtgcgt ctggctggag gagatggacc ctgctcaggg   2100
cgagtagaag tgcattctgg agaagcctgg accccagtgt ctgatggaaa cttcacactc   2160
cccactgccc aggtcatctg tgcagagctg ggatgtggca aggctgtgtc tgtcctggga   2220
cacatgccat tcagagagtc cgatggccag gtctgggctg aagagttcag gtgtgatggg   2280
ggggagcctg agctctggtc ctgccccaga gtgccctgtc caggaggcac atgtctccac   2340
agtggagctg ctcaggttgt ctgttcagtg tacacagaag tccagcttat gaaaaacggc   2400
acctctcaat gtgaggggca ggtggagatg aagatctctg gacgatggag agcgctctgt   2460
gcctcccact ggagtctggc caatgccaat gttgtctgtc gtcagctcgg ctgtggagtc   2520
gccatctcca cccccagagg accacacttg gtggaaggag gtgatcagat ctcaacagcc   2580
caatttcact gctcaggggc tgagtccttc ctgtggagtt gtcctgtgac tgccttgggt   2640
gggcctgact gttcccatgg caacacagcc tctgtgatct gctcaggaaa ccacacccag   2700
gtgctgcccc agtgcaacga cttcctgtct caacctgcag gctctgcggc ctcagaggag   2760
agttctccct actgctcaga cagcaggcag ctccgcctgg tggacggggg cggtccctgc   2820
ggcgggagag tggagatcct tgaccagggc tcctggggca ccatctgtga tgatgactgg   2880
gacctggacg atgcccgtgt ggtgtgcagg cagctgggct gtggagaagc cctcaatgcc   2940
acggggtctg ctcacttcgg ggcaggatca gggcccatct ggctggacga cctgaactgc   3000
acaggaaagg agtcccacgt gtggaggtgc ccttcccggg gctgggggcg gcacgactgc   3060
agacacaagg aggacgccgg ggtcatctgc tcagagttcc tggccctcag gatggtgagc   3120
gaggaccagc agtgtgctgg gtggctggag gttttctaca acgggacctg gggcagtgtc   3180
tgccgcagcc ccatggaaga tatcactgtg tccgtgatct gcagacagct tggatgtggg   3240
gacagtggaa gtctcaacac ctctgttggt ctcagggaag gttctagacc ccggtgggta   3300
gatttaattc agtgtcggaa aatggatacc tctctctggc agtgtccttc tggcccatgg   3360
aaatacagtt catgctctcc aaaggaggaa gcctacatct catgtgaagg aagaagaccc   3420
aagagctgtc caactgctgc cgcctgcaca gacagagaga agctccgcct caggggagga   3480
gacagcgagt gctcagggcg ggtggaggtg tggcacaacg gctcctgggg caccgtgtgc   3540
```

-continued

```
gatgactcct ggagcctggc agaggctgag gtggtgtgtc agcagctggg ctgtggccag   3600
gccctggaag ccgtgcggtc tgcagcattt ggccctggaa atgggagcat ctggctggac   3660
gaggtgcagt gcgggggccg ggagtcctcc ctgtgggact gtgttgcgga gccctggggg   3720
cagagcgact gcaagcacga ggaggatgct ggtgtgaggt gctctggtgt aaggacaaca   3780
ttgcccacga ccacagcagg gaccagaaca acctcaaatt ctctccctgg catcttctcc   3840
ctgcctgggg ttctctgcct tatcctgggg tcgcttctct tcctggtcct cgtcatcctg   3900
gtgactcagc tactcagatg gagagcagag cgcagagcct tatccagcta tgaagatgct   3960
cttgctgaag ctgtgtatga ggagctcgat taccttctga cacagaagga aggtctgggc   4020
agcccagatc agatgactga tgtccctgat gaaaattatg atgatgctga agaagtacca   4080
gtgcctggaa ctccttctcc ctctcagggg aatgaggagg aagtgccccc agagaaggag   4140
gacggggtga ggtcctctca gacaggctct ttcctgaact tctccagaga ggcagctaat   4200
cctggggaag gagaagagag cttctggctg ctccagggga agaaagggga tgctgggtat   4260
gatgatgttg aactcagtgc cctgggaaca tccccagtga ctttctcg                4308
```

TANGO 294, A LIPASE-LIKE PROTEIN

CROSS REFERENCE TO RELATED APPLICATIONS

This application is a continuation-in-part of co-pending U.S. patent application Ser. No. 09/333,159, filed Jun. 14, 1999.

BACKGROUND OF THE INVENTION

The molecular bases underlying many human and animal physiological states (e.g., diseased and homeostatic states of various tissues) remain unknown. Nonetheless, it is well understood that these states result from interactions among the proteins and nucleic acids present in the cells of the relevant tissues. In the past, the complexity of biological systems overwhelmed the ability of practitioners to understand the molecular interactions giving rise to normal and abnormal physiological states. More recently, though, the techniques of molecular biology, transgenic and null mutant animal production, computational biology, pharmacogenomics, and the like have enabled practitioners to discern the role and importance of individual genes and proteins in particular physiological states.

Knowledge of the sequences and other properties of genes (particularly including the portions of genes encoding proteins) and the proteins encoded thereby enables the practitioner to design and screen agents which will affect, prospectively or retrospectively, the physiological state of an animal tissue in a favorable way. Such knowledge also enables the practitioner, by detecting the levels of gene expression and protein production, to diagnose the current physiological state of a tissue or animal and to predict such physiological states in the future. This knowledge furthermore enables the practitioner to identify and design molecules which bind with the polynucleotides and proteins, in vitro, in vivo, or both.

The present invention provides sequence information for polynucleotides derived from human and murine genes and for proteins encoded thereby, and thus enables the practitioner to assess, predict, and affect the physiological state of various human and murine tissues.

SUMMARY OF THE INVENTION

The present invention is based, at least in part, on the discovery of a variety of human and murine cDNA molecules which encode proteins which are herein designated TANGO 202, TANGO 234, TANGO 265, TANGO 273, TANGO 286, TANGO 294, and INTERCEPT 296. These seven proteins, fragments thereof, derivatives thereof, and variants thereof are collectively referred to herein as the polypeptides of the invention or the proteins of the invention. Nucleic acid molecules encoding polypeptides of the invention are collectively referred to as nucleic acids of the invention.

The nucleic acids and polypeptides of the present invention are useful as modulating agents in regulating a variety of cellular processes. Accordingly, in one aspect, the present invention provides isolated nucleic acid molecules encoding a polypeptide of the invention or a biologically active portion thereof. The present invention also provides nucleic acid molecules which are suitable as primers or hybridization probes for the detection of nucleic acids encoding a polypeptide of the invention.

The invention also features nucleic acid molecules which are at least 40% (or 50%, 60%, 70%, 80%, 90%, 95%, or 98%) identical to the nucleotide sequence of any of SEQ ID NOs: 1, 2, 9, 10, 17, 18, 25, 26, 33, 34, 45, 46, 53, 54, 67, 68, 72, and 73, the nucleotide sequence of a cDNA clone deposited with ATCC® as one of Accession numbers 207219, 207184, 207228, 207185, 207220, and 207221 ("a cDNA of a clone deposited as one of ATCC® 207219, 207184, 207228, 207185, 207220, and 207221"), or a complement thereof.

The invention features nucleic acid molecules which include a fragment of at least 15 (25, 40, 60, 80, 100, 150, 200, 250, 300, 350, 400, 450, 550, 650, 700, 800, 900, 1000, 1200, 1400, 1600, 1800, 2000, 2200, 2400, 2600, 2800, 3000, 3500, 4000, 4500, or 4928) consecutive nucleotide residues of any of SEQ ID NOs: 1, 2, 9, 10, 17, 18, 25, 26, 33, 34, 45, 46, 53, 54, 67, 68, 72, and 73, the nucleotide sequence of a cDNA of a clone deposited as one of ATCC® 207219, 207184, 207228, 207185, 207220, and 207221, or a complement thereof.

The invention also features nucleic acid molecules which include a nucleotide sequence encoding a protein having an amino acid sequence that is at least 50% (or 60%, 70%, 80%, 90%, 95%, or 98%) identical to the amino acid sequence of any of SEQ ID NOs: 3–8, 11–16, 19–24, 27–32, 35–44, 47–52, 55–66, 69, and 74, or the amino acid sequence encoded by a cDNA of a clone deposited as one of ATCC® 207219, 207184, 207228, 207185, 207220, and 207221, or a complement thereof.

In preferred embodiments, the nucleic acid molecules have the nucleotide sequence of any of SEQ ID NOs: 1, 2, 9, 10, 17, 18, 25, 26, 33, 34, 45, 46, 53, 54, 67, 68, 72, and 73, or the nucleotide sequence of a cDNA of a clone deposited as one of ATCC4 207219, 207184, 207228, 207185, 207220, and 207221.

Also within the invention are nucleic acid molecules which encode a fragment of a polypeptide having the amino acid sequence of any of SEQ ID NOs: 3–8, 11–16, 19–24, 27–32, 35–44, 47–52, 55–66, 69, and 74, or the amino acid sequence encoded by a cDNA of a clone deposited as one of ATCC® 207219, 207184, 207228, 207185, 207220, and 207221, the fragment including at least 8 (10, 15, 20, 25, 30, 40, 50, 75, 100, 125, 150, or 200) consecutive amino acids of any of SEQ ID NOs: 3–8, 11–16, 19–24, 27–32, 35–44, 47–52, 55–66, 69, and 74, or the amino acid sequence encoded by a cDNA of a clone deposited as one of ATCC® 207219, 207184, 207228, 207185, 207220, and 207221.

The invention includes nucleic acid molecules which encode a naturally occurring allelic variant of a polypeptide comprising the amino acid sequence of any of SEQ ID NOs: 3–8, 11–16, 19–24, 27–32, 35–44, 47–52, 55–66, 69, and 74, or the amino acid sequence encoded by a cDNA of a clone deposited as one of ATCC® 207219, 207184, 207228, 207185, 207220, and 207221, wherein the nucleic acid molecule hybridizes under stringent conditions to a nucleic acid molecule having a nucleic acid sequence encoding any of SEQ ID NOs: 1, 2, 9, 10, 17, 18, 25, 26, 33, 34, 45, 46, 53, 54, 67, 68, 72, and 73, the nucleotide sequence of a cDNA of a clone deposited as one of ATCC® 207219, 207184, 207228, 207185, 207220, and 207221, or a complement thereof.

Also within the invention are isolated polypeptides or proteins having an amino acid sequence that is at least about 50%, preferably 60%, 75%, 90%, 95%, or 98% identical to the amino acid sequence of any of SEQ ID NOs: 3–8, 11–16, 19–24, 27–32, 35–44, 47–52, 55–66, 69, and 74.

Also within the invention are isolated polypeptides or proteins which are encoded by a nucleic acid molecule having a nucleotide sequence that is at least about 40%, preferably 50%, 75%, 85%, or 95% identical the nucleic acid sequence encoding any of SEQ ID NOs: 3–8, 11–16, 19–24, 27–32, 35–44, 47–52, 55–66, 69, and 74, and isolated polypeptides or proteins which are encoded by a nucleic acid molecule consisting of the nucleotide sequence which hybridizes under stringent hybridization conditions to a nucleic acid molecule having the nucleotide sequence of any of SEQ ID NOs: 1, 2, 9, 10, 17, 18, 25, 26, 33, 34, 45, 46, 53, 54, 67, 68, 72, and 73.

Also within the invention are polypeptides which are naturally occurring allelic variants of a polypeptide that includes the amino acid sequence of any of SEQ ID NOs: 3–8, 11–16, 19–24, 27–32, 35–44, 47–52, 55–66, 69, and 74, or the amino acid sequence encoded by a cDNA of a clone deposited as one of ATCC® 207219, 207184, 207228, 207185, 207220, and 207221, wherein the polypeptide is encoded by a nucleic acid molecule which hybridizes under stringent conditions to a nucleic acid molecule having the nucleotide sequence of any of SEQ ID NOs: 1, 2, 9, 10, 17, 18, 25, 26, 33, 34, 45, 46, 53, 54, 67, 68, 72, and 73, or a complement thereof.

The invention also features nucleic acid molecules that hybridize under stringent conditions to a nucleic acid molecule having the nucleotide sequence of any of SEQ ID NOs: 1, 2, 9, 10, 17, 18, 25, 26, 33, 34, 45, 46, 53, 54, 67, 68, 72, and 73, the nucleotide sequence of a cDNA of a clone deposited as one of ATTC® 207219, 207184, 207228, 207185, 207220, and 207221, or a complement thereof. In other embodiments, the nucleic acid molecules are at least 15 (25, 40, 60, 80, 100, 150, 200, 250, 300, 350, 400, 450, 550, 650, 700, 800, 900, 1000, 1200, 1400, 1600, 1800, 2000, 2200, 2400, 2600, 2800, 3000, 3500, 4000, 4500, or 4928) nucleotides in length and hybridize under stringent conditions to a nucleic acid molecule having the nucleotide sequence of any of SEQ ID NOs: 1, 2, 9, 10, 17, 18, 25, 26, 33, 34, 45, 46, 53, 54, 67, 68, 72, and 73, the nucleotide sequence of a cDNA of a clone deposited as one of ATCC® 207219, 207184, 207228, 207185, 207220, and 207221, or a complement thereof. In some embodiments, the isolated nucleic acid molecules encode a cytoplasmic, transmembrane, extracellular, or other domain of a polypeptide of the invention. In other embodiments, the invention provides an isolated nucleic acid molecule which is antisense to the coding strand of a nucleic acid of the invention.

Another aspect of the invention provides vectors, e.g., recombinant expression vectors, comprising a nucleic acid molecule of the invention. In another embodiment, the invention provides isolated host cells, e.g., mammalian and non-mammalian cells, containing such a vector or a nucleic acid of the invention. The invention also provides methods for producing a polypeptide of the invention by culturing, in a suitable medium, a host cell of the invention containing a recombinant expression vector encoding a polypeptide of the invention such that the polypeptide of the invention is produced.

Another aspect of this invention features isolated or recombinant proteins and polypeptides of the invention. Preferred proteins and polypeptides possess at least one biological activity possessed by the corresponding naturally-occurring human polypeptide. An activity, a biological activity, and a functional activity of a polypeptide of the invention refers to an activity exerted by a protein or polypeptide of the invention on a responsive cell as determined in vivo, or in vitro, according to statndard techniques.

Such activities can be a direct activity, such as an association with or an association with or an enzymatic activity on a second protein, or an indirect activity, such as a cellular process (e.g., signaling activity) mediated by interaction of the protein with a second protein. Such activities include, by way of example, formation of protein-protein interactions with proteins of one or more signaling pathways (e.g., with a protein with which the naturally-occuring polypeptide interacts); binding with a ligand of the naturally-occuring protein; and binding with an intracellular target of the naturally-occuring protein. Other activities include modulation of one or more of cellular proliferation, of cellular differentiation, of chemotaxis, of cellular migration, and of cell death (e.g., apoptosis).

By way of example, TANGO 202 exhibits the ability to affect growth, proliferation, survival, differentiation, and activity of human hematopoietic cells (e.g., bone marrow stromal cells) and fetal cells. TANGO 202 modulates cellular binding to one or more mediators, modulates proteolytic activity in vivo, modulates developmental processes, and modulates cell growth, proliferation, survival, differentiation, and activity. Thus, TANGO 202 can be used to prevent, diagnose, or treat disorders relating to aberrant cellular protease activity, inappropriate interaction (or non-interaction) of cells with mediators, inappropriate development, and blood and hematopoietic cell-related disorders. Exemplary disorders for which TANGO 202 is useful include immune disorders, infectious diseases, autoimmune disorders, vascular and cardiovascular disorders, disorders related to mal-expression of growth factors, cancers, hematological disorders, various cancers, birth defects, developmental defects, and the like.

Further by way of example, TANGO 234 exhibits the ability to affect growth, proliferation, survival, differentiation, and activity of human lung, hematopoietic, and fetal cells and of (e.g., bacterial or fungal) cells and viruses which infect humans. TANGO 234 modulates growth, proliferation, survival, differentiation, and activity of gamma delta T cells, for example. Furthermore, TANGO 234 modulates cholesterol deposition on human arterial walls, and is involved in uptake and metabolism of low density lipoprotein and regulation of serum cholesterol levels. Thus, TANGO 234 can be used to affect development and persistence of atherogenesis and arteriosclerosis, as well as other vascular and cardiovascular disorders. Other exemplary disorders for which TANGO 234 is useful include immune development disorders and disorders involving generation and persistence of an immune response to bacterial, fungal, and viral infections.

Still further by way of example, TANGO 265 modulates growth and regeneration of neuronal and epithelial tissues, and guides neuronal axon development. TANGO 265 is a transmembrane protein which mediates cellular interaction with cells, molecules and structures (e.g., extracellular matrix) in the extracellular environment. TANGO 265 is therefore involved in growth, organization, and adhesion of tissues and the cells which constitute those tissues. Furthermore, TANGO 265 modulates growth, proliferation, survival, differentiation, and activity of neuronal cells and immune system cells. Thus, TANGO 265 can be used, for example, to prevent, diagnose, or treat disorders characterized by aberrant organization or development of a tissue or organ, for guiding neural axon development, for modulating differentiation of cells of the immune system, for modulating cytokine production by cells of the immune system, for modulating reactivity of cells of the immune system toward cytokines, for modulating initiation and persistence of an inflammatory response, and for modulating proliferation of epithelial cells.

Yet further by way of example, TANGO 273 protein mediates one or more physiological responses of cells to bacterial infection, e.g., by mediating one or more of detection of bacteria in a tissue in which it is expressed, movement of cells with relation to sites of bacterial infection, production of biological molecules which inhibit bacterial infection, and production of biological molecules which alleviate cellular or other physiological damage wrought by bacterial infection. TANGO 273, a transmembrane protein, is also involved in transmembrane signal transduction, and therefore mediates transmission of signals between the extracellular and intracellular environments of cells. TANGO 273 mediates regulation of cell growth and proliferation, endocytosis, activation of respiratory burst, and other physiological processes triggered by transmission of a signal via a protein with which TANGO 273 interacts. The compositions and methods of the invention can therefore be used to prevent, diagnose, and treat disorders involving one or more physiological activities mediated by TANGO 273 protein. Such disorders include, for example, various bone-related disorders such as metabolic, homeostatic, and developmental bone disorders (e.g., osteoporosis, various cancers, skeletal development disorders, bone fragility and the like), disorders caused by or related to bacterial infection, and disorders characterized by aberrant transmembrane signal transduction by TANGO 273.

As an additional example, TANGO 286 protein is involved in lipid-binding physiological processes such as lipid transport, metabolism, serum lipid particle regulation, host anti-microbial defensive mechanisms, and the like. Thus, the compositions and methods of the invention can therefore be used to prevent, diagnose, and treat disorders involving one or more physiological activities mediated by TANGO 286 protein. Such disorders include, for example, lipid transport disorders, lipid metabolism disorders, obesity, disorders of serum lipid particle regulation, disorders involving insufficient or inappropriate host anti-microbial defensive mechanisms, vasculitis, bronchiectasis, LPS-related disorders such as shock, disseminated intravascular coagulation, anemia, thrombocytopenia, adult respiratory distress syndrome, renal failure, liver disease, and disorders associated with Gran negative bacterial infections, such as bacteremia, endotoxemia, sepsis, and the like.

Further by way of example, TANGO 294 protein is involved in facilitating absorption and metabolism of fat. Thus, the compositions and methods of the invention can therefore be used to prevent, diagnose, and treat disorders involving one or more physiological activities mediated by TANGO 294 protein. Such disorders include, for example, inadequate expression of gastric/pancreatic lipase, cystic fibrosis, exocrine pancreatic insufficiency, medical treatments which alter fat absorption, obesity, and the like.

As another example, INTERCEPT 296 protein is involved in physiological processes related to disorders of the human lung and esophagus. Thus, the compositions and methods of the invention can be used to prevent, diagnose, and treat these disorders. Such disorders include, for example, various cancers, bronchitis, cystic fibrosis, respiratory infections (e.g., influenza, bronchiolitis, pneumonia, and tuberculosis), asthma, emphysema, chronic bronchitis, bronchiectasis, pulmonary edema, pleural effusion, pulmonary embolus, adult and infant respiratory distress syndromes, heartburn, and gastric reflux esophageal disease.

In one embodiment, a polypeptide of the invention has an amino acid sequence sufficiently identical to an identified domain of a polypeptide of the invention. As used herein, the term "sufficiently identical" refers to a first amino acid or nucleotide sequence which contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences which contain a common structural domain having about 65% identity, preferably 75% identity, more preferably 85%, 95%, or 98% identity are defined herein as sufficiently identical.

In one embodiment, the isolated polypeptide of the invention lacks both a transmembrane and a cytoplasmic domain. In another embodiment, the polypeptide lacks both a transmembrane domain and a cytoplasmic domain and is soluble under physiological conditions.

The polypeptides of the present invention, or biologically active portions thereof, can be operably linked to a heterologous amino acid sequence to form fusion proteins. The invention further features antibody substances that specifically bind a polypeptide of the invention such as monoclonal or polyclonal antibodies, antibody fragments, single-chain antibodies, and the like. In addition, the polypeptides of the invention or biologically active portions thereof can be incorporated into pharmaceutical compositions, which optionally include pharmaceutically acceptable carriers. These antibody substances can be made, for example, by providing the polypeptide of the invention to an immunocompetent vertebrate and thereafter harvesting blood or serum from the vertebrate.

In another aspect, the present invention provides methods for detecting the presence of the activity or expression of a polypeptide of the invention in a biological sample by contacting the biological sample with an agent capable of detecting an indicator of activity such that the presence of activity is detected in the biological sample.

In another aspect, the invention provides methods for modulating activity of a polypeptide of the invention comprising contacting a cell with an agent that modulates (inhibits or enhances) the activity or expression of a polypeptide of the invention such that activity or expression in the cell is modulated. In one embodiment, the agent is an antibody that specifically binds to a polypeptide of the invention.

In another embodiment, the agent modulates expression of a polypeptide of the invention by modulating transcription, splicing, or translation of an mRNA encoding a polypeptide of the invention. In yet another embodiment, the agent is a nucleic acid molecule having a nucleotide sequence that is antisense with respect to the coding strand of an mRNA encoding a polypeptide of the invention.

The present invention also provides methods to treat a subject having a disorder characterized by aberrant activity of a polypeptide of the invention or aberrant expression of a nucleic acid of the invention by administering an agent which is a modulator of the activity of a polypeptide of the invention or a modulator of the expression of a nucleic acid of the invention to the subject. In one embodiment, the modulator is a protein of the invention. In another embodiment, the modulator is a nucleic acid of the invention. In other embodiments, the modulator is a peptide, peptidomimetic, or other small molecule (e.g., a small organic molecule).

The present invention also provides diagnostic assays for identifying the presence or absence of a genetic lesion or mutation characterized by at least one of: (i) aberrant modification or mutation of a gene encoding a polypeptide of the invention, (ii) mis-regulation of a gene encoding a polypeptide of the invention, and (iii) aberrant post-translational modification of a polypeptide of the invention wherein a wild-type form of the gene encodes a polypeptide having the activity of the polypeptide of the invention.

In another aspect, the invention provides a method for identifying a compound that binds to or modulates the activity of a polypeptide of the invention. In general, such methods entail measuring a biological activity of the polypeptide in the presence and absence of a test compound and identifying those compounds which alter the activity of the polypeptide.

The invention also features methods for identifying a compound which modulates the expression of a polypeptide or nucleic acid of the invention by measuring the expression of the polypeptide or nucleic acid in the presence and absence of the compound.

In yet a further aspect, the invention provides substantially purified antibodies or fragments thereof (i.e., antibody substances), including non-human antibodies or fragments thereof, which specifically bind with a polypeptide of the invention or with a portion thereof. In various embodiments, these substantially purified antibodies/fragments can be human, non-human, chimeric, and/or humanized antibodies. Non-human antibodies included in the invention include, by way of example, goat, mouse, sheep, horse, chicken, rabbit, and rat antibodies. In addition, the antibodies of the invention can be polyclonal antibodies or monoclonal antibodies.

In a particularly preferred embodiment, the antibody substance of the invention specifically binds with an extracellular domain of one of TANGO 202, TANGO 234, TANGO 265, TANGO 273, TANGO 286, TANGO 294, and INTERCEPT 296. Preferably, the extracellular domain with which the antibody substance binds has an amino acid sequence selected from the group consisting of SEQ ID NOs: 5, 6, 14, 22, 30, 37, 49, 50, and 56–58.

Any of the antibody substances of the invention can be conjugated with a therapeutic moiety or with a detectable substance. Non-limiting examples of detectable substances that can be conjugated with the antibody substances of the invention include an enzyme, a prosthetic group, a fluorescent material (i.e., a fluorophore), a luminescent material, a bioluminescent material, and a radioactive material (e.g., a radionuclide or a substituent comprising a radionuclide).

The invention also provides a kit containing an antibody substance of the invention conjugated with a detectable substance, and instructions for use. Still another aspect of the invention is a pharmaceutical composition comprising an antibody substance of the invention and a pharmaceutically acceptable carrier. In preferred embodiments, the pharmaceutical composition contains an antibody substance of the invention, a therapeutic moiety (preferably conjugated with the antibody substance), and a pharmaceutically acceptable carrier.

Other features and advantages of the invention will be apparent from the following detailed description and claims.

BRIEF DESCRIPTION OF THE DRAWINGS

FIG. 1 comprises FIGS. 1A–1M. The nucleotide sequence (SEQ ID NO: 1) of a cDNA encoding the human TANGO 202 protein described herein is listed in FIGS. 1A–1D. The open reading frame (ORF; residues 34 to 1458; SEQ ID NO: 2) of the cDNA is indicated by nucleotide triplets, above which the amino acid sequence (SEQ ID NO: 3) of human TANGO 202 is listed. The nucleotide sequence (SEQ ID NO: 67) of a cDNA encoding the murine TANGO 202 protein described herein is listed in FIGS. 1E–1I. The ORF (residues 81 to 1490; SEQ ID NO: 68) of the cDNA is indicated by nucleotide triplets, above which the amino acid sequence (SEQ ID NO: 69) of murine TANGO 202 is listed. An alignment of the amino acid sequences of human ("Hum."; SEQ ID NO: 3) and murine ("Mur."; SEQ ID NO: 69) TANGO 202 protein is shown in FIGS. 1J and 1K, wherein identical amino acid residues are indicated by ":" and similar amino acid residues are indicated by ".".

FIG. 2 comprises FIGS. 2A–2Qxvii. The nucleotide sequence (SEQ ID NO: 9) of a cDNA encoding the human TANGO 234 protein described herein is listed in FIGS. 2A–2I. The ORF (residues 28 to 4386; SEQ ID NO: 10) of the cDNA is indicated by nucleotide triplets, above which the amino acid sequence (SEQ ID NO: 11) of human TANGO 234 is listed.

FIG. 3 comprises FIGS. 3A–3U. The nucleotide sequence (SEQ ID NO: 17) of a cDNA encoding the human TANGO 265 protein described herein is listed in FIGS. 3A–3E. The ORF (residues 32 to 2314; SEQ ID NO: 18) of the cDNA is indicated by nucleotide triplets, above which the amino acid sequence (SEQ ID NO: 19) of human TANGO 265 is listed. An alignment of the amino acid sequences of human TANGO 265 protein ("Hum."; SEQ ID NO: 19) and murine semaphorin B protein ("Mur."; SEQ ID NO: 70; GenBank Accession No. X85991) is shown in FIGS. 3F–3H, wherein identical amino acid residues are indicated by ":" and similar amino acid residues are indicated by ".". In FIGS. 3I–3T, an alignment of the nucleotide sequences of the cDNA encoding human TANGO 265 protein ("Hum."; SEQ ID NO: 17) and the nucleotide sequences of the cDNA encoding murine semaphorin B protein ("Mur."; SEQ ID NO: 71; GenBank Accession No. X85991) is shown.

FIG. 4 comprises FIGS. 4A–4J. The nucleotide sequence (SEQ ID NO: 25) of a cDNA encoding the human TANGO 273 protein described herein is listed in FIGS. 4A–4C. The ORF (residues 135 to 650; SEQ ID NO: 26) of the cDNA is indicated by nucleotide triplets, above which the amino acid sequence (SEQ ID NO: 27) of human TANGO 273 is listed. The nucleotide sequence (SEQ ID NO: 72) of a cDNA encoding the murine TANGO 273 protein described herein is listed in FIGS. 4D–4G. The ORF (residues 137 to 652; SEQ ID NO: 73) of the cDNA is indicated by nucleotide triplets, above which the amino acid sequence (SEQ ID NO: 74) of murine TANGO 273 is listed. An alignment of the amino acid sequences of human ("Hum."; SEQ ID NO: 27) and murine ("Mur."; SEQ ID NO: 74) TANGO 273 protein is shown in FIG. 4H, wherein identical amino acid residues are indicated by ":" and similar amino acid residues are indicated by ".".

FIG. 5 comprises FIGS. 5A–5I. The nucleotide sequence (SEQ ID NO: 33) of a cDNA encoding the human TANGO 286 protein described herein is listed in FIGS. 5A–5D. The ORF (residues 133 to 1497; SEQ ID NO: 34) of the cDNA is indicated by nucleotide triplets, above which the amino acid sequence (SEQ ID NO: 35) of human TANGO 286 is listed.

FIG. 6 comprises FIGS. 6A–6H. The nucleotide sequence (SEQ ID NO: 45) of a cDNA encoding the human TANGO 294 protein described herein is listed in FIGS. 6A–6C. The ORF (residues 126 to 1394; SEQ ID NO: 46) of the cDNA is indicated by nucleotide triplets, above which the amino acid sequence (SEQ ID NO: 47) of human TANGO 294 is listed. An alignment of the amino acid sequences of human TANGO 294 protein ("294"; SEQ ID NO: 47) and a known human lipase protein ("HLP"; SEQ ID NO: 75; GenBank Accession No. NP_004181) is shown in FIGS. 6D and 6E, wherein identical amino acid residues are indicated by ":" and similar amino acid residues are indicated by ".".

FIG. 7 comprises FIGS. 7A–7F. The nucleotide sequence (SEQ ID NO: 53) of a cDNA encoding the human INTERCEPT 296 protein described herein is At listed in FIGS. 7A–7C. The ORF (residues 70 to 1098; SEQ ID NO: 54) of the cDNA is indicated by nucleotide triplets, above which the amino acid sequence (SEQ ID NO: 55) of human INTERCEPT 296 protein is listed.

DETAILED DESCRIPTION OF THE INVENTION

Figure 1L:
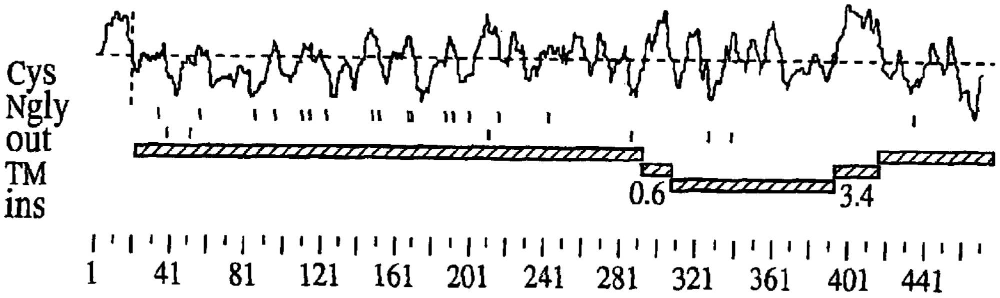
FIG. 1L is a hydrophilicity plot of human TANGO 202 protein, in which the locations of cysteine residues ("Cys") and potential N-glycosylation sites ("Ngly") are indicated by vertical bars and the predicted extracellular ("out"), intracellular ("ins"), or transmembrane ("TM") locations of the protein backbone is indicated by a horizontal bar.

The present invention is based, at least in part, on the discovery of a variety of human and murine cDNA molecules which encode proteins which are herein designated TANGO 202, TANGO 234, TANGO 265, TANGO 273, TANGO 286, TANGO 294, and INTERCEPT 296. These proteins exhibit a variety of physiological activities, and are included in a single application for the sake of convenience. It is understood that the allowability or non-allowability of claims directed to one of these proteins has no bearing on the allowability of claims directed to the others. The characteristics of each of these proteins and the cDNAs encoding them are now described separately.

TANGO 202

A cDNA clone (designated jthke096b05) encoding at least a portion of human TANGO 202 protein was isolated from a human fetal skin cDNA library. The corresponding murine cDNA was isolated as a clone (designated jtmMa044f07) from a bone marrow stromal cell cDNA library. The human TANGO 202 protein is predicted by structural analysis to be a type I membrane protein, although it can exist in a secreted form as well. The murine TANGO 202 protein is predicted by structural analysis to be a secreted protein.

The full length of the cDNA encoding human TANGO 202 protein (FIG. 1; SEQ ID NO: 1) is 1656 nucleotide residues. The open reading frame (ORF) of this cDNA, nucleotide residues 34 to 1458 of SEQ ID NO: 1 (i.e., SEQ ID NO: 2), encodes a 475-amino acid transmembrane protein (FIG. 1; SEQ ID NO: 3).

The invention thus includes purified human TANGO 202 protein, both in the form of the immature 475 amino acid residue protein (SEQ ID NO: 3) and in the form of the mature 456 amino acid residue protein (SEQ ID NO: 5). The invention also includes purified murine TANGO 202 protein, both in the form of the immature 470 amino acid residue protein (SEQ ID NO: 67) and in the form of the mature 451 amino acid residue protein (SEQ ID NO: 43). Mature human or murine TANGO 202 proteins can be synthesized without the signal sequence polypeptide at the amino terminus thereof, or they can be synthesized by generating immature TANGO 202 protein and cleaving the signal sequence therefrom.

In addition to full length mature and immature human and murine TANGO 202 proteins, the invention includes fragments, derivatives, and variants of these TANGO 202 proteins, as described herein. These proteins, fragments, derivatives, and variants are collectively referred to herein as polypeptides of the invention or proteins of the invention.

The invention also includes nucleic acid molecules which encode a polypeptide of the invention. Such nucleic acids include, for example, a DNA molecule having the nucleotide sequence listed in SEQ ID NO: 1 or some portion thereof or SEQ ID NO: 67 or some portion thereof, such as the portion which encodes mature human or murine TANGO 202 protein, immature human or murine TANGO 202 protein, or a domain of human or murine TANGO 202 protein. These nucleic acids are collectively referred to as nucleic acids of the invention.

TANGO 202 proteins and nucleic acid molecules encoding them comprise a family of molecules having certain conserved structural and functional features. As used herein, the term "family" is intended to mean two or more proteins or nucleic acid molecules having a common or similar domain structure and having sufficient amino acid or nucleotide sequence identity as defined herein. Family members can be from either the same or different species (e.g., human and mouse, as described herein). For example, a family can comprise two or more proteins of human origin, or can comprise one or more proteins of human origin and one or more of non-human origin.

A common domain present in TANGO 202 proteins is a signal sequence. As used herein, a signal sequence includes a peptide of at least about 10 amino acid residues in length which occurs at the amino terminus of membrane-bound and secreted proteins and which contains at least about 45% hydrophobic amino acid residues such as alanine, leucine, isoleucine, phenylalanine, proline, tyrosine, tryptophan, or valine. In a preferred embodiment, a signal sequence contains at least about 10 to 35 amino acid residues, preferably about 10 to 20 amino acid residues, and has at least about 35–60%, more preferably 40–50%, and more preferably at least about 45% hydrophobic residues. A signal sequence serves to direct a protein containing such a sequence to a lipid bilayer. Thus, in one embodiment, a TANGO 202 protein contains a signal sequence corresponding to amino acid residues 1 to 19 of SEQ ID NO: 3 (SEQ ID NO: 4) or to amino acid residues 1 to 19 of SEQ ID NO: 69 (SEQ ID NO: 42). The signal sequence is cleaved during processing of the mature protein.

TANGO 202 proteins can also include an extracellular domain. As used herein, an "extracellular domain" refers to a portion of a protein which is localized to the non-cytoplasmic side of a lipid bilayer of a cell when a nucleic acid encoding the protein is expressed in the cell. The human TANGO 202 protein extracellular domain is located from about amino acid residue 20 to about amino acid residue 392 of SEQ ID NO: 3 in the non-secreted form, and from about amino acid residue 20 to amino acid residue 475 of SEQ ID NO: 3 (i.e., the entire mature human protein). The murine TANGO 202 protein extracellular domain is located from about amino acid residue 20 to amino acid residue 470 of SEQ ID NO: 69 (i.e., the entire mature murine protein).

TANGO 202 proteins of the invention can also include a transmembrane domain. As used herein, a "transmembrane domain" refers to an amino acid sequence having at least about 20 to 25 amino acid residues in length and which contains at least about 65–70% hydrophobic amino acid residues such as alanine, leucine, phenylalanine, protein, tyrosine, tryptophan, or valine. In a preferred embodiment, a transmembrane domain contains at least about 15 to 30 amino acid residues, preferably about 20–25 amino acid residues, and has at least about 60–80%, more preferably 65–75%, and more preferably at least about 70% hydrophobic residues. Thus, in one embodiment, a TANGO 202 protein of the invention contains a transmembrane domain corresponding to about amino acid residues 393 to 415 of SEQ ID NO: 3 (SEQ ID NO: 7).

In addition, TANGO 202 proteins of the invention can include a cytoplasmic domain, particularly including a carboxyl-terminal cytoplasmic domain. As used herein, a "cytoplasmic domain" refers to a portion of a protein which is localized to the cytoplasmic side of a lipid bilayer of a cell when a nucleic acid encoding the protein is expressed in the cell. The cytoplasmic domain is located from about amino acid residue 416 to amino acid residue 475 of SEQ ID NO: 3 (SEQ ID NO: 8) in the non-secreted form of human TANGO 202 protein.

TANGO 202 proteins typically comprise a variety of potential post-translational modification sites (often within an extracellular domain), such as those described herein in Tables I (for human TANGO 202) and II (for murine TANGO 202), as predicted by computerized sequence analysis of TANGO 202 proteins using amino acid sequence comparison software (comparing the amino acid sequence of TANGO 202 with the information in the PROSITE database {rel. 12.2; February 1995} and the Hidden Markov Models database {Rel. PFAM 3.3}).

TABLE I

| Type of Potential Modification Site or Domain | Amino Acid Residues of SEQ ID NO: 3 | Amino Acid Sequence |
|---|---|---|
| N-glycosylation site | 47 to 50 | NWTA |
| | 61 to 64 | NETF |

TABLE I-continued

| Type of Potential Modification Site or Domain | Amino Acid Residues of SEQ ID NO: 3 | Amino Acid Sequence |
|---|---|---|
| | 219 to 222 | NYSA |
| | 295 to 298 | NVSL |
| | 335 to 338 | NQTV |
| | 347 to 350 | NLSV |
| Protein kinase C phosphorylation site | 70 to 72 | TLK |
| | 137 to 139 | TSK |
| | 141 to 143 | SNK |
| | 155 to 157 | SQR |
| | 238 to 240 | TGR |
| | 245 to 247 | TIR |
| | 277 to 279 | THR |
| | 307 to 309 | SDR |
| | 355 to 357 | SSK |
| | 387 to 389 | SHR |
| | 418 to 420 | TFK |
| | 421 to 423 | SHR |
| Casein kinase II phosphorylation site | 337 to 340 | TVAE |
| | 438 to 441 | TSGE |
| | 464 to 467 | SQQD |
| N-myristoylation site | 53 to 58 | GGKPCL |
| | 120 to 125 | GNLGCY |
| | 136 to 141 | GTSKTS |
| | 162 to 167 | GMESGY |
| | 214 to 219 | GACGGN |
| Kringle domain signature | 85 to 90 | YCRNPD |
| Kringle Domain | 34 to 116 | See FIG. 1 |
| CUB domain | 216 to 320 | See FIG. 1 |

TABLE II

| Type of Potential Modification Site or Domain | Amino Acid Residues of SEQ ID NO: 69 | Amino Acid Sequence |
|---|---|---|
| N-glycosylation site | 59 to 62 | NETF |
| | 217 to 220 | NYSA |
| | 255 to 258 | NFTL |
| | 293 to 296 | NVSL |
| | 333 to 336 | NQTL |
| | 345 to 348 | NLSV |
| cAMP- or cGMP-dependent protein kinase phosphorylation site | 455 to 458 | RRSS |
| Protein kinase C phosphorylation site | 68 to 70 | TLK |
| | 135 to 137 | TSK |
| | 139 to 141 | SNK |
| | 153 to 155 | SQR |
| | 236 to 238 | TGR |
| | 243 to 245 | TIR |
| | 275 to 277 | THR |
| | 283 to 285 | SGR |
| | 305 to 307 | SDR |
| | 353 to 355 | SSK |
| | 408 to 410 | SQR |
| | 453 to 455 | SLR |
| | 457 to 459 | SSR |
| Casein kinase II phosphorylation site | 28 to 31 | SGPE |
| | 257 to 260 | TLFD |
| | 321 to 324 | TKEE |
| | 335 to 338 | TLAE |
| | 384 to 387 | TATE |
| N-myristoylation site | 51 TO 56 | GGKPCL |
| | 118 TO 123 | GNLGCY |
| | 134 TO 139 | GTSKTS |
| | 160 TO 165 | GMESGY |
| | 212 TO 217 | GACGGN |
| | 391 TO 396 | GLCTAW |
| | 429 TO 434 | GTVVSL |
| Kringle domain signature | 83 to 88 | YCRNPD |
| Kringle Domain | 32 to 114 | See FIG. 1 |
| CUB domain | 214 to 318 | See FIG. 1 |

As used herein, the term "post-translational modification site" refers to a protein domain that includes about 3 to 10 amino acid residues, more preferably about 3 to 6 amino acid residues wherein the domain has an amino acid sequence which comprises a consensus sequence which is recognized and modified by a protein-modifying enzyme. Exemplary protein-modifying enzymes include amino acid glycosylases, cAMP- and cGMP-dependent protein kinases, protein kinase C, casein kinase II, myristoylases, and prenyl transferases. In various embodiments, the protein of the invention has at least 1, 2, 4, 6, 10, 15, or 20 or more of the post-translational modification sites described herein in Tables I and II.

Exemplary additional domains present in human and murine TANGO 202 protein include Kringle domains and CUB domains. In one embodiment, the protein of the invention has at least one domain that is at least 55%, preferably at least about 65%, more preferably at least about 75%, yet more preferably at least about 85%, and most preferably at least about 95% identical to one of the domains described herein in Tables I and II. Preferably, the protein of the invention has at least one Kringle domain and one CUB domain.

A Kringle domain has a characteristic profile that has been described in the art (Castellino and Beals (1987) *J. Mol. Evol.* 26:358–369; Patthy (1985) *Cell* 41:657–663; Ikeo et al. (1991) *FEBS Lett.* 287:146–148). Many, but not all, Kringle domains comprise a conserved hexapeptide signature sequence, namely (F or Y)-C-R-N-P-(D or N or R).

The cysteine residue is involved in a disulfide bond.

Kringle domains are triple-looped, disulfide cross-linked domains found in a varying number of copies in, for example, some serine proteases and plasma proteins. Kringle domains have a role in binding mediators (e.g., membranes, other proteins, or phospholipids) and in regulation of proteolytic activity. Kringle domains have been identified in the following proteins, for example: apolipoprotein A, blood coagulation factor XII (Hageman factor), hepatocyte growth factor (HGF), HGF-like protein (Friezner Degen et al., (1991) *Biochemistry* 30:9781–9791), HGF activator (Miyazawa et al., (1993) *J. Biol. Chem.* 268:10024–10028), plasminogen, thrombin, tissue plasminogen activator, urokinase-type plasminogen activator, and four influenza neuraminidases. The presence of a Kringle domain in each of human and murine TANGO 202 protein indicates that TANGO 202 is involved in one or more physiological processes in which these other Kringle domain-containing proteins are involved, has biological activity in common with one or more of these other Kringle domain-containing proteins, or both.

CUB domains are extracellular domains of about 110 amino acid residues which occur in functionally diverse, mostly developmentally regulated proteins (Bork and Beckmann (1993) *J. Mol. Biol.* 231:539–545; Bork (1991) *FEBS Lett.* 282:9–12). Many CUB domains contain four conserved cysteine residues, although some, like that of TANGO 202, contain only two of the conserved cysteine residues. The structure of the CUB domain has been predicted to assume a beta-barrel configuration, similar to that of immunoglobulins. Other proteins which have been found to comprise one or more CUB domains include, for example, mammalian complement sub-components Cls and Clr, hamster serine protease Casp, mammalian complement activating component of Ra-reactive factor, vertebrate enteropeptidase, vertebrate bone morphogenic protein 1, sea urchin blastula proteins BP10 and SpAN, *Caenorhabditis elegans* hypothetical proteins F42A10.8 and R151.5, neuropilin (A5 antigen), sea urchin fibropellins I and III, mammalian hyaluronate-binding protein TSG6 (PS4), mammalian spermadhesins, and Xenopus embryonic protein UVS.2. The presence of a CUB domain in each of human and murine TANGO 202 protein indicates that TANGO 202 is involved in one or more physiological processes in which these other CUB domain-containing proteins are involved, has biological activity in common with one or more of these other CUB domain-containing proteins, or both.

The signal peptide prediction program SIGNALP (Nielsen et al. (1997) *Protein Engineering* 10:1–6) predicted that human TANGO 202 protein includes a 19 amino acid signal peptide (amino acid residues 1 to 19 of SEQ ID NO: 3; SEQ ID NO: 4) preceding the mature TANGO 202 protein (amino acid residues 20 to 475 of SEQ ID NO: 3; SEQ ID NO: 5). Human TANGO 202 protein includes an extracellular domain (amino acid residues 20 to 392 of SEQ ID NO: 3; SEQ ID NO: 6); a transmembrane domain (amino acid residues 393 to 415 of SEQ ID NO: 3; SEQ ID NO: 7); and a cytoplasmic domain (amino acid residues 416 to 475 of SEQ ID NO: 3; SEQ ID NO: 8). The murine homolog of TANGO 202 protein is predicted to be a secreted protein. Thus, it is recognized that human TANGO 202 can also exist in the to form of a secreted protein, likely being translated from an alternatively spliced TANGO 202 mRNA. In a variant form of the protein, an extracellular portion of TANGO 202 protein (e.g., amino acid residues 20 to 392 of SEQ ID NO: 3) can be cleaved from the mature protein to generate a soluble fragment of TANGO 202.

FIG. 1L depicts a hydrophilicity plot of human TANGO 202 protein. Relatively hydrophobic regions are above the dashed horizontal line, and relatively hydrophilic regions are below the dashed horizontal line. The hydrophobic region which corresponds to amino acid residues 1 to 19 of SEQ ID NO: 3 is the signal sequence of human TANGO 202 (SEQ ID NO: 4). The hydrophobic region which corresponds to amino acid residues 393 to 415 of SEQ ID NO: 3 is the transmembrane domain of human TANGO 202 (SEQ ID NO: 7). As described elsewhere herein, relatively hydrophilic regions are generally located at or near the surface of a protein, and are more frequently effective immunogenic epitopes than are relatively hydrophobic regions. For example, the region of human TANGO 202 protein from about amino acid residue 61 to about amino acid residue 95 appears to be located at or near the surface of the protein, while the region from about amino acid residue 395 to about amino acid residue 420 appears not to be located at or near the surface.

The predicted molecular weight of human TANGO 202 protein without modification and prior to cleavage of the signal sequence is about 51.9 kilodaltons. The predicted molecular weight of the mature human TANGO 202 protein without modification and after cleavage of the signal sequence is about 50.1 kilodaltons.

The full length of the cDNA encoding murine TANGO 202 protein (FIG. 1; SEQ ID NO: 67) is 4928 nucleotide residues. The ORF of this cDNA, nucleotide residues 81 to 1490 of SEQ ID NO: 67 (i.e., SEQ ID NO: 68), encodes a 470-amino acid secreted protein (FIG. 1; SEQ ID NO: 69).

The signal peptide prediction program SIGNALP (Nielsen et al. (1997) *Protein Engineering* 10:1–6) predicted that murine TANGO 202 protein includes a 19 amino acid signal peptide (amino acid residues 1 to 19 of SEQ ID NO: 69; SEQ ID NO: 42) preceding the mature TANGO 202 protein (amino acid residues 20 to 470 of SEQ ID NO: 69; SEQ ID NO: 43). Murine TANGO 202 protein is a secreted protein.

Figure 1M:
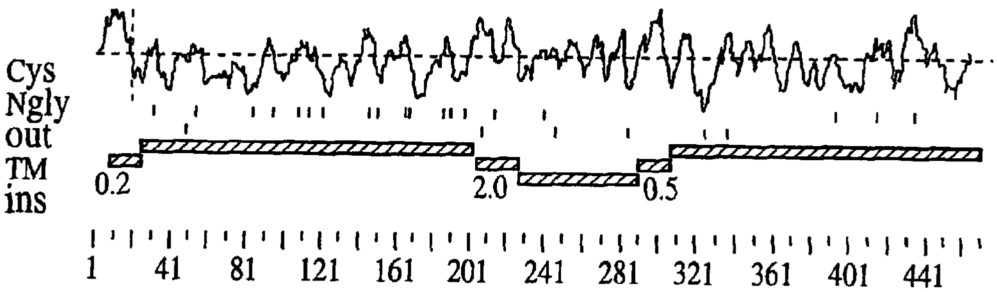
FIG. 1M is a hydrophilicity plot of murine TANGO 202 protein.

FIG. 1M depicts a hydrophilicity plot of murine TANGO 202 protein. Relatively hydrophobic regions are above the dashed horizontal line, and relatively hydrophilic regions are below the dashed horizontal line. The hydrophobic region which corresponds to amino acid residues 1 to 19 of SEQ ID NO: 69 is the signal sequence of murine TANGO 202 (SEQ ID NO: 42). As described elsewhere herein, relatively hydrophilic regions are generally located at or near the surface of a protein, and are more frequently effective immunogenic epitopes than are relatively hydrophobic regions. For example, the region of murine TANGO 202 protein from about amino acid residue 61 to about amino acid residue 95 appears to be located at or near the surface of the protein, while the region from about amino acid residue 295 to about amino acid residue 305 appears not to be located at or near the surface The predicted molecular weight of murine TANGO 202 protein without modification and prior to cleavage of the signal sequence is about 51.5 kilodaltons. The predicted molecular weight of the mature murine TANGO 202 protein without modification and after cleavage of the signal sequence is about 49.7 kilodaltons.

Human and murine TANGO 202 proteins exhibit considerable sequence similarity, as indicated herein in FIGS. 1J and 1K. FIGS. 1J and 1K depict an alignment of human and murine TANGO 202 amino acid sequences (SEQ ID NOs: 3 and 69, respectively). In this alignment (made using the ALIGN software {Myers and Miller (1989) *CABIOS*, ver. 2.0}; pam120.mat scoring matrix; gap penalties −12/−4), the proteins are 76.5% identical. The human and murine ORFs encoding TANGO 202 are 87.4% identical, as assessed using the same software and parameters.

In situ hybridization experiments in mouse tissues indicated that mRNA corresponding to the cDNA encoding TANGO 202 is expressed in the tissues listed in Table III, wherein "+" indicates detectable expression and "++" indicates a greater level of expression than "+".

TABLE III

| Animal | Tissue | Relative Level of Expression |
|---|---|---|
| Mouse (Adult) | bladder, especially in transitional epithelium | ++ |
| | renal glomeruli | + |
| | brain | + |
| | heart | + |
| | liver | + |
| | spleen | + |
| | placenta | + |
| Mouse (Embryo) | ubiquitous | + |

Biological Function of TANGO 202 Proteins, Nucleic Acids, and Modulators Thereof TANGO 202 proteins are involved in disorders which affect both tissues in which they are normally expressed and tissues in which they are normally not expressed. Based on the observation that TANGO 202 is expressed in human fetal skin, ubiquitously in fetal mouse tissues, in adult murine bone marrow stromal cells, and in cells of adult murine bladder, renal glomeruli, brain, heart, liver, spleen and placenta, TANGO 202 protein is involved in one or more biological processes which occur in these tissues. In particular, TANGO 202 is involved in modulating growth, proliferation, survival, differentiation, and activity of cells of these tissues including, but not limited to, hematopoietic and fetal cells. Thus, TANGO 202 has a role in disorders which affect these cells and their growth, proliferation, survival, differentiation, and activity. Ubiquitous expression of TANGO 202 in fetal murine tissues, contrasted with limited expression in adult murine tissues further indicates that TANGO 202 is involved in disorders in which it is inappropriately expressed (e.g., disorders in which TANGO 202 is expressed in adult murine tissues other than bone marrow stromal cells and disorders in which TANGO 202 is not expressed in one or more developing fetal tissues).

The presence of a Kringle domain in both the murine and human TANGO 202 proteins indicates that this protein is involved in modulating cellular binding to one or more mediators (e.g., proteins, phospholipids, intracellular organelles, or other cells), in modulating proteolytic activity, or both. The presence of a Kringle domain in other proteins (e.g., growth factors) indicates activities that these proteins share with TANGO 202 protein (e.g., modulating cell dissociation and migration into and through extracellular matrices). The presence of Kringle domains in numerous plasma proteins, particularly coupled with the observation that TANGO 202 is expressed in adult murine bone marrow stromal cells, indicates a role for TANGO 202 protein in modulating binding of blood or hematopoietic cells (or both) to one or more mediators. Thus, TANGO 202 is involved in disorders relating to aberrant cellular protease activity, inappropriate interaction or non-interaction of cells with mediators, and in blood and hematopoietic cell-related disorders. Such disorders include, by way of example and not limitation, immune disorders, infectious diseases, autoimmune disorders, vascular and cardiovascular disorders, disorders related to mal-expression of growth factors, cancers, hematological disorders, and the like.

The cDNA encoding TANGO 202 exhibits significant nucleotide sequence similarity with a polynucleotide encoding a kringle-domain-containing protein (designated HTHBZ47) described in the European Patent Application No. EP 0 911 399 A2 (published Apr. 28, 1999). Thus, the TANGO 202 protein can exhibit one or more of the activities exhibited by HTHBZ47, and can be used to prevent, inhibit, diagnose, and treat one or more disorders for which HTHBZ47 is useful. These disorders include cancer, inflammation, autoimmune disorders, allergic disorders, asthma, rheumatoid arthritis, inflammation of central nervous system tissues, cerebellar degeneration, Alzheimer's disease, Parkinson's disease, multiple sclerosis, amylotrophic lateral sclerosis, head injury damage and other neurological abnormalities, septic shock, sepsis, stroke, osteoporosis, osteoarthritis, ischemic reperfusion injury, cardiovascular disease, kidney disease, liver disease, ischemic injury, myocardial infarction, hypotension, hypertension, AIDS, myelodysplastic syndromes and other hematologic abnormalities, aplastic anemia, male pattern baldness, and bacterial, fungal, protozoan, and viral infections.

The presence of a CUB domain in both the murine and human TANGO 202 proteins indicates that this protein is involved in biological processes common to other CUB domain-containing proteins, such as developmental processes and binding to mediators. Therefore, TANGO 202 protein has a role in disorders which involve inappropriate developmental processes (e.g., abnormally high proliferation or un-differentiation of a differentiated tissue or abnormally low differentiation or proliferation of a non-developed or non-differentiated tissue) and modulation of cell growth, proliferation, survival, differentiation, and activity. Such disorders include, by way of example and not limitation, various cancers and birth and developmental defects.

Thus, proteins and nucleic acids of the invention which are identical to, similar to, or derived from human and murine TANGO 202 proteins and nucleic acids encoding them are useful for preventing, diagnosing, and treating, among others, vascular and cardiovascular disorders, hematological disorders, disorders related to mal-expression of growth factors, and cancer. Other uses for these proteins and nucleic acids of the invention relate to modulating cell growth (e.g., angiogenesis), proliferation (e.g., cancers), survival (e.g., apoptosis), differentiation (e.g., hematopoiesis), and activity (e.g., ligand-binding capacity). TANGO 202 proteins and nucleic acids encoding them are also useful for modulating cell dissociation and modulating migration of cells in extracellular matrices.

TANGO 234

A cDNA clone (designated jthsa104d11) encoding at least a portion of human TANGO 234 protein was isolated from a human fetal spleen cDNA library. The human TANGO 234 protein is predicted by structural analysis to be a transmembrane protein, although it can exist in a secreted form as well.

The full length of the cDNA encoding human TANGO 234 protein (FIG. 2; SEQ ID NO: 9) is 4628 nucleotide residues. The ORF of this cDNA, nucleotide residues 28 to 4386 of SEQ ID NO: 9 (i.e., SEQ ID NO: 10), encodes a 1453-amino acid transmembrane protein (FIG. 2; SEQ ID NO: 11).

The invention thus includes purified human TANGO 234 protein, both in the form of the immature 1453 amino acid residue protein (SEQ ID NO: 11) and in the form of the mature 1413 amino acid residue protein (SEQ ID NO: 13). Mature human TANGO 234 protein can be synthesized without the signal sequence polypeptide at the amino terminus thereof, or it can be synthesized by generating immature TANGO 234 protein and cleaving the signal sequence therefrom.

In addition to full length mature and immature human TANGO 234 proteins, the invention includes fragments, derivatives, and variants of these TANGO 234 proteins, as described herein. These proteins, fragments, derivatives, and variants are collectively referred to herein as polypeptides of the invention or proteins of the invention.

The invention also includes nucleic acid molecules which encode a polypeptide of the invention. Such nucleic acids include, for example, a DNA molecule having the nucleotide sequence listed in SEQ ID NO: 9 or some portion thereof, such as the portion which encodes mature TANGO 234 protein, immature TANGO 234 protein, or a domain of TANGO 234 protein. These nucleic acids are collectively referred to as nucleic acids of the invention.

TANGO 234 proteins and nucleic acid molecules encoding them comprise a family of molecules having certain conserved structural and functional features, as indicated by the conservation of amino acid sequence between human TANGO 234 protein and bovine WC1 protein, as shown in FIGS. 2K through 2P, and the conservation of nucleotide sequence between the ORFs encoding human TANGO 234 protein and bovine WC1 protein, as shown in FIGS. 2Qi through 2Qxvii.

A common domain present in TANGO 234 proteins is a signal sequence. As used herein, a signal sequence includes a peptide of at least about 10 amino acid residues in length which occurs at the amino terminus of membrane-bound proteins and which contains at least about 45% hydrophobic amino acid residues such as alanine, leucine, isoleucine, phenylalanine, proline, tyrosine, tryptophan, or valine. In a preferred embodiment, a signal sequence contains at least about 10 to 35 amino acid residues, preferably about 10 to 20 amino acid residues, and has at least about 35–60%, more preferably 40–50%, and more preferably at least about 45% hydrophobic residues. A signal sequence serves to direct a protein containing such a sequence to a lipid bilayer. Thus, in one embodiment, a TANGO 234 protein contains a signal sequence corresponding to amino acid residues 1 to 40 of SEQ ID NO: 11 (SEQ ID NO: 12). The signal sequence is cleaved during processing of the mature protein.

TANGO 234 proteins can include an extracellular domain. The human TANGO 234 protein extracellular domain is located from about amino acid residue 41 to about amino acid residue 1359 of SEQ ID NO: 3. TANGO 234 can alternately exist in a secreted form, such as a mature protein having the amino acid sequence of amino acid residues 41 to 1453 or residues 41 to about 1359 of SEQ ID NO: 11.

In addition, TANGO 234 include a transmembrane domain. In one embodiment, a TANGO 234 protein of the invention contains a transmembrane domain corresponding to about amino acid residues 1360 to 1383 of SEQ ID NO: 11 (SEQ ID NO: 15).

The present invention includes TANGO 234 proteins having a cytoplasmic domain, particularly including proteins having a carboxyl-terminal cytoplasmic domain. The human TANGO 234 cytoplasmic domain is located from about amino acid residue 1384 to amino acid residue 1453 of SEQ ID NO: 11 (SEQ ID NO: 16).

TANGO 234 proteins typically comprise a variety of potential post-translational modification sites (often within an extracellular domain), such as those described herein in Table IV, as predicted by computerized sequence analysis of TANGO 234 proteins using amino acid sequence comparison software (comparing the amino acid sequence of TANGO 234 with the information in the PROSITE database {rel. 12.2; February 1995} and the Hidden Markov Models database {Rel. PFAM 3.3}). In certain embodiments, a protein of the invention has at least 1, 2, 4, 6, 10, 15, or 20 or more of the post-translational modification sites listed in Table IV.

TABLE IV

| Type of Potential Modification Site or Domain | Amino Acid Residues of SEQ ID NO: 11 | Amino Acid Sequence |
|---|---|---|
| N-glycosylation site | 42 to 45 | NGTD |
| | 78 to 81 | NTTA |
| | 120 to 123 | NESA |
| | 161 to 164 | NNSC |
| | 334 to 337 | NESF |
| | 377 to 380 | NCSG |
| | 441 to 444 | NESA |
| | 548 to 551 | NESN |
| | 637 to 640 | NAST |
| | 972 to 975 | NESL |
| | 1013 to 1016 | NVSD |
| | 1084 to 1087 | NATV |
| | 1104 to 1107 | NCTG |
| | 1161 to 1164 | NGTW |
| | 1171 to 1174 | NITT |
| | 1318 to 1321 | NESF |
| | 1354 to 1357 | NASS |
| Glycosaminoglycan attachment site | 558 to 561 | SGWG |
| | 665 to 668 | SGWG |
| cAMP- or cGMP-dependent protein kinase phosphorylation site | 1229 to 1232 | RRIS |
| | 1399 to 1402 | RRGS |
| Protein kinase C phosphorylation site | 165 to 167 | SGR |
| | 268 to 270 | TNR |
| | 379 to 381 | SGR |
| | 419 to 421 | SRR |
| | 469 to 471 | SDK |
| | 506 to 508 | STR |
| | 589 to 591 | SNR |

TABLE IV-continued

| Type of Potential Modification Site or Domain | Amino Acid Residues of SEQ ID NO: 11 | Amino Acid Sequence |
|---|---|---|
| | 593 to 595 | SGR |
| | 661 to 663 | SCR |
| | 696 to 698 | SSR |
| | 746 to 748 | TER |
| | 805 to 807 | SGR |
| | 815 to 817 | TWR |
| | 959 to 961 | SVR |
| | 1256 to 1258 | SGR |
| | 1349 to 1351 | SLK |
| | 1396 to 1398 | STR |
| Casein kinase II phosphorylation site | 44 to 47 | TDLE |
| | 71 to 74 | TVCD |
| | 178 to 181 | TICD |
| | 245 to 248 | SHNE |
| | 253 to 256 | TCYD |
| | 258 to 261 | SDLE |
| | 319 to 322 | SGSD |
| | 332 to 335 | SGNE |
| | 392 to 395 | TICD |
| | 439 to 442 | TGNE |
| | 606 to 609 | TVCD |
| | 622 to 625 | SQLD |
| | 673 to 676 | SHSE |
| | 686 to 689 | SDME |
| | 760 to 763 | TGGE |
| | 765 to 768 | SLWD |
| | 818 to 821 | SVCD |
| | 845 to 848 | SVGD |
| | 857 to 860 | TWAE |
| | 907 to 910 | SQCD |
| | 923 to 926 | SLCD |
| | 927 to 930 | THWD |
| | 974 to 977 | SLLD |
| | 1059 to 1062 | TICD |
| | 1106 to 1109 | TGTE |
| | 1145 to 1148 | SETE |
| | 1233 to 1236 | SPAE |
| | 1241 to 1244 | TCED |
| | 1269 to 1272 | TVCD |
| | 1402 to 1405 | SLEE |
| | 1425 to 1428 | TSDD |
| N-myristoylation site | 67 to 72 | GQWGTV |
| | 90 to 95 | GCPFSF |
| | 101 to 106 | GQAVTR |
| | 119 to 124 | GNESAL |
| | 133 to 138 | GSHNCY |
| | 160 to 165 | GNNSCS |
| | 197 to 202 | GCPSSF |
| | 226 to 231 | GNELAL |
| | 240 to 245 | GNHDCS |
| | 267 to 272 | GTNRCM |
| | 304 to 309 | GCGTAL |
| | 328 to 333 | GVSCSG |
| | 374 to 379 | GSNNCS |
| | 411 to 416 | GCPFSV |
| | 418 to 423 | GSRRAK |
| | 440 to 445 | GNESAL |
| | 465 to 470 | GVICSD |
| | 547 to 552 | GNESNI |
| | 588 to 593 | GSNRCS |
| | 632 to 637 | GMGLGN |
| | 668 to 673 | GNNDCS |
| | 679 to 684 | GVICSD |
| | 695 to 700 | GSSRCA |
| | 712 to 717 | GILCAN |
| | 720 to 725 | GMNIAE |
| | 758 to 763 | GCTGGE |
| | 853 to 858 | GNGLTW |
| | 891 to 896 | GVVCSR |
| | 944 to 949 | GTALST |
| | 985 to 990 | GAPPCI |
| | 992 to 997 | GNTVSV |
| | 1078 to 1083 | GCGVAF |
| | 1121 to 1126 | GQHDCR |
| | 1132 to 1137 | GVICSE |
| | 1162 to 1167 | GTWGSV |

TABLE IV-continued

| Type of Potential Modification Site or Domain | Amino Acid Residues of SEQ ID NO: 11 | Amino Acid Sequence |
|---|---|---|
| | 1185 to 1190 | GCGENG |
| | 1265 to 1270 | GSWGTV |
| | 1288 to 1293 | GCGSAL |
| | 1302 to 1307 | GQGTGT |
| | 1331 to 1336 | GQSDCG |
| | 1342 to 1347 | GVRCSG |
| | 1422 to 1427 | GTRTSD |
| | 1443 to 1438 | GCEDAS |
| | 1444 to 1449 | GVLPAS |
| Amidation site | 1167 to 1170 | VGRR |
| Speract receptor repeated (SRR) domain signature | 53 to 90 | See FIG. 2 |
| | 160 to 197 | See FIG. 2 |
| | 267 to 304 | See FIG. 2 |
| | 1041 to 1078 | See FIG. 2 |
| | 1251 to 1288 | See FIG. 2 |
| Scavenger receptor cysteine-rich (SRCR) domain | 51 to 148 | See FIG. 2 |
| | 158 to 255 | See FIG. 2 |
| | 265 to 362 | See FIG. 2 |
| | 372 to 469 | See FIG. 2 |
| | 479 to 576 | See FIG. 2 |
| | 586 to 683 | See FIG. 2 |
| | 693 to 790 | See FIG. 2 |
| | 798 to 895 | See FIG. 2 |
| | 903 to 1000 | See FIG. 2 |
| | 1039 to 1136 | See FIG. 2 |
| | 1146 to 1243 | See FIG. 2 |
| | 1249 to 1346 | See FIG. 2 |

Among the domains that occur in TANGO 234 protein are SRR domains and SRCR domains. In one embodiment, the protein of the invention has at least one domain that is at least 55%, preferably at least about 65%, more preferably at least about 75%, yet more preferably at least about 85%, and most preferably at least about 95% identical to one of these domains. In other embodiments, the protein has at least two of the SRR and SRCR domains described herein in Table IV. In other embodiments, the protein has at least one SRR domain and at least one SRCR domain.

The SRR domain is named after a receptor domain identified in a sea urchin egg protein designated speract. The consensus sequence of this domain (using standard one-letter amino acid codes, wherein X is any amino acid residue) is as follows.

$$-G-X_5-G-X_2-E-X_6-W-G-X_2-C-X_3-(F \text{ or } Y \text{ or } W)-X_8-C-X_3-G-.$$

Speract is a transmembrane glycoprotein of 500 amino acid residues (Dangott et al. (1989) *Proc. Natl. Acad. Sci. USA* 86:2128–2132). Structurally, this receptor consists of a large extracellular domain of 450 residues, followed by a transmembrane region and a small cytoplasmic domain of 12 amino acid residues. The extracellular domain contains four repeats of an approximately 115 amino acid domain. There are 17 amino acid residues that are perfectly conserved in the four repeats in speract, including six cysteine residues, six glycine residues, and two glutamate residues. TANGO 234 has five SRR domains, in which 16 of the 17 conserved speract residues are present of four of the SRR domains and 15 are present in the remaining SRR domain. This domain is designated the speract receptor repeated domain. The amino acid sequence of mammalian macrophage scavenger receptor type I (MSRI) exhibits such a domain (Freeman et al. (1990) *Proc. Natl. Acad. Sci. USA* 87:8810–8814). MSRI proteins are membrane glycoproteins implicated in the pathologic deposition of cholesterol in arterial walls during atherogenesis. TANGO 234 is involved in one or more physiological processes related to cholesterol deposition and atherogenesis, as well as other vascular and cardiovascular disorders.

Scavenger receptor cysteine-rich (SRCR) domains are disulfide rich extracellular domains which are present in certain cell surface and secreted proteins. Proteins having SRCR domains exhibit diverse ligand binding specificity. For example, in addition to modified lipoproteins, some of these proteins bind a variety of surface components of pathogenic microorganisms, and some of the proteins bind apoptotic cells. SRCR domains are also involved in mediating immune development and response. Other SRCR-containing proteins are involved in binding of modified lipoproteins (e.g., oxidized low density lipoprotein {LDL}) by specialized macrophages, leading to the formation of macrophages filled with cholesteryl ester droplets (i.e., foam cells). TANGO 234 is involved in one or more physiological processes in which these other SRCR domain-containing proteins are involved, such as LDL uptake and metabolism, regulation of serum cholesterol level, atherogenesis, atherosclerosis, bacterial or viral infections, immune development, and generation and perseverance of immune responses.

WC1 is a ruminant protein having an SRCR domain. WC1 and gamma delta T-cell receptor are the only known gamma delta T-cell specific antigens. Antibodies which bind specifically with WC1 induce growth arrest in IL-2-dependent gamma delta T-cell and augment proliferation of gamma delta T-cells in an autologous mixed lymphocyte reaction or in the presence of anti-CD2 or anti-CD5 antibodies. Injection of antibodies which bind specifically with WC1 into calves results in long-lasting depletion of gamma delta T-cells. Furthermore, antibodies which bind specifically with WC1 can be used to purify gamma delta T-cells.

Gamma delta T-cells are involved in a variety of physiological processes. For example, these cells are potential mediators of allergic airway inflammation and lyme disease. Furthermore, these cells are involved in natural resistance to viral infections and can mediate autoimmune diseases. Elimination of gamma delta T-cells by injection of antibodies which bind specifically therewith can affect the outcomes of these disorders.

TANGO 234 is likely the human orthologue of ruminant protein WC1, and thus is involved with the physiological processes described above in humans. An alignment of the amino acid sequences of (human) TANGO 234 and bovine WC1 protein is shown in FIGS. 2K–2P. In this alignment (made using the ALIGN software {Myers and Miller (1989) *CABIOS*, ver. 2.0}; pam120.mat scoring matrix; gap penalties −12/−4), the proteins are 40.4% identical. An alignment of the nucleotide sequences of the ORFs encoding (human) TANGO 234 and bovine WC1 protein is shown in FIGS. 2Qi–2Qxvii. The two ORFs are 54.3% identical, as assessed using the same software and parameters.

The signal peptide prediction program SIGNALP (Nielsen et al. (1997) *Protein Engineering* 10: 1–6) predicted that human TANGO 234 protein includes a 40 amino acid signal peptide (amino acid residues 1 to 40 of SEQ ID NO: 11; SEQ ID NO: 12) preceding the mature TANGO 234 protein (amino acid residues 41 to 4386 of SEQ ID NO: 11; SEQ ID NO: 13). Human TANGO 234 protein includes an extracellular domain (amino acid residues 41 to 1359 of SEQ ID NO: 11; SEQ ID NO: 14); a transmembrane domain (amino acid residues 1360 to 1383 of SEQ ID NO: 11; SEQ ID NO: 15); and a cytoplasmic domain (amino acid residues 1384 to 1453 of SEQ ID NO: 11; SEQ ID NO: 16).

Figure 2J:
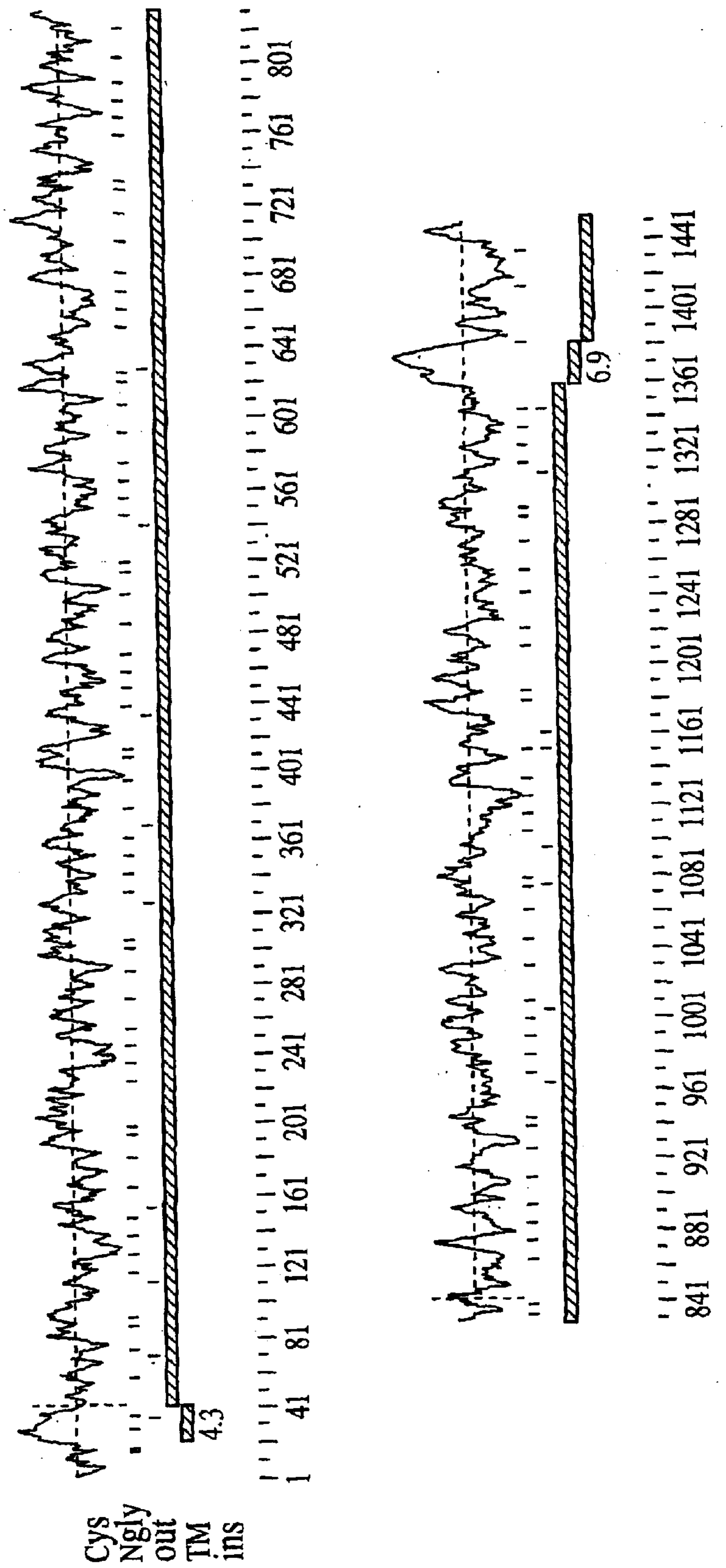
FIG. 2J is a hydrophilicity plot of human TANGO 234 protein. An alignment of the amino acid sequences of human TANGO 234 ("Hum"; SEQ ID NO: 11) and bovine WC1 ("WC1"; SEQ ID NO: 78) proteins is shown in FIGS. 2K–2P, wherein identical amino acid residues are indicated by ":" and similar amino acid residues are indicated by ".". An alignment of the nucleotide sequences of an ORF encoding human TANGO 234 ("Hum"; SEQ ID NO: 10) and an ORF encoding bovine WC1 ("WC1"; SEQ ID NO: 79) proteins is shown in FIGS. 2Qi–2Qxvii, wherein identical nucleotide residues are indicated by ":".

FIG. 2J depicts a hydrophilicity plot of human TANGO 234 protein. Relatively hydrophobic regions are above the dashed horizontal line, and relatively hydrophilic regions are below the dashed horizontal line. The hydrophobic region which corresponds to amino acid residues 1 to 40 of SEQ ID NO: 11 is the signal sequence of human TANGO 234 (SEQ ID NO: 12). The hydrophobic region which corresponds to amino acid residues 1360 to 1383 of SEQ ID NO: 11 is the transmembrane domain of human TANGO 234 (SEQ ID NO: 15). As described elsewhere herein, relatively hydrophilic regions are generally located at or near the surface of a protein, and are more frequently effective immunogenic epitopes than are relatively hydrophobic regions. For example, the region of human TANGO 234 protein from about amino acid residue 225 to about amino acid residue 250 appears to be located at or near the surface of the protein, while the region from about amino acid residue 990 to about amino acid residue 1000 appears not to be located at or near the surface.

The predicted molecular weight of human TANGO 234 protein without modification and prior to cleavage of the signal sequence is about 159.3 kilodaltons. The predicted molecular weight of the mature human TANGO 234 protein without modification and after cleavage of the signal sequence is about 154.7 kilodaltons.

Chromosomal mapping to identify the location of the gene encoding human TANGO 234 protein indicated that the gene was located at chromosomal location h12p13 (with synteny to mo6). Flanking chromosomal markers include WI-6980 and GATA8A09.43. Nearby human loci include IBD2 (inflammatory bowel disease 2), FPF (familial periodic fever), and HPDR2 (hypophosphatemia vitamin D resistant rickets 2). Nearby genes are KLRC (killer cell receptor cluster), DRPLA (dentatorubro-pallidoluysian atrophy), GAPD (glyceraldehyde-3-phosphate) dehydrogenase, and PXR1 (peroxisome receptor 1). Murine chromosomal mapping indicated that the murine orthologue is located near the scr (scruffy) locus. Nearby mouse genes include drpla (dentatorubral phillidoluysian atrophy), prp (proline rich protein), and kap (kidney androgen regulated protein).

Northern analysis experiments indicated that mRNA corresponding to the cDNA encoding TANGO 234 is expressed in the tissues listed in Table V, wherein "++" indicates moderate expression, "+" indicates lower expression, and "−" indicates no detectable expression.

TABLE V

| Animal | Tissue | Relative Level of Expression |
|---|---|---|
| Human | spleen | ++ |
| | fetal lung | ++ |
| | lung | + |
| | thymus | + |
| | bone marrow | − |
| | peripheral blood leukocytes | − |

Biological Function of TANGO 234 Proteins, Nucleic Acids, and Modulators Thereof TANGO 234 proteins are involved in disorders which affect both tissues in which they are normally expressed and tissues in which they are normally not expressed. Based on the observation that TANGO 234 is expressed in human fetal lung, spleen, and, to a lesser extent in adult lung and thymus tissue, TANGO 234 protein is involved in one or more biological processes which occur in these tissues. In particular, TANGO 234 is involved in modulating growth, proliferation, survival, differentiation, and activity of cells including, but not limited to, lung, spleen, thymus bone marrow, hematopoietic, peripheral blood leukocytes, and fetal cells of the animal in which it is normally expressed. Thus, TANGO 234 has a role in disorders which affect these cells and their growth, proliferation, survival, differentiation, and activity. Expression of TANGO 234 in an animal is also involved in modulating growth, proliferation, survival, differentiation, and activity of cells and viruses which are foreign to the host (i.e., bacterial, fungal, and viral infections).

Homology of human TANGO 234 with bovine WC1 protein indicates that TANGO 234 has physiological functions in humans analogous to the functions of WC1 in ruminants. Thus, TANGO 234 is involved in modulating growth, proliferation, survival, differentiation, and activity of gamma delta T cells. For example, TANGO 234 affects the ability of gamma delta T cells to interact with chemokines such as interleukin-2. TANGO 234 therefore is involved in the physiological processes associated with allergic airway inflammation, lyme arthritis, resistance to viral infection, auto-immune diseases, and the like.

In addition, presence in TANGO 234 of SRR and SRCR domains indicates that TANGO 234 is involved in physiological functions identical or analogous to the functions performed by other proteins having such domains. For example, like other SRR domain-containing proteins, TANGO 234 modulates cholesterol deposition in arterial walls, and is thus involved in development and persistence of atherogenesis and arteriosclerosis, as well as other vascular and cardiovascular disorders. Like other SRCR domain-containing proteins, TANGO 234 is involved in uptake and metabolism of LDL, regulation of serum cholesterol level, and can modulate these processes as well as the processes of atherogenesis, arteriosclerosis, immune development, and generation and perseverance of immune responses to bacterial, fungal, and viral infections.

TANGO 265

A cDNA clone (designated jthsa079g01) encoding at least a portion of human TANGO 265 protein was isolated from a human fetal spleen cDNA library. The human TANGO 265 protein is predicted by structural analysis to be a transmembrane membrane protein, although it can exist in a secreted form as well.

The full length of the cDNA encoding human TANGO 265 protein (FIG. 3; SEQ ID NO: 17) is 3104 nucleotide residues. The ORF of this cDNA, nucleotide residues 32 to 2314 of SEQ ID NO: 17 (i.e., SEQ ID NO: 18), encodes a 761-amino acid transmembrane protein (FIG. 3; SEQ ID NO: 19).

The invention thus includes purified TANGO 265 protein, both in the form of the immature 761 amino acid residue protein (SEQ ID NO: 19) and in the form of the mature 730 amino acid residue protein (SEQ ID NO: 21). Mature TANGO 265 protein can be synthesized without the signal sequence polypeptide at the amino terminus thereof, or it can be synthesized by generating immature TANGO 265 protein and cleaving the signal sequence therefrom.

In addition to full length mature and immature TANGO 265 proteins, the invention includes fragments, derivatives, and variants of TANGO 265 protein, as described herein. These proteins, fragments, derivatives, and variants are collectively referred to herein as polypeptides of the invention or proteins of the invention.

The invention also includes nucleic acid molecules which encode a polypeptide of the invention. Such nucleic acids include, for example, a DNA molecule having the nucleotide sequence listed in SEQ ID NO: 17 or some portion thereof, such as the portion which encodes mature TANGO 265 protein, immature TANGO 265 protein, or a domain of TANGO 265 protein. These nucleic acids are collectively referred to as nucleic acids of the invention.

TANGO 265 proteins and nucleic acid molecules encoding them comprise a family of molecules having certain conserved structural and functional features.

A common domain present in TANGO 265 proteins is a signal sequence. As used herein, a signal sequence includes a peptide of at least about 10 amino acid residues in length which occurs at the amino terminus of membrane-bound proteins and which contains at least about 45% hydrophobic amino acid residues such as alanine, leucine, isoleucine, phenylalanine, proline, tyrosine, tryptophan, or valine. In a preferred embodiment, a signal sequence contains at least about 10 to 35 amino acid residues, preferably about 10 to 20 amino acid residues, and has at least about 35–60%, more preferably 40–50%, and more preferably at least about 45% hydrophobic residues. A signal sequence serves to direct a protein containing such a sequence to a lipid bilayer. Thus, in one embodiment, a TANGO 265 protein contains a signal sequence corresponding to amino acid residues 1 to 31 of SEQ ID NO: 19 (SEQ ID NO: 20). The signal sequence is cleaved during processing of the mature protein.

TANGO 265 proteins can also include an extracellular domain. The human TANGO 265 protein extracellular domain is located from about amino acid residue 32 to about amino acid residue 683 of SEQ ID NO: 17. TANGO 265 can alternately exist in a secreted form, such as a mature protein having the amino acid sequence of amino acid residues 32 to 761 or residues 32 to about 683 of SEQ ID NO: 19.

TANGO 265 proteins can also include a transmembrane domain. In one embodiment, a TANGO 265 protein of the invention contains a transmembrane domain corresponding to about amino acid residues 684 to 704 of SEQ ID NO: 19 (SEQ ID NO: 23).

In addition, TANGO 265 proteins include a cytoplasmic domain, particularly including proteins having a carboxyl-terminal cytoplasmic domain. The human TANGO 265 cytoplasmic domain is located from about amino acid residue 705 to amino acid residue 761 of SEQ ID NO: 19 (SEQ ID NO: 24).

TANGO 265 proteins typically comprise a variety of potential post-translational modification sites (often within an extracellular domain), such as those described herein in Table VI, as predicted by computerized sequence analysis of TANGO 265 proteins using amino acid sequence comparison software (comparing the amino acid sequence of TANGO 265 with the information in the PROSITE database {rel. 12.2; February 1995} and the Hidden Markov Models database {Rel. PFAM 3.3}). In certain embodiments, a protein of the invention has at least 1, 2, 4, 6, 10, 15, or 20 or more of the post-translational modification sites listed in Table VI.

TABLE IV

| Type of Potential Modification Site or Domain | Amino Acid Residues of SEQ ID NO: 19 | Amino Acid Sequence |
|---|---|---|
| N-glycosylation site | 120 to 123 | NETQ |
| | 135 to 138 | NVTH |
| | 496 to 499 | NCSV |
| | 607 to 610 | NGLS |
| Glycosaminoglycan attachment site | 70 to 73 | SGDG |
| cAMP- or cGMP-dependent protein kinase phosphorylation site | 108 to 111 | RKKS |
| | 116 to 119 | KKKS |
| | 281 to 284 | KKWT |
| Protein kinase C phosphorylation site | 106 to 108 | SDR |
| | 262 to 264 | TSR |
| | 361 to 363 | TSR |
| | 366 to 368 | TYR |
| | 385 to 387 | SDK |

TABLE IV-continued

| Type of Potential Modification Site or Domain | Amino Acid Residues of SEQ ID NO: 19 | Amino Acid Sequence |
|---|---|---|
| | 533 to 535 | SWK |
| | 555 to 557 | SLR |
| | 721 to 723 | TLR |
| | 738 to 740 | SPK |
| Casein kinase II phosphorylation site | 152 to 155 | TFIE |
| | 176 to 179 | SPFD |
| | 250 to 253 | TASE |
| | 342 to 345 | SLLD |
| | 411 to 414 | SGVE |
| | 498 to 501 | SVYE |
| | 502 to 505 | SCVD |
| | 574 to 577 | SILE |
| | 738 to 741 | SPKE |
| | 745 to 748 | SASD |
| N-myristoylation site | 79 to 84 | GAREAI |
| | 191 to 196 | GMLYSG |
| | 331 to 336 | GGTRSS |
| | 412 to 417 | GVEYTR |
| | 437 to 442 | GTTTGS |
| | 620 to 625 | GLYQCW |
| | 671 to 676 | GAALAA |
| Sema domain | 64 to 478 | See FIG. 3 |

An exemplary domains which occurs in TANGO 265 proteins is a sema domain. In one embodiment, the protein of the invention has at least one domain that is at least 55%, preferably at least about 65%, more preferably at least about 75%, yet more preferably at least about 85%, and most preferably at least about 95% identical to one of the sema domains described herein in Table VI.

Sema domains occur in semaphorin proteins. Semaphorins are a large family of secreted and transmembrane proteins, some of which function as repellent signals during neural axon guidance. The sema domain and a variety of semaphorin proteins in which it occurs are described, for example, in Winberg et al. (1998 *Cell* 95:903–916). Sema domains also occur in human hepatocyte growth factor receptor (Swissprot Accession no. P08581) and the similar neuronal and epithelial transmembrane receptor protein (Swissprot Accession no. P51805). The presence of an sema domain in human TANGO 265 protein indicates that TANGO 265 is involved in one or more physiological processes in which the semaphorins are involved, has biological activity in common with one or more of the semaphorins, or both.

Human TANGO 265 protein exhibits considerable sequence similarity to murine semaphorin B protein (GenBank Accession no. X85991), as indicated herein in FIGS. 3F–3H. FIGS. 3F–3H depict an alignment of the amino acid sequences of human TANGO 265 protein (SEQ ID NO: 19) and murine semaphorin B protein (SEQ ID NO: 76). In this alignment (pam120.mat scoring matrix, gap penalties −12/−4), the amino acid sequences of the proteins are 82.3% identical. FIGS. 3I through 3T depict an alignment of the nucleotide sequences of cDNA encoding human TANGO 265 protein (SEQ ID NO: 17) and murine cDNA encoding semaphorin B protein (SEQ ID NO: 77). In this alignment (pam120.mat scoring matrix, gap penalties −12/−4), the nucleic acid sequences of the cDNAs are 76.2% identical. Thus, TANGO 265 is the human orthologue of murine semaphorin B and shares functional similarities to that protein.

It is known that semaphorins are bi-functional, capable of functioning either as attractive axonal guidance proteins or as repellent axonal guidance proteins (Wong et al. (1997) *Development* 124:3597–3607). Furthermore, semaphorins bind with neuronal cell surface proteins designated plexins, which are expressed on both neuronal cells and cells of the immune system (Comeau et al. (1998) *Immunity* 8:473–482; Jin and Strittmatter (1997) *J. Neurosci.* 17:6256–6263).

The signal peptide prediction program SIGNALP (Nielsen et al. (1997) *Protein Engineering* 10:1–6) predicted that human TANGO 265 protein includes a 31 amino acid signal peptide (amino acid residues 1 to 31 of SEQ ID NO: 19; SEQ ID NO: 20) preceding the mature TANGO 265 protein (amino acid residues 32 to 761 of SEQ ID NO: 19; SEQ ID NO: 21). Human TANGO 265 protein includes an extracellular domain (amino acid residues 32 to 683 of SEQ ID NO: 19; SEQ ID NO: 22); a transmembrane domain (amino acid residues 684 to 704 of SEQ ID NO: 19; SEQ ID NO: 23); and a cytoplasmic domain (amino acid residues 705 to 761 of SEQ ID NO: 19; SEQ ID NO: 24).

Figure 3U:
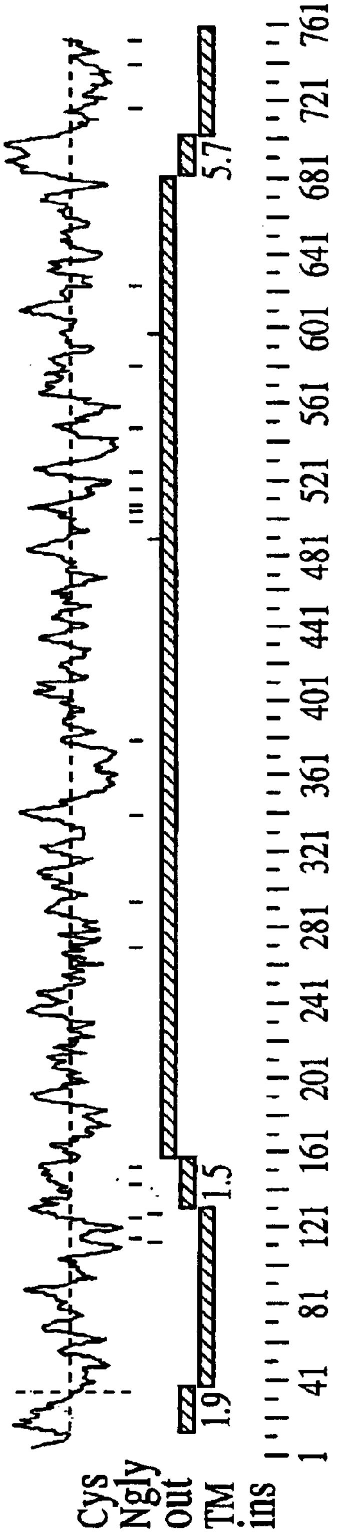
FIG. 3U is a hydrophilicity plot of TANGO 265 protein.

FIG. 3U depicts a hydrophilicity plot of human TANGO 265 protein. Relatively hydrophobic regions are above the dashed horizontal line, and relatively hydrophilic regions are below the dashed horizontal line. The hydrophobic region which corresponds to amino acid residues 1 to 31 of SEQ ID NO: 19 is the signal sequence of human TANGO 265 (SEQ ID NO: 20). The hydrophobic region which corresponds to amino acid residues 684 to 704 of SEQ ID NO: 19 is the transmembrane domain of human TANGO 265 (SEQ ID NO: 23). As described elsewhere herein, relatively hydrophilic regions are generally located at or near the surface of a protein, and are more frequently effective immunogenic epitopes than are relatively hydrophobic regions. For example, the region of human TANGO 265 protein from about amino acid residue 350 to about amino acid residue 375 appears to be located at or near the surface of the protein, while the region from about amino acid residue 230 to about amino acid residue 250 appears not to be located at or near the surface.

The predicted molecular weight of human TANGO 265 protein without modification and prior to cleavage of the signal sequence is about 83.6 kilodaltons. The predicted molecular weight of the mature human TANGO 265 protein without modification and after cleavage of the signal sequence is about 80.2 kilodaltons.

Chromosomal mapping was performed by computerized comparison of TANGO 265 cDNA sequences against a chromosomal mapping database in order to identify the approximate location of the gene encoding human TANGO 265 protein. This analysis indicated that the gene was located on chromosome 1 between markers D1S305 and D1S2635.

Biological Function of TANGO 265 Proteins, Nucleic Acids, and Modulators Thereof TANGO 265 proteins are involved in disorders which affect both tissues in which they are normally expressed and tissues in which they are normally not expressed. Based on the observation that TANGO 265 is expressed in human fetal spleen, involvement of TANGO 202 protein in immune system development and modulation is indicated.

The presence of the sema domain in TANGO 265 indicates that this protein is involved in development of neuronal and epithelial tissues and also functions as a repellant protein which guides axonal development. TANGO 265 modulates nerve growth and regeneration and also modulates growth and regeneration of other epithelial tissues.

The observation that TANGO 265 shares significant identity with murine semaphorin B suggests that it has activity identical or analogous to the activity of this protein. These observations indicate that TANGO 265 modulates growth, proliferation, survival, differentiation, and activity of neuronal cells and immune system cells. Thus, TANGO 265 protein is useful, for example, for guiding neural axon development, for modulating differentiation of cells of the immune system, for modulating cytokine production by cells of the immune system, for modulating reactivity of cells of the immune system toward cytokines, for modulating initiation and persistence of an inflammatory response, and for modulating proliferation of epithelial cells.

TANGO 273

A cDNA clone (designated jthoc028g06) encoding at least a portion of human TANGO 273 protein was isolated from a lipopolysaccharide-(LPS-)stimulated human osteoblast cDNA library. The corresponding murine cDNA clone (designated jtmoa001c04) was isolated from an LPS-stimulated murine osteoblast cDNA library. The human and murine TANGO 273 proteins are predicted by structural analysis to be transmembrane proteins.

The full length of the cDNA encoding human TANGO 273 protein (FIG. 4; SEQ ID NO: 25) is 2964 nucleotide residues. The ORF of this cDNA, nucleotide residues 135 to 650 of SEQ ID NO: 25 (i.e., SEQ ID NO: 26), encodes a 172-amino acid transmembrane protein (FIG. 4; SEQ ID NO: 27).

The invention thus includes purified human TANGO 273 protein, both in the form of the immature 172 amino acid residue protein (SEQ ID NO: 27) and in the form of the mature 150 amino acid residue protein (SEQ ID NO: 29). The invention also includes purified murine TANGO 273 protein, both in the form of the immature 172 amino acid residue protein (SEQ ID NO: 74) and in the form of the mature 150 amino acid residue protein (SEQ ID NO: 44). Mature human or murine TANGO 273 proteins can be synthesized without the signal sequence polypeptide at the amino terminus thereof, or they can be synthesized by generating immature TANGO 273 protein and cleaving the signal sequence therefrom.

In addition to full length mature and immature human and murine TANGO 273 proteins, the invention includes fragments, derivatives, and variants of these TANGO 273 proteins, as described herein. These proteins, fragments, derivatives, and variants are collectively referred to herein as polypeptides of the invention or proteins of the invention.

The invention also includes nucleic acid molecules which encode a polypeptide of the invention. Such nucleic acids include, for example, a DNA molecule having the nucleotide sequence listed in SEQ ID NO: 25 or some portion thereof or SEQ ID NO: 73 or some portion thereof, such as the portion which encodes mature TANGO 273 protein, immature TANGO 273 protein, or a domain of TANGO 273 protein. These nucleic acids are collectively referred to as nucleic acids of the invention.

TANGO 273 proteins and nucleic acid molecules encoding them comprise a family of molecules having certain conserved structural and functional features. This family includes, by way of example, the human and murine TANGO 273 proteins.

A common domain of TANGO 273 proteins is a signal sequence. As used herein, a signal sequence includes a peptide of at least about 10 amino acid residues in length which occurs at the amino terminus of membrane-bound proteins and which contains at least about 45% hydrophobic amino acid residues such as alanine, leucine, isoleucine, phenylalanine, proline, tyrosine, tryptophan, or valine. In a preferred embodiment, a signal sequence contains at least about 10 to 35 amino acid residues, preferably about 10 to 20 amino acid residues, and has at least about 35–60%, more preferably 40–50%, and more preferably at least about 45% hydrophobic residues. A signal sequence serves to direct a protein containing such a sequence to a lipid bilayer. Thus, in one embodiment, a TANGO 273 protein contains a signal sequence corresponding to amino acid residues 1 to 22 of SEQ ID NO: 27 (SEQ ID NO: 28) or to amino acid residues 1 to 22 of SEQ ID NO: 74. The signal sequence is cleaved during processing of the mature protein.

TANGO 273 proteins can also include an extracellular domain. The human TANGO 273 protein extracellular domain is located from about amino acid residue 23 to about amino acid residue 60 of SEQ ID NO: 27, and the murine TANGO 273 protein extracellular domain is located from about amino acid residue 23 to about amino acid residue 60 of SEQ ID NO: 74.

The present invention also includes TANGO 273 proteins having a transmembrane domain. As used herein, a "transmembrane domain" refers to an amino acid sequence having at least about 15 to 30 amino acid residues in length and which contains at least about 65–70% hydrophobic amino acid residues such as alanine, leucine, phenylalanine, protein, tyrosine, tryptophan, or valine. In a preferred embodiment, a transmembrane domain contains at least about 15 to 20 amino acid residues, preferably about 20 to 25 amino acid residues, and has at least about 60–80%, more preferably 65–75%, and more preferably at least about 70% hydrophobic residues. Thus, in one embodiment, a human TANGO 273 protein of the invention contains a transmembrane domain corresponding to about amino acid residues 61 to 81 of SEQ ID NO: 27 (SEQ ID NO: 31). In another embodiment, a murine TANGO 273 protein of the invention contains a transmembrane domain corresponding to about amino acid residues 61 to 81 of SEQ ID NO: 74.

In addition, TANGO 273 proteins include a cytoplasmic domain. The human TANGO 273 cytoplasmic domain is located from about amino acid residue 82 to amino acid residue 172 of SEQ ID NO: 27 (SEQ ID NO: 32), and the murine TANGO 273 cytoplasmic domain is located from about amino acid residue 82 to amino acid residue 172 of SEQ ID NO: 74.

TANGO 273 proteins typically comprise a variety of potential post-translational modification sites (often within an extracellular domain), such as those described herein in Tables VII and VIII, as predicted by computerized sequence analysis of human and murine TANGO 273 proteins using amino acid sequence comparison software (comparing the amino acid sequence of TANGO 273 with the information in the PROSITE database {rel. 12.2; February 1995} and the Hidden Markov Models database {Rel. PFAM 3.3}). In certain embodiments, a protein of the invention has at least 1, 2, 3, 4, 5, or all 6 of the post-translational modification sites listed in Table VII. In other embodiments, the protein of the invention has at least 1, 2, 3, 4, 5, 6, or all 7 of the post-translational modification sites listed in Table VIII.

TABLE VII

| Type of Potential Modification Site or Domain | Amino Acid Residues of SEQ ID NO: 27 | Amino Acid Sequence |
|---|---|---|
| N-glycosylation site | 97 to 100 | NVSY |
| Casein kinase II phosphorylation site | 41 to 44 | SYED |
| N-myristoylation site | 31 to 36 | GLYPTY |
| | 47 to 52 | GSRCCV |
| | 70 to 75 | GVLFCC |
| | 131 to 136 | GNSMAM |

TABLE VII-continued

| Type of Potential Modification Site or Domain | Amino Acid Residues of SEQ ID NO: 27 | Amino Acid Sequence |
|---|---|---|
| Src Homology 3 (SR3) domain binding site | 86 to 90 | YPPPL |
| | 103 to 107 | QPPNP |
| | 113 to 117 | QPGPP |
| | 121 to 125 | DPGGP |
| | 140 to 145 | VPPNSP |
| | 151 to 155 | CPPPP |
| | 160 to 164 | TPPPP |

TABLE VIII

| Type of Potential Modification Site or Domain | Amino Acid Residues of SEQ ID NO: 74 | Amino Acid Sequence |
|---|---|---|
| N-glycosylation site | 97 to 100 | NVSY |
| Casein kinase II phosphorylation site | 41 to 44 | SYED |
| N-myristoylation site | 31 to 36 | GLYPTY |
| | 47 to 52 | GSRCCV |
| | 70 to 75 | GVLFCC |
| | 131 to 136 | GNTMAM |
| Src Homology 3 (SH3) domain binding site | 86 to 90 | YPPPL |
| | 103 to 107 | QPPNP |
| | 115 to 119 | GPPYY |
| | 121 to 125 | DPGGP |
| | 141 to 145 | QPNSP |
| | 151 to 155 | YPPPP |
| | 160 to 164 | TPPPP |
| Amidation site | 1 to 4 | MGRR |

The amino acid sequence of TANGO 273 protein includes about seven potential proline-rich Src homology 3 (SH3) domain binding sites nearer the cytoplasmic portion of the protein. SH3 domains mediate specific assembly of protein complexes, presumably by interacting with proline-rich protein domains (Morton and Campbell (1994) *Curr. Biol.* 4:615–617). SH3 domains also mediate interactions between proteins involved in transmembrane signal transduction. Coupling of proteins mediated by SH3 domains has been implicated in a variety of physiological systems, including those involving regulation of cell growth and proliferation, endocytosis, and activation of respiratory burst.

SH3 domains have been described in the art (e.g., Mayer et al. (1988) *Nature* 332:272–275; Musacchio et al. (1992) *FEBS Lett.* 307:55–61; Pawson and Schlessinger (1993) *Curr. Biol.* 3:434–442; Mayer and Baltimore (1993) *Trends Cell Biol.* 3:8–13; Pawson (1993) *Nature* 373:573–580), and occur in a variety of cytoplasmic proteins, including several (e.g., protein tyrosine kinases) involved in transmembrane signal transduction. Among the proteins in which one or more SH3 domains occur are protein tyrosine kinases such as those of the Src, Abl, Bkt, Csk and ZAP70 families, mammalian phosphatidylinositol-specific phospholipases C-gamma-1 and -2, mammalian phosphatidylinositol 3-kinase regulatory p85 subunit, mammalian Ras GTPase-activating protein (GAP), proteins which mediate binding of guanine nucleotide exchange factors and growth factor receptors (e.g., vertebrate GRB2, *Caenorhabditis elegans* sem-5, and Drosophila DRK proteins), mammalian Vav oncoprotein, guanidine nucleotide releasing factors of the CDC 25 family (e.g., yeast CDC25, yeast SCD25, and fission yeast ste6 proteins), MAGUK proteins (e.g., mammalian light junction protein ZO-1, vertebrate erythrocyte membrane protein p55, *C. elegans* protein lin-2, rat protein CASK, and mammalian synaptic proteins SAP90/PSD-95, CHAPSYN-110/PSD-93, SAP97/DLG1, and SAP102), proteins which interact with vertebrate receptor protein tyrosine kinases (e.g., mammalian cytoplasmic protein Nck and oncoprotein Crk), chicken Src substrate p80/85 protein (cortactin), human hemopoietic lineage cell specific protein Hs1, mammalian dihydrouridine-sensitive L-type calcium channel beta subunit, human myasthenic syndrome antigen B (MSYB), mammalian neutrophil cytosolic activators of NADPH oxidase (e.g., p47 {NCF-1}, p67 {NCF-2}, and *C. elegans* protein B0303.7) myosin heavy chains (MYO3) from amoebae, from slime molds, and from yeast, vertebrate and Drosophila spectrin and fodrin alpha chain proteins, human amphiphysin, yeast actin-binding proteins ABP1 and SLA3, yeast protein BEM1, fission yeast protein scd2 (ral3), yeast BEM1-binding proteins BOI2 (BEB1) and BOB1 (BOI1), yeast fusion protein FUS1, yeast protein RSV167, yeast protein SSU81, yeast hypothetical proteins YAR014c, YFR024c, YHL002w, YHR016c, YJL020C, and YHR114w, hypothetical fission yeast protein SpAC12C2.05c, and *C. elegans* hypothetical protein F42H10.3. Of these proteins, multiple SH3 domains occur in vertebrate GRB2 protein, *C. elegans* sem-5 protein, Drosophila DRK protein, oncoprotein Crk, mammalian neutrophil cytosolic activators of NADPH oxidase p47 and p67, yeast protein BEM1, fission yeast protein scd2, yeast hypothetical protein YHR114w, mammalian cytoplasmic protein Nck, *C. elegans* neutrophil cytosolic activator of NADPH oxidase B0303.7, and yeast actin-binding protein SLA1. Of these proteins, three or more SH3 domains occur in mammalian cytoplasmic protein Nck, *C. elegans* neutrophil cytosolic activator of NADPH oxidase B0303.7, and yeast actin-binding protein SLA1. The presence of SH3 domain binding sites in TANGO 273 indicates that TANGO 273 interacts with one or more of these and other SH3 domain-containing proteins and is thus involved in physiological processes in which one or more of these or other SH3 domain-containing proteins are involved.

The signal peptide prediction program SIGNALP (Nielsen et al. (1997) *Protein Engineering* 10:1–6) predicted that human TANGO 273 protein includes a 22 amino acid signal peptide (amino acid residues 1 to 22 of SEQ ID NO: 27; SEQ ID NO: 28) preceding the mature TANGO 273 protein (amino acid residues 23 to 172 of SEQ ID NO: 27; SEQ ID NO: 29). Human TANGO 273 protein includes an extracellular domain (amino acid residues 23 to 60 of SEQ ID NO: 27; SEQ ID NO: 30); a transmembrane domain (amino acid residues 61 to 81 of SEQ ID NO: 27; SEQ ID NO: 31); and a cytoplasmic domain (amino acid residues 82 to 172 of SEQ ID NO: 27; SEQ ID NO: 32).

Figure 4I:
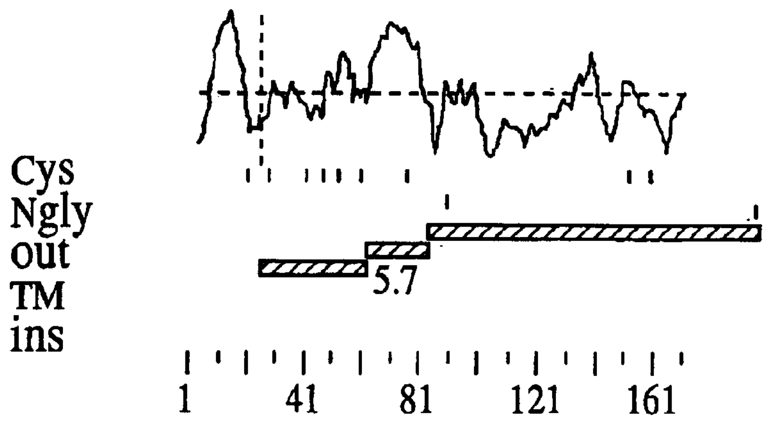
FIG. 4I is a hydrophilicity plot of human TANGO 273 protein.

FIG. 4I depicts a hydrophilicity plot of human TANGO 273 protein. Relatively hydrophobic regions are above the dashed horizontal line, and relatively hydrophilic regions are below the dashed horizontal line. The hydrophobic region which corresponds to amino acid residues 1 to 22 of SEQ ID NO: 27 is the signal sequence of human TANGO 273 (SEQ ID NO: 28). The hydrophobic region which corresponds to amino acid residues 61 to 81 of SEQ ID NO: 27 is the transmembrane domain of human TANGO 273 (SEQ ID NO: 31). As described elsewhere herein, relatively hydrophilic regions are generally located at or near the surface of a protein, and are more frequently effective immunogenic epitopes than are relatively hydrophobic regions. For example, the region of human TANGO 273 protein from about amino acid residue 100 to about amino acid residue 120 appears to be located at or near the surface of the protein, while the region from about amino acid residue 130 to about amino acid residue 140 appears not to be located at or near the surface.

Chromosomal mapping was performed by computerized comparison of TANGO 273 cDNA sequences against a chromosomal mapping database in order to identify the approximate location of the gene encoding human TANGO 273 protein. This analysis indicated that the gene was located on chromosome 7 between markers D7S2467 and D7S2552.

The predicted molecular weight of human TANGO 273 protein without modification and prior to cleavage of the signal sequence is about 19.2 kilodaltons. The predicted molecular weight of the mature human TANGO 273 protein without modification and after cleavage of the signal sequence is about 16.8 kilodaltons.

Northern analysis experiments indicated that mRNA corresponding to the cDNA encoding TANGO 273 is expressed in the tissues listed in Table VIIa, wherein "++" indicates moderate expression and "+" indicates lower expression.

TABLE VIIa

| Animal | Tissue | Relative Level of Expression |
|---|---|---|
| Human | heart | ++ |
| | brain | ++ |
| | skeletal muscle | ++ |
| | pancreas | ++ |
| | placenta | + |
| | lung | + |
| | liver | + |
| | kidney | + |

The full length of the cDNA encoding murine TANGO 273 protein (FIG. 4; SEQ ID NO: 72) is 2915 nucleotide residues. The ORF of this cDNA, nucleotide residues 137 to 650 of SEQ ID NO: 72 (i.e., SEQ ID NO: 73), encodes a 172-amino acid transmembrane protein (FIG. 4; SEQ ID NO: 74).

The signal peptide prediction program SIGNALP (Nielsen et al. (1997) *Protein Engineering* 10:1–6) predicted that murine TANGO 273 protein includes a 22 amino acid signal peptide (amino acid residues 1 to 22 of SEQ ID NO: 74) preceding the mature TANGO 273 protein (amino acid residues 23 to 172 of SEQ ID NO: 74; SEQ ID NO: 44). Murine TANGO 273 protein includes an extracellular domain (amino acid residues 23 to 60 of SEQ ID NO: 74); a transmembrane domain (amino acid residues 61 to 81 of SEQ ID NO: 74); and a cytoplasmic domain (amino acid residues 82 to 172 of SEQ ID NO: 74).

Figure 4J:
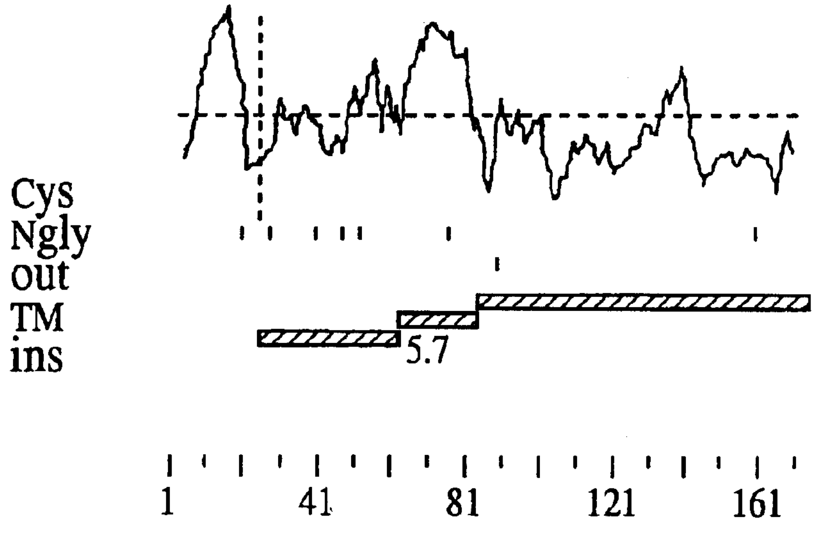
FIG. 4J is a hydrophilicity plot of murine TANGO 273 protein.

FIG. 4J depicts a hydrophilicity plot of murine TANGO 273 protein. Relatively hydrophobic regions are above the dashed horizontal line, and relatively hydrophilic regions are below the dashed horizontal line. The hydrophobic region which corresponds to amino acid residues 1 to 22 of SEQ ID NO: 74 is the signal sequence of murine TANGO 273. As described elsewhere herein, relatively hydrophilic regions are generally located at or near the surface of a protein, and are more frequently effective immunogenic epitopes than are relatively hydrophobic regions. For example, the region of murine TANGO 273 protein from about amino acid residue 100 to about amino acid residue 120 appears to be located at or near the surface of the protein, while the region from about amino acid residue 130 to about amino acid residue 140 appears not to be located at or near the surface.

The predicted molecular weight of murine TANGO 273 protein without modification and prior to cleavage of the signal sequence is about 19.4 kilodaltons. The predicted molecular weight of the mature murine TANGO 273 protein without modification and after cleavage of the signal sequence is about 17.1 kilodaltons.

In situ analysis of murine TANGO 273 mRNA indicated that TANGO 273 is expressed with central nervous system (CNS) tissues during embryogenesis and into adulthood. Expression of TANGO 273 is widely observed in murine CNS tissues, including brain, spinal cord, eye, and olfactory epithelium at all embryonic ages examined (i.e., at embryonic days 13.5, 14.5, 15.5, 16.5, and 18.5 and at post-natal day 1.5).

Human and murine TANGO 273 cDNA sequences exhibit significant nucleotide sequence identity with an expressed sequence tag (EST) isolated from a library of ESTs corresponding to proteins secreted from prostate tissue, as described in PCT publication number WO 99/06550, published Feb. 11, 1999.

Human and murine TANGO 273 proteins exhibit considerable sequence similarity, as indicated herein in FIG. 4H. FIG. 4H depicts an alignment of human and murine TANGO 273 protein amino acid sequences (SEQ ID NOs: 27 and 74, respectively). In this alignment (pam120.mat scoring matrix, gap penalties −12/−4), the proteins are 89.5% identical. Alignment of the ORF encoding human TANGO 273 protein and the ORF encoding murine TANGO 273 protein using the same software and parameters indicated that the nucleotide sequences are 84.1% identical.

Biological Function of TANGO 273 Proteins, Nucleic Acids, and Modulators Thereof cDNAs encoding the human and murine TANGO 273 proteins were each isolated from LPS-stimulated osteoblast cDNA libraries. These proteins are involved in bone-related metabolism, homeostasis, and development disorders. Thus, proteins and nucleic acids of the invention which are identical to, similar to, or derived from human and murine TANGO 273 proteins and nucleic acids encoding them are useful for preventing, diagnosing, and treating, among others, bone-related disorders such as osteoporosis, cancer, skeletal development disorders, bone fragility, and the like.

Expression of TANGO 273 in heart, brain, skeletal muscle, and pancreas, placenta, lung, liver, and kidney tissues is an indication that TANGO 273 proteins, nucleic acids encoding them, and agents that modulate activity or expression of either of these can be used to modulate growth, proliferation, survival, differentiation, adhesion, and activity of cells of these tissues, or to prognosticate, diagnose, and treat one or more disorders which affect these tissues.

The fact that TANGO 273 is expressed at high levels in neurological tissues is an indication that TANGO 273 proteins, nucleic acids, and modulators thereof can be used to modulate proliferation, differentiation, or function of neurological cells in these tissues (e.g., neuronal cells). Thus, TANGO 273 proteins, nucleic acids, and modulators thereof can be used to prognosticate, diagnose, and treat one or more neurological disorders. Examples of such disorders include CNS disorders, CNS-related disorders, focal brain disorders, global-diffuse cerebral disorders, and other neurological and cerebrovascular disorders.

CNS disorders include, but are not limited to cognitive and neurodegenerative disorders such as Alzheimer's disease, senile dementia, Huntington's disease, amyotrophic lateral sclerosis, and Parkinson's disease, as well as Gilles de la Tourette's syndrome, autonomic function disorders such as hypertension and sleep disorders (e.g., insomnia, hypersomnia, parasomnia, and sleep apnea); neuropsychiatric disorders (e.g., schizophrenia, schizoaffective disorder, attention deficit disorder, dysthymic disorder, major depressive disorder, mania, and obsessive-compulsive disorder); psychoactive substance use disorders; anxiety; panic disorder; and bipolar affective disorders (e.g., severe bipolar affective disorder and bipolar affective disorder with hypomania and major depression).

CNS-related disorders include disorders associated with developmental, cognitive, and autonomic neural and neurological processes, such as pain, appetite, long term memory, and short term memory.

Exemplary focal brain disorders include aphasia, apraxia, agnosia, and amnesias (e.g., posttraumatic amnesia, transient global amnesia, and psychogenic amnesia). Global-diffuse cerebral disorders with which TANGO 273 can be associated include coma, stupor, obtundation, and disorders of the reticular formation.

Other neurological disorders with which TANGO 273 can be associated include ischemic syndromes (e.g., stroke), hypertensive encephalopathy, hemorrhagic disorders, and disorders involving aberrant function of the blood-brain barrier (e.g., CNS infections such as meningitis and encephalitis, aseptic meningitis, metastasis of non-CNS tumor cells into the CNS, various pain disorders such as migraine, blindness and other vision problems, and CNS-related adverse drug reactions such as head pain, sleepiness, and confusion). TANGO 273 proteins, nucleic acids encoding them, and agents that modulate activity or expression of either of these can be used to prognosticate, diagnose, and treat one or more of these disorders.

Developmental regulation of TANGO 273 expression in fetal neurological tissues, as described herein, is an indication that TANGO 273 proteins, nucleic acids, and modulators thereof can be used to prognosticate, diagnose, and treat one or more disorders which involve aberrant fetal neurological development. Examples of such disorders include blindness, deafness, fetal death, mental retardation, dysraphia, anencephaly, malformation of cerebral hemispheres, encephalocele, porencephaly, hydranencephaly, hydrocephalus, and spina bifida.

The fact that TANGO 273 is expressed in tissues which were exposed to LPS indicates that TANGO 273 mediates one or more physiological responses of cells to bacterial infection. Thus, TANGO 273 is involved in one or more of detection of bacteria in a tissue in which it is expressed, movement of cells with relation to sites of bacterial infection, production of biological molecules which inhibit bacterial infection, and production of biological molecules which alleviate cellular or other physiological damage wrought by bacterial infection.

Presence in TANGO 273 protein of multiple SH3 domain binding sites indicates that TANGO 273 protein interacts with one or more SH3 domain-containing proteins. Thus, TANGO 273 protein mediates binding of proteins (i.e., binding of proteins to TANGO 273 and to one another to form protein complexes) in cells in which it is expressed. TANGO 273 is also involved in transduction of signals between the exterior environment of cells (i.e., including from other cells) and the interior of cells in which it is expressed. TANGO 273 mediates regulation of cell growth and proliferation, endocytosis, activation of respiratory burst, and other physiological processes triggered by transmission of a signal via a protein with which TANGO 273 interacts.

Sequence similarity of TANGO 273 cDNA with an EST expressed in prostate tissue indicates that TANGO 273 can be expressed in prostate tissue, and can thus be involved in disorders of the prostate. Thus, TANGO 273 proteins, nucleic acids encoding them, and agents that modulate activity or expression of either of these can be used to treat prostate disorders. Examples of prostate disorders which can be treated in this manner include inflammatory prostatic diseases (e.g., acute and chronic prostatitis and granulomatous prostatitis), prostatic hyperplasia (e.g., benign prostatic hypertrophy or hyperplasia), and prostate tumors (e.g., carcinomas).

In another example, TANGO 273 polypeptides, nucleic acids, or modulators thereof, can be used to treat cardiovascular disorders, such as ischemic heart disease (e.g., angina pectoris, myocardial infarction, and chronic ischemic heart disease), hypertensive heart disease, pulmonary heart disease, valvular heart disease (e.g., rheumatic fever and rheumatic heart disease, endocarditis, mitral valve prolapse, and aortic valve stenosis), congenital heart disease (e.g., valvular and vascular obstructive lesions, atrial or ventricular septal defect, and patent ductus arteriosus), or myocardial disease (e.g., myocarditis, congestive cardiomyopathy, and hypertrophic cardiomyopathy).

In another example, TANGO 273 polypeptides, nucleic acids, or modulators thereof, can be used to treat disorders of the brain, such as cerebral edema, hydrocephalus, brain herniations, iatrogenic disease (due to, e.g., infection, toxins, or drugs), inflammations (e.g., bacterial and viral meningitis, encephalitis, and cerebral toxoplasmosis), cerebrovascular diseases (e.g., hypoxia, ischemia, and infarction, intracranial hemorrhage and vascular malformations, and hypertensive encephalopathy), and tumors (e.g., neuroglial tumors, neuronal tumors, tumors of pineal cells, meningeal tumors, primary and secondary lymphomas, intracranial tumors, and medulloblastoma), and to treat injury or trauma to the brain.

In another example, TANGO 273 polypeptides, nucleic acids, or modulators thereof, can be used to treat disorders of skeletal muscle, such as muscular dystrophy (e.g., Duchenne muscular dystrophy, Becker muscular dystrophy, Emery-Dreifuss muscular dystrophy, limbgirdle muscular dystrophy, facioscapulohumeral muscular dystrophy, myotonic dystrophy, oculopharyngeal muscular dystrophy, distal muscular dystrophy, and congenital muscular dystrophy), motor neuron diseases (e.g., amyotrophic lateral sclerosis, infantile progressive spinal muscular atrophy, intermediate spinal muscular atrophy, spinal bulbar muscular atrophy, and adult spinal muscular atrophy), myopathies (e.g., inflammatory myopathies such as dermatomyositis and polymyositis, myotonia congenita, paramyotonia congenita, central core disease, nemaline myopathy, myotubular myopathy, and periodic paralysis), and metabolic diseases of muscle (e.g., phosphorylase deficiency, acid maltase deficiency, phosphofructokinase deficiency, debrancher enzyme deficiency, mitochondrial myopathy, carnitine deficiency, carnitine palmityl transferase deficiency, phosphoglycerate kinase deficiency, phosphoglycerate mutase deficiency, lactate dehydrogenase deficiency, and myoadenylatc deaminase deficiency).

In another example, TANGO 273 polypeptides, nucleic acids, or modulators thereof, can be used to treat pancreatic disorders, such as pancreatitis (e.g., acute hemorrhagic pancreatitis and chronic pancreatitis), pancreatic cysts (e.g., congenital cysts, pseudocysts, and benign or malignant neoplastic cysts), pancreatic tumors (e.g., pancreatic carcinoma and adenoma), diabetes mellitus (e.g., insulin- and non-insulin-dependent types, impaired glucose tolerance, and gestational diabetes), or islet cell tumors (e.g., insulinomas, adenomas, Zollinger-Ellison syndrome, glucagonomas, and somatostatinoma).

In another example, TANGO 273 polypeptides, nucleic acids, or modulators thereof, can be used to treat placental disorders, such as toxemia of pregnancy (e.g., preeclampsia and eclampsia), placentitis, or spontaneous abortion.

In another example, TANGO 273 polypeptides, nucleic acids, or modulators thereof, can be used to treat pulmonary disorders, such as atelectasis, cystic fibrosis, rheumatoid lung disease, pulmonary congestion or edema, chronic obstructive airway disease (e.g., emphysema, chronic bronchitis, bronchial asthma, and bronchiectasis), diffuse interstitial diseases (e.g., sarcoidosis, pneumoconiosis, hypersensitivity pneumonitis, Goodpasture's syndrome, idiopathic pulmonary hemosiderosis, pulmonary alveolar proteinosis, desquamative interstitial pneumonitis, chronic interstitial pneumonia, fibrosing alveolitis, hamman-rich syndrome, pulmonary eosinophilia, diffuse interstitial fibrosis, Wegener's granulomatosis, lymphomatoid granulomatosis, and lipid pneumonia), or tumors (e.g., bronchogenic carcinoma, bronchioalveolar carcinoma, bronchial carcinoid, hamartoma, and mesenchymal tumors).

In another example, TANGO 273 polypeptides, nucleic acids, or modulators thereof, can be used to treat hepatic (liver) disorders, such as jaundice, hepatic failure, hereditary hyperbilirubinemias (e.g., Gilbert's syndrome, Crigler-Naijar syndromes, and Dubin-Johnson and Rotor's syndromes), hepatic circulatory disorders (e.g., hepatic vein thrombosis and portal vein obstruction and thrombosis) hepatitis (e.g., chronic active hepatitis, acute viral hepatitis, and toxic and drug-induced hepatitis) cirrhosis (e.g., alcoholic cirrhosis, biliary cirrhosis, and hemochromatosis), or malignant tumors (e.g., primary carcinoma, hepatoblastoma, and angiosarcoma).

In another example, TANGO 273 polypeptides, nucleic acids, or modulators thereof, can be used to treat renal (kidney) disorders, such as glomerular diseases (e.g., acute and chronic glomerulonephritis, rapidly progressive glomerulonephritis, nephrotic syndrome, focal proliferative glomerulonephritis, glomerular lesions associated with systemic disease such as systemic lupus erythematosus, Goodpasture's syndrome, multiple myeloma, diabetes, neoplasia, sickle cell disease, and chronic inflammatory diseases), tubular diseases (e.g., acute tubular necrosis and acute renal failure, polycystic renal disease, medullary sponge kidney, medullary cystic disease, nephrogenic diabetes, and renal tubular acidosis), tubulointerstitial diseases (e.g., pyelonephritis, drug and toxin induced tubulointerstitial nephritis, hypercalcemic nephropathy, and hypokalemic nephropathy) acute and rapidly progressive renal failure, chronic renal failure, nephrolithiasis, vascular diseases (e.g., hypertension and nephrosclerosis, microangiopathic hemolytic anemia, atheroembolic renal disease, diffuse cortical necrosis, and renal infarcts), or tumors (e.g., renal cell carcinoma and nephroblastoma).

TANGO 286

A cDNA clone (designated jthkf042e03) encoding at least a portion of human TANGO 286 protein was isolated from a human keratinocyte cDNA library. The human TANGO 286 protein is predicted by structural analysis to be a secreted protein.

The full length of the cDNA encoding TANGO 286 protein (FIG. 5; SEQ ID NO: 33) is 1980 nucleotide residues. The ORF of this cDNA, nucleotide residues 133 to 1497 of SEQ ID NO: 33 (i.e., SEQ ID NO: 34), encodes a 455-amino acid secreted protein (FIG. 5; SEQ ID NO: 35).

The invention thus includes purified TANGO 286 protein, both in the form of the immature 455 amino acid residue protein (SEQ ID NO: 35) and in the form of the mature 432 amino acid residue protein (SEQ ID NO: 37). Mature TANGO 286 protein can be synthesized without the signal sequence polypeptide at the amino terminus thereof, or it can be synthesized by generating immature TANGO 286 protein and cleaving the signal sequence therefrom.

In addition to full length mature and immature TANGO 286 proteins, the invention includes fragments, derivatives, and variants of these TANGO 286 proteins, as described herein. These proteins, fragments, derivatives, and variants are collectively referred to herein as polypeptides of the invention or proteins of the invention.

The invention also includes nucleic acid molecules which encode a polypeptide of the invention. Such nucleic acids include, for example, a DNA molecule having the nucleotide sequence listed in SEQ ID NO: 33 or some portion thereof, such as the portion which encodes mature TANGO 286 protein, immature TANGO 286 protein, or a domain of TANGO 286 protein. These nucleic acids are collectively referred to as nucleic acids of the invention.

TANGO 286 proteins and nucleic acid molecules encoding them comprise a family of molecules having certain conserved structural and functional features.

A common domain of TANGO 286 proteins is a signal sequence. As used herein, a signal sequence includes a peptide of at least about 10 amino acid residues in length which occurs at the amino terminus of membrane-bound proteins and which contains at least about 45% hydrophobic amino acid residues such as alanine, leucine, isoleucine, phenylalanine, proline, tyrosine, tryptophan, or valine. In a preferred embodiment, a signal sequence contains at least about 10 to 35 amino acid residues, preferably about 10 to 20 amino acid residues, and has at least about 35–60%, more preferably 40–50%, and more preferably at least about 45% hydrophobic residues. A signal sequence serves to direct a protein containing such a sequence to a lipid bilayer. Thus, in one embodiment, a TANGO 286 protein contains a signal sequence corresponding to amino acid residues 1 to 23 of SEQ ID NO: 35 (SEQ ID NO: 36). The signal sequence is cleaved during processing of the mature protein.

TANGO 286 is a secreted soluble protein (i.e., a secreted protein having a single extracellular domain), as indicated by computerized sequence analysis and comparison of the amino acid sequence of TANGO 286 with related proteins, such as the soluble proteins designated bactericidal permeability increasing (BPI) protein and recombinant endotoxin neutralizing polypeptide (RENP).

TANGO 286 proteins typically comprise a variety of potential post-translational modification sites (often within an extracellular domain), such as those described herein in Table IX, as predicted by computerized sequence analysis of TANGO 286 proteins using amino acid sequence comparison software (comparing the amino acid sequence of TANGO 286 with the information in the PROSITE database {rel. 12.2; February 1995} and the Hidden Markov Models database {Rel. PFAM 3.3}). In certain embodiments, a protein of the invention has at least 1, 2, 4, 6, 10, 15, or 20 or more of the post-translational modification sites listed in Table IX.

TABLE IX

| Type of Potential Modification Site or Domain | Amino Acid Residues of SEQ ID NO: 35 | Amino Acid Sequence |
|---|---|---|
| N-glycosylation site | 79 to 82 | NFSN |
| | 92 to 95 | NTSL |
| | 113 to 116 | NIST |
| | 161 to 164 | NLST |
| | 173 to 176 | NYTL |
| | 205 to 208 | NLTD |
| | 249 to 252 | NLTL |
| | 303 to 306 | NFTL |
| | 320 to 323 | NSTV |
| | 363 to 366 | NRSN |
| Protein kinase C phosphorylation site | 35 to 37 | TQR |
| | 362 to 364 | SNR |
| | 429 to 431 | SSK |

TABLE IX-continued

| Type of Potential Modification Site or Domain | Amino Acid Residues of SEQ ID NO: 35 | Amino Acid Sequence |
|---|---|---|
| Casein kinase II phosphorylation site | 63 to 66 | SGSE |
| | 130 to 133 | SFAE |
| | 163 to 166 | STLE |
| | 169 to 172 | TKID |
| | 175 to 178 | TLLD |
| | 183 to 186 | SSPE |
| | 253 to 256 | STEE |
| | 321 to 324 | STVE |
| | 365 to 368 | SNIE |
| | 409 to 412 | SDIE |
| N-myristoylation site | 42 to 47 | GYQAGM |
| | 269 to 274 | GNVLSR |
| Lipid-binding serum glycoprotein domain | 12 to 427 | see FIG. 5 |

Certain lipid-binding serum glycoproteins, such as LPS-binding protein (LBP), bactericidal permeability-increasing protein (BPI), cholesteryl ester transfer protein (CETP), and phospholipid transfer protein (PLTP), share regions of sequence similarity which are herein designated a lipid-binding serum glycoprotein domain (Schumann et al., (1990) *Science* 249:1429–1431; Gray et al., (1989) *J. Biol. Chem.* 264:9505–9509; Day et al., (1994) *J. Biol. Chem.* 269:9388–9391). The consensus pattern of lipid-binding serum glycoprotein domains is as follows (using standard single letter amino acid abbreviations wherein X is any amino acid residue).

-(P or A)-(G or A)-(L or I or V or M or C)-$X_2$-R-(I or V)-(S or T)-$X_3$-L-$X_{(4\ or\ 5)}$-(E or Q)-$X_4$-(L or I or V or M)-$X_{(0\ or\ 1)}$-(E or Q or K)-$X_8$-P-

(e.g., amino acid residues 28–60 of SEQ ID NO: 35).

Proteins in which a lipid-binding serum glycoprotein domain occurs are often structurally related and exhibit related physiological activities. LBP binds to lipid A moieties of bacterial LPS and, once bound thereto, induces secretion of α-tumor necrosis factor, apparently by interacting with the CD14 receptor. BPI also binds LPS and exerts a cytotoxic effect on Gram-negative bacteria (Elsbach, (1998) *J. Leukoc. Biol.* 64:14–18). CETP is involved in transfer of insoluble cholesteryl esters during reverse cholesterol transport. PLTP appears to be involved in phospholipid transport and modulation of serum HDL particles.

The signal peptide prediction program SIGNALP (Nielsen et al. (1997) *Protein Engineering* 10:1–6) predicted that TANGO 286 protein includes a 23 amino acid signal peptide (amino acid residues 1 to 23 of SEQ ID NO: 35; SEQ ID NO: 36) preceding the mature TANGO 286 protein (amino acid residues 24 to 455 of SEQ ID NO: 35; SEQ ID NO: 37). Human TANGO 286 protein is a secreted soluble protein.

Figure 5E:
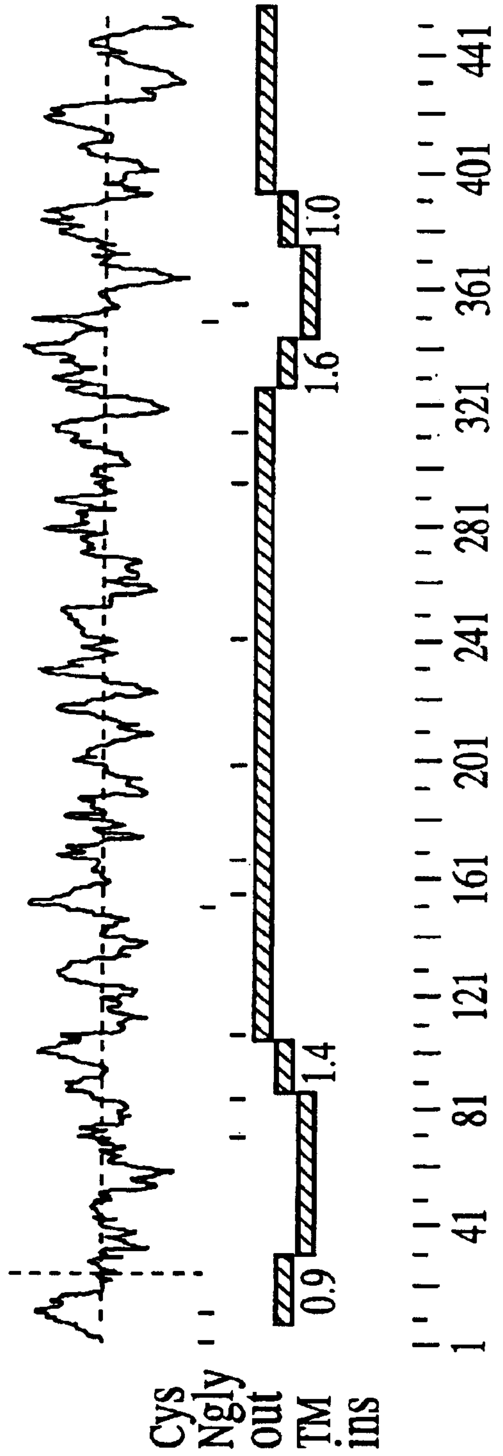
FIG. 5E is a hydrophilicity plot of TANGO 286 protein. An alignment of the amino acid sequences of human TANGO 286 ("286"; SEQ ID NO: 35) and BPI protein ("BPI"; SEQ ID NO: 38) protein is shown in FIGS. 5F and 5G, wherein identical amino acid residues are indicated by ":" and similar amino acid residues are indicated by ".". An alignment of the amino acid sequences of human TANGO 286 ("286"; SEQ ID NO: 35) and RENP protein ("RENP"; SEQ ID NO: 39) is shown in FIGS. 5H and 5I, wherein identical amino acid residues are indicated by ":" and similar amino acid residues are indicated by ".".

FIG. 5E depicts a hydrophilicity plot of TANGO 286 protein. Relatively hydrophobic regions are above the dashed horizontal line, and relatively hydrophilic regions are below the dashed horizontal line. As described elsewhere herein, relatively hydrophilic regions are generally located at or near the surface of a protein, and are more frequently effective immunogenic epitopes than are relatively hydrophobic regions. For example, the region of human TANGO 286 protein from about amino acid residue 420 to about amino acid residue 435 appears to be located at or near the surface of the protein, while the region from about amino acid residue 325 to about amino acid residue 345 appears not to be located at or near the surface.

The predicted molecular weight of TANGO 286 protein without modification and prior to cleavage of the signal sequence is about 50.9 kilodaltons. The predicted molecular weight of the mature TANGO 286 protein without modification and after cleavage of the signal sequence is about 48.2 kilodaltons.

The gene encoding human TANGO 286 protein was determined to be located on chromosome 22 by comparison of matching genomic clones such as the clones assigned GenBank Accession numbers W16806 and AL021937.

A portion of TANGO 286 protein exhibits significant amino acid homology with a region of the human chromosome region 22q12–13 genomic nucleotide sequence having GenBank Accession number AL021937. Alignment of a 45 kilobase nucleotide sequence encoding TANGO 286 with AL021937, however, indicated the presence in TANGO 286 of exons which differ from those disclosed in L021937 (pam120.mat scoring matrix; gap penalties −12/−4). This region of chromosome 22 comprises an immunoglobulin lambda chain C (IGLC) pseudogene, the Ret finger protein-like 3 (RFPL3) and Ret finger protein-like 3 antisense (RFPL3S) genes, a gene encoding a novel immunoglobulin lambda chain V family protein, a novel gene encoding a protein similar both to mouse RGDS protein (RALGDS, RALGEF, guanine nucleotide dissociation stimulator A) and to rabbit oncogene RSC, a novel gene encoding the human orthologue of worm F16A11.2 protein, a novel gene encoding a protein similar both to BPI and to rabbit liposaccharide-binding protein, and a 5'-portion of a novel gene. This region also comprises various ESTs, STSs, GSSs, genomic marker D22S1175, a ca repeat polymorphism and putative CpG islands. TANGO 286 protein thus shares one or more structural or functional features of these molecules.

TANGO 286 protein exhibits considerable sequence similarity with BPI protein, having 23.9% amino acid sequence identity therewith, as assessed using the ALIGN v. 2.0 computer software using a pam120.mat scoring matrix and gap penalties of −12/−4. TANGO 286 protein also exhibits considerable sequence similarity with recombinant endotoxin neutralizing polypeptide (RENP), having 24.5% amino acid sequence identity therewith, as assessed using the ALIGN software. Physiological activities of BPI protein and RENP have been described (e.g., Gabay et al., (1989) *Proc. Natl. Acad. Sci. USA* 86:5610–5614; Elsbach, (1998) *J. Leukoc. Biol.* 64:14–18; Mahadeva et al., (1997) *Chest* 112:1699–1701; International patent application WO96/34873). RENP, for example, binds LPS and neutralizes bacterial endotoxins. BPI, RENP, and other proteins in which a lipid-binding serum glycoprotein domain occurs bind LPS and neutralize bacterial endotoxins, and are therefore useful for preventing, detecting, and treating LPS-related disorders such as shock, disseminated intravascular coagulation, anemia, thrombocytopenia, adult respiratory distress syndrome, renal failure, liver disease, and disorders associated with Gram negative bacterial infections. In addition to the physiological conditions described above, BPI protein is known to be involved in vasculitis and bronchiectasis, in that antibodies which bind specifically with BPI protein are present in at least some patients afflicted with these disorders (Mahadeva et al., supra).

Biological Function of TANGO 286 Proteins, Nucleic Acids, and Modulators Thereof Expression of TANGO 286 in keratinocyte library indicates that this protein is involved in a disorders which involve keratinocytes. Such disorders include, for example, disorders involving extracellular matrix abnormalities, dermatological disorders, ocular disorders, inappropriate hair growth (e.g., baldness), infections of the nails of the fingers and toes, scalp disorders (e.g., dandruff), and the like.

The fact that TANGO 286 protein contains a lipid-binding serum glycoprotein domain indicates that TANGO 286 is involved in one or more physiological processes in which these other lipid-binding serum glycoprotein domain-containing proteins are involved. Thus, TANGO 286 is involved in one or more of lipid transport, metabolism, serum lipid particle regulation, host anti-microbial defensive mechanisms, and the like.

Human TANGO 286 shares physiological functionality with other proteins in which a lipid-binding serum glycoprotein domains occurs (e.g., LBP, BPI protein, CETP, and PLTP). Based on the amino acid sequence similarity of TANGO 286 with BPI protein and with RENP, TANGO 286 protein exhibits physiological activities exhibited by these proteins. Thus, TANGO 286 proteins are useful for preventing, diagnosing, and treating, among others, lipid transport disorders, lipid metabolism disorders, disorders of serum lipid particle regulation, obesity, disorders involving insufficient or inappropriate host anti-microbial defensive mechanisms, vasculitis, bronchiectasis, LPS-related disorders such as shock, disseminated intravascular coagulation, anemia, thrombocytopenia, adult respiratory distress syndrome, renal failure, liver disease, and disorders associated with Gram negative bacterial infections, such as bacteremia, endotoxemia, sepsis, and the like.

TANGO 294

A cDNA clone (designated jthrc145g07) encoding at least a portion of human TANGO 294 protein was isolated from a human pulmonary artery smooth muscle cell cDNA library. The human TANGO 294 protein is predicted by structural analysis to be a transmembrane membrane protein. No expression of DNA encoding TANGO 294 was detected in human heart, brain, placenta, lung, liver, skeletal muscle, kidney, or pancreas tissues.

The full length of the cDNA encoding TANGO 294 protein (FIG. 6; SEQ ID NO: 45) is 2044 nucleotide residues. The ORF of this cDNA, nucleotide residues 126 to 1394 of SEQ ID NO: 45 (i.e., SEQ ID NO: 46), encodes a 423-amino acid transmembrane protein (FIG. 6; SEQ ID NO: 47).

The invention includes purified TANGO 294 protein, both in the form of the immature 423 amino acid residue protein (SEQ ID NO: 47) and in the form of the mature 390 amino acid residue protein (SEQ ID NO: 49). Mature TANGO 294 protein can be synthesized without the signal sequence polypeptide at the amino terminus thereof, or it can be synthesized by generating immature TANGO 294 protein and cleaving the signal sequence therefrom.

In addition to full length mature and immature TANGO 294 proteins, the invention includes fragments, derivatives, and variants of TANGO 294 protein, as described herein. These proteins, fragments, derivatives, and variants are collectively referred to herein as polypeptides of the invention or proteins of the invention.

The invention also includes nucleic acid molecules which encode a polypeptide of the invention. Such nucleic acids include, for example, a DNA molecule having the nucleotide sequence listed in SEQ ID NO: 45 or some portion thereof, such as the portion which encodes mature TANGO 294 protein, immature .TANGO 294 protein, or a domain of TANGO 294 protein. These nucleic acids are collectively referred to as nucleic acids of the invention.

TANGO 294 proteins and nucleic acid molecules encoding them comprise a family of molecules having certain conserved structural and functional features.

Also included within the scope of the invention are TANGO 294 proteins having a signal sequence. As used herein, a signal sequence includes a peptide of at least about 10 amino acid residues in length which occurs at the amino terminus of membrane-bound proteins and which contains at least about 45% hydrophobic amino acid residues such as alanine, leucine, isoleucine, phenylalanine, proline, tyrosine, tryptophan, or valine. In a preferred embodiment, a signal sequence contains at least about 10 to 35 amino acid residues, preferably about 10 to 20 amino acid residues, and has at least about 35–60%, more preferably 40–50%, and more preferably at least about 45% hydrophobic residues. A signal sequence serves to direct a protein containing such a sequence to a lipid bilayer. Thus, in one embodiment, a TANGO 294 protein contains a signal sequence corresponding to amino acid residues 1 to 33 of SEQ ID NO: 47 (SEQ ID NO: 48). The signal sequence is cleaved during processing of the mature protein.

The naturally-occurring form of TANGO 294 protein is a secreted protein (i.e., not comprising the predicted signal sequence). However, in variant forms, TANGO 294 proteins can be transmembrane proteins which include an extracellular domain. In this transmembrane variant form, the predicted TANGO 294 protein extracellular domain is located from about amino acid residue 34 to about amino acid residue 254 of SEQ ID NO: 47, the predicted cytoplasmic domain is located from about amino acid residue 280 to amino acid residue 423 of SEQ ID NO: 47 (SEQ ID NO: 52), and the predicted transmembrane domain is located from about amino acid residues 255 to 279 of SEQ ID NO: 47 (SEQ ID NO: 51).

TANGO 294 proteins typically comprise a variety of potential post-translational modification sites (often within an extracellular domain), such as those described herein in Table X, as predicted by computerized sequence analysis of TANGO 294 proteins using amino acid sequence comparison software (comparing the amino acid sequence of TANGO 294 with the information in the PROSITE database {rel. 12.2; February 1995} and the Hidden Markov Models database {Rel. PFAM 3.3}). In certain embodiments, a protein of the invention has at least 1, 2, 4, 6, 10, 15, or 20 or more of the post-translational modification sites listed in Table X.

TABLE X

| Type of Potential Modification Site or Domain | Amino Acid Residues of SEQ ID NO: 47 | Amino Acid Sequence |
|---|---|---|
| N-glycosylation site | 48 to 51 | NISE |
| | 113 to 116 | NNSL |
| | 285 to 288 | NMSR |
| | 413 to 416 | NLSQ |
| Protein kinase C phosphorylation site | 12 to 14 | SHR |
| | 138 to 140 | SRK |
| | 217 to 219 | TVK |
| Casein kinase II phosphorylation site | 155 to 158 | SYDE |
| | 175 to 178 | TGQE |
| | 198 to 201 | TMPE |
| | 360 to 363 | SNPE |
| Tyrosine kinase phosphorylation site | 174 to 182 | KTGQEKIYY |
| N-myristoylation site | 99 to 104 | GLVGGA |
| | 130 to 135 | GNSRGN |
| | 188 to 193 | GTTMGF |
| | 277 to 282 | GGFNTN |
| Amidation site | 240 to 243 | FGKK |
| Lipase serine active site | 180 to 189 | IYYVGYSQGT |
| Alpha/beta hydrolase fold domain | 125 to 404 | See FIG. 6 |

Alpha/beta hydrolase fold domains occur in a wide variety of enzymes (Ollis et al., (1992) *Protein Eng.* 5:197–211).

The alpha/beta fold domain is a conserved topological domain in which sequence homology is not necessarily conserved. Conservation of topology in the alpha/beta fold domain preserves arrangement of catalytic residues, even though those residues, and the reactions they catalyze, can vary. In many enzymes, particularly including alpha/beta hydrolases, this domain encompasses the active site of the enzyme. In one embodiment, the protein of the invention has at least one domain that is at least 55%, preferably at least about 65%, more preferably at least about 75%, yet more preferably at least about 85%, and most preferably at least about 95% identical to the alpha/beta hydrolase fold domain described herein in Table X.

The signal peptide prediction program SIGNALP (Nielsen et al. (1997) *Protein Engineering* 10:1–6) predicted that human TANGO 294 protein includes a 33 amino acid signal peptide (amino acid residues 1 to 33 of SEQ ID NO: 47; SEQ ID NO: 48) preceding the mature TANGO 294 protein (amino acid residues 34 to 423 of SEQ ID NO: 47; SEQ ID NO: 49). Human TANGO 294 protein is a soluble secreted protein. However, in the transmembrane variant form, human TANGO 294 protein includes an extracellular domain (amino acid residues 34 to 254 of SEQ ID NO: 47; SEQ ID NO: 50); a transmembrane domain (amino acid residues 255 to 279 of SEQ ID NO: 47; SEQ ID NO: 51), and a cytoplasmic domain (amino acid residues 280 to 423 of SEQ ID NO: 47; SEQ ID NO: 52)

Figure 6F:
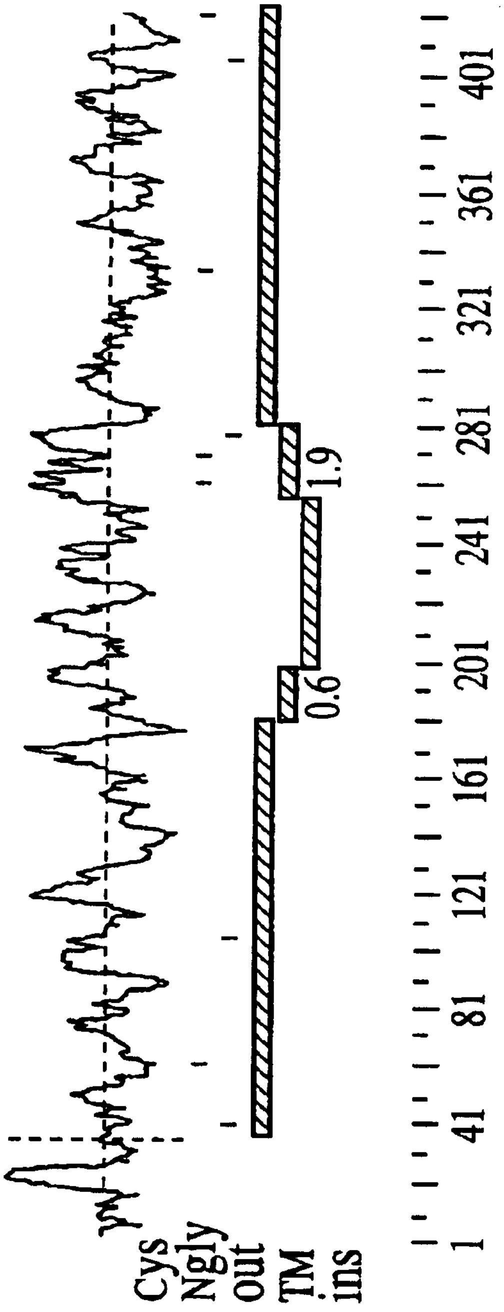
FIG. 6F is a hydrophilicity plot of TANGO 294 protein. An alignment of the amino acid sequences of human TANGO 294 protein ("294"; SEQ ID NO: 47) and a known human lysosomal acid lipase protein ("LAL"; SEQ ID NO: 41) is shown in FIGS. 6G and 6H, wherein identical amino acid residues are indicated by ":" and similar amino acid residues are indicated by ".".

FIG. 6F depicts a hydrophilicity plot of human TANGO 294 protein. Relatively hydrophobic regions are above the dashed horizontal line, and relatively hydrophilic regions are below the dashed horizontal line. The hydrophobic region which corresponds to amino acid residues 1 to 33 of SEQ ID NO: 47 is the signal sequence of human TANGO 294 (SEQ ID NO: 49). The hydrophobic region which corresponds to amino acid residues 255 to 279 of SEQ ID NO: 47 is the predicted transmembrane domain of human TANGO 294 (SEQ ID NO: 51). As described elsewhere herein, relatively hydrophilic regions are generally located at or near the surface of a protein, and are more frequently effective immunogenic epitopes than are relatively hydrophobic regions. For example, the region of human TANGO 294 protein from about amino acid residue 130 to about amino acid residue 150 appears to be located at or near the surface of the protein, while the region from about amino acid residue 90 to about amino acid residue 100 appears not to be located at or near the surface.

The predicted molecular weight of human TANGO 294 protein without modification and prior to cleavage of the signal sequence is about 48.2 kilodaltons. The predicted molecular weight of the mature human TANGO 294 protein without modification and after cleavage of the signal sequence is about 44.2 kilodaltons.

It may be that amino acid residues 1 to 15 of SEQ ID NO: 47 do not occur in TANGO 294 protein. However, it is recognized that amino acid residues 16 to 33 of SEQ ID NO: 47 form a functional signal sequence even in the absence of residues 1 to 15. The amino acid sequence (and hence the properties) of mature TANGO 294 protein are unaffected by presence or absence of amino acid residues 1 to 15 of immature TANGO 294 protein.

Human TANGO 294 protein exhibits considerable sequence similarity (i.e., about 75% amino acid sequence identity) to lingual and gastric lipase proteins of rat (Swissprot Accession no. P04634; Docherty et al. (1985) *Nucleic Acids Res.* 13:1891–1903), dog (Swissprot Accession no. P80035; Carriere et al. (1991) *Eur. J. Biochem.* 202:75–83), and human (Swissprot Accession no. P07098; Bernbaeck and Blaeckberg (1987) *Biochim. Biophys. Acta* 909:237–244), as assessed using the ALIGN v.2.0 computer software using a pam12.mat scoring matrix and gap penalties of −12/−4. TANGO 294 is distinct from the known human lipase, as indicated in FIGS. 6D and 6E. FIGS. 6D and 6E depict an alignment of the amino acid sequences of human TANGO 294 protein (SEQ ID NO: 47) and the known human lipase protein (SEQ ID NO: 75), as assessed using the same software and parameters. In this alignment (pam120.mat scoring matrix, gap penalties −12/−4), the amino acid sequences of the proteins are 49.8% identical. TANGO 294 also is distinct from the known human lysosomal acid lipase, as indicated in FIGS. 6G and 6H. FIGS. 6G and 6H depicts an alignment of the amino acid sequences of human TANGO 294 protein (SEQ ID NO: 47) and the known human lysosomal acid lipase protein (SEQ ID NO: 41). In this alignment (pam120.mat scoring matrix, gap penalties −12/−4), the amino acid sequences of the proteins are 56.9% identical.

TANGO 294 is a human lipase distinct from the known human lipase and the known human lysosomal acid lipase. Furthermore, in view of the comparisons of the amino acid sequences of TANGO 294 and the two human lipases and the nature of transcriptional initiation sites, it is recognized that the transcriptional start site can correspond to either of the methionine residues located at residues 1 and 15 of SEQ ID NO: 47 The present invention thus includes proteins in which the initially transcribed amino acid residue is the methionine residue at position 1 of SEQ ID NO: 47 and proteins in which the initially transcribed amino acid residue is the methionine residue at position 15 of SEQ ID NO: 47 (i.e., proteins in which the amino acid sequence of TANGO 294 does not include residues 1 to 14 of SEQ ID NO: 47). Furthermore, because amino acid residues 1 to 14 of SEQ ID NO: 47 are predicted to be part of a signal sequence, it is recognized that the protein not comprising this portion of the amino acid sequence will nonetheless exhibit a functional signal sequence at its amino terminus.

Biological Function of TANGO 294 Proteins, Nucleic Acids, and Modulators Thereof The sequence similarity of TANGO 294 and mammalian lingual, gastric, and lysosomal acid lipase proteins indicates that TANGO 294 is involved in physiological processes identical or analogous to those involving these lipases. Thus, TANGO 294 is involved in facilitating absorption and metabolism of fat. TANGO 294 can thus be used, for example, to prevent, detect, and treat disorders relating to fat absorption and metabolism, such as inadequate expression of gastric/pancreatic lipase, cystic fibrosis, exocrine pancreatic insufficiency, obesity, medical treatments which alter fat absorption, and the like.

TANGO 294 protein is known to be expressed in human pulmonary artery smooth muscle tissue. This indicates that TANGO 294 protein is involved in transportation and metabolism of fats and lipids in the human vascular and cardiovascular systems. Thus, TANGO 294 proteins of the invention can be used to prevent, detect, and treat disorders involving these body systems.

INTERCEPT 296

A cDNA clone (designated jthEa030h09) encoding at least a portion of human INTERCEPT 296 protein was isolated from a human esophagus cDNA library. The human INTERCEPT 296 protein is predicted by structural analysis to be a transmembrane protein having three or more transmembrane domains. Expression of DNA encoding INTERCEPT 296 tissue has been detected by northern analysis of human lung tissue. In human lung tissue, two moieties corresponding to INTERCEPT 296 have been identified in Northern blots. It is recognized that these two moieties may represent alternatively polyadenylated INTERCEPT 296 mRNAs or alternatively spliced INTERCEPT 296 mRNAs. It has furthermore been observed that INTERCEPT 296 does not appear to be expressed in any of heart, brain, placenta, skeletal muscle, kidney, and pancreas tissues.

The full length of the cDNA encoding INTERCEPT 296 protein (FIG. 7; SEQ ID NO: 53) is 2133 nucleotide residues. The ORF of this cDNA, nucleotide residues 70 to 1098 of SEQ ID NO: 53 (i.e., SEQ ID NO: 54), encodes a 343-amino acid transmembrane protein (FIG. 7; SEQ ID NO: 55).

The invention includes purified INTERCEPT 296 protein, which has the amino acid sequence listed in SEQ ID NO: 55. In addition to full length INTERCEPT 296 proteins, the invention includes fragments, derivatives, and variants of these INTERCEPT 296 proteins, as described herein. These proteins, fragments, derivatives, and variants are collectively referred to herein as polypeptides of the invention or proteins of the invention.

The invention also includes nucleic acid molecules which encode a polypeptide of the invention. Such nucleic acids include, for example, a DNA molecule having the nucleotide sequence SEQ ID NO: 53 or some portion thereof, such as the portion which encodes INTERCEPT 296 protein or a domain thereof. These nucleic acids are collectively referred to as nucleic acids of the invention.

INTERCEPT 296 proteins and nucleic acid molecules encoding them comprise a family of molecules having certain conserved structural and functional features, such as the five transmembrane domains which occur in the protein.

INTERCEPT 296 comprises at least five transmembrane domains, at least three cytoplasmic domains, and at least two extracellular domains. INTERCEPT 296 does not appear to comprise a cleavable signal sequence. Amino acid residues 1 to 70 of SEQ ID NO: 55 likely directs insertion of the protein into the cytoplasmic membrane. There are at least two mechanisms by which this can occur. Sequence analysis of residues 1 to 70 of SEQ ID NO: 55 indicates that this entire region may represent a signal sequence or that residues 1 to 47 represent a signal sequence, with residues 48–70 representing a transmembrane region. Human INTERCEPT 296 protein extracellular domains are located from about amino acid residue 70 to about amino acid residue 182 (SEQ ID NO: 57) and from about amino acid residue 228 to about amino acid residue 249 (SEQ ID NO: 58) of SEQ ID NO: 55. Human INTERCEPT 296 cytoplasmic domains are located from about amino acid residue 43 to amino acid residue 50 (SEQ ID NO: 64), from about amino acid residue 205 to amino acid residue 210 (SEQ ID NO: 65), and from amino acid residue 272 to amino acid residue 343 (SEQ ID NO: 66) of SEQ ID NO: 55. The five transmembrane domains of INTERCEPT 296 are located from about amino acid residues 24 to 42 (SEQ ID NO: 59), 51 to 70 (SEQ ID NO: 60), 183 to 204 (SEQ ID NO: 61), 211 to 227 (SEQ ID NO: 62), and 250 to 271 (SEQ ID NO: 63) of SEQ ID NO: 55.

INTERCEPT 296 proteins typically comprise a variety of potential post-translational modification sites (often within an extracellular domain), such as those described herein in Table XI, as predicted by computerized sequence analysis of INTERCEPT 296 proteins using amino acid sequence comparison software (comparing the amino acid sequence of INTERCEPT 296 with the information in the PROSITE database {rel. 12.2; February 1995} and the Hidden Markov Models database {Rel. PFAM 3.3}). In certain embodiments, a protein of the invention has at least 1, 2,4, 6, 10, 15, or 20 or more of the post-translational modification sites listed in Table XI.

TABLE XI

| Type of Potential Modification Site or Domain | Amino Acid Residues of SEQ ID NO: 55 | Amino Acid Sequence |
|---|---|---|
| N-glycosylation site | 71 to 74 | NFSS |
| | 84 to 87 | NTSY |
| | 109 to 112 | NITL |
| | 121 to 124 | NETI |
| | 284 to 287 | NQSV |
| Protein kinase C phosphorylation site | 86 to 88 | SYK |
| | 131 to 133 | TWR |
| | 162 to 164 | TPR |
| | 304 to 306 | SPR |
| | 313 to 315 | SPK |
| | 326 to 328 | STK |
| Casein kinase II phosphorylation site | 286 to 289 | SVDE |
| | 296 to 299 | SPEE |
| | 309 to 312 | SMAD |
| Tyrosine kinase phosphorylation site | 148 to 156 | KGLPDPVLY |
| N-myristoylation site | 79 to 84 | GQVSTN |
| | 100 to 105 | GLQVGL |
| | 107 to 112 | GVNITL |
| | 265 to 270 | GLAMAV |

Figure 7D:
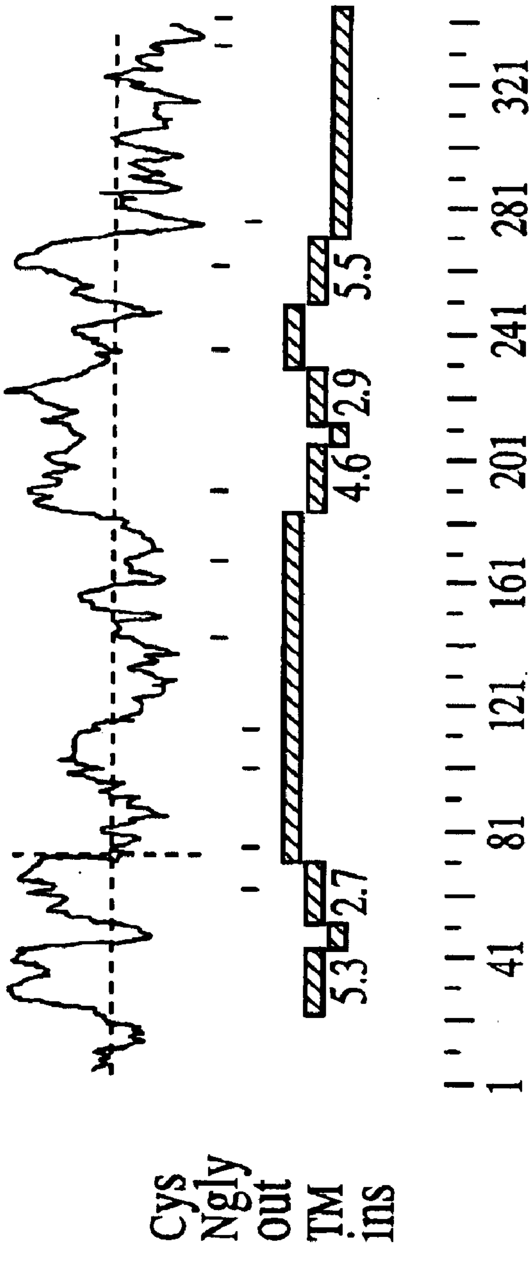
FIG. 7D is a hydrophilicity plot of INTERCEPT 296 protein. An alignment of the amino acid sequences of human INTERCEPT 296 protein ("296"; SEQ ID NO: 55) and *C. elegans* C06E1.3 related protein ("CRP"; SEQ ID NO: 40) is shown in FIGS. 7E and 7F, wherein identical amino acid residues are indicated by ":" and similar amino acid residues are indicated by ".".

FIG. 7D depicts a hydrophilicity plot of INTERCEPT 296 protein. Relatively hydrophobic regions are above the dashed horizontal line, and relatively hydrophilic regions are below the dashed horizontal line. The hydrophobic regions which corresponds to amino acid residues 24 to 42, 51 to 70, 183 to 204, 211 to 227, and 250 to 271 of SEQ ID NO: 55 are the transmembrane domains of human INTERCEPT 296 (SEQ ID NOs: 59 through 63, respectively). As described elsewhere herein, relatively hydrophilic regions are generally located at or near the surface of a protein, and are more frequently effective immunogenic epitopes than are relatively hydrophobic regions. For example, the region of human INTERCEPT 296 protein from about amino acid residue 120 to about amino acid residue 140 appears to be located at or near the surface of the protein, while the region from about amino acid residue 95 to about amino acid residue 110 appears not to be located at or near the surface.

The predicted molecular weight of INTERCEPT 296 protein without modification and prior to cleavage of the signal sequence is about 37.8 kilodaltons. The predicted molecular weight of the mature INTERCEPT 296 protein without modification and after cleavage of the signal sequence is about 30.2 kilodaltons.

FIGS. 7E and 7F depicts an alignment of the amino acid sequences of human INTERCEPT 296 protein (SEQ ID NO: 55) and *Caenorhabditis elegans* C06E1.3 related protein (SEQ ID NO: 399). In this alignment (pam120.mat scoring matrix, gap penalties −12/−4), the amino acid sequences of the proteins are 26.8% identical. The *C. elegans* protein has five predicted transmembrane domains.

Biological Function of INTERCEPT 296 Proteins, Nucleic Acids, and Modulators Thereof The cDNA encoding INTERCEPT 296 protein was obtained from a human esophagus cDNA library, and INTERCEPT 296 is expressed in lung tissue. The INTERCEPT 296-related proteins and nucleic acids of the invention are therefore useful for prevention, detection, and treatment of disorders of the human lung and esophagus. Such disorders include, for example, various cancers, bronchitis, cystic fibrosis, respiratory infections (e.g., influenza, bronchiolitis, pneumonia, and tuberculosis), asthma, emphysema, chronic bronchitis, bronchiectasis, pulmonary edema, pleural effusion, pulmonary embolus, adult and infant respiratory distress syndromes, heartburn, and gastric reflux esophageal disease.

Tables A and B summarize sequence data corresponding to the human proteins herein designated TANGO 202, TANGO 234, TANGO 265, TANGO 273, TANGO 286, TANGO 294, and INTERCEPT 296.

TABLE A

| Protein Designation | SEQ ID NOs | | | Depicted in FIG. # | ATCC® Accession # |
|---|---|---|---|---|---|
| | cDNA | ORF | Protein | | |
| TANGO 202 | 1 | 2 | 3 | 1 | 207219 |
| TANGO 234 | 9 | 10 | 11 | 2 | 207184 |
| TANGO 265 | 17 | 18 | 19 | 3 | 207228 |
| TANGO 273 | 25 | 26 | 27 | 4 | 207185 |
| TANGO 286 | 33 | 34 | 35 | 5 | 207220 |
| TANGO 294 | 45 | 46 | 47 | 6 | 207220 |
| INTERCEPT 296 | 53 | 54 | 55 | 7 | 207220 |

TABLE B

| Protein Desig. | Signal Sequence | | Mature Protein | | Extracellular Domain(s) | | Transmembrane Domain(s) | | Cytoplasmic Domain(s) | |
|---|---|---|---|---|---|---|---|---|---|---|
| | SEQ ID NOs | | | | | | | | | |
| TANGO 202 | 1 to 19 | | 4 | 20 to 475 | 5 | 20 to 392 | 6 | 393 to 415 | 7 | 416 to 475 | 8 |
| (variant) | (1 to 19) | | (4) | (20 to 475) | (5) | (20 to 475) | (5) | (N/A) | | (N/A) | |
| TANGO 234 | 1 to 40 | | 12 | 41 to 1453 | 13 | 41 to 1359 | 14 | 1360 to 1383 | 15 | 1384 to 1453 | 16 |
| TANGO 265 | 1 to 31 | | 20 | 32 to 761 | 21 | 32 to 683 | 22 | 684 to 704 | 23 | 705 to 761 | 24 |
| TANGO 273 | 1 to 22 | | 28 | 23 to 172 | 29 | 23 to 60 | 30 | 61 to 81 | 31 | 82 to 172 | 32 |
| TANGO 286 | 1 to 23 | | 36 | 24 to 455 | 37 | 24 to 455 | 37 | N/A | | N/A | |
| TANGO 294 | 1 to 33 | | 48 | 34 to 423 | 49 | 34 to 254 | 50 | 255 to 279 | 51 | 280 to 423 | 52 |
| (variant 1) | (15 to 33) | | (40) | (34 to 423) | (49) | (34 to 254) | (50) | (255 to 279) | (51) | (280 to 423) | (52) |
| <variant 2> | <1 to 33> | | <48> | <34 to 423> | <49> | <34 to 423> | <49> | <N/A> | | <N/A> | |
| {variant 3} | {15 to 33} | | {40} | {34 to 423} | {49} | {34 to 423} | {49} | {N/A} | | {N/A} | |
| INTERCEPT 296 | N/A | | | 1 to 343 | 55 | 1 to 23 | 56 | 24 to 42 | 59 | 43 to 50 | 64 |
| | | | | | | 71 to 182 | 57 | 51 to 70 | 60 | 205 to 210 | 65 |
| | | | | | | 228 to 249 | 58 | 183 to 204 | 61 | 272 to 343 | 66 |
| | | | | | | | | 211 to 227 | 62 | | |
| | | | | | | | | 250 to 271 | 63 | | |
| | | | | | Amino Acid Residues | | | | | |

Various aspects of the invention are described in further detail in the following subsections.

I. Isolated Nucleic Acid Molecules

One aspect of the invention pertains to isolated nucleic acid molecules that encode a polypeptide of the invention or a biologically active portion thereof, as well as nucleic acid molecules sufficient for use as hybridization probes to identify nucleic acid molecules encoding a polypeptide of the invention and fragments of such nucleic acid molecules suitable for use as PCR primers for the amplification or mutation of nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of all or a portion of any of SEQ ID NOs: 1, 2, 9, 10, 17, 18, 25, 26, 33, 34, 45, 46, 53, 54, 67, 68, 72, and 73, or a complement thereof, or which has a nucleotide sequence comprising one of these sequences, can be isolated using standard molecular biology techniques and the sequence information provided herein. Using a nucleic acid comprising at least one of the sequences of SEQ ID NOs: 1, 2, 9, 10, 17, 18, 25, 26, 33, 34, 45, 46, 53, 54, 67, 68, 72, and 73 as a hybridization probe, nucleic acid molecules of the invention can be isolated using standard hybridization and cloning techniques (e.g., as described in Sambrook et al., eds., *Molecular Cloning: A Laboratory Manual*, 2nd ed., Cold Spring Harbor Laboratory, Cold Spring Harbor Laboratory Press, Cold Spring Harbor, N.Y., 1989).

A nucleic acid molecule of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which is a complement of the nucleotide sequence of any of SEQ ID NOs: 1, 2, 9, 10, 17, 18, 25, 26, 33, 34, 45, 46, 53, 54, 67, 68, 72, and 73, or a portion thereof. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule of the invention can comprise only a portion of a nucleic acid sequence encoding a full length polypeptide of the invention for example, a fragment which can be used as a probe or primer or a fragment encoding a biologically active portion of a polypeptide of the invention. The nucleotide sequence determined from the cloning one gene allows for the generation of probes and primers designed for use in identifying and/or cloning homologs in other cell types, e.g., from other tissues, as well as homologs from other mammals. The probe/primer typically comprises substantially purified oligonucleotide. The oligonucleotide typically comprises a region of nucleotide sequence that hybridizes under stringent conditions to at least about 15, preferably about 25, more preferably about 50, 75, 100, 125, 150, 175, 200, 250, 300, 350, or 400 or more consecutive nucleotides of the sense or anti-sense sequence of any of SEQ ID NOs: 1, 2, 9, 10, 17, 18, 25, 26, 33, 34, 45, 46, 53, 54, 67, 68, 72, and 73, or of a naturally occurring mutant of any of SEQ ID NOs: 1, 2, 9, 10, 17, 18, 25, 26, 33, 34, 45, 46, 53, 54, 67, 68, 72, and 73.

Probes based on the sequence of a nucleic acid molecule of the invention can be used to detect transcripts or genomic sequences encoding the same protein molecule encoded by a selected nucleic acid molecule. The probe comprises a label group attached thereto, e.g., a radioisotope, a fluorescent compound, an enzyme, or an enzyme co-factor. Such probes can be used as part of a diagnostic test kit for identifying cells or tissues which mis-express the protein, such as by measuring levels of a nucleic acid molecule encoding the protein in a sample of cells from a subject, e.g., detecting mRNA levels or determining whether a gene encoding the protein has been mutated or deleted.

A nucleic acid fragment encoding a biologically active portion of a polypeptide of the invention can be prepared by isolating a portion of any of SEQ ID NOs: 2, 10, 18, 26, 34, 46, 54, 68, and 73, expressing the encoded portion of the polypeptide protein (e.g., by recombinant expression in vitro), and assessing the activity of the encoded portion of the polypeptide.

The invention further encompasses nucleic acid molecules that differ from the nucleotide sequence of any of SEQ ID NOs: 1, 2, 9, 10, 17, 18, 25, 26, 33, 34, 45, 46, 53, 54, 67, 68, 72, and 73 due to degeneracy of the genetic code and thus encode the same protein as that encoded by the nucleotide sequence of any of SEQ ID NOs: 2, 10, 18, 26, 34, 46, 54, 68, and 73.

In addition to the nucleotide sequences of SEQ ID NOs: 2, 10, 18, 26, 34, 46, 54, 68, and 73, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus.

As used herein, the phrase "allelic variant" refers to a nucleotide sequence which occurs at a given locus or to a polypeptide encoded by the nucleotide sequence. For example, chromosomal mapping has been used to locate the gene encoding human TANGO 234 at chromosomal location h12p13 (with synteny to mo6), between chromosomal markers WI-6980 and GATA8A09.43. Thus, human TANGO 234 allelic variants can include TANGO 234 nucleotide sequence polymorphisms (e.g., nucleotide sequences that vary from SEQ ID NO: 9) that map to this chromosomal region. Similarly, chromosomal mapping has been used to locate the gene encoding human TANGO 265 protein on chromosome 1, between markers D1S305 and D1S2635. Allelic variants of TANGO 265 occur at this chromosomal location. Further by way of example, the gene encoding human TANGO 273 protein has been located by chromosomal mapping on chromosome 7, between markers D7S2467 and D7S2552. Allelic variants of TANGO 273 occur at this chromosomal location.

As used herein, the terms "gene" and "recombinant gene" refer to nucleic acid molecules comprising an open reading frame encoding a polypeptide of the invention. Such natural allelic variations can typically result in 1–5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

Moreover, nucleic acid molecules encoding proteins of the invention from other species (homologs), which have a nucleotide sequence which differs from that of the specific proteins described herein are intended to be within the scope of the invention. Nucleic acid molecules corresponding to natural allelic variants and homologs of a cDNA of the invention can be isolated based on their homology with nucleic acid molecules described herein, using the specific cDNAs described herein, or a portion thereof, as a hybridization probe according to standard hybridization techniques under stringent hybridization conditions. For example, a cDNA encoding a soluble form of a membrane-bound protein of the invention isolated based on its hybridization to a nucleic acid molecule encoding all or part of the membrane-bound form. Likewise, a cDNA encoding a membrane-bound form can be isolated based on its hybridization to a nucleic acid molecule encoding all or part of the soluble form.

Accordingly, in another embodiment, an isolated nucleic acid molecule of the invention is at least 15 (25, 40, 60, 80, 100, 150, 200, 250, 300, 350, 400, 450, 550, 650, 700, 800, 900, 1000, 1200, 1400, 1600, 1800, 2000, 2200, 2400, 2600, 2800, 3000, 3500, 4000, 4500, or 4928) nucleotides in length and hybridizes under stringent conditions to the nucleic acid molecule comprising the nucleotide sequence, preferably the coding sequence, of any of SEQ ID NOs: 1, 2, 9, 10, 17, 18, 25, 26, 33, 34, 45, 46, 53, 54, 67, 68, 72, and 73, or a complement thereof. As used herein, the term "hybridizes-under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6×sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions with the sequence of any of SEQ ID NOs: 1, 2, 9, 10, 17, 18, 25, 26, 33, 34, 45, 46, 53, 54, 67, 68, 72, and 73, or a complement thereof, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of a nucleic acid molecule of the invention sequence that can exist in the population, the skilled artisan will further appreciate that changes can be introduced by mutation thereby leading to changes in the amino acid sequence of the encoded protein, without altering the biological activity of the protein. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the invention pertains to nucleic acid molecules encoding a polypeptide of the invention that contain changes in amino acid residues that are not essential for activity. Such polypeptides differ in amino acid sequence from the sequence of any of SEQ ID NOs: 3–8, 11–16, 19–24, 27–32, 35–44, 47–52, 55–66, 69, and 74, yet retain biological activity. In one embodiment, the isolated nucleic acid molecule includes a nucleotide sequence encoding a protein that includes an amino acid sequence that is at least about 40% identical, 50%, 60%, 70%, 80%, 90%, 95%, or 98% identical to the amino acid sequence of any of SEQ ID NOs: 3–8, 11–16, 19–24, 27–32, 35–44, 47–52, 55–66, 69, and 74.

An isolated nucleic acid molecule encoding a variant protein can be created by introducing one or more nucleotide substitutions, additions or deletions into the nucleotide sequence of any of SEQ ID NOs: 1, 2, 9, 10, 17, 18, 25, 26, 33, 34, 45, 46, 53, 54, 67, 68, 72, and 73, such that one or more amino acid residue substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In a preferred embodiment, a mutant polypeptide that is a variant of a polypeptide of the invention can be assayed for: (1) the ability to form protein:protein interactions with one or more polypeptides of the invention (e.g., in a signaling pathway); (2) the ability to bind a ligand of a polypeptide of the invention (e.g., another protein identified herein); (3) the ability to bind to an intracellular target protein of a polypeptide of the invention (e.g., a modulator or substrate of the polypeptide); or (4) the ability to modulate a physiological activity of the protein, such as one of those disclosed herein (e.g., ability to modulate cell proliferation, cell migration, chemotaxis, or cellular differentiation).

The present invention encompasses antisense nucleic acid molecules, i.e., molecules which are complementary to a sense nucleic acid encoding a polypeptide of the invention, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to all or part of a non-coding region of the coding strand of a nucleotide sequence encoding a polypeptide of the invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, $N_6$-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a selected polypeptide of the invention to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an alpha-anomeric nucleic acid molecule. An $\alpha$-anomeric nucleic acid molecule forms specific double-stranded hybrids with complementary RNA in which, contrary to the usual beta-units, the strands run parallel to each other (Gaultier et al. (1987) *Nucleic Acids Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach (1988) *Nature* 334:585–591) can be used to catalytically cleave mRNA transcripts to thereby inhibit translation of the protein encoded by the mRNA. A ribozyme having specificity for a nucleic acid molecule encoding a polypeptide of the invention can be designed based upon the nucleotide sequence of a cDNA disclosed herein. For example, a derivative of a Tetrahymena L-19 IVS RNA can be constructed in which the nucleotide sequence of the active site is complementary to the nucleotide sequence to be cleaved in a Cech et al. U.S. Pat. No. 4,987,071; and Cech et al. U.S. Pat. No. 5,116,742. Alternatively, an mRNA encoding a polypeptide of the invention can be used to select a catalytic RNA having a specific ribonuclease activity from a pool of RNA molecules. See, e.g., Bartel and Szostak (1993) *Science* 261:1411–1418.

The invention also encompasses nucleic acid molecules which form triple helical structures. For example, expression of a polypeptide of the invention can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569–84; Helene (1992) *Ann N.Y. Acad. Sci.* 660:27–36; and Maher (1992) *Bioassays* 14(12):807–15.

In various embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4(1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93: 14670–675.

PNAs can be used in therapeutic and diagnostic applications. For example, PNAs can be used as antisense or anti-gene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup (1996), supra; Perry-O'Keefe et al. (1996) *Proc. Natl. Acad. Sci. USA* 93: 14670–675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996), supra). The synthesis of PNA-DNA chimeras can be performed as described in Hymp (1996), supra, and Finn et al. (1996) *Nucleic Acids Res.* 24(17):3357–63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al. (1989) *Nucleic Acids Res.* 17:5973–88). PNA monomers are then coupled in a step-wise manner to produce a chimeric molecule with a 5' PNA segment and a 3' DNA segment (Finn et al. (1996) *Nucleic Acids Res.* 24(17):3357–63). Alternatively, chimeric molecules can be synthesized with a 5' DNA segment and a 3' PNA segment (Peterser et al. (1975) *Bioorganic Med. Chem. Lett.* 5:1119–11124).

In other embodiments, the oligonucleotide can include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) *Bio/Techniques* 6:958–976) or intercalating agents (see, e.g., Zon (1988) *Pharm. Res.* 5:539–549). To this end, the oligonucleotide can be conjugated to another molecule, e.g., a peptide, hybridization triggered cross-linking agent, transport agent, hybridization-triggered cleavage agent, etc.

II. Isolated Proteins and Antibodies

One aspect of the invention pertains to isolated proteins, and biologically active portions thereof, as well as polypeptide fragments suitable for use as immunogens to raise antibodies directed against a polypeptide of the invention. In one embodiment, the native polypeptide can be isolated from cells or tissue sources by an appropriate purification scheme using standard protein purification techniques. In another embodiment, polypeptides of the invention are produced by recombinant DNA techniques. Alternative to recombinant expression, a polypeptide of the invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a polypeptide of the invention include polypeptides comprising amino acid sequences sufficiently identical to or derived from the amino acid sequence of the protein (e.g., the amino acid sequence shown in any of SEQ ID NOs: 3–8, 11–16, 19–24, 27–32, 35–44, 47–52, 55–66, 69, and 74), which include fewer amino acids than the full length protein, and exhibit at least one activity of the corresponding full-length protein. Typically, biologically active portions comprise a domain or motif with at least one activity of the corresponding protein. A biologically active portion of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the invention.

Preferred polypeptides have the amino acid sequence of any of SEQ ID NOs: 3–8, 11–16, 19–24, 27–32, 35–44, 47–52, 55–66, 69, and 74. Other useful proteins are substantially identical (e.g., at least about 40%, preferably 50%, 60%, 70%, 80%, 90%, 95%, or 99%) to any of SEQ ID NOs: 3–8, 11–16, 19–24, 27–32, 35–44, 47–52, 55–66, 69, and 74 and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264–2268, modified as in Karlin and Altschul (1993) *Proc. Natl. Acad. Sci. USA* 90:5873–5877. Such an algorithm is incorporated into the NBLAST and XBLAST programs of Altschul, et al. (1990) *J. Mol. Biol.* 215:403–410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.* 25:3389–3402. Alternatively, PSI-Blast can be used to perform an iterated search which detects distant relationships between molecules. Id. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) *CABIOS* 4:11–17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, only exact matches are counted.

The invention also provides chimeric or fusion proteins. As used herein, a "chimeric protein" or "fusion protein" comprises all or part (preferably biologically active) of a polypeptide of the invention operably linked to a heterologous polypeptide (i.e., a polypeptide other than the same polypeptide of the invention). Within the fusion protein, the term "operably linked" is intended to indicate that the polypeptide of the invention and the heterologous polypeptide are fused in-frame to each other. The heterologous polypeptide can be fused to the amino-terminus or the carboxyl-terminus of the polypeptide of the invention.

One useful fusion protein is a GST fusion protein in which the polypeptide of the invention is fused to the carboxyl terminus of GST sequences. Such fusion proteins can facilitate the purification of a recombinant polypeptide of the invention.

In another embodiment, the fusion protein contains a heterologous signal sequence at its amino terminus. For example, the native signal sequence of a polypeptide of the invention can be removed and replaced with a signal sequence from another protein. For example, the gp67 secretory sequence of the baculovirus envelope protein can be used as a heterologous signal sequence (*Current Protocols in Molecular Biology*, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an immunoglobulin fusion protein in which all or part of a polypeptide of the invention is fused to sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a polypeptide of the invention. Inhibition of ligand/receptor interaction can be useful therapeutically, both for treating proliferative and differentiative disorders and for modulating (e.g., promoting or inhibiting) cell survival. Moreover, the immunoglobulin fusion proteins of the invention can be used as immunogens to produce antibodies directed against a polypeptide of the invention in a subject, to purify ligands and in screening assays to identify molecules which inhibit the interaction of receptors with ligands.

Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence of a polypeptide of the invention (e.g., the signal sequence in one of SEQ ID NOs: 3, 4, 11, 12, 19, 20, 27, 28, 35, 36, 47, 48, 69, and 74) can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to the signal sequence itself and to the polypeptide in the absence of the signal sequence (i.e., the cleavage products). In one embodiment, a nucleic acid sequence encoding a signal sequence of the invention can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

In another embodiment, the signal sequences of the present invention can be used to identify regulatory sequences, e.g., promoters, enhancers, repressors. Since signal sequences are the most amino-terminal sequences of a peptide, it is expected that the nucleic acids which flank the signal sequence on its amino-terminal side will be regulatory sequences which affect transcription. Thus, a nucleotide sequence which encodes all or a portion of a signal sequence can be used as a probe to identify and isolate signal sequences and their flanking regions, and these flanking regions can be studied to identify regulatory elements therein.

The present invention also pertains to variants of the polypeptides of the invention. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a protein of the invention which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of the coding sequence of a polypeptide of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, re-naturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) *Proc. Natl. Acad. Sci. USA* 89:7811–7815; Delgrave et al. (1993) *Protein Engineering* 6(3):327–331).

An isolated polypeptide of the invention, or a fragment thereof, can be used as an immunogen to generate antibodies using standard techniques for polyclonal and monoclonal antibody preparation. The full-length polypeptide or protein can be used or, alternatively, the invention provides antigenic peptide fragments for use as immunogens. The antigenic peptide of a protein of the invention comprises at least 8 (preferably 10, 15, 20, or 30 or more) amino acid residues of the amino acid sequence of any of SEQ ID NOs: 3–8, 11–16, 19–24, 27–32, 35–44, 47–52, 55–66, 69, and 74, and encompasses an epitope of the protein such that an antibody raised against the peptide forms a specific immune complex with the protein.

Preferred epitopes encompassed by the antigenic peptide are regions that are located on the surface of the protein, e.g., hydrophilic regions. FIGS. 1L, 1M, 2J, 3U, 4I, 4J, 5E, 6F, and 7D are hydrophobicity plots of the proteins of the invention. These plots or similar analyses can be used to identify hydrophilic regions.

An immunogen typically is used to prepare antibodies by immunizing a suitable (i.e., immunocompetent) subject such as a rabbit, goat, mouse, or other mammal or vertebrate. An appropriate immunogenic preparation can contain, for example, recombinantly-expressed or chemically-synthesized polypeptide. The preparation can further include an adjuvant, such as Freund's complete or incomplete adjuvant, or a similar immunostimulatory agent.

Accordingly, another aspect of the invention pertains to antibodies directed against a polypeptide of the invention. The terms "antibody" and "antibody substance" as used interchangeably herein refer to immunoglobulin molecules and immunologically active portions of immunoglobulin molecules, i.e., molecules that contain an antigen binding site which specifically binds an antigen, such as a polypeptide of the invention (e.g., an epitope of a polypeptide of the invention). A molecule which specifically binds to a given polypeptide of the invention is a molecule which binds the polypeptide, but does not substantially bind other molecules in a sample, e.g., a biological sample, which naturally contains the polypeptide. Examples of immunologically active portions of immunoglobulin molecules include F(ab) and $F(ab')_2$ fragments which can be generated by treating the antibody with an enzyme such as pepsin. The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope.

Polyclonal antibodies can be prepared as described above by immunizing a suitable subject with a polypeptide of the invention as an immunogen. Preferred polyclonal antibody compositions are ones that have been selected for antibodies directed against (i.e., which bind specifically with) one or more polypeptides of the invention. Particularly preferred polyclonal antibody preparations are ones that contain only antibodies directed against one or more polypeptides of the invention. Particularly preferred immunogen compositions are those that contain no other human proteins such as, for example, immunogen compositions made using a non-human host cell for recombinant expression of a polypeptide of the invention. In such a manner, the only human epitope or epitopes recognized by the resulting antibody compositions raised against this immunogen will be present as part of a polypeptide or polypeptides of the invention.

The antibody titer in the immunized subject can be monitored over time by standard techniques, such as with an enzyme linked immunosorbent assay (ELISA) using immobilized polypeptide. If desired, the antibody molecules can be harvested or isolated from the subject (e.g., from the blood or serum of the subject) and further purified by well-known techniques, such as protein A chromatography to obtain the IgG fraction. Alternatively, antibodies which bind specifically with a protein or polypeptide of the invention can be selected or purified (e.g., partially purified) using chromatographic methods, such as affinity chromatography. For example, a recombinantly expressed and purified (or partially purified) protein of the invention can be produced as described herein, and covalently or non-covalently coupled with a solid support such as, for example, a chromatography column. The column thus exhibits specific affinity for antibody substances which bind specifically with the protein of the invention, and these antibody substances can be purified from a sample containing antibody substances directed against a large number of different epitopes, thereby generating a substantially purified antibody substance composition, i.e., one that is substantially free of antibody substances which do not bind specifically with the protein. A substantially purified antibody composition, in this context, means an antibody sample that contains at most only 30% (by dry weight) of contaminating antibodies directed against epitopes other than those on the desired protein or polypeptide of the invention, preferably at most 20%, more preferably at most 10%, most preferably at most 5% (by dry weight of the sample is contaminating antibodies). A purified antibody composition means that at least 99% of the antibodies in the composition are directed against the desired protein or polypeptide of the invention.

At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77–96) or trioma techniques. The technology for producing hybridomas is well known (see generally *Current Protocols in Immunology* (1994) Coligan et al. (eds.) John Wiley & Sons, Inc., New York, N.Y.). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System*, Catalog No. 27-9400-01; and the Stratagene SURFZAP™ *Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92,20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions of the antibody amino acid sequence are derived from different animal species, such as those having a variable region derived from a murine monoclonal antibody and a constant region derived from a human immunoglobulin. (See, e.g., Cabilly et al., U.S. Pat. No. 4,816,567; and Boss et al., U.S. Pat. No. 4,816,397). Humanized antibodies are antibody molecules which are obtained from non-human species, which have one or more complementarity-determining regions (CDRs) derived from the non-human species, and which have a framework region derived from a human immunoglobulin molecule. (See, e.g., Queen, U.S. Pat. No. 5,585,089). Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison (1985) *Science* 229:1202–1207; Oi et al. (1986) *Bio/Techniques* 4:214; U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human patients. Such antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, *Int. Rev. Immunol.* 13:65–93). For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; and 5,545,806. In addition, companies such as Abgenix, Inc. (Freemont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope (Jespers et al. (1994) *Bio/technology* 12:899–903).

An antibody directed against a polypeptide of the invention (e.g., monoclonal antibody) can be used to isolate the polypeptide by standard techniques, such as affinity chromatography or immunoprecipitation. Moreover, such an antibody can be used to detect the protein (e.g., in a cellular lysate or cell supernatant) in order to evaluate the abundance and pattern of expression of the polypeptide. The antibodies can also be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Further, an antibody substance can be conjugated with a therapeutic moiety such as a cytotoxin, a therapeutic agent, or a radioactive metal ion. Cytotoxins and cytotoxic agents include any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithrarnycin, actinomycin D, 1-dehydrotestosterone, glucocorticoids, procaine, tetracaine, lidocaine, propranolol, puromycin, and analogs or homologs of these compounds. Therapeutic agents include, antimetabolites (e.g., methotrexate, 6-mercaptopurine, 6-thioguanine, cytarabine, 5-fluorouracil, and decarbazine), alkylating agents (e.g., mechlorethamine, thioepa chlorambucil, melphalan, carmustine {BSNU}, lomustine {CCNU}, cyclothosphamide, busulfan, dibromomannitol, streptozotocin, mitomycin C, and cis-dichlorodiamine platinum (II) (DDP) cisplatin), anthracyclines (e.g., daunorubicin {formerly daunomycin} and doxorubicin), antibiotics (e.g., dactinomycin {formerly actinomycin}, bleomycin, mithramycin, and anthramycin {AMC}), and anti-mitotic agents (e.g., vincristine and vinblastine).

The conjugates of the invention can be used to modify a biological response; the drug moiety is not to be construed as limited to classical chemical therapeutic agents. For example, the drug moiety can be a protein or polypeptide which exhibits a desired biological activity. Such proteins include, for example, toxins such as abrin, ricin A, pseudomonas exotoxin, or diphtheria toxin; proteins such as tumor necrosis factor, alpha-interferon, beta-interferon, nerve growth factor, platelet derived growth factor, tissue plasminogen activator; and biological response modifiers such as lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), and other growth factors.

Techniques for conjugating a therapeutic moiety with an antibody substance are well known (see, e.g., Arnon et al., "Monoclonal Antibodies For Immunotargeting Of Drugs In Cancer Therapy", in *Monoclonal Antibodies and Cancer Therapy*, Reisfeld et al., eds., pp. 243–256, Alan R. Liss, Inc., 1985; Hellstrom et al., "Antibodies For Drug Delivery", in *Controlled Drug Delivery,* 2nd Ed., Robinson et al., eds., pp. 623–653, Marcel Dekker, Inc., 1987; Thorpe, "Antibody Carriers Of Cytotoxic Agents In Cancer Therapy: A Review", in *Monoclonal Antibodies '84: Biological and Clinical Applications*, Pinchera et al., eds., pp. 475–506, 1985; "Analysis, Results, And Future Prospective Of The Therapeutic Use Of Radiolabeled Antibody In Cancer Therapy", in *Monoclonal Antibodies for Cancer Detection and Therapy*, Baldwin et al., eds., pp. 303–316, Academic Press, 1985; and Thorpe et al., "The Preparation And Cytotoxic Properties Of Antibody-Toxin Conjugates", Immunol. Rev. 62:119–58, 1982). Alternatively, an antibody can be conjugated with a second antibody to form an antibody heteroconjugate as described by Segal in U.S. Pat. No. 4,676,980.

Accordingly, in one aspect, the invention provides substantially purified antibodies or fragment thereof, and non-human antibodies or fragments thereof, which antibodies or fragments specifically bind with a polypeptide having an amino acid sequence which comprises a sequence selected from the group consisting of:

(i) SEQ ID NOs: 3–8, 11–16, 19–24, 27–32, 35–44, 47–52, 55–66, 69, and 74;

(ii) the amino acid sequence encoded by a cDNA of a clone deposited as one of ATCC® 207219, 207184, 207228, 207185, 207220, and 207221;

(iii) at least 15 amino acid residues of the amino acid sequence of any of SEQ ID NOs: 3–8, 11–16, 19–24, 27–32, 35–44, 47–52, 55–66, 69, and 74;

(iv) an amino acid sequence which is at least 95% identical to the amino acid sequence of any of SEQ ID NOs: 3–8, 11–16, 19–24, 27–32, 35–44, 47–52, 55–66, 69, and 74, wherein the percent identity is determined using the ALIGN program of the GCG software package with a PAM120 weight residue table, a gap length penalty of 12, and a gap penalty of 4; and (v) an amino acid sequence which is encoded by a nucleic acid molecule which hybridizes with a nucleic acid having a sequence selected from the group consisting of SEQ ID NOs: 1, 2, 9, 10, 17, 18, 25, 26, 33, 34, 45, 46, 53, 54, 67, 68, 72, and 73 under conditions of hybridization of 6×SSC (standard saline citrate) at 45° C. and washing in 0.2×SSC, 0.1% SDS at 65° C.

In another aspect, the invention provides non-human antibodies or fragments thereof, which antibodies or fragments specifically bind with a polypeptide having an amino acid sequence which comprises a sequence selected from the group consisting of:

(i) SEQ ID NOs: 3–8, 11–16, 19–24, 27–32, 35–44, 47–52, 55–66, 69, and 74;

(ii) the amino acid sequence encoded by a cDNA of a clone deposited as one of ATCC® 207219, 207184, 207228, 207185, 207220, and 207221;

(iii) at least 15 amino acid residues of the amino acid sequence of any of SEQ ID NOs: 3–8, 11–16, 19–24, 27–32, 35–44, 47–52, 55–66, 69, and 74;

(iv) an amino acid sequence which is at least 95% identical to the amino acid sequence of any of SEQ ID NOs: 3–8, 11–16, 19–24, 27–32, 35–44, 47–52, 55–66, 69, and 74, wherein the percent identity is determined using the ALIGN program of the GCG software package with a PAM120 weight residue table, a gap length penalty of 12, and a gap penalty of 4; and (v) an amino acid sequence which is encoded by a nucleic acid molecule which hybridizes with a nucleic acid having a sequence selected from the group consisting of SEQ ID NOs: 1, 2, 9, 10, 17, 18, 25, 26, 33, 34, 45, 46, 53, 54, 67, 68, 72, and 73 under conditions of hybridization of 6×SSC (standard saline citrate) at 45° C. and washing in 0.2×SSC, 0.1% SDS at 65° C. Such non-human antibodies can be goat, mouse, sheep, horse, chicken, rabbit, or rat antibodies. Alternatively, the non-human antibodies of the invention can be chimeric and/or humanized antibodies. In addition, the non-human antibodies of the invention can be polyclonal antibodies or monoclonal antibodies.

In still a further aspect, the invention provides monoclonal antibodies or fragments thereof, which antibodies or fragments specifically bind with a polypeptide having an amino acid sequence which comprises a sequence selected from the group consisting of:

(i) SEQ ID NOs: 3–8, 11–16, 19–24, 27–32, 35–44, 47–52, 55–66, 69, and 74;

(ii) the amino acid sequence encoded by a cDNA of a clone deposited as one of ATCC® 207219, 207184, 207228, 207185, 207220, and 207221;

(iii) at least 15 amino acid residues of the amino acid sequence of any of SEQ ID NOs: 3–8, 11–16, 19–24, 27–32, 35–44, 47–52, 55–66, 69, and 74;

(iv) an amino acid sequence which is at least 95% identical to the amino acid sequence of any of SEQ ID NOs: 3–8, 11–16, 19–24, 27–32, 35–44, 47–52, 55–66, 69, and 74, wherein the percent identity is determined using the ALIGN program of the GCG software package with a PAM120 weight residue table, a gap length penalty of 12, and a gap penalty of 4; and (v) an amino acid sequence which is encoded by a nucleic acid molecule which hybridizes with a nucleic acid having a sequence selected from the group consisting of SEQ ID NOs: 1, 2, 9, 10, 17, 18, 25, 26, 33, 34, 45, 46, 53, 54, 67, 68, 72, and 73 under conditions of hybridization of 6×SSC (standard saline citrate) at 45° C. and washing in 0.2×SSC, 0.1% SDS at 65° C. The monoclonal antibodies can be human, humanized, chimeric and/or non-human antibodies.

The substantially purified antibodies or fragments thereof can specifically bind with a signal peptide, a secreted sequence, an extracellular domain, a transmembrane or a cytoplasmic domain cytoplasmic membrane of a polypeptide of the invention. In a particularly preferred embodiment, the substantially purified antibodies or fragments thereof, the non-human antibodies or fragments thereof, and/or the monoclonal antibodies or fragments thereof, of the invention specifically bind with a secreted sequence or with an extracellular domain of one of TANGO 202, TANGO 234, TANGO 265, TANGO 273, TANGO 286, TANGO 294, and INTERCEPT 296. Preferably, the extracellular domain with which the antibody substance binds has an amino acid sequence selected from the group consisting of SEQ ID NOs: 5, 6, 14, 22, 30, 37, 49, 50, and 56–58.

Any of the antibody substances of the invention can be conjugated with a therapeutic moiety or to a detectable substance. Non-limiting examples of detectable substances that can be conjugated with the antibody substances of the invention include an enzyme, a prosthetic group, a fluorescent material (i.e., a fluorophore), a luminescent material, a bioluminescent material, and a radioactive material (e.g., a radionuclide or a substituent comprising a radionuclide).

The invention also provides a kit containing an antibody substance of the invention conjugated with a detectable substance, and instructions for use. Still another aspect of the invention is a pharmaceutical composition comprising an antibody substance of the invention and a pharmaceutically acceptable carrier. In preferred embodiments, the pharmaceutical composition contains an antibody substance of the invention, a therapeutic moiety (preferably conjugated with the antibody substance), and a pharmaceutically acceptable carrier.

Still another aspect of the invention is a method of making an antibody that specifically recognizes one of TANGO 202, TANGO 234, TANGO 265, TANGO 273, TANGO 286, TANGO 294, and INTERCEPT 296. This method comprises immunizing a vertebrate (e.g., a mammal such as a rabbit, goat, or pig) with a polypeptide. The polypeptide used as an immunogen has an amino acid sequence that comprises a sequence selected from the group consisting of:

(i) SEQ ID NOs: 3–8, 11–16, 19–24, 27–32, 35–44, 47–52, 55–66, 69, and 74;

(ii) the amino acid sequence encoded by a cDNA of a clone deposited as one of ATTC® 207219, 207184, 207228, 207185, 207220, and 207221;

(iii) at least 15 amino acid residues of the amino acid sequence of any of SEQ ID NOs: 3–8, 11–16, 19–24, 27–32, 35–44, 47–52, 55–66, 69, and 74;

(iv) an amino acid sequence which is at least 95% identical to the amino acid sequence of any of SEQ ID NOs: 3–8, 11–16, 19–24, 27–32, 35–44, 47–52, 55–66, 69, and 74, wherein the percent identity is determined using the ALIGN program of the GCG software package with a PAM120 weight residue table, a gap length penalty of 12, and a gap penalty of 4; and (v) an amino acid sequence which is encoded by a nucleic acid molecule which hybridizes with a nucleic acid having a sequence selected from the group consisting of SEQ ID NOs: 1, 2, 9, 10, 17, 18, 25, 26, 33, 34, 45, 46, 53, 54, 67, 68, 72, and 73 under conditions of hybridization of 6×SSC (standard saline citrate) at 45° C. and washing in 0.2×SSC, 0.1% SDS at 65° C.

After immunization, a sample is collected from the vertebrate that contains an antibody that specifically recognizes the polypeptide with which the vertebrate was immunized. Preferably, the polypeptide is recombinantly produced using a non-human host cell. Optionally, an antibody substance can be further purified from the sample using techniques well known to those of skill in the art. The method can further comprise making a monoclonal antibody-producing cell from a cell of the vertebrate. Optionally, antibodies can be collected from the antibody-producing cell.

III. Recombinant Expression Vectors and Host Cells

Another aspect of the invention pertains to vectors, preferably expression vectors, containing a nucleic acid encoding a polypeptide of the invention (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses; adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

The recombinant expression vectors of the invention can be designed for expression of a polypeptide of the invention in prokaryotic (e.g., *E. coli*) or eukaryotic cells (e.g., insect cells (using baculovirus expression vectors), yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* a with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:3140), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174(DE3) from a resident lambda prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec1 (Baldari et al. (1987) *EMBO J.* 6:229–234), pMFa (Kuran and Herskowitz, (1982) *Cell* 30:933–943), pJRY88 (Schultz et al. (1987) *Gene* 54:113–123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (*Reviews—Trends in Genetics*, Vol. 1(1)1986).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

In another embodiment, the expression characteristics of an endogenous nucleic acid within a cell, cell line, or microorganism (e.g., a TANGO 202, TANGO 234, TANGO 265, TANGO 273, TANGO 286, TANGO 294, or INTERCEPT 296 nucleic acid, as described herein) can be modified by inserting a heterologous DNA regulatory element (i.e., one that is heterologous with respect to the endogenous gene) into the genome of the cell, stable cell line, or cloned microorganism. The inserted regulatory element can be operatively linked with the endogenous gene (e.g., TANGO 202, TANGO 234, TANGO 265, TANGO 273, TANGO 286, TANGO 294, or INTERCEPT 296) and thereby control, modulate, or activate the endogenous gene. For example, an endogenous TANGO 202, TANGO 234, TANGO 265, TANGO 273, TANGO 286, TANGO 294, or INTERCEPT 296 gene which is normally "transcriptionally silent" (i.e., a TANGO 202, TANGO 234, TANGO 265, TANGO 273, TANGO 286, TANGO 294, or INTERCEPT 296 gene which is normally not expressed, or is normally expressed only at only a very low level) can be activated by inserting a regulatory element which is capable of promoting expression of the gene in the cell, cell line, or microorganism. Alternatively, a transcriptionally silent, endogenous TANGO 202, TANGO 234, TANGO 265, TANGO 273, TANGO 286, TANGO 294, or INTERCEPT 296 gene can be activated by inserting a promiscuous regulatory element that works across cell types.

A heterologous regulatory element can be inserted into a stable cell line or cloned microorganism such that it is operatively linked with and activates expression of an endogenous TANGO 202, TANGO 234, TANGO 265, TANGO 273, TANGO 286, TANGO 294, or INTERCEPT 296 gene, using techniques, such as targeted homologous recombination, which are well known to those of skill in the art (described e.g., in Chappel, U.S. Pat. No. 5,272,071; PCT publication No. WO 91/06667, published May 16, 1991).

A host cell of the invention, such as a prokaryotic or eukaryotic host cell in culture, can be used to produce a polypeptide of the invention. Accordingly, the invention further provides methods for producing a polypeptide of the invention using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

The host cells of the invention can also be used to produce non-human transgenic animals. For example, in one embodiment, a host cell of the invention is a fertilized oocyte or an embryonic stem cell into which a sequences encoding a polypeptide of the invention have been introduced. Such host cells can then be used to create non-human transgenic animals in which exogenous sequences encoding a polypeptide of the invention have been introduced into their genome or homologous recombinant animals in which endogenous encoding a polypeptide of the invention sequences have been altered. Such animals are useful for studying the function and/or activity of the polypeptide and for identifying and/or evaluating modulators of polypeptide activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing nucleic acid encoding a polypeptide of the invention (or a homologue thereof) into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, 4,873,191, in Hogan, *Manipulating the Mouse Embryo*, Cold Spring Harbor Laboratory Press, Cold Spring Harbor, N.Y., 1986, and in Wakayama et al., 1999, Proc. Natl. Acad. Sci. USA 96:14984–14989. Similar methods can be used to produce other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create a homologous recombinant animal, a vector is prepared which contains at least a portion of a gene encoding a polypeptide of the invention into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation) and cells in which the introduced gene has homologously recombined with the endogenous gene are selected (see, e.g., Li et al. (1992) *Cell* 69:915). The selected cells are then injected into a blastocyst of an animal (e.g., a mouse) to form aggregation chimeras (see, e.g., Bradley in *Teratocarcinomas and Embryonic Stem Cells: A Practical Approach*, Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823–829 and in PCT Publication Nos. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813 and PCT Publication Nos. WO 97/07668 and WO 97/07669.

IV. Pharmaceutical Compositions

The nucleic acid molecules, polypeptides, and antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of the invention. Such methods comprise formulating a pharmaceutically acceptable carrier with an agent which modulates expression or activity of a polypeptide or nucleic acid of the invention. Such compositions can further include additional active agents. Thus, the invention further includes methods for preparing a pharmaceutical composition by formulating a pharmaceutically acceptable carrier with an agent which modulates expression or activity of a polypeptide or nucleic acid of the invention and one or more additional active compounds.

The agent which modulates expression or activity can, for example, be a small molecule other than a nucleic acid, polypeptide, or antibody of the invention. For example, such small molecules include peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents and protein or polypeptide agents depends upon a number of factors within the ken of the ordinarily skilled physician, veterinarian, or researcher. The dose(s) of these agents will vary, for example, depending upon the identity, size, and condition of the subject or sample being treated, further depending upon the route by which the composition is to be administered, if applicable, and the effect which the practitioner desires the agent to have upon the nucleic acid or polypeptide of the invention. Exemplary doses of a small molecule include milligram or microgram amounts per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). Exemplary doses of a protein or polypeptide include gram, milligram or microgram amounts per kilogram of subject or sample weight (e.g., about 1 microgram per kilogram to about 5 grams per kilogram, about 100 micrograms per kilogram to about 500 milligrams per kilogram, or about 1 milligram per kilogram to about 50 milligrams per kilogram). It is furthermore understood that appropriate doses of one of these agents depend upon the potency of the agent with respect to the expression or activity to be modulated. Such appropriate doses can be determined using the assays described herein. When one or more of these agents is to be administered to an animal (e.g., a human) in order to modulate expression or activity of a polypeptide or nucleic acid of the invention, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific agent employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium, and then incorporating the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches, and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes which can be targeted to bind with virus-infected cells using a monoclonal antibody which binds specifically with a viral antigen) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The nucleic acid molecules of the invention can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologs, and antibodies described herein can be used in one or more of the following methods: a) screening assays; b) detection assays (e.g., chromosomal mapping, tissue typing, forensic biology); c) predictive medicine (e.g., diagnostic assays, prognostic assays, monitoring clinical trials, and pharmacogenomics); and d) methods of treatment (e.g., therapeutic and prophylactic). For example, polypeptides of the invention can to used for all of the purposes identified herein in portions of the disclosure relating to individual types of protein of the invention (e.g., TANGO 202 proteins, TANGO 234 proteins, TANGO 265 proteins, TANGO 273 proteins, TANGO 286 proteins, TANGO 294 proteins, and INTERCEPT 296 proteins). Polypeptides of the invention can also be used to modulate cellular proliferation, cellular differentiation, cellular adhesion, or some combination of these. The isolated nucleic acid molecules of the invention can be used to express proteins (e.g., via a recombinant expression vector in a host cell in gene therapy applications), to detect mRNA (e.g., in a biological sample) or a genetic lesion, and to modulate activity of a polypeptide of the invention. In addition, the polypeptides of the invention can be used to screen drugs or compounds which modulate activity or expression of a polypeptide of the invention as well as to treat disorders characterized by insufficient or excessive production of a protein of the invention or production of a form of a protein of the invention which has decreased or aberrant activity compared to the wild type protein. In addition, the antibodies of the invention can be used to detect and isolate a protein of the and modulate activity of a protein of the invention.

This invention further pertains to novel agents identified by the above-described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind to polypeptide of the invention or have a stimulatory or inhibitory effect on, for example, expression or activity of a polypeptide of the invention.

In one embodiment, the invention provides assays for screening candidate or test compounds which bind to or modulate the activity of the membrane-bound form of a polypeptide of the invention or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds can be presented in solution (e.g., Houghten (1992) *Bio/Techniques* 13:412–421), or on beads (Lam (1991) *Nature* 354:82–84), chips (Fodor (1993) *Nature* 364:555–556), bacteria (U.S. Pat. No. 5,223,409), spores (U.S. Pat. Nos. 5,571,698; 5,403,484; and 5,223,409), plasmids (Cull et al. (1992) *Proc. Natl. Acad. Sci. USA* 89:1865–1869) or phage (Scott and Smith (1990) *Science* 249:386–390; Devlin (1990) *Science* 249:404–406; Cwirla et al. (1990) *Proc. Natl. Acad. Sci. USA* 87:6378–6382; and Felici (1991) *J. Mol. Biol.* 222:301–310).

In one embodiment, an assay is a cell-based assay in which a cell which expresses a membrane-bound form of a polypeptide of the invention, or a biologically active portion thereof, on the cell surface is contacted with a test compound and the ability of the test compound to bind to the polypeptide determined. The cell, for example, can be a yeast cell or a cell of mammalian origin. Determining the ability of the test compound to bind to the polypeptide can be accomplished, for example, by coupling the test compound with a radioisotope or enzymatic label such that binding of the test compound to the polypeptide or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radio-emission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses a membrane-bound form of a polypeptide of the invention, or a biologically active portion thereof, on the cell surface with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide or a biologically active portion thereof as compared to the known compound.

In another embodiment, the assay involves assessment of an activity characteristic of the polypeptide, wherein binding of the test compound with the polypeptide or a biologically active portion thereof alters (i.e., increases or decreases) the activity of the polypeptide.

In another embodiment, an assay is a cell-based assay comprising contacting a cell expressing a membrane-bound form of a polypeptide of the invention, or a biologically active portion thereof, on the cell surface with a test compound and determining the ability of the test compound to modulate (e.g., stimulate or inhibit) the activity of the polypeptide or biologically active portion thereof. Determining the ability of the test compound to modulate the activity of the polypeptide or a biologically active portion thereof can be accomplished, for example, by determining the ability of the polypeptide to bind to or interact with a target molecule or to transport molecules across the cytoplasmic membrane.

Determining the ability of a polypeptide of the invention to bind to or interact with a target molecule can be accomplished by one of the methods described above for determining direct binding. As used herein, a "target molecule" is a molecule with which a selected polypeptide (e.g., a polypeptide of the invention binds or interacts with in nature, for example, a molecule on the surface of a cell which expresses the selected protein, a molecule on the surface of a second cell, a molecule in the extracellular milieu, a molecule associated with the internal surface of a cell membrane or a cytoplasmic molecule. A target molecule can be a polypeptide of the invention or some other polypeptide or protein. For example, a target molecule can be a component of a signal transduction pathway which facilitates transduction of an extracellular signal (e.g., a signal generated by binding of a compound to a polypeptide of the invention) through the cell membrane and into the cell or a second intercellular protein which has catalytic activity or a protein which facilitates the association of downstream signaling molecules with a polypeptide of the invention. Determining the ability of a polypeptide of the invention to bind to or interact with a target molecule can be accomplished by determining the activity of the target molecule. For example, the activity of the target molecule can be determined by detecting induction of a cellular second messenger of the target (e.g., an mRNA, intracellular $Ca^{2+}$, diacylglycerol, IP3, and the like), detecting catalytic/enzymatic activity of the target on an appropriate substrate, detecting the induction of a reporter gene (e.g., a regulatory element that is responsive to a polypeptide of the invention operably linked to a nucleic acid encoding a detectable marker, e.g. luciferase), or detecting a cellular response, for example, cellular differentiation, or cell proliferation.

In yet another embodiment, an assay of the present invention is a cell-free assay comprising contacting a polypeptide of the invention or biologically active portion thereof with a test compound and determining the ability of the test compound to bind to the polypeptide or biologically active portion thereof. Binding of the test compound to the polypeptide can be determined either directly or indirectly as described above. In a preferred embodiment, the assay includes contacting the polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide or biologically active portion thereof as compared to the known compound.

In another embodiment, an assay is a cell-free assay comprising contacting a polypeptide of the invention or biologically active portion thereof with a test compound and determining the ability of the test compound to modulate (e.g., stimulate or inhibit) the activity of the polypeptide or biologically active portion thereof. Determining the ability of the test compound to modulate the activity of the polypeptide can be accomplished, for example, by determining the ability of the polypeptide to bind to a target molecule by one of the methods described above for determining direct binding. In an alternative embodiment, determining the ability of the test compound to modulate the activity of the polypeptide can be accomplished by determining the ability of the polypeptide of the invention to further modulate the target molecule. For example, the catalytic activity, the enzymatic activity, or both, of the target molecule on an appropriate substrate can be determined as previously described.

In yet another embodiment, the cell-free assay comprises contacting a polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the polypeptide to preferentially bind to or modulate the activity of a target molecule.

The cell-free assays of the present invention are amenable to use of both a soluble form or the membrane-bound form of a polypeptide of the invention. In the case of cell-free assays comprising the membrane-bound form of the polypeptide, it can be desirable to utilize a solubilizing agent such that the membrane-bound form of the polypeptide is maintained in solution. Examples of such solubilizing agents include non-ionic detergents such as n-octylglucoside, n-dodecylglucoside, n-octylmaltoside, octanoyl-N-methylglucamide, decanoyl-N-methylglucamide, Triton X-100, Triton X-114, Thesit, Isotridecypoly(ethylene glycol ether)n, 3-[(3-cholamidopropyl)dimethylamminio]-1-propane sulfonate (CHAPS), 3-[(3-cholamidopropyl) dimethylamminio]-2-hydroxy-1-propane sulfonate (CHAPSO), or N-dodecyl-N,N-dimethyl-3-ammonio-1-propane sulfonate.

In one or more embodiments of the above assay methods of the present invention, it can be desirable to immobilize either the polypeptide of the invention or its target molecule to facilitate separation of complexed from non-complexed forms of one or both of the proteins, as well as to accommodate automation of the assay. Binding of a test compound to the polypeptide, or interaction of the polypeptide with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase fusion proteins or glutathione-S-transferase fusion proteins can be adsorbed onto glutathione SEPHAROSE™ beads (Sigma Chemical; St. Louis, Mo.) or glutathione derivatized microtiter plates, which are then combined with the test compound or the test compound and either the non-adsorbed target protein or A polypeptide of the invention, and the mixture incubated under conditions conducive to complex formation (e.g., at physiological conditions for salt and pH). Following incubation, the beads or microtiter plate wells are washed to remove any unbound components and complex formation is measured either directly or indirectly, for example, as described above. Alternatively, the complexes can be dissociated from the matrix, and the level of binding or activity of the polypeptide of the invention can be determined using standard techniques.

Other techniques for immobilizing proteins on matrices can also be used in the screening assays of the invention. For example, either the polypeptide of the invention or its target molecule can be immobilized uitilizing conjugation of biotin and streptavidin. Biotinylated polypeptide of the invention or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with the polypeptide of the invention or target molecules but which do not interfere with binding of the polypeptide of the invention to its target molecule can be derivatized to the wells of the plate, and unbound target or polypeptide of the invention trapped in the wells by antibody conjugation. Methods for detecting such complexes, in addition to those described above for the GST-immobilized complexes, include immunodetection of complexes using antibodies reactive with the polypeptide of the invention or target molecule, as well as enzyme-linked assays which rely on detecting an enzymatic activity associated with the polypeptide of the invention or target molecule.

In another embodiment, modulators of expression of a polypeptide of the invention are identified in a method in which a cell is contacted with a candidate compound and the expression of the selected mRNA or protein (i.e., the mRNA or protein corresponding to a polypeptide or nucleic acid of the invention) in the cell is determined. The level of expression of the selected mRNA or protein in the presence of the candidate compound is compared to the level of expression of the selected mRNA or protein in the absence of the candidate compound. The candidate compound can then be identified as a modulator of expression of the polypeptide of the invention based on this comparison. For example, when expression of the selected mRNA or protein is greater (i.e., statistically significantly greater) in the presence of the candidate compound than in its absence, the candidate compound is identified as a stimulator of the selected mRNA or protein expression. Alternatively, when expression of the selected mRNA or protein is less (i.e., statistically significantly less) in the presence of the candidate compound than in its absence, the candidate compound is identified as an inhibitor of the selected mRNA or protein expression. The level of the selected mRNA or protein expression in the cells can be determined by methods described herein.

In yet another aspect of the invention, a polypeptide of the inventions can be used as "bait proteins" in a two-hybrid assay or three hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Bio/Techniques* 14:920–924; Iwabuchi et al. (1993) *Oncogene* 8:1693–1696; and PCT Publication No. WO 94/10300), to identify other proteins, which bind to or interact with the polypeptide of the invention and modulate activity of the polypeptide of the invention. Such binding proteins are also likely to be involved in the propagation of signals by the polypeptide of the inventions as, for example, upstream or downstream elements of a signaling pathway involving the polypeptide of the invention.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. Accordingly, nucleic acid molecules described herein or fragments thereof, can be used to map the location of the corresponding genes on a chromosome. The mapping of the sequences to chromosomes is an important first step in correlating these sequences with genes associated with disease.

Briefly, genes can be mapped to chromosomes by preparing PCR primers (preferably 15–25 base pairs in length) from the sequence of a gene of the invention. Computer analysis of the sequence of a gene of the invention can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the gene sequences will yield an amplified fragment. For a review of this technique, see D'Eustachio et al. ((1983) *Science* 220:919–924).

PCR mapping of somatic cell hybrids is a rapid procedure for assigning a particular sequence to a particular chromosome. Three or more sequences can be assigned per day using a single thermal cycler. Using the nucleic acid sequences of the invention to design oligonucleotide primers, sub-localization can be achieved with panels of fragments from specific chromosomes. Other mapping strategies which can similarly be used to map a gene to its chromosome include in situ hybridization (described in Fan et al. (1990) *Proc. Natl. Acad. Sci. USA* 87:6223–27), pre-screening with labeled flow-sorted chromosomes, and pre-selection by hybridization to chromosome specific cDNA libraries. Fluorescence in situ hybridization (FISH) of a DNA sequence to a metaphase chromosomal spread can further be used to provide a precise chromosomal location in one step. For a review of this technique, see Verma et al. (Human Chromosomes: A Manual of Basic Techniques (Pergamon Press, New York, 1988)).

Reagents for chromosome mapping can be used individually to mark a single chromosome or a single site on that chromosome, or panels of reagents can be used for marking multiple sites and/or multiple chromosomes. Reagents corresponding to non-coding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) *Nature* 325:783–787.

Moreover, differences in the DNA sequences between individuals affected and unaffected with a disease associated with a gene of the invention can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Furthermore, the nucleic acid sequences disclosed herein can be used to perform searches against "mapping databases", e.g., BLAST-type search, such that the chromosome position of the gene is identified by sequence homology or identity with known sequence fragments which have been mapped to chromosomes.

In the instant case, the human gene for TANGO 265 is located on chromosome 1 between markers D1S305 and D1S2635, and the human gene for TANGO 273 is located on chromosome 7 between markers D7S2467 and D7S2552.

In the instant case, the human gene for TANGO 286 exhibits significant amino acid homology with a region of the human chromosome region 22q12–13 genomic nucleotide sequence having GenBank Accession number AL021937. Alignment of a 45 kilobase nucleotide sequence encoding TANGO 286 with AL021937, however, indicated the presence in TANGO 286 of exons which differ from those disclosed in L021937 (pam120.mat scoring matrix; gap penalties −12/−4). This region of chromosome 22 comprises an immunoglobulin lambda chain C (IGLC) pseudogene, the Ret finger protein-like 3 (RFPL3) and Ret finger protein-like 3 antisense (RFPL3S) genes, a gene encoding a novel immunoglobulin lambda chain V family protein, a novel gene encoding a protein similar both to mouse RGDS protein (RALGDS, RALGEF, guanine nucleotide dissociation stimulator A) and to rabbit oncogene RSC, a novel gene encoding the human orthologue of worm F16A11.2 protein, a novel gene encoding a protein similar both to BPI and to rabbit liposaccharide-binding protein, and a 5'-portion of a novel gene. This region also comprises various ESTs, STSs, GSSs, genomic marker D22S1175, a ca repeat polymorphism and putative CpG islands.

A polypeptide and fragments and sequences thereof and antibodies which bind specifically with such polypeptides/fragments can be used to map the location of the gene encoding the polypeptide on a chromosome. This mapping can be performed by specifically detecting the presence of the polypeptide/fragments in members of a panel of somatic cell hybrids between cells obtained from a first species of animal from which the protein originates and cells obtained from a second species of animal, determining which somatic cell hybrid(s) expresses the polypeptide, and noting the chromosome(s) of the first species of animal that it contains. For examples of this technique (see Pajunen et al., 1988, Cytogenet. Cell Genet. 47:37–41 and Van Keuren et al., 1986, Hum. Genet. 74:34–40). Alternatively, the presence of the polypeptide in the somatic cell hybrids can be determined by assaying an activity or property of the polypeptide (e.g., enzymatic activity, as described in Bordelon-Riser et al., 1979, Som. Cell Genet. 5:597–613 and Owerbach et al., 1978, Proc. Natl. Acad. Sci. USA 75:5640–5644).

In the instant case, the human gene for TANGO 234 protein indicated that the gene is located at chromosomal location h12p13. Flanking chromosomal markers include WI-6980 and GATA8A09.43. Nearby human loci include IBD2 (inflammatory bowel disease 2), FPF (familial periodic fever), and HPDR2 (hypophosphatemia vitamin D resistant rickets 2). Nearby genes are KLRC (killer cell receptor cluster), DRPLA (dentatorubro-pallidoluysian atrophy), GAPD (glyceraldehyde-3-phosphate) dehydrogenase, and PXR1 (peroxisome receptor 1). This region is syntenic to mouse chromosome mo6. Murine chromosomal mapping indicated that the murine orthologue is located near the scr (scruffy) locus. Nearby mouse genes include drpla (dentatorubral phillidoluysian atrophy), prp (proline rich protein), and kap (kidney androgen regulated protein).

2. Tissue Typing

The nucleic acid sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the nucleic acid sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The nucleic acid sequences of the invention uniquely represent portions of the human genome. Allelic variation occurs to some degree in the coding regions of these sequences, and to a greater degree in the non-coding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the non-coding regions, fewer sequences are necessary to differentiate individuals. The non-coding sequences of any of SEQ ID NOs: 1, 9, 17, 25, 33, 45, and 53 can comfortably provide positive individual identification with a panel of perhaps 10 to 1,000 primers which each yield a non-coding amplified sequence of 100 bases. If predicted coding sequences, such as those in any of SEQ ID NOs: 2, 10, 18, 26, 34, 46, and 54 are used, a more appropriate number of primers for positive individual identification would be 500–2,000.

If a panel of reagents from the nucleic acid sequences described herein is used to generate a unique identification database for an individual, those same reagents can later be used to identify tissue from that individual. Using the unique identification database, positive identification of the individual, living or dead, can be made from extremely small tissue samples.

3. Use of Partial Gene Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). As mentioned above, actual base sequence information can be used for identification as an accurate alternative to patterns formed by restriction enzyme generated fragments. Sequences targeted to non-coding regions are particularly appropriate for this use as greater numbers of polymorphisms occur in the non-coding regions, making it easier to differentiate individuals using this technique. Examples of polynucleotide reagents include the nucleic acid sequences of the invention or portions thereof, e.g., fragments derived from non-coding regions having a length of at least 20 or 30 bases.

The nucleic acid sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such probes can be used to identify tissue by species and/or by organ type.

C. Predictive Medicine

The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining expression of a polypeptide or nucleic acid of the invention and/or activity of a polypeptide of the invention (e.g., expression or activity of one of TANGO 202, TANGO 234, TANGO 265, TANGO 273, TANGO 286, TANGO 294, or INTERCEPT 296 genes or proteins), in the context of a biological sample (e.g., blood, serum, cells, tissue) to thereby determine whether an individual is afflicted with a disease or disorder, or is at risk of developing a disorder, associated with aberrant expression or activity of a polypeptide of the invention. The invention also provides for prognostic (or predictive) assays for determining whether an individual is at risk of developing a disorder associated with aberrant expression or activity of a polypeptide of the invention. For example, mutations in a gene of the invention can be assayed in a biological sample. Such assays can be used for prognostic or predictive purpose to thereby prophylactically treat an individual prior to the onset of a disorder characterized by or associated with aberrant expression or activity of a polypeptide of the invention.

As an alternative to making determinations based on the absolute expression level of a selected gene, determinations can be based on normalized expression levels of the gene. A gene expression level is normalized by correcting the absolute expression level of the gene (e.g., a TANGO 202, TANGO 234, TANGO 265, TANGO 273, TANGO 286, TANGO 294, or INTERCEPT 296 gene as described herein) by comparing its expression to expression of a gene for which expression is not believed to be co-regulated with the gene of interest, e.g., a housekeeping gene that is constitutively expressed. Suitable genes for normalization include housekeeping genes such as the actin gene. Such normalization allows comparison of the expression level in one sample, e.g., a patient sample, with the expression level in another sample, e.g., a sample obtained from a patient known not to be afflicted with a disease or condition, or between samples obtained from different sources.

Alternatively, the expression level can be assessed as a relative expression level. To assess a relative expression level for a gene (e.g., a TANGO 202, TANGO 234, TANGO 265, TANGO 273, TANGO 286, TANGO 294, or INTERCEPT 296 gene, as described herein), the level of expression of the gene is determined for 10 or more samples (preferably 50 or more samples) of different isolates of cells in which the gene is believed to be expressed, prior to assessing the level of expression of the gene in the sample of interest. The mean expression level of the gene detected in the large number of samples is determined, and this value is used as a baseline expression level for the gene. The expression level of the gene assessed in the test sample (i.e., its absolute level of expression) is divided by the mean expression value to yield a relative expression level. Such a method can identify tissues or individuals which are afflicted with a disorder associated with aberrant expression of a gene of the invention.

Preferably, the samples used in the baseline determination are generated either using cells obtained from a tissue or individual known to be afflicted with a disorder (e.g., a disorder associated with aberrant expression of one of the TANGO 202, TANGO 234, TANGO 265, TANGO 273, TANGO 286, TANGO 294, or INTERCEPT 296 genes) or using cells obtained from a tissue or individual known not to be afflicted with the disorder. Alternatively, levels of expression of these genes in tissues or individuals known to be or not to be afflicted with the disorder can be used to assess whether the aberrant expression of the gene is associated with the disorder (e.g., with onset of the disorder, or as a symptom of the disorder over time).

Another aspect of the invention pertains to monitoring the influence of agents (e.g., drugs or other compounds) on the expression or activity of one or more of TANGO 202, TANGO 234, TANGO 265, TANGO 273, TANGO 286, TANGO 294, and INTERCEPT 296 in clinical trials. These and other agents are described in further detail in the following sections.

1. Diagnostic Assays

An exemplary method for detecting the presence or absence of a polypeptide or nucleic acid of the invention in a biological sample involves obtaining a biological sample from a test subject and contacting the biological sample with a compound or an agent capable of detecting a polypeptide or nucleic acid (e.g., mRNA, genomic DNA) of the invention such that the presence of a polypeptide or nucleic acid of the invention is detected in the biological sample. A preferred agent for detecting mRNA or genomic DNA encoding a polypeptide of the invention is a labeled nucleic acid probe capable of hybridizing to mRNA or genomic DNA encoding a polypeptide of the invention. The nucleic acid probe can be, for example, a full-length cDNA, such as the nucleic acid of any of SEQ ID NOs: 1, 9, 17, 25, 33, 45, 53, 67, and 72, or a portion thereof, such as an oligonucleotide of at least 15, 30, 50, 100, 250 or 500 nucleotides in length and sufficient to specifically hybridize under stringent conditions to a mRNA or genomic DNA encoding a polypeptide of the invention. Other suitable probes for use in the diagnostic assays of the invention are described herein.

A preferred agent for detecting a polypeptide of the invention is an antibody capable of binding to a polypeptide of the invention, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect mRNA, protein, or genomic DNA in a biological sample in vitro as well as in vivo. For example, in vitro techniques for detection of mRNA include Northern hybridizations and in situ hybridizations. In vitro techniques for detection of a polypeptide of the invention include enzyme linked immunosorbent assays (ELISAs), Western blots, immunoprecipitations and immunofluorescence. In vitro techniques for detection of genomic DNA include Southern hybridizations. Furthermore, in vivo techniques for detection of a polypeptide of the invention include introducing into a subject a labeled antibody directed against the polypeptide. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting a polypeptide of the invention or mRNA or genomic DNA encoding a polypeptide of the invention, such that the presence of the polypeptide or mRNA or genomic DNA encoding the polypeptide is detected in the biological sample, and comparing the presence of the polypeptide or mRNA or genomic DNA encoding the polypeptide in the control sample with the presence of the polypeptide or mRNA or genomic DNA encoding the polypeptide in the test sample.

The invention also encompasses kits for detecting the presence of a polypeptide or nucleic acid of the invention in a biological sample (a test sample). Such kits can be used to determine if a subject is suffering from or is at increased risk of developing a disorder associated with aberrant expression of a polypeptide of the invention (e.g., one of the disorders described in the section of this disclosure wherein the individual polypeptide of the invention is discussed). For example, the kit can comprise a labeled compound or agent capable of detecting the polypeptide or mRNA encoding the polypeptide in a biological sample and means for determining the amount of the polypeptide or mRNA in the sample (e.g., an antibody which binds the polypeptide or an oligonucleotide probe which binds to DNA or mRNA encoding the polypeptide). Kits can also include instructions for observing that the tested subject is suffering from or is at risk of developing a disorder associated with aberrant expression of the polypeptide if the amount of the polypeptide or mRNA encoding the polypeptide is above or below a normal level.

For antibody-based kits, the kit can comprise, for example: (1) a first antibody (e.g., attached to a solid support) which binds to a polypeptide of the invention; and, optionally, (2) a second, different antibody which binds to either the polypeptide or the first antibody and is conjugated to a detectable agent.

For oligonucleotide-based kits, the kit can comprise, for example: (1) an oligonucleotide, e.g., a detectably labeled oligonucleotide, which hybridizes to a nucleic acid sequence encoding a polypeptide of the invention or (2) a pair of primers useful for amplifying a nucleic acid molecule encoding a polypeptide of the invention. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of the polypeptide.

2. Prognostic Assays

The methods described herein can furthermore be utilized as diagnostic or prognostic assays to identify subjects having or at risk of developing a disease or disorder associated with aberrant expression or activity of a polypeptide of the invention. For example, the assays described herein, such as the preceding diagnostic assays or the following assays, can be utilized to identify a subject having or at risk of developing a disorder associated with aberrant expression or activity of a polypeptide of the invention (e.g., one of the disorders described in the section of this disclosure wherein the individual polypeptide of the invention is discussed).

Alternatively, the prognostic assays can be utilized to identify a subject having or at risk for developing such a disease or disorder. Thus, the present invention provides a method in which a test sample is obtained from a subject and a polypeptide or nucleic acid (e.g., mRNA, genomic DNA) of the invention is detected, wherein the presence of the polypeptide or nucleic acid is diagnostic for a subject having or at risk of developing a disease or disorder associated with aberrant expression or activity of the polypeptide. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant expression or activity of a polypeptide of the invention. For example, such methods can be used to determine whether a subject can be effectively treated with a specific agent or class of agents (e.g., agents of a type which decrease activity of the polypeptide). Thus, the present invention provides methods for determining whether a subject can be effectively treated with an agent for a disorder associated with aberrant expression or activity of a polypeptide of the invention in which a test sample is obtained and the polypeptide or nucleic acid encoding the polypeptide is detected (e.g., wherein the presence of the polypeptide or nucleic acid is diagnostic for a subject that can be administered the agent to treat a disorder associated with aberrant expression or activity of the polypeptide).

The methods of the invention can also be used to detect genetic lesions or mutations in a gene of the invention, thereby determining if a subject with the lesioned gene is at risk for a disorder characterized aberrant expression or activity of a polypeptide of the invention. In preferred embodiments, the methods include detecting, in a sample of cells from the subject, the presence or absence of a genetic lesion or mutation characterized by at least one of an alteration affecting the integrity of a gene encoding the polypeptide of the invention, or the mis-expression of the gene encoding the polypeptide of the invention. For example, such genetic lesions or mutations can be detected by ascertaining the existence of at least one of: 1) a deletion of one or more nucleotides from the gene; 2) an addition of one or more nucleotides to the gene; 3) a substitution of one or more nucleotides of the gene; 4) a chromosomal rearrangement of the gene; 5) an alteration in the level of a messenger RNA transcript of the gene; 6) an aberrant modification of the gene, such as of the methylation pattern of the genomic DNA; 7) the presence of a non-wild type splicing pattern of a messenger RNA transcript of the gene; 8) a non-wild type level of the protein encoded by the gene; 9) an allelic loss of the gene; and 10) an inappropriate post-translational modification of the protein encoded by the gene. As described herein, there are a large number of assay techniques known in the art which can be used for detecting lesions in a gene.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in a gene (see, e.g., Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to the selected gene under conditions such that hybridization and amplification of the gene (if present) occurs, and detecting the presence or absence of an amplification product, or detecting the size of the amplification product and comparing the length to a control sample. PCR and/or LCR can be desirable to use as a preliminary amplification step in conjunction with any of the techniques used for detecting mutations described herein.

Alternative amplification methods include: self-sustained sequence replication (Guatelli et al. (1990) *Proc. Natl. Acad. Sci. USA* 87:1874–1878), transcriptional amplification system (Kwoh, et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a selected gene from a sample cell can be identified by alterations in restriction enzyme cleavage patterns. For example, sample and control DNA is isolated, (optionally) amplified, digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations can be identified by hybridizing a sample and control nucleic acids, e.g., DNA or RNA, to high density arrays containing hundreds or thousands of oligonucleotides probes (Cronin et al. (1996) *Human Mutation* 7:244–255; Kozal et al. (1996) *Nature Medicine* 2:753–759). For example, genetic mutations can be identified in two-dimensional arrays containing light-generated DNA probes as described in Cronin et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the selected gene and detect mutations by comparing the sequence of the sample nucleic acids with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in a selected gene include methods in which protection from cleavage agents is used to detect mismatched bases in RNA/RNA or RNA/DNA heteroduplexes (Myers et al. (1985) *Science* 230:1242). In general, the technique of mismatch cleavage entails providing heteroduplexes formed by hybridizing (labeled) RNA or DNA containing the wild-type sequence with potentially mutant RNA or DNA obtained from a tissue sample. The double-stranded duplexes are treated with an agent which cleaves single-stranded regions of the duplex such as which will exist due to base pair mismatches between the control and sample strands. RNA/DNA duplexes can be treated with RNase to digest mismatched regions, and DNA/DNA hybrids can be treated with S1 nuclease to digest mismatched regions.

In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al. (1988) *Proc. Natl. Acad. Sci. USA* 85:4397; Saleeba et al. (1992) *Methods Enzymol* 217:286–295. In a preferred embodiment, the control DNA or RNA can be labeled for detection.

In still another embodiment, the mismatch cleavage reaction employs one or more proteins that recognize mismatched base pairs in double-stranded DNA (so called DNA mismatch repair enzymes) in defined systems for detecting and mapping point mutations in cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a selected sequence, e.g., a wild-type sequence, is hybridized to a cDNA or other DNA product from a test cell(s). The duplex is treated with a DNA mismatch repair enzyme, and the cleavage, products, if any, can be detected from electrophoresis protocols or the like. See, e.g., U.S. Pat. No. 5,459,039.

In other embodiments, alterations in electrophoretic mobility will be used to identify mutations in genes. For example, single strand conformation polymorphism (SSCP) can be used to detect differences in electrophoretic mobility between mutant and wild type nucleic acids (Orita et al. (1989) *Proc. Natl. Acad. Sci. USA* 86:2766; see also Cotton (1993) *Mutat. Res.* 285:125–144; Hayashi (1992) *Genet. Anal. Tech. Appl.* 9:73–79). Single-stranded DNA fragments of sample and control nucleic acids will be denatured and allowed to re-nature. The secondary structure of single-stranded nucleic acids varies according to sequence, and the resulting alteration in electrophoretic mobility enables the detection of even a single base change. The DNA fragments can be labeled or detected with labeled probes. The sensitivity of the assay can be enhanced by using RNA (rather than DNA), in which the secondary structure is more sensitive to a change in sequence. In a preferred embodiment, the subject method utilizes heteroduplexes analysis to separate double stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a 'GC clamp' of approximately 40 base pairs of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers can be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification can be used in conjunction with the instant invention. Oligonucleotides used as primers for specific amplification can carry the mutation of interest in the center of the molecule (so that amplification depends on differential hybridization; Gibbs et al. (1989) *Nucleic Acids Res.* 17:2437–2448) or at the extreme 3' end of one primer where, under appropriate conditions, mismatching can prevent or reduce polymerase extension (Prossner (1993) *Tibtech* 11:238). In addition, it can be desirable to introduce a novel restriction site in the region of the mutation to create cleavage-based detection (Gasparini et al. (1992) *Mol. Cell Probes* 6:1). Amplification can also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein can be performed, for example, using pre-packaged diagnostic kits comprising at least one probe nucleic acid or antibody reagent described herein, which can be conveniently used, e.g., in clinical settings to diagnose patients exhibiting symptoms or family history of a disease or illness involving a gene encoding a polypeptide of the invention. Furthermore, any cell type or tissue, preferably peripheral blood leukocytes, in which the polypeptide of the invention is expressed can be utilized in the prognostic assays described herein.

3. Pharmacogenomics

Agents, or modulators which have a stimulatory or inhibitory effect on activity or expression of a polypeptide of the invention as identified by a screening assay described herein can be administered to individuals to treat (prophylactically or therapeutically) disorders associated with aberrant activity of the polypeptide. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of a polypeptide of the invention, expression of a nucleic acid of the invention, or mutation content of a gene of the invention in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of a polypeptide of the invention, expression of a nucleic acid encoding the polypeptide, or mutation content of a gene encoding the polypeptide in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a modulator of activity or expression of the polypeptide, such as a modulator identified by one of the exemplary screening assays described herein.

4. Monitoring of Effects During Clinical Trials

Monitoring the influence of agents (e.g., drug compounds) on the expression or activity of a polypeptide of the invention (e.g., the ability to modulate aberrant cell proliferation chemotaxis, and/or differentiation) can be applied not only in basic drug screening, but also in clinical trials. For example, the effectiveness of an agent, as determined by a screening assay as described herein, to increase gene expression, protein levels, or protein activity, can be monitored in clinical trials of subjects exhibiting decreased gene expression, protein levels, or protein activity. Alternatively, the effectiveness of an agent, as determined by a screening assay, to decrease gene expression, protein levels or protein activity, can be monitored in clinical trials of subjects exhibiting increased gene expression, protein levels, or protein activity. In such clinical trials, expression or activity of a polypeptide of the invention and preferably, that of other polypeptide that have been implicated in for example, a cellular proliferation disorder, can be used as a marker of the immune responsiveness of a particular cell.

For example, and not by way of limitation, genes, including those of the invention, that are modulated in cells by treatment with an agent (e.g., compound, drug or small molecule) which modulates activity or expression of a polypeptide of the invention (e.g., as identified in a screening assay described herein) can be identified. Thus, to study the effect of agents on cellular proliferation disorders, for example, in a clinical trial, cells can be isolated and RNA prepared and analyzed for the levels of expression of a gene of the invention and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of a gene of the invention or other genes. In this way, the gene expression pattern can serve as a marker, indicative of the physiological response of the cells to the agent. Accordingly, this response state can be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of the polypeptide or nucleic acid of the invention in the pre-administration sample; (iii) obtaining one or more post-administration samples from the subject; (iv) detecting the level the of the polypeptide or nucleic acid of the invention in the post-administration samples; (v) comparing the level of the polypeptide or nucleic acid of the invention in the pre-administration sample with the level of the polypeptide or nucleic acid of the invention in the post-administration sample or samples; and (vi) altering the administration of the agent to the subject accordingly. For example, increased administration of the agent can be desirable to increase the expression or activity of the polypeptide to higher levels than detected, i.e., to increase the effectiveness of the agent. Alternatively, decreased administration of the agent can be desirable to decrease expression or activity of the polypeptide to lower levels than detected, i.e., to decrease the effectiveness of the agent.

C. Methods of Treatment

The present invention provides for both prophylactic and therapeutic methods of treating a subject at risk of (or susceptible to) a disorder or having a disorder associated with aberrant expression or activity of a polypeptide of the invention and/or in which the polypeptide of the invention is involved. Disorders characterized by aberrant expression or activity of the polypeptides of the invention are described elsewhere in this disclosure.

1. Prophylactic Methods

In one aspect, the invention provides a method for preventing in a subject, a disease or condition associated with an aberrant expression or activity of a polypeptide of the invention, by administering to the subject an agent which modulates expression or at least one activity of the polypeptide. Subjects at risk for a disease which is caused or contributed to by aberrant expression or activity of a polypeptide of the invention can be identified by, for example, any or a combination of diagnostic or prognostic assays as described herein. Administration of a prophylactic agent can occur prior to the manifestation of symptoms characteristic of the aberrance, such that a disease or disorder is prevented or, alternatively, delayed in its progression. Depending on the type of aberrance, for example, an agonist or antagonist agent can be used for treating the subject. The appropriate agent can be determined based on screening assays described herein.

2. Therapeutic Methods

Another aspect of the invention pertains to methods of modulating expression or activity of a polypeptide of the invention for therapeutic purposes. The modulatory method of the invention involves contacting a cell with an agent that modulates one or more of the activities of the polypeptide. An agent that modulates activity can be an agent as described herein, such as a nucleic acid or a protein, a naturally-occurring cognate ligand of the polypeptide, a peptide, a peptidomimetic, or other small molecule. In one embodiment, the agent stimulates one or more of the biological activities of the polypeptide. Examples of such stimulatory agents include the active polypeptide of the invention and a nucleic acid molecule encoding the polypeptide of the invention that has been introduced into the cell. In another embodiment, the agent inhibits one or more of the biological activities of the polypeptide of the invention. Examples of such inhibitory agents include antisense nucleic acid molecules and antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a polypeptide of the invention. In one embodiment, the method involves administering an agent (e.g., an agent identified by a screening assay described herein), or combination of agents that modulates (e.g., up-regulates or down-regulates) expression or activity. In another embodiment, the method involves administering a polypeptide of the invention or a nucleic acid molecule of the invention as therapy to compensate for reduced or aberrant expression or activity of the polypeptide.

Stimulation of activity is desirable in situations in which activity or expression is abnormally low or down-regulated and/or in which increased activity is likely to have a beneficial effect. Conversely, inhibition of activity is desirable in situations in which activity or expression is abnormally high or up-regulated and/or in which decreased activity is likely to have a beneficial effect.

The contents of all references, patents, and published patent applications cited throughout this application are hereby incorporated by reference.

Deposit of Clones

Each of these deposits was made merely as a convenience to those of skill in the art. These deposits are not an admission that a deposit is required under 35 U.S.C. §112.

Clone EpT202, encoding human TANGO 202 was deposited with the American Type Culture Collection (ATCC®, 10801 University Boulevard, Manassas, Va. 20110-2209) on Apr. 21, 1999 and was assigned Accession Number 207219. This deposit will be maintained under the terms of the Budapest Treaty on the International Recognition of the Deposit of Microorganisms for the Purposes of Patent Procedure.

Clone EpTm202, encoding murine TANGO 202 was deposited with ATCC® on Apr. 21, 1999 and was assigned (composite) Accession Number 207221. This deposit will be maintained under the terms of the Budapest Treaty on the International Recognition of the Deposit of Microorganisms for the Purposes of Patent Procedure.

Clone EpT234, encoding human TANGO 234 was deposited with ATTC® on Apr. 2, 1999 and was assigned Accession Number 207184. This deposit will be maintained under the terms of the Budapest Treaty on the International Recognition of the Deposit of Microorganisms for the Purposes of Patent Procedure.

Clone EpT265, encoding human TANGO 265 was deposited with ATCC® on Apr. 28, 1999 and was assigned Accession Number 207228. This deposit will be maintained under the terms of the Budapest Treaty on the International Recognition of the Deposit of Microorganisms for the Purposes of Patent Procedure.

Clone EpT273, encoding human TANGO 273 was deposited with ATCC® on Apr. 2, 1999 and was assigned Accession Number 207185. This deposit will be maintained under the terms of the Budapest Treaty on the International Recognition of the Deposit of Microorganisms for the Purposes of Patent Procedure.

Clone EpTm273, encoding murine TANGO 273 was deposited with ATCC® on Apr. 2, 1999 and was assigned (composite) Accession Number 207221. This deposit will be maintained under the terms of the Budapest Treaty on the International Recognition of the Deposit of Microorganisms for the Purposes of Patent Procedure.

Clone EpT286, encoding human TANGO 286 was deposited with ATTC® on Apr. 20, 1999 and was assigned (composite) Accession Number 207220. This deposit will be maintained under the terms of the Budapest Treaty on the International Recognition of the Deposit of Microorganisms for the Purposes of Patent Procedure.

Clone EpT294, encoding human TANGO 294 was deposited with ATCC® on Apr. 20, 1999 and was assigned (composite) Accession Number 207220. This deposit will be maintained under the terms of the Budapest Treaty on the International Recognition of the Deposit of Microorganisms for the Purposes of Patent Procedure.

Clone EpT296, encoding human INTERCEPT 296 was deposited with ATTC® on Apr. 20, 1999 and was assigned (composite) Accession Number 207220. This deposit will be maintained under the terms of the Budapest Treaty on the International Recognition of the Deposit of Microorganisms for the Purposes of Patent Procedure.

Clones containing cDNA molecules encoding human TANGO 286, human TANGO 294, and INTERCEPT 296 were deposited with ATTC® on Apr. 21, 1999 as Accession Number 207220, as part of a composite deposit representing a mixture of five strains, each carrying one recombinant plasmid harboring a particular cDNA clone.

To distinguish the strains and isolate a strain harboring a particular cDNA clone, an aliquot of the mixture is streaked out to single colonies on nutrient medium (e.g., LB plates) supplemented with 100 mg/ml ampicillin, single colonies are grown, and then plasmid DNA is extracted using a standard mini-preparation procedure. Next, a sample of the DNA mini-preparation is digested with a combination of the restriction enzymes SalI, NotI, and DraII and the resulting products are resolved on a 0.8% agarose gel using standard DNA electrophoresis conditions. This digestion procedure liberates fragments as follows:

1. human TANGO 286 (clone EpT286): 1.85 kB and 0.1 kB (human TANGO 286 has a DraII cut site at about base pair 1856).
2. human TANGO 294 (clone EpT294): 1.4 kB and 0.6 kB (human TANGO 294 has a DraII cut site at about base pair 1447).
3. human INTERCEPT 296 (clone EpT296): 0.4 kB, 1.6 kB, and 0.1 kB (human INTERCEPT 296 has DraII cut sites at about base pair 410 and at about base pair 1933).

The identity of the strains can be inferred from the fragments liberated.

Clones containing cDNA molecules encoding mouse TANGO 202 and mouse TANGO 273 were deposited with ATCC® on Apr. 21, 1999 and were assigned Accession Number 207221, as part of a composite deposit representing a mixture of five strains, each carrying one recombinant plasmid harboring a particular cDNA clone.

To distinguish the strains and isolate a strain harboring a particular cDNA clone, an aliquot of the mixture is streaked out to single colonies on nutrient medium (e.g., LB plates) supplemented with 100 mg/ml ampicillin, single colonies are grown, and then plasmid DNA is extracted using a standard mini-preparation procedure. Next, a sample of the DNA mini-preparation is digested with a combination of the restriction enzymes Sal I, Not I, and Apa I, and the resultant products are resolved on a 0.8% agarose gel using standard DNA electrophoresis conditions. This digestion procedure liberates fragments as follows:

1. mouse TANGO 202 (clone EpTm202): 3.5 kB and 1.4 kB (mouse TANGO 202 has a Apa I cut site at about base pair 3519).
2. mouse TANGO 273 (clone EpTm273): 0.3 kB and 2.6 kB (mouse TANGO 273 has a Apa I cut site at about base pair 298).

The identity of the strains can be inferred from the fragments liberated.

Human TANGO 202, human TANGO 234, human TANGO 265, and human TANGO 273 were each deposited as single deposits. Their clone names, deposit dates, and accession numbers are as follows:

1. human TANGO 202: clone EpT202 was deposited with ATCC® on Apr. 21, 1999, and was assigned Accession Number 207219.
2. human TANGO 234: clone EpT234 was deposited with ATCC® on Apr. 2, 1999, and was assigned Accession Number 207184.
3. human TANGO 265: clone EpT265 was deposited with ATCC® on Apr. 28, 1999, and was assigned Accession Number 207228.
4. human TANGO 273: clone EpT273 was deposited with ATCC® on Apr. 2, 1999, and was assigned Accession Number 207185.

All publications, patents, and patent applications referenced in this specification are incorporated by reference into the specification to the same extent as if each individual publication, patent, or patent application had been specifically and individually indicated to be incorporated herein by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated polypeptide selected from the group consisting of:

a) a polypeptide which is encoded by a nucleic acid molecule comprising a nucleotide sequence which is at least 90% identical to the nucleotide sequence of SEQ ID NO:45 or SEQ ID NO:46;

b) a polypeptide which is encoded by a nucleic acid molecule comprising a nucleotide sequence which is at least 90% identical to the nucleotide sequence of the DNA insert of clone EpT294, which was deposited with ATCC as Accession Number 207220;

c) a polypeptide which is at least 90% identical to the amino acid sequence of SEQ ID NO:47;

d) a polypeptide which is at least 90% identical to residues 15–423 of the amino acid sequence of SEQ ID NO:47; and e) a polypeptide which is at least 90% identical to the amino acid sequence of SEQ ID NO: 49;

wherein the polypeptide exhibits a lipase activity.

2. The isolated polypeptide of claim 1, wherein the polypeptide is encoded by a nucleic acid molecule comprising a nucleotide sequence which is at least 95% identical to the nucleotide sequence of SEQ ID NO:45 or SEQ ID NO:46.

3. The isolated polypeptide of claim 1, wherein the polypeptide is encoded by a nucleic acid molecule comprising a nucleotide sequence which is at least 95% identical to the nucleotide sequence of the DNA insert of clone EpT294, which was deposited with ATCC as Accession Number 207220.

4. The isolated polypeptide of claim 1, wherein the polypeptide is at least 95% identical to the amino acid sequence of SEQ ID NO:47.

5. The isolated polypeptide of claim 1, wherein the polypeptide is at least 95% identical to residues 15–423 of the amino acid sequence of SEQ ID NO:47.

6. The isolated polypeptide of claim 1, wherein the polypeptide is at least 95% identical to the amino acid sequence of SEQ ID NO:49.

7. The isolated polypeptide of claim 1, wherein the amino acid sequence of the polypeptide further comprises heterologous amino acid residues.

8. The isolated polypeptide of claim 1, admixed with a pharmaceutically acceptable carrier.

9. An isolated polypeptide which is encoded by a nucleic acid molecule comprising the nucleotide sequence of SEQ ID NO:45 or SEQ ID NO:46.

10. The isolated polypeptide of claim 9, wherein the amino acid sequence of the polypeptide further comprises heterologous amino acid residues.

11. The isolated polypeptide of claim 9, admixed with a pharmaceutically acceptable carrier.

12. An isolated polypeptide which is encoded by the nucleotide sequence of the DNA insert of clone EpT294, which was deposited with ATCC as Accession Number 207220.

13. The isolated polypeptide of claim 12, wherein the amino acid sequence of the polypeptide further comprises heterologous amino acid residues.

14. The isolated polypeptide of claim 12, admixed with a pharmaceutically acceptable carrier.

15. An isolated polypeptide comprising the amino acid sequence of SEQ ID NO:47.

16. The isolated polypeptide of claim 15, wherein the amino acid sequence of the polypeptide further comprises heterologous amino acid residues.

17. The isolated polypeptide of claim 15, admixed with a pharmaceutically acceptable carrier.

18. An isolated polypeptide comprising the amino acid sequence of SEQ ID NO:49.

19. The isolated polypeptide of claim 18, wherein the amino acid sequence of the polypeptide further comprises heterologous amino acid residues.

20. The isolated polypeptide of claim 18, admixed with a pharmaceutically acceptable carrier.

* * * * *